(12) United States Patent
Heise et al.

(10) Patent No.: US 7,875,624 B2
(45) Date of Patent: Jan. 25, 2011

(54) MODULATING AND MEASURING CELLULAR ADHESION

(75) Inventors: Carla Heise, Benicia, CA (US); Sang H. Lee, Waltham, MA (US)

(73) Assignee: Novartis Vaccines and Diagnostics, Inc., Emeryville, CA (US)

( * ) Notice: Subject to any disclaimer, the term of this patent is extended or adjusted under 35 U.S.C. 154(b) by 558 days.

(21) Appl. No.: 11/061,386

(22) Filed: Feb. 18, 2005

(65) Prior Publication Data

US 2005/0239825 A1 Oct. 27, 2005

Related U.S. Application Data

(60) Provisional application No. 60/546,395, filed on Feb. 20, 2004, provisional application No. 60/547,103, filed on Feb. 23, 2004, provisional application No. 60/554,771, filed on Mar. 19, 2004.

(51) Int. Cl.
  *A01N 43/42* (2006.01)
  *A61K 31/44* (2006.01)

(52) U.S. Cl. ......................... 514/287; 546/64

(58) Field of Classification Search .................. 514/312
  See application file for complete search history.

(56) References Cited

U.S. PATENT DOCUMENTS

| | | | |
|---|---|---|---|
| 3,663,606 A | 5/1972 | Yoshikazu | |
| 4,659,657 A | 4/1987 | Harnisch et al. | |
| 4,882,342 A | 11/1989 | Von der Saal et al. | |
| 5,073,492 A | 12/1991 | Chen et al. | |
| 5,151,360 A * | 9/1992 | Handa et al. | 435/375 |
| 5,330,992 A | 7/1994 | Eissenstat et al. | |
| 5,414,088 A | 5/1995 | Von Der Saal et al. | |
| 5,480,883 A | 1/1996 | Spada et al. | |
| 5,585,380 A | 12/1996 | Bianco et al. | |
| 5,646,153 A | 7/1997 | Spada et al. | |
| 5,710,158 A | 1/1998 | Myers et al. | |
| 5,763,441 A | 6/1998 | App et al. | |
| 5,792,771 A | 8/1998 | App et al. | |
| 5,801,212 A | 9/1998 | Okamoto et al. | |
| 5,855,866 A | 1/1999 | Thorpe et al. | |
| RE36,256 E | 7/1999 | Spada et al. | |
| 5,942,385 A | 8/1999 | Hirth | |
| 5,981,569 A | 11/1999 | App et al. | |
| 6,057,320 A | 5/2000 | Spada et al. | |
| 6,111,110 A | 8/2000 | Brenan et al. | |
| 6,137,010 A | 10/2000 | Joo et al. | |
| 6,174,912 B1 | 1/2001 | Beck et al. | |
| 6,258,951 B1 | 7/2001 | Lohmann et al. | |
| 6,268,391 B1 | 7/2001 | Dickerson et al. | |
| 6,303,600 B1 | 10/2001 | Cox et al. | |
| 6,306,874 B1 | 10/2001 | Fraley et al. | |
| 6,313,138 B1 | 11/2001 | Fraley et al. | |
| RE37,650 E | 4/2002 | Myers et al. | |
| 6,420,382 B2 | 7/2002 | Fraley et al. | |
| 6,479,512 B1 | 11/2002 | Fraley et al. | |
| 6,593,344 B1 | 7/2003 | Biedermann et al. | |
| 6,605,617 B2 | 8/2003 | Renhowe et al. | |
| 6,756,383 B2 | 6/2004 | Renhowe et al. | |
| 6,759,417 B2 | 7/2004 | Renhowe et al. | |
| 6,762,194 B2 | 7/2004 | Renhowe et al. | |
| 6,774,237 B2 | 8/2004 | Renhowe et al. | |
| 6,774,327 B1 | 8/2004 | Wong | |
| 6,800,760 B2 | 10/2004 | Renhowe et al. | |
| 7,064,215 B2 | 6/2006 | Renhowe et al. | |
| 7,179,912 B2 | 2/2007 | Halbrook et al. | |
| 7,470,709 B2 | 12/2008 | Barsanti et al. | |
| 2002/0103230 A1 | 8/2002 | Renhowe et al. | |
| 2002/0107392 A1 | 8/2002 | Renhowe et al. | |
| 2002/0165218 A1 | 11/2002 | Halbrook et al. | |
| 2003/0028018 A1 | 2/2003 | Renhowe et al. | |
| 2003/0087854 A1 | 5/2003 | Monia et al. | |
| 2003/0158224 A1 | 8/2003 | Renhowe et al. | |
| 2003/0159702 A1 | 8/2003 | Lindell et al. | |
| 2003/0207883 A1 | 11/2003 | Renhowe et al. | |
| 2004/0002518 A1 | 1/2004 | Renhowe et al. | |
| 2004/0006101 A1 | 1/2004 | Renhowe et al. | |
| 2004/0092535 A1 | 5/2004 | Barsanti et al. | |
| 2004/0097545 A1 | 5/2004 | Renhowe et al. | |

(Continued)

FOREIGN PATENT DOCUMENTS

AU 2003290699 6/2004

(Continued)

OTHER PUBLICATIONS

Yoo et al., Synchronous Elevation of Soluble Intercellular Adhesion Molecule-1 (ICAM-1) and Vascular Cell Adhesion Molecule-1 (VCAM-1) Correlates with Gastric Cancer Progression, 1998, Yonsei Medical Journal, vol. 39. No. 1, pp. 27-36.*

(Continued)

*Primary Examiner*—James D Anderson
*Assistant Examiner*—Meghan Finn
(74) *Attorney, Agent, or Firm*—Foley & Lardner LLP

(57) ABSTRACT

Methods of using compounds having Structure I or the salts or tautomers of the compounds in the treatment of disorders relating to cell adhesion and metastatic processes are presented herein.

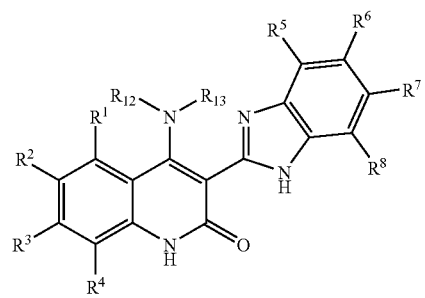

18 Claims, 9 Drawing Sheets

U.S. PATENT DOCUMENTS

| | | | |
|---|---|---|---|
| 2004/0220196 A1 | 11/2004 | Hannah et al. | |
| 2005/0054672 A1 | 3/2005 | Renhowe et al. | |
| 2005/0137399 A1 | 6/2005 | Cai et al. | |
| 2005/0203101 A1 | 9/2005 | Barsanti et al. | |
| 2005/0209247 A1 | 9/2005 | Cai et al. | |
| 2005/0256157 A1 | 11/2005 | Gesner et al. | |
| 2005/0261307 A1* | 11/2005 | Cai et al. | 514/253.07 |
| 2006/0261307 A1 | 11/2006 | Black et al. | |

FOREIGN PATENT DOCUMENTS

| | | |
|---|---|---|
| CA | 2421120 | 3/2002 |
| CL | 23463 | 11/2003 |
| DE | 2363459 | 6/1975 |
| DE | 3634066 | 4/1988 |
| DE | 19841985 | 3/2000 |
| EP | 0290153 | 11/1988 |
| EP | 0 509 717 | 4/1992 |
| EP | 0 508 800 | 10/1992 |
| EP | 0 747 771 | 12/1996 |
| EP | 0 797 376 | 9/1997 |
| EP | 0 290 153 | 11/1998 |
| EP | 1 086 705 | 3/2001 |
| HU | P0104752 | 7/2002 |
| JP | 59-130284 | 7/1984 |
| JP | 63-230687 | 9/1988 |
| JP | 02-229165 | 9/1990 |
| JP | 6-9952 | 1/1994 |
| JP | 7-43896 | 2/1995 |
| JP | 8-29973 | 2/1996 |
| JP | 63-258903 | 10/1998 |
| WO | WO 91/04974 | 4/1991 |
| WO | WO 92/18483 | 10/1992 |
| WO | WO 92/20642 | 11/1992 |
| WO | WO-94/11337 | 5/1994 |
| WO | WO 95/15758 | 6/1995 |
| WO | WO-95/18622 | 7/1995 |
| WO | WO 95/18801 | 7/1995 |
| WO | WO 97/03069 | 1/1997 |
| WO | WO-97/21436 | 6/1997 |
| WO | WO 97/34876 | 9/1997 |
| WO | WO 97/48694 | 12/1997 |
| WO | WO 98/13350 | 4/1998 |
| WO | WO 98/55124 | 12/1998 |
| WO | WO 99/10349 | 3/1999 |
| WO | WO 99/16755 | 4/1999 |
| WO | WO-99/48868 | 9/1999 |
| WO | WO 99/50263 | 10/1999 |
| WO | WO 99/65897 | 12/1999 |
| WO | WO 00/00481 | 1/2000 |
| WO | WO 00/03990 | 1/2000 |
| WO | WO 00/11709 | 3/2000 |
| WO | WO 00/20400 | 4/2000 |
| WO | WO 00/27379 | 5/2000 |
| WO | WO 00/31049 | 6/2000 |
| WO | WO 00/35492 | 6/2000 |
| WO | WO 00/58315 | 10/2000 |
| WO | WO 00/71129 | 11/2000 |
| WO | WO 00/74683 | 12/2000 |
| WO | WO 01/02369 | 1/2001 |
| WO | WO 01/12169 | 2/2001 |
| WO | WO 01/28993 | 4/2001 |
| WO | WO 01/29025 | 4/2001 |
| WO | WO 01/52875 | 7/2001 |
| WO | WO 01/52904 | 7/2001 |
| WO | WO 01/53268 | 7/2001 |
| WO | WO 01/55114 | 8/2001 |
| WO | WO 01/62251 | 8/2001 |
| WO | WO 01/62252 | 8/2001 |
| WO | WO 01/74296 | 10/2001 |
| WO | WO 02/18383 | 3/2002 |
| WO | WO 02/22598 | 3/2002 |
| WO | WO 02/26716 | 4/2002 |
| WO | WO 02/32861 | 4/2002 |
| WO | WO 02/058697 | 8/2002 |
| WO | WO 03/004488 | 1/2003 |
| WO | WO 03/033472 | 4/2003 |
| WO | WO 03/087095 | 10/2003 |
| WO | WO 2004/018419 | 3/2004 |
| WO | WO 2004/030620 | 4/2004 |
| WO | WO 20041031401 | 4/2004 |
| WO | WO 2004/043389 | 5/2004 |
| WO | WO 2004/063151 | 7/2004 |
| WO | WO 2004/063170 | 7/2004 |
| WO | WO-2004/073631 | 9/2004 |
| WO | WO 2004/087153 | 10/2004 |
| WO | WO-2004/103274 | 12/2004 |
| WO | WO 2005/009967 | 2/2005 |
| WO | WO-2005/037306 | 4/2005 |
| WO | WO 2005/046589 | 5/2005 |
| WO | WO 2005/046590 | 5/2005 |
| WO | WO 2005/047244 | 5/2005 |
| WO | WO 2005/053692 | 6/2005 |
| WO | WO 2005/082340 | 9/2005 |
| WO | WO 2006/081445 | 8/2006 |
| WO | WO 2006/27926 | 11/2006 |

OTHER PUBLICATIONS

Blakey et al., Anti-cancer drug discovery and development summit, 2003, Expert Opin. Investig. Drugs, vol. 12, No. 9, pp. 1577-1582.*

Gontero, et al., "Metastasis Markers in Bladder Cancer: A Review of the Literature and Clinical Considerations", European Urology, vol. 46, pp. 296-311 (2004).

Kirstein, Ca 145:201781, abstract only of Recent Patents on Anti-cancer Drug Discovery, vol. 1(2), pp. 153-161 (2006).

Grand, et al., Targeting FGFR3 in Multiple Myeloma: Inhibition of t(4;14) Positive Cells by SU5402 and PD173074, Leukemia, 2004, vol. 18, pp. 962-966.

Dalton, et al., "Multiple Myeloma," Hematology, Am. Soc. Hematol. Educ. Program, 2001, 157-77.

Ukrainets, et al., "Effective Synthesis of 3-(Benzimidazol-2-yl)-4-Hydroxy-2-Oxo-1,2-Dihydroquinolines," Tetrahedron Letters, vol. 36, No. 42, 1995, pp. 7747-7748.

Carla Heise, et al., "In vivo Preclinical Evaluation of Tyrosine Kinase Inhibitors with Potent Effects on Tumor Angiogenesis, Growth and Metastasis," Abstract and presentation material for a presentation at the American Association for Cancer Research meeting held in Apr. 2002.

U.S. Appl. No. 10/644,055, filed Aug. 2003, Barsanti, et al.
U.S. Appl. No. 10/839,793, filed May 2004, Barsanti, et al.
U.S. Appl. No. 10/982,543, filed Nov. 2004, Cai, et al.

Cecil, Textbook of Medicine, 21$^{st}$ Edition (2000), Goldman & Bennett (Editors), W.B. Saunders Company (Publisher), Chapter 198, pp. 1060-1074.

Ukrainets et al., "Effective Synthesis of 3-(Benzimidazol-2-yl)-4-Hydroxy-2-Oxo-1,2, Dihydroquinolines"*Tetrahedron Letters* 36(42), 7747-7749, 1995.

Zetter, B. R., "Angiogenesis and Tumor Metastasis," Annu. Rev. Med., 1998, vol. 49, pp. 407-424; published by Annual Review Inc.

MSNBC News Services, "Mixed results on new cancer drug," Nov. 9, 2000.

Gura, T., "Systems for Identifying New Drugs Are Often Faulty," *Science*, 1997, vol. 278, pp. 1041-1042.

Dermer, G. B., "Another Anniversary for the War on Cancer," *Biotechnology*, 1994, vol. 12, p. 320.

Freshney, R. I., *Culture of Animal Cells—A Manual of Basic Technique*, 1983, pp. 1-4; published by Alan R. Liss, Inc.

Angiogenesis Foundation, "New Study Shows That Acute Myeloid Leukemia is Angiogenesis-Dependent," Jan. 4, 2000; www.angio.org/newsandviews/ archive2000/jan_4_2000.html.

Hussong, J. W. et al., "Evidence of increased angiogenesis in acute myeloid leukemia,"*Blood*, 2000, vol. 95(1), pp. 309-313; The American Society of Hematology.

Kerbel, R. S., "Tumor Angiogenesis: Past, Present and Near Future," *Carcinogenesis*, 2000, vol. 21(3), pp. 505-515; Oxford University Press.

Lundberg, L. G. et al., "Bone Marrow in Polycythemia Vera, Chronic Myelocytic Leukemia, and Myelofibrosis Has an Increased Vascularity," *American Journal of Pathology*, 2000, vol. 157(1), pp. 15-19.

Dankbar, B. et al., "Vascular endothelial growth factor and interleukin-6 in paracrine tumor-stromal cell interactions in multiple myeloma," *Blood*, 2000, vol. 5(8), pp. 2630-2636.

Menzel, T. et al., "Elevated Intracellular Level of Basic Fibroblast Growth Factor Correlates with Stage of Chronic Lymphocytic Leukemia and is Associated With Resistance to Fludarabine," *Blood*, 1996, vol. 87(3), pp. 1056-1063.

Gruber, G. et al., "Basic Fibroblast Growth Factor is Expressed in CD19/CD11c-Positive Cells in Hairy Cell Leukemia," *Blood*, 1999, vol. 94(3), pp. 1077-1085.

U.S. Appl. No. 10/982,543, filed Nov. 5, 2004, Cai et al.

U.S. Appl. No. 10/982,757, filed Nov. 5, 2004, Cai et al.

U.S. Appl. No. 10/983,174, filed Nov. 5, 2004, Cai et al.

U.S. Appl. No. 11/041,191, filed Jan. 21, 2005, Gesner et al.

Aprelikova, O., et al., "FLT4, a novel Class III Receptor Tyrosine Kinase in chromosome 5q33-qter1," *Cancer Res.*, vol. 52, pp. 746-748, Feb. 1, 1992, published by the American Association for Cancer Research, Stanford University Libraries' High Wire Press, California, United States of America.

Beals, C. R. et al., "Nuclear Export of NF-ATc Enhanced by Glycogen Synthase Kinase-3," *Science*, vol. 275, pp. 1930-1933, Mar. 28, 1997.

Brownlees, J. et al., "Tau phosphorylation in transgenic mice expressing glycogen synthase kinase-3β transgenes," *NeuroReport*, vol. 8, No. 15, pp. 3251-3255, Oct. 20, 1997; published by Rapid Science Publishers.

Carmeliet, P. et al. "Angiogenesis in Cancer and Other Diseases," Nature, 407, pp. 249-257 (2000).

Chan, T. A. et al., "14-3-3σ is required to prevent mitotic catastrophe after DNA damage," *Nature*, vol. 401, pp. 616-620, Oct. 7, 1999; published by Macmillan Magazines Ltd.

Chen, G. et al., "The Mood-Stabilizing Agent Valproate Inhibits the Activity of Glycogen Synthase Kinase-3," *J. Neurochem.*, vol. 72, No. 3, 1999, pp. 1327-1330; published by Lippincott Williams & Wilkins, Inc., Philadelphia.

Chesi, M. et al., "Activated fibroblast growth factor receptor 3 is an oncogene that contributes to tumor progression in multiple myeloma," *Blood*, vol. 97, No. 3, pp. 729-736, Feb. 1, 2001; published by The American Society of Hematology.

Connolly, D., et al., "Human Vascular Permeability Factor," *J. Biol. Chem.*, vol. 264, pp. 20017-20024, 1989, published by the American Society For Biochemistry and Molecular Biology, Inc., Stanford University Libraries' High Wire Press, California, United States of America.

Connolly, D., et al., "Tumor Vascular Permeability Factor Stimulates Endothelial Cell Growth and Angiogenesis," *J. Clin. Invest.*, vol. 84, pp. 1470-1478, Nov. 1989, published by the American Society for Clinical Investigation, Inc., Stanford University Libraries' High Wire Press, California, United States of America.

Cross, A. E. et al., "The inhibition of glycogen synthase kinase-3 by insulin or insulin-like growth factor 1 in the rat skeletal muscle cell line L6 blocked by wortmannin, but not by rapamycin: evidence that wortmannin blocks activation of the mitogen-activated protein kinase pathway in L6 cells between Ras and Raf," *Biochem J.*, vol. 303, pp. 21-26, 1994; (printed in Great Britain).

DeVries, C., et al., "The fms-Like Tyrosine Kinase, a Receptor for Vascular Endothelial Growth Factor," *Science*, vol. 255, pp. 989-991, Feb. 21, 1992, published by The American Society for the Advancement of Science, Stanford University Libraries' High Wire Press, California, United States of America.

Doukas, M. A. et al., "Effect of Lithium on Stem Cell and Stromal Cell Proliferation in vitro," *Exp. Hematol.*, vol. 14, pp. 215-221, 1986; published by International Society for Experimental Hematology.

Ferrara, N., et al., "The Biology of Vascular Endothelial Growth Factor," *Endocrinol. Rev.*, vol. 18, No. 1, pp. 4-25, 1997, published by the Endocrine Society, Stanford University Libraries' High Wire Press, California, United States of America.

Flückiger-Isler, R. E. et al., "Stimulation of rat liver glycogen synthesis by the adenosine kinase inhibitor 5-iodotubercidin," *Biochem. J.*, vol. 292, pp. 85-91, 1993; (printed in Great Britain).

Folkman, J., "Fighting Cancer by Attacking Its Blood Supply," *Scientific American*, vol. 275, pp. 150-154, Sep. 1996, published by Scientific American, Inc., New York, New York, United States of America.

Hammond, W. P. et al., "Lithium Therapy of Canine Cyclic Hematopoiesis," *Blood*, vol. 55, No. 1, pp. 26-28, Jan. 1980.

Heinrich, M. C. et al., "Inhibition of KIT Tyrosine Kinase Activity: A Novel Molecular Approach to the Treatment of KIT-Positive Malignancies," *J. Clin. Oncol.*, vol. 20, No. 6, pp. 1692-1703, Mar. 15, 2002.

Hennequin, L. F., et al., Design and Structure—Activity Relationship of a New Class of Potent VEGF Receptor Tyrosine Kinase Inhibitors,: *J. Med. Chem.*, vol. 42, No. 26, pp. 5369-5389, 1999; published by American Chemical Society, Washington, D.C.

Hirao, A. et al., "DNA Damage-Induced Activation of p53 by the Checkpoint Kinase CHk2," *Science*, vol. 287, pp. 1824-1827, Mar. 10, 2000.

Klein, P. S. et al., "A molecular mechanism for the effect of lithium on development," *Proc. Natl. Acad. Sci. USA*, vol. 93, pp. 8455-8459, Aug. 1996.

Lee, J. et al., "Positive Regulation of Wee1 by Chk1 and 14-3-3 Proteins," *Molecular Biology of the Cell*, vol. 12, pp. 551-563, Mar. 2001; published by the American Society for Cell Biology.

Leung, D., et al., "Vascular Endothelial Growth Factor Is a Secreted Angiogenic Mitogen," *Science*, vol. 246, pp. 1306-1309, Dec. 8, 1989, published by the American Society for the Advancement of Science, Stanford University Libraries' High Wire Press, California, United States of America.

Levis, M. et al., "A FLT3-targeted tyrosine kinase inhibitor is cytotoxic to leukemia cells in vitro and in vivo," *Blood*, vol. 99, No. 11, pp. 3885-3891, Jun. 1, 2002; published by the American Society of Hematology.

Liu, Q. et al., "Chk1 is an essential kinase that is regulated by Atr and required for the $G_2/M$ DNA damage checkpoint," *Genes & Development*, vol. 14, 2000, pp. 1448-1459; published by Cold Springs Harbor Laboratory Press.

Lopez-Girona, A. et al., "Nuclear localization of Cdc25 is regulated by DNA damage and a 14-3-3 protein," *Nature*, vol. 397, pp. 172-175, Jan. 14, 1999; published by Macmillan Magazines Ltd.

Lovestone, S. et al., "Alzheimer's disease-like phosphorylation of the microtubule-associated protein tau by glycogen synthase kinase-3 in transfected mammalian cells," *Current Biology*, vol. 4, pp. 1077-1086, Dec. 1, 1994; published by Elsevier Science Ltd.

Lymboussaki, A., "Vascular endothelial growth factors and their receptors in embryos, adults, and in tumors," Academic Dissertation, University of Helsinki, Molecular/Cancer Biology Laboratory and Department of Pathology, Haartman Institute, 1999.

Maguire, M.P., et al., "A New Series of PDGF Receptor Tyrosine Kinase Inhibitors: 3-Substituted Quinoline Derivatives," *J. Med. Chem.*, vol. 37, No. 14, pp. 2129-2137, 1994; published by American Chemical Society, Washington, D.C.

Massillon, D. et al., "Identification of the glycogenic compound 5-iodotubercidin as a general protein kinase inhibitor," *Biochem. J.*, vol. 299, pp. 123-128, 1994; printed in Great Britain.

Matei, S., et al., "Condensation of ethyl 2-benzimidazoleacetate with carbonyl compounds," *Rev. Chim.*, vol. 33, No. 6, pp. 527-530, 1989, published by the Central Institute of Chemistry, Bucharest, Romania.

Mustonen, T., et al., "Endothelial Receptor Tyrosine Kinases Involved in Angiogenesis," *J. Cell Biology*, vol. 129, No. 4, pp. 895-898, May 1995, published by the Rockfeller University Press, New York, New York, United States of America.

Nonaka, S. et al., "Chronic lithium treatment robustly protects neurons in the central nervous system against excitotoxicity by inhibiting N-methyl-D-aspartate receptor-mediated calcium influx," *Proc. Natl. Acad. Sci. USA*, vol. 95, pp. 2642-2647, Mar. 1998.

Parker, L. L. et al., "Inactivation of the p34cdc2-Cyclin B Complex by the Human WEE1 Tyrosine Kinase," *Science*, vol. 257, pp. 1955-1957, Sep. 25, 1992.

Pei, J.-J. et al., "Distribution, Levels, and Activity of Glycogen Synthase Kinase-3 in the Alzheimer. Disease Brain," *Journal of Neuropathology and Experimental Neurology*, vol. 56, No. 1, pp. 70-78, Jan. 1997; published by the American Association of Neuropathologists.

Peng, C.-Y. et al., "Mitotic and $G_2$ Checkpoint Control: Regulation of 14-3-3 Protein Binding by Phosphorylation of Cdc25C on Serine-216," *Science*, vol. 277, pp. 1501-1505, Sep. 5, 1997.

Plouet, J., et al., "Isolation and characterization of a newly identified endothelial cell mitogen produced by AtT-20 cells," *EMBO J.*, vol. 8, No. 12, pp. 3801-3806, 1989, published by IRL Press.

Quinn, T., et al., "Fetal liver kinase 1 is a receptor for vascular endothelial growth factor and is selectively expressed in vascular endothelium," *Proc. Natl. Acad. Sci. USA*, vol. 90, pp. 7533-7537, Aug. 1993.

Saito, Y. et al., "The mechanism by which epidermal growth factor inhibits glycogen synthase kinase 3 in A431 cells," *Biochem. J.*, vol. 303, pp. 27-31, 1994; printed in Great Britain.

Sanchez, Y. et al., "Conservation of the Chk1 Checkpoint Pathway in Mammals: Linkage of DNA Damage to Cdk Regulation Through Cdc25," *Science*, vol. 277, pp. 1497-1501, Sep. 5, 1997.

Shibuya, M., et al., "Nucleotide sequence and expression of a novel human receptor-type tyrosine kinase gene (fit) closely related to the fms family," *Oncogene*, vol. 5, pp. 519-524, 1990, published by Macmillan Press Ltd., Stockton Press Company, Great Britain.

Smolich, B.D. et al., "The antiangiogenic protein kinase inhibitors SU5416 and SU6668 inhibit the SCF receptor (c-kit) in a human myeloid leukemia cell line and in acute myeloid leukemia blasts," *Blood*, vol. 97, No. 5, pp. 1413-1421, Mar. 1, 2001; published by the American Society of Hematology.

Stambolic, V. et al., "Lithium inhibits glycogen synthase kinase-3 activity and mimics Wingless signaling in intact cells," *Current Biology*, vol. 6, No. 12, pp. 1664-1668, 1996; published by Current Biology Ltd. ISSN 0960-9822.

Stover, D. R., "Recent advances in protein kinase inhibition: Current molecular scaffolds used for inhibitor synthesis," *Current Opinion in Drug Discovery & Development*, vol. 2, No. 4, pp. 274-285, 1999; published by PharmaPress Ltd., London, United Kingdom.

Sun, T-Q. et al.. "PAR-1 is a Dishevelled-associated kinase and a positive regulator of Wnt signalling," *Nature Cell Biology*, vol. 3, pp. 628-636, Jul. 2001; published by Macmillan Magazines Ltd.

Takashima, A. et al., "tau protein kinase I is essential for amyloid β-protein-induced neurotoxicity," *Proc. Natl. Acad. Sci. USA*, vol. 90, pp. 7789-7793, Aug. 1993.

Takashima, A. et al., "Presenilin 1 associates with glycogen synthase kinase-3β and its substrate tau," *Proc. Natl. Acad. Sci. USA*, vol. 95, pp. 9837-9641, Aug. 1998; published by The National Academy of Sciences.

Terman, B., et al., "Identification of a new endothelial cell growth factor receptor tyrosine kinase," *Oncogene*, vol. 6, pp. 1677-1683, 1991, published by Macmillan Press Ltd., Stockton Press Company, Great Britain.

Thomas, M.D., R. J. et al., "Progress in Geriatrics: Excitatory Amino Acids in Health and Disease," *J. of the American Geriatrics Society*, vol. 43, No. 11, Nov. 1995; published by American Geriatrics Society.

Ukrainets, I., "Effective Synthesis of 3-(Benzimidazol-2-yl)-4-Hydroxy-2-Oxo-1,2-Dihydroquinolines," *Tet. Lett.*, vol, 36, No. 42, pp. 7747-7748, 1995, published by Elsevier Science Ltd., Great Britain.

Ukrainets, I., et al., "2-Carbethoxymethyl-4H-3,1-Benzoxazin-4-One. 3. *Condensation of o-Phenylenediamine," pp. 198-200, translated from *Khimiya Geterotsiklicheskikh Soedinii*, No. 2, pp. 239-241, Feb. 1992, published by Plenum Publ. Corp., London, Great Britain.

Ukrainets, I., et al., "4-Hydroxy-2-Quinolones 7. *Synthesis and Biological Properties of 1-R-3-(2-Benzimidazolyl)-4-Hydroxy-2-Quinolones," pp. 92-94, translated from *Khimiya Geterotsiklicheskikh Soedinii*, No. 1, pp. 105-108, Jan. 1993, published by Plenum Publ. Corp., London, Great Britain.

Ukrainets, I., et al., "4-Hydroxy-2-Quinolones. 16.* Condensation of N-R-Substituted Amides of 2-Carboxy-Malonanilic Acid With o-Phenylenediamine," pp. 941-944, translated from *Khimiya Geterotsiklicheskikh Soedinii*, vol. 8, pp. 1105-1108, Aug. 1993, published by Plenum Publ. Corp., London, Great Britain.

Ukrainets, I., et al., "4-Hydroxy-2-Quinolones. 32.* Synthesis and Antithyroid Activity of Thio Analogs of 1H-2-OXO-3-(2-Benzimidazolyl)-4-HydroxyQuinoline," *Chem. Heterocyclic Comp.*, vol. 33, No. 5, pp. 600-604, 1997, published by Kluwer Academic Publishers, London, Great Britain.

Ullrich, A., et al., "Signal Transduction by Receptors with Tyrosine Kinase Activity," *Cell*, vol. 61, pp. 203-212, Apr. 20, 1990, published by Cell Press, Cambridge, Massachusetts, United States of America.

van der Geer, P., et al., "Receptor Protein-Tyrosine Kinases and Their Signal Transduction Pathways," *Annu. Rev. Cell Biol.*, vol. 10, pp. 251-337, 1994, published by Annual Reviews, Inc., Palo Alto, California, United States of America.

Vogelstein, B. et al., "Surfing the p53 network," *Nature*, vol. 408, pp. 307-310, Nov. 16, 2000; published by Macmillan Magazines Ltd.

Welsh, G. I. et al., "Glycogen synthase kinase-3 is rapidly inactivated in response to insulin and phosphorylates eukaryotic initiation factor eIF-2B," *Biochem. J.*, vol. 294, pp. 625-629, 1993; printed in Great Britain.

Yamasaki, Y. et al., "Pioglitazone (AD-4833) Ameliorates Insulin Resistance in Patients with NIDDM," *Tohoku J. Exp. Med.*, vol. 183, pp. 173-183, 1997.

Zhao, H. et al., "ATR-Mediated Checkpoint Pathways Regulate Phosphorylation and Activation of Human Chk1," *Molecular and Cellular Biology*, vol. 21, No. 13, pp. 4129-4139, Jul. 2001; published by American Society for Microbiology.

Zhang, Z. et al., "Destabilization of β-catenin by mutations in presenilin-1 potentiates neuronal apoptosis," *Nature*, vol. 395, pp. 698-702, Oct. 15, 1998; published by Macmillan Publishers Ltd.

List of compounds purchased from various vendors (3 pages).

CAS printout for 304876-79-7 Registry File, entry date into Registry File Nov. 29, 2000; and CAS printout for 300591-52-0 Registry File, entry date into Registry File Oct. 31, 2000.

Salmon S.E., et al., "Basic & Clinical Pharmacology, Seventh Edition," edited by B. Katzung, Appleton & Lange, pp. 29, 881-884 (1998).

Milauer, B. et al., "Glioblastoma Growth Inhibited In Vivo by a Dominant-Negative Flk-1 Mutant" Nature, vol. 367, pp. 576-579 (1994); published by the Nature Publishing Group.

Pinedo, H.M. et al., "Translational Research: The Role of VEGF in Tumor Angiogenesis," The Oncologist 2000 vol. 5(supp 1) pp. 1-2 (2000).

McMahon G. "VEGF Receptor Signaling in Tumor Angiogenesis," The Oncologist 2000 vol. 5(supp 1) pp. 3-10 (2000).

Antonios-McCrea, W. R. et al., "LHMDS mediated tandem acylation-cyclization of 2-aminobenzenecarbonitriles with 2-benzymidazol-2-yl acetates: a short and efficient route to the synthesis of 4-amino-3-benzimidazol-2-ylhydroquinolin-2-ones," *Tetrahedron Letters*, vol. 47, 2006, pp. 657-660; published by Elsevier Ltd.

Bastin et al. Salt selection and Optimisation procedures for pharmaceutical new chemical entities, organic process research & development 2000, 4, 427-35.

Beck, J. R., "A Direct Synthesis of Benzo[b]thiophene-2-carboxylate Esters Involving Nitro Displacement," *J. Org. Chem.*, vol. 37, No. 21, 1972, pp. 3224-3226.

Beebe, J. S. et al., "Pharmacological Characterization of CP-547,632, a Novel Vascular Endothelial Growth Factor Receptor-2 Tyrosine Kinase Inhibitor for Cancer Therapy," *Cancer Research*, vol. 63, pp. 7301-7309, Nov. 2003.

Berge, S. et al., "Pharmaceutical Salts," *J. Pharm. Sci.*, vol. 66, No. 1, 1977, pp. 1-19.

Berwanger, B. et al., "Loss of a *FYN*-regulated differentiation and growth arrest pathway in advanced stage neuroblastoma," *Cancer Cell*, vol. 2, Nov. 2002, pp. 377-386; published by Cell Press.

Caira, Mino R., "Crystalline polymorphism of Organic Compounds," *Topics in Current Chemistry*, vol. 198, Springer Verlag 1998.

Guideline for the Format and Content of the Human Pharmacokinetic and Bioavailability Section of an Application, *Center for Drugs and Biologics*, FDA, Department of Health and Human Services, Feb. 1997, pp. 1-18.

Hiyama, T. et al., "A New Synthesis of 3-Amino-2-Alkenoates," *Tetrahedron Letters*, vol. 23, No. 15, 1982, pp. 1597-1600; published by Pergamon Press Ltd.

Johnson et al., "Relationships between drug activity in NCI preclinical in vitro and in vivo models and early clinical trials," *British Journal of Cancer*, vol. 84, No. 10, 2001, pp. 1424-1431.

Kreimeyer, A. et al., "Evaluation and Biological Properties of Reactive Ligands for the Mapping of the Glycine Site on the *N*-Methyl-D-aspartate (NMDA) Receptor," *J. Med. Chem.*, vol. 42, 1999, pp. 4394-4404; published by American Chemical Society.

Lee, S. H. et al., "In vivo Target Modulation and Biological Activity of CHIR-258, a Multitargeted Growth Factor Receptor Kinase Inhibitor, in Colon Cancer Models," *Clin. Cancer Res.*, vol. 11, No. 10, pp. 3633-3641, May 15, 2005.

Lopes de Menezes, D. E. et al., "CHIR-258: A Potent Inhibitor of FLT3 Kinase in Experimental Tumor Xenograft Models of Human Acute Myelogenous Leukemia," *Clin. Cancer Res.*, vol. 11, No. 14, pp. 5281-5291, Jul. 15, 2005.

Majolini, M. B. et al., "Dysregulation of the Protein Tyrosine Kinase LCK in Lymphoproliferative Disorders and in Other Neoplasias," *Leukemia and Lymphoma*, vol. 35(3-4), 1999, pp. 245-254; published by OPA (Overseas Publishers Association) N.V.

Mundy, "Preclinical models of bone metastases," *Semin. Oncol.*, 28(4 Suppl. 11), 2001, pp. 2-8.

Siemeister, G. et al., "Two Independent Mechanisms Essential for Tumor Angiogenesis: Inhibition of Human Melanoma Xenograft Growth by Interfering with either the Vascular Endothelial Growth Factor Receptor Pathway or the Tie-2 Pathway," *Cancer Research*, vol. 59, Jul. 1, 1999, pp. 3185-3191.

Suggitt et al., "50 Years of Preclinical Anticancer Drug Screening: Empirical to Target-Driven Approaches," *Clinical Cancer Research*, vol. 11, 2005, pp. 971-981.

Trudel, S. et al., "CHIR-258, a novel, multitargeted tyrosine kinase inhibitor for the potential treatment of t(f;14) multiple myeloma," *Blood*, vol. 105, No. 7, Apr. 1, 2005; published by the American Society of Hematology.

Valtola, R. et al., "VEGFR-3 and Its Ligand VEGF-C Are Associated with Angiogenesis in Breast Cancer," *American Journal of Pathology*, vol. 154, No. 5, May 1999, pp. 1381-1390; published by American Society for Investigative Pathology.

Wedge, S. R. et al., "ZD6474 Inhibits Vascular Endothelial Growth Factor Signaling, Angiogenesis, and Tumor Growth following Oral Administration," *Cancer Research*, vol. 62, pp. 4645-4655, Aug. 15, 2002.

Winstead, E., "p53 Gene May Help Fight Tumors," *NCI Cancer Bulletin*, vol. 4, No. 5, pp. 1-2, 2007.

Yao et al., "Cell-specific but p53-independent Regulation of Vascular Endothelial Growth Factor Expression by Interferons in Human Glioblastoma Cells," *Journal of Neuro-Oncology*, vol. 76, pp. 219-225, 2006.

Zeng et al., "HDAC3 is crucial in shear- and VEGF-induced stem cell differentiation toward endothelial cells," *The Journal of Cell Biology*, vol. 174, No. 7, pp. 1059-1069, 2006.

Danish Search Report for Singapore Patent Application No. 200501676-1 dated Feb. 28, 2006.

Danish Written Opinion for Singapore Patent Application No. 200501676-1 dated Sep. 20, 2007.

European Communication for EP 01973722.0 dated Mar. 16, 2004.

European Communication for EP 03746614.1 dated Nov. 6, 2007.

European Partial Search Report for EP 07011978.9 dated Sep. 19, 2007.

European Supplementary Search Report for EP 03746614.1 dated May 24, 2007.

International Search Report for PCT/US00/13420 dated Aug. 14, 2000.

International Search Report for PCT/US01/42131 dated Mar. 6, 2002.

International Search Report for PCT/US03/10463 dated Jun. 12, 2003.

International Preliminary Examination Report for PCT/US03/10463 dated Jun. 8, 2004.

International Search Report for PCT/US2005/005316 dated Nov. 28, 2005.

International Search Report for PCT/US06/19349 dated Sep. 11, 2006.

International Search Report for PCT/US2006/020296 dated Nov. 14, 2006.

Carling, R. W. et al., "4-Substituted-3-phenylguinolin-2(1H)-ones: Acidic and Nonacidic Glycine Site N-Methyl-D-aspartate Antagonists with in Vivo Activity," J. Med. Chem., vol. 40, 1997, pp. 754-765; published by American Chemical Society.

Charvát, T. et al., "Diethyl Acetonedicarboxylate—a Precursor for the Synthesis of New Substituted 4-Aminoquinolines and Fused 4-Aminopyridines," Monatshefte für Chemie, vol. 126, 1995, pp. 333-340.

First Office Action in Australian Application No. 2005216904 dated Sep. 30, 2009.

Foekens et al. "Cancer Research," 2001, vol. 61, pp. 5407-5414.

Gewald, K. et al., "4-Amino-3-pyridiniochinolin-2(1H)-on-chloride und 3,4-Diaminochinolin-2(1H)-one," Chem. Ber., vol. 124, 1991, pp. 1237-1241, Eng. Abstract provided; published by VCH Verlagsgesellschaft mbH.

Parham, W. E, et al., "Elaboration of Bromoarylnitriles," J. Org. Chem., vol. 41, No. 7, 1976, pp. 1187-1191.

Schäfer, H. et al., "Zur Synthese von 4-Aminochinolinen und—chinolinonen-(2) aus Anthranilsäurenitril," Journal f. prakt. Chemie, Band 321, Heft 4, 1979, pp. 695-698, Eng. Abstract included. Only English Abstract Considered.

Susa. M. et al., "Src inhibitors: drugs for the treatment of osteoporosis, cancer or both?," TiPS, vol. 21, Dec. 2000, pp. 489-495; published by Elsevier Science Ltd.

Timmer et al.; "Lithium Intoxication," J. Am. Soc. Nephrol; vol. 10, pp. 666-674; 1999.

U.S. Notice of Allowance in U.S. Appl. No. 10/886,950 mailed Jun. 12, 2009.

Veronese, A. C. et al., "Tin (IV) Chloride-promoted Synthesis of 4-Aminopyridines and 4-Aminoquinolines," Tetrahedron, vol. 51, No. 45, 1995, pp. 12277-12284; published by Elsevier Science Ltd.

Veronese, A. C. et al., "Tin(IV) Choloride-promoted vs. Metal β-Carbonyl-enolate-catalysed Reactions off β-Dicarbonyls with Nitriles," J. Chem Research (S), 1988, pp. 246-247.

Bulusu V. R., "Irinotecan and 5-Flourouracil in Colorectal Cancer: Time for a Pause?," European Journal of Cancer, vol. 34, No. 3, 1998, pp. 286-289.

European Search Report received for EP Appln. No. 03783281.3 mailed Jan. 15, 2010.

European Search Report received for EP Appln. No. 04816941.1 mailed Jan. 14, 2010.

Supplementary Search Report received in Malaysian Appln. No. PI20034345 completed Jan. 14, 2010.

Chekhun (Tschechun), et al., "Current View on the Mechanisms of Drug Resistance of Tumors," Onkologijya, 2000, T.2, Nos. 1-2, pp. 11-15. (English Summary: p. 15.).

Andre, T., et al., "CPT-11 (Irinotecan) Addition to Bimonthly, High-dose Leucovorin and Bolus and Continuous-infusion 5-Fluorouracil (FOLFIRI) for Pretreated Metastic Colorectal Cancer," European Journal of Cancer, vol. 35, No. 9, 1999, pp. 1343-1347. Compound summary also attached.

Glade-Bender, J., et al., "VEGF blocking therapy in the treatment of cancer," Expert Opinion on Biological Therapy, vol. 3, No. 2, Apr. 2003, pp. 263-276.

Jackman, A.L., et al., "Combination of Raltitrexed with other Cytotoxic Agents: Rationale and Preclinical Observations," European Journal of Cancer, vol. 35, Suppl. 1, Mar. 1999, pp. S3-S8. Compound summary also attached.

Magne, N., et al., "Sequence-dependent effects of ZD 1839 (Iressa) in combination with cytotoxic treatment in human head and neck cancer," British Journal of Cancer, 2002, pp. 819-827.

Morin, Michael J., "From oncogene to drug: development of small molecule tyrosine kinase inhibitors as anti-tumor and anti-angiogenic agents," Oncogene, 2000, pp. 6574-6583.

Noble, et al., "Protein Kinase Inhibitors: Insights into Drug Design from Structure," Science, vol. 303, Mar. 19, 2004, pp. 1800-1805.

European Search Report for EP 05017665.0 dated Feb. 28, 2006.

International Search Report for PCT/US04/36956 dated Oct. 2, 2006.

Notice of Allowance received for U.S. Appl. No. 10/706,328 dated Jun. 11, 2010.
Notice of Allowance received for U.S. Appl. No. 10/983,174 dated Jul. 8, 2010.

Supplementary European Search Report received for European Appln. No. 04810468.1 dated May 25, 2010 and mailed Jun. 1, 2010.

\* cited by examiner

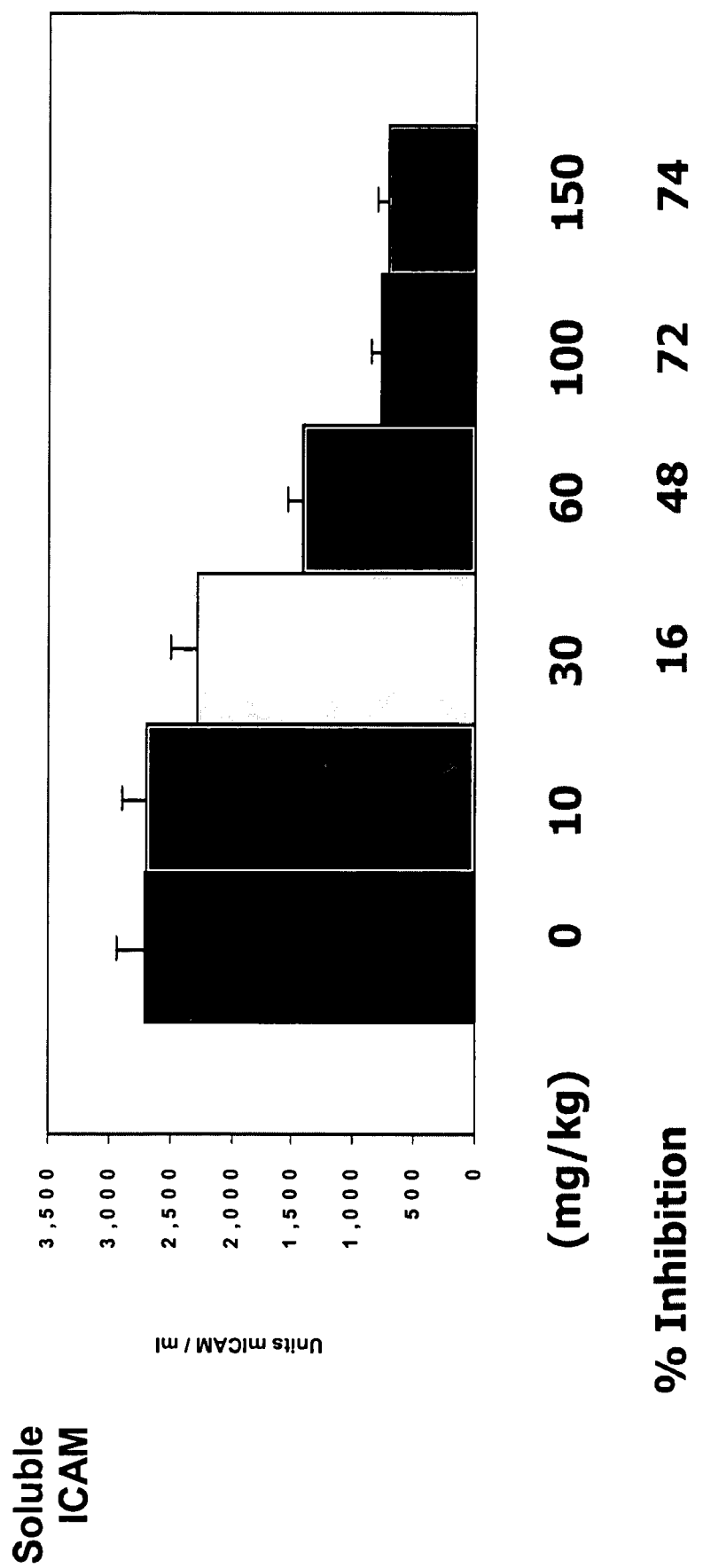

MODULATING AND MEASURING CELLULAR ADHESION

CROSS REFERENCES TO RELATED APPLICATIONS

This application claims priority to U.S. Provisional Application No. 60/546,395 filed Feb. 20, 2004, U.S. Provisional Application No. 60/547,103 filed Feb. 23, 2004, and U.S. Provisional Application No. 60/554,771 filed Mar. 19, 2004, the entire disclosures of which are each incorporated herein by reference and for all purposes as if fully set forth herein.

FIELD OF THE INVENTION

The present invention provides methods for using compounds to modulate inflammatory responses and processes related to tumor metastasis. The invention further provides methods for monitoring the effects of the compounds of the invention by measuring the levels of ICAM, VCAM, or E-selectin molecules in a subject treated with the compounds.

BACKGROUND OF THE INVENTION

Amino quinolinone benzimidazolyl compounds such as 4-amino-5-fluoro-3-[6-(4-methylpiperazin-1-yl)-1H-benzimidazol-2-yl]quinolin-2(1H)-one and their tautomers and salts are potent inhibitors of various class kinases such as VEGFR2 (KDR, Flk-1), FGFR1 and PDGFRβ with $IC_{50}$s ranging from 10-27 nM. See U.S. Pat. No. 6,605,617, U.S. patent application Ser. No. 10/644,055, and U.S. patent application Ser. No. 10/706,328, each of which is hereby incorporated by reference in its entirety and for all purposes as if fully set forth herein, for a list of various tyrosine and serine/threonine kinases for which 4-amino-5-fluoro-3-[6-(4-methylpiperazin-1-yl)-1H-benzimidazol-2-yl]quinolin-2(1H)-one has shown activity and for assay procedures. Such kinases are important for the initiation and maintenance of new blood vessel growth as well as tumor proliferation. Consequently these inhibitors have direct applications in the treatment of various disorders such as solid and hematological cancers. The identification of plasma biomarkers in subjects treated with these kinase inhibitors would therefore provide a convenient method for monitoring the subject's physiological response to the treatment.

Cell adhesion molecules play important roles in tumor cell invasion, metastasis, and interaction with immune cells. VCAM (vascular cell adhesion molecule) is a transmembrane glycoprotein and expressed in endothelial cells and various cancer types such as bladder, breast, gastrointestinal, ovarian, renal, and Hodgkin's and non-Hodgkin's lymphoma. VCAM is induced by VEGF and is predominantly expressed in activated endothelial cells. ICAM (inducible cell adhesion molecule) is also expressed in endothelial cells and various cells including fibroblasts, hematopoietic cells, and tumor cells. The soluble form of ICAM present in the plasma is generated by proteolytic cleavage of membrane-associated molecules. E-Selectin (endothelial leukocyte adhesion molecule) is a transmembrane glycoprotein expressed in endothelial cells and mediates adhesion of neutrophils, monocytes, and T cells to endothelial cells. E-selectin also mediates tumor progression and metastasis.

A high concentration of soluble ICAM, VCAM, and E-selectin is considered a marker of endothelial cell activation during tumor development, metastasis, and inflammatory responses. These cell adhesion molecules localized on endothelial cells can mediate adhesion of metastatic tumor cells and allow extravasation into the vessels. It is of interest that these molecules are inducible, being poorly expressed on normal endothelial cells but capable of being expressed highly after exposure to cytokines such as IL-1 or TNF-a. In addition, some of these molecules are preferentially expressed in different vascular beds, with VCAM being abundant in the lung and E-selectin in the liver.

Matrix metalloproteases (MMPs) are a class of proteases that degrade most components of the extracellular matrix (ECM). Under normal physiological conditions they play an important role in development, tissue remodeling and morphogenesis. However, elevated levels of certain metalloproteases have been implicated in pathological diseases such as cancer and inflammation. Degradation of the extracellular matrix in the basement membrane is essential for tissue invasion by tumor cells and metastasis at various sites, and this degradation is dependent on the activity of MMPs. The family of MMPs includes more than 20 members. Two of these proteases are MMP-2 (gelatinase A, 72 KD) and MMP-9 (gelatinase B, 92 KD). MMP-2 and MMP-9 are important regulators of cancer progression and metastasis and their levels are frequently elevated in various cancer patients.

A report by Bergers et al. (Matrix metalloproteinase-9 triggers the angiogenic switch during carcinogenesis; Berger, G. et al., Nature Cell Biology, 2:737-744; 2000) discloses that MMP-9/gelatinase B is a functional component of an angiogenic switch during multistage pancreatic carcinogenesis by increasing the release of VEGF.

Various quinolinone benzimidazole compounds useful in inhibiting angiogenesis and vascular endothelial growth factor receptor tyrosine kinases and in inhibiting other tyrosine and serine/threonine kinases including 4-amino-5-fluoro-3-[5-(4-methylpiperazin-1-yl)-1H-benzimidazol-2-yl]quinolin-2(1H)-one or a tautomer thereof and the synthesis thereof are disclosed in the following documents which are each hereby incorporated by reference in their entireties and for all purposes as if fully set forth herein: U.S. Pat. No. 6,605,617; U.S. Pat. No. 6,756,383; U.S. patent application Ser. No. 10/116,117 filed (published on Feb. 6, 2003, as U.S. 2003/0028018 A1); U.S. patent application Ser. No. 10/644,055 (published on May 13, 2004, U.S. Patent Application No. 2004/0092535); U.S. patent application Ser. No. 10/983,174; U.S. patent application Ser. No. 10/706,328 (published on Nov. 4, 2004, as 2004/0220196); U.S. patent application Ser. No. 10/982,757; and U.S. patent application Ser. No. 10/982,543.

An important need exists for methods for modulating levels of cellular adhesion molecules and matrix metalloproteases. Such methods would therefore constitute important and needed therapies in the treatment of inflammatory and metastatic diseases mediated by cellular adhesion molecules and matrix metalloproteases.

SUMMARY OF THE INVENTION

The present invention relates to methods of treating a human or animal subject with, and uses in a human or animal subject of, a compound of Structure I, a tautomer of the compound, a pharmaceutically acceptable salt of the compound, a pharmaceutically acceptable salt of the tautomer, or a mixture thereof. The invention also relates to the use of the compound, tautomer, salt of the compound, salt of the tautomer, or the mixture thereof in the preparation of a medicament for use in the methods described herein.

In one aspect, the invention provides a method of modulating an inflammatory response or reducing cellular adhesion in a subject. Such methods include administering to the subject a compound of Structure I, a tautomer of the compound, a pharmaceutically acceptable salt of the compound, a pharmaceutically acceptable salt of the tautomer, or a mixture thereof. The inflammatory response is modulated in the subject and/or cellular adhesion is reduced in the subject after administration of the compound, the tautomer, the pharmaceutically acceptable salt of the compound, the pharmaceutically acceptable salt of the tautomer, or the mixture thereof.

In one aspect, the compound, tautomer, salt of the compound, salt of the tautomer, or the mixture thereof are used to modulate an inflammatory response.

In another aspect, the compound, tautomer, salt of the compound, salt of the tautomer, or the mixture thereof are used to reduce cellular adhesion.

In another aspect, the compound, tautomer, salt of the compound, salt of the tautomer, or the mixture thereof are used to decrease ICAM, VCAM, or E-selectin levels.

In another aspect, the compound, tautomer, salt of the compound, salt of the tautomer, or the mixture thereof used to reduce the levels of circulating cell adhesion molecules.

In another aspect, the compound, tautomer, salt of the compound, salt of the tautomer, or the mixture thereof are used to decrease circulating ICAM, VCAM, or E-selectin levels.

In another aspect, the invention provides a method of monitoring the progression of a disease or treatment in a human or animal subject. The method includes measuring the amount of at least one cell adhesion molecule in the subject after administration of a compound of Structure I, a tautomer of the compound, a pharmaceutically acceptable salt of the compound, a pharmaceutically acceptable salt of the tautomer, or a mixture thereof to the subject. In some embodiments, the cell adhesion molecule is selected from inducible cell adhesion molecule (ICAM), vascular cell adhesion molecule (VCAM), or endothelial leukocyte adhesion molecule (E-Selectin). Some such methods further include withdrawing a sample of blood from the subject and then measuring the amount of the at least one cell adhesion molecule in at least a portion of the sample. Other embodiments include administering the compound, the tautomer, the pharmaceutically acceptable salt of the compound, the pharmaceutically acceptable salt of the tautomer, or the mixture thereof to the subject.

In another aspect, the invention provides a method of identifying a subject in need of a compound of Structure I, a tautomer of the compound, a pharmaceutically acceptable salt of the compound, a pharmaceutically acceptable salt of the tautomer, or a mixture thereof. The method includes measuring the amount of at least one cell adhesion molecule in the subject before, during, or after administration of the compound of Structure I, the tautomer of the compound, the pharmaceutically acceptable salt of the compound, the pharmaceutically acceptable salt of the tautomer, or the mixture thereof to the subject. In some embodiments, the cell adhesion molecule is selected from inducible cell adhesion molecule, vascular cell adhesion molecule, or endothelial leukocyte adhesion molecule. In some embodiments, the method further includes administering the compound of Structure I, the tautomer of the compound, the pharmaceutically acceptable salt of the compound, the pharmaceutically acceptable salt of the tautomer, or the mixture thereof to the subject after measuring the amount of the cell adhesion molecule in the subject.

Structure I has the following formula:

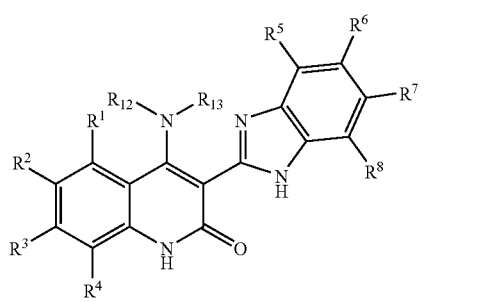

wherein, $R^1$, $R^2$, $R^3$, and $R^4$ may be the same or different and are independently selected from the group consisting of H, Cl, Br, F, I, —CN, —NO$_2$, —OH, —OR$^{15}$ groups, —NR$^{16}$R$^{17}$ groups, substituted and unsubstituted amidinyl groups, substituted and unsubstituted guanidinyl groups, substituted and unsubstituted primary, secondary, and tertiary alkyl groups, substituted and unsubstituted aryl groups, substituted and unsubstituted alkenyl groups, substituted and unsubstituted alkynyl groups, substituted and unsubstituted heterocyclyl groups, substituted and unsubstituted aminoalkyl groups, substituted and unsubstituted alkylaminoalkyl groups, substituted and unsubstituted dialkylaminoalkyl groups, substituted and unsubstituted arylaminoalkyl groups, substituted and unsubstituted diarylaminoalkyl groups, substituted and unsubstituted (alkyl)(aryl)aminoalkyl groups, substituted and unsubstituted heterocyclylalkyl groups, and —C(=O)R$^{18}$ groups;

$R^5$, $R^6$, $R^7$, and $R^8$ may be the same or different and are independently selected from the group consisting of H, Cl, Br, F, I, —NO$_2$, —OH, —OR$^{19}$ groups, —NR$^{20}$R$^{21}$ groups, —SH, —SR$^{22}$ groups, —S(=O)R$^{23}$ groups, —S(=O)$_2$R$^{24}$ groups, —CN, substituted and unsubstituted amidinyl groups, substituted and unsubstituted guanidinyl groups, substituted and unsubstituted primary, secondary, and tertiary alkyl groups, substituted and unsubstituted aryl groups, substituted and unsubstituted alkenyl groups, substituted and unsubstituted alkynyl groups, substituted and unsubstituted heterocyclyl groups, substituted and unsubstituted alkylaminoalkyl groups, substituted and unsubstituted dialkylaminoalkyl groups, substituted and unsubstituted arylaminoalkyl groups, substituted and unsubstituted diarylaminoalkyl groups, substituted and unsubstituted (alkyl)(aryl)aminoalkyl groups, substituted and unsubstituted heterocyclylalkyl groups, —C(=O)R$^{25}$ groups, substituted and unsubstituted aminoalkyl groups, substituted and unsubstituted heterocyclylaminoalkyl groups, substituted and unsubstituted hydroxyalkyl groups, substituted and unsubstituted alkoxyalkyl groups, substituted and unsubstituted aryloxyalkyl groups, and substituted and unsubstituted heterocyclyloxyalkyl groups;

$R^{12}$ is selected from the group consisting of H, substituted and unsubstituted alkyl groups, substituted and unsubstituted aryl groups, and substituted and unsubstituted heterocyclyl groups;

$R^{13}$ is selected from the group consisting of H, substituted and unsubstituted alkyl groups, substituted and unsubstituted aryl groups, substituted and unsubstituted heterocyclyl groups, —OH, alkoxy groups, aryloxy groups, —NH₂, substituted and unsubstituted heterocyclylalkyl groups, substituted and unsubstituted aminoalkyl groups, substituted and unsubstituted alkylaminoalkyl groups, substituted and unsubstituted dialkylaminoalkyl groups, substituted and unsubstituted arylaminoalkyl groups, substituted and unsubstituted diarylaminoalkyl groups, substituted and unsubstituted (alkyl)(aryl)aminoalkyl groups, substituted and unsubstituted alkylamino groups, substituted and unsubstituted arylamino groups, substituted and unsubstituted dialkylamino groups, substituted and unsubstituted diarylamino groups, substituted and unsubstituted (alkyl)(aryl) amino groups, —C(=O)H, —C(=O)-alkyl groups, —C(=O)-aryl groups, —C(=O)O-alkyl groups, —C(=O)O-aryl groups, —C(=O)NH₂, —C(=O)NH(alkyl) groups, —C(=O)NH(aryl) groups, —C(=O)N(alkyl)₂ groups, —C(=O)N(aryl)₂ groups, —C(=O)N(alkyl)(aryl) groups, —C(=O)-heterocyclyl groups, —C(=O)—O-heterocyclyl groups, —C(=O)NH(heterocyclyl) groups, —C(=O)—N(heterocyclyl)₂ groups, —C(=O)—N(alkyl)(heterocyclyl) groups, —C(=O)—N(aryl)(heterocyclyl) groups, substituted and unsubstituted heterocyclylaminoalkyl groups, substituted and unsubstituted hydroxyalkyl groups, substituted and unsubstituted alkoxyalkyl groups, substituted and unsubstituted aryloxyalkyl groups, and substituted and unsubstituted heterocyclyloxyalkyl groups;

$R^{15}$ and $R^{19}$ may be the same or different and are independently selected from the group consisting of substituted and unsubstituted alkyl groups, substituted and unsubstituted aryl groups, substituted and unsubstituted heterocyclyl groups, substituted and unsubstituted heterocyclylalkyl groups, —C(=O)H, —C(=O)-alkyl groups, —C(=O)-aryl groups, —C(=O)NH₂, —C(=O)NH(alkyl) groups, —C(=O)NH(aryl) groups, —C(=O)N(alkyl)₂ groups, —C(=O)N(aryl)₂ groups, —C(=O)N(alkyl)(aryl) groups, substituted and unsubstituted aminoalkyl groups, substituted and unsubstituted alkylaminoalkyl groups, substituted and unsubstituted dialkylaminoalkyl groups, substituted and unsubstituted arylaminoalkyl groups, substituted and unsubstituted diarylaminoalkyl groups, substituted and unsubstituted (alkyl)(aryl)aminoalkyl groups, substituted and unsubstituted heterocyclylaminoalkyl, substituted and unsubstituted diheterocyclylaminoalkyl, substituted and unsubstituted (heterocyclyl)(alkyl)aminoalkyl, substituted and unsubstituted (heterocyclyl)(aryl)aminoalkyl, substituted and unsubstituted alkoxyalkyl groups, substituted and unsubstituted hydroxyalkyl groups, substituted and unsubstituted aryloxyalkyl groups, and substituted and unsubstituted heterocyclyloxyalkyl groups;

$R^{16}$ and $R^{20}$ may be the same or different and are independently selected from the group consisting of H, substituted and unsubstituted alkyl groups, substituted and unsubstituted aryl groups, and substituted and unsubstituted heterocyclyl groups;

$R^{17}$ and $R^{21}$ may be the same or different and are independently selected from the group consisting of H, substituted and unsubstituted alkyl groups, substituted and unsubstituted aryl groups, substituted and unsubstituted heterocyclyl groups, —C(=O)H, —C(=O)-alkyl groups, —C(=O)-aryl groups, —C(=O)NH₂, —C(=O)NH(alkyl) groups, —C(=O)NH(aryl) groups, —C(=O)N(alkyl)₂ groups, —C(=O)N(aryl)₂ groups, —C(=O)N(alkyl)(aryl) groups, —C(=O)O-alkyl groups, —C(=O)O-aryl groups, substituted and unsubstituted heterocyclylalkyl groups, substituted and unsubstituted aminoalkyl groups, substituted and unsubstituted alkylaminoalkyl groups, substituted and unsubstituted dialkylaminoalkyl groups, substituted and unsubstituted arylaminoalkyl groups, substituted and unsubstituted diarylaminoalkyl groups, substituted and unsubstituted (alkyl)(aryl)aminoalkyl groups, —C(=O)-heterocyclyl groups, —C(=O)—O-heterocyclyl groups, —C(=O)NH(heterocyclyl) groups, —C(=O)—N(heterocyclyl)₂ groups, —C(=O)—N(alkyl)(heterocyclyl) groups, —C(=O)—N(aryl)(heterocyclyl) groups, substituted and unsubstituted heterocyclylaminoalkyl groups, substituted and unsubstituted hydroxyalkyl groups, substituted and unsubstituted alkoxyalkyl groups, substituted and unsubstituted aryloxyalkyl groups, and substituted and unsubstituted heterocyclyloxyalkyl groups;

$R^{18}$, $R^{23}$, $R^{24}$, and $R^{25}$ may be the same or different and are independently selected from the group consisting of H, —NH₂, —NH(alkyl) groups, —NH(aryl) groups, —N(alkyl)₂ groups, —N(aryl)₂ groups, —N(alkyl)(aryl) groups, —NH(heterocyclyl) groups, —N(heterocyclyl)(alkyl) groups, —N(heterocyclyl)(aryl) groups, —N(heterocyclyl)₂ groups, substituted and unsubstituted alkyl groups, substituted and unsubstituted aryl groups, —OH, substituted and unsubstituted alkoxy groups, substituted and unsubstituted aryloxy groups, substituted and unsubstituted heterocyclyl groups, —NHOH, —N(alkyl)OH groups, —N(aryl)OH groups, —N(alkyl)O-alkyl groups, —N(aryl)O-alkyl groups, —N(alkyl)O-aryl groups, and —N(aryl)O-aryl groups; and $R^{22}$ is selected from the group consisting of substituted and unsubstituted alkyl groups, substituted and unsubstituted aryl groups, and substituted and unsubstituted heterocyclyl groups.

Further objects, features and advantages of the invention will be apparent from the following detailed description.

BRIEF DESCRIPTION OF THE DRAWINGS

FIGS. 2A and 2B are graphs showing the dose-dependent reduction of soluble ICAM (FIG. 2A; greater than 70% inhibition with 100 or 150 mg/kg) and soluble VCAM (FIG. 2B; 44-47% inhibition with 100 or 150 mg/kg) in the serum of mice with 4T1 breast tumors when dosed with varying amounts of 4-amino-5-fluoro-3-[6-(4-methylpiperazin-1-yl)-1H-benzimidazol-2-yl]quinolin-2(1H)-one.

FIG. 6 is a scanned image showing the decrease in the expression of ICAM, and VCAM when HUVECs in culture were treated with 4-amino-5-fluoro-3-[6-(4-methylpiperazin-1-yl)-1H-benzimidazol-2-yl]quinolin-2(1H).

DETAILED DESCRIPTION OF THE INVENTION

Figure 1:
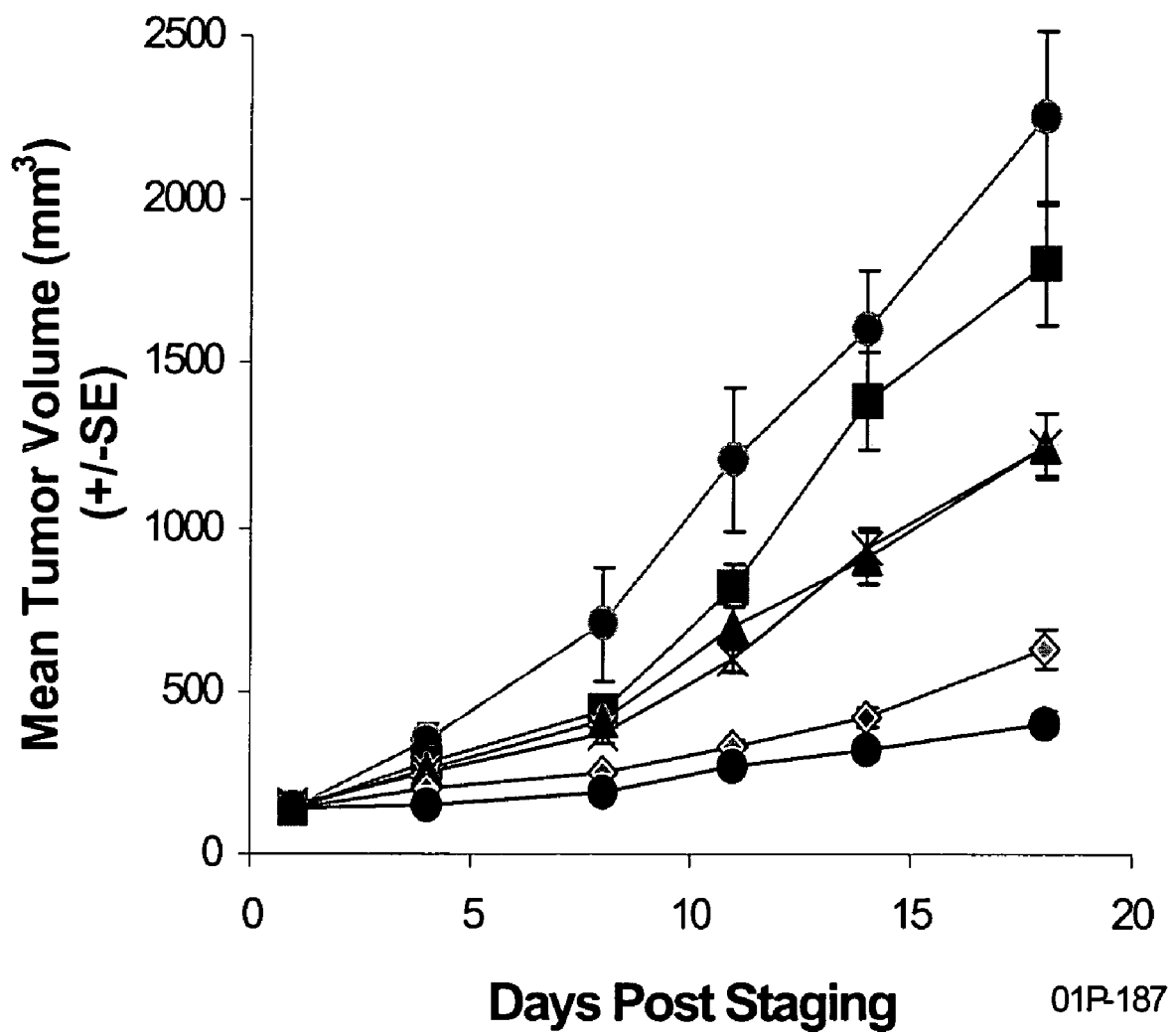
FIG. 1 is a graph showing the effects of various amount of 4-amino-5-fluoro-3-[6-(4-methylpiperazin-1-yl)-1H-benzimidazol-2-yl]quinolin-2(1H)-one (Compound 1) on a 4T1 murine breast tumor model (vehicle (grey outlined circle); 10 mpk (square); 30 mpk (grey triangle); 60 mpk (X); 100 mpk (diamond); and 150 mpk (filed circle)). The growth of the subcutaneous tumor was inhibited (40-80% compared to control), liver metastases were completely inhibited, and lung metastases were inhibited by 60-97% after 18 days of dosing.
Figure 2B:
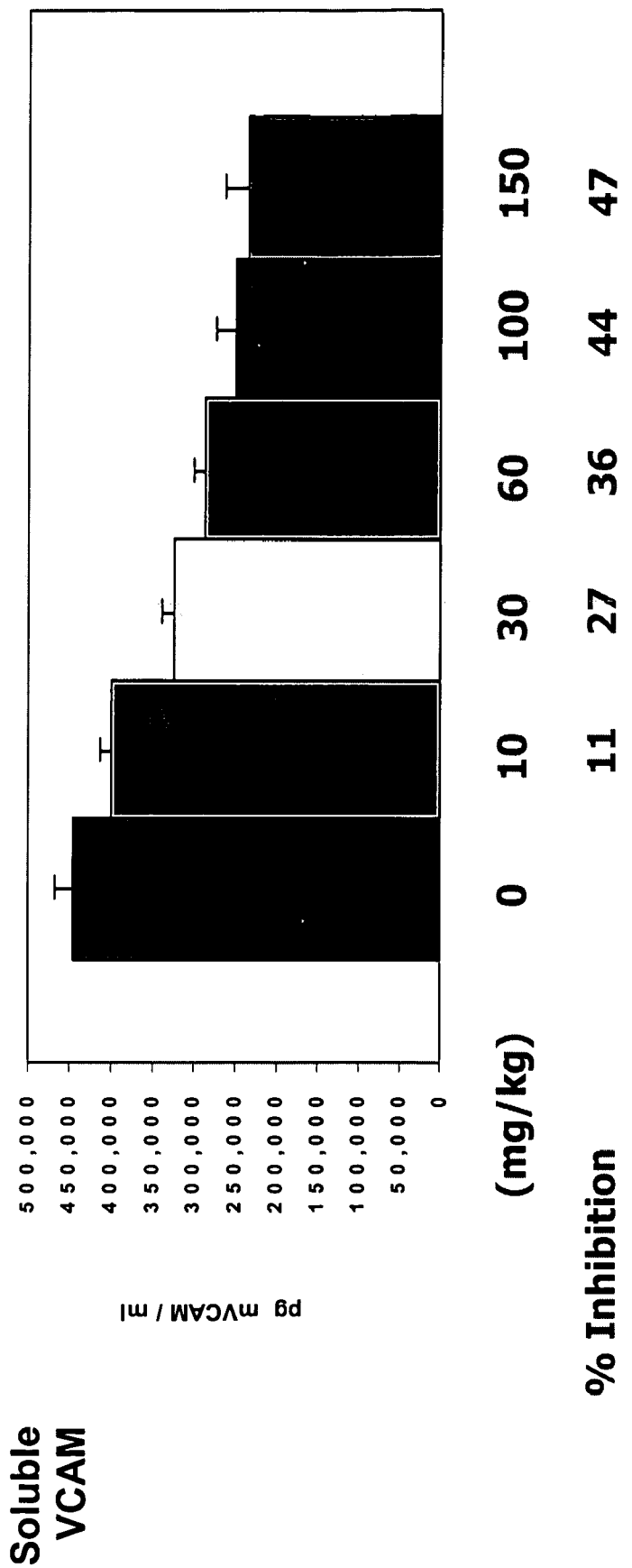
Figure 3:
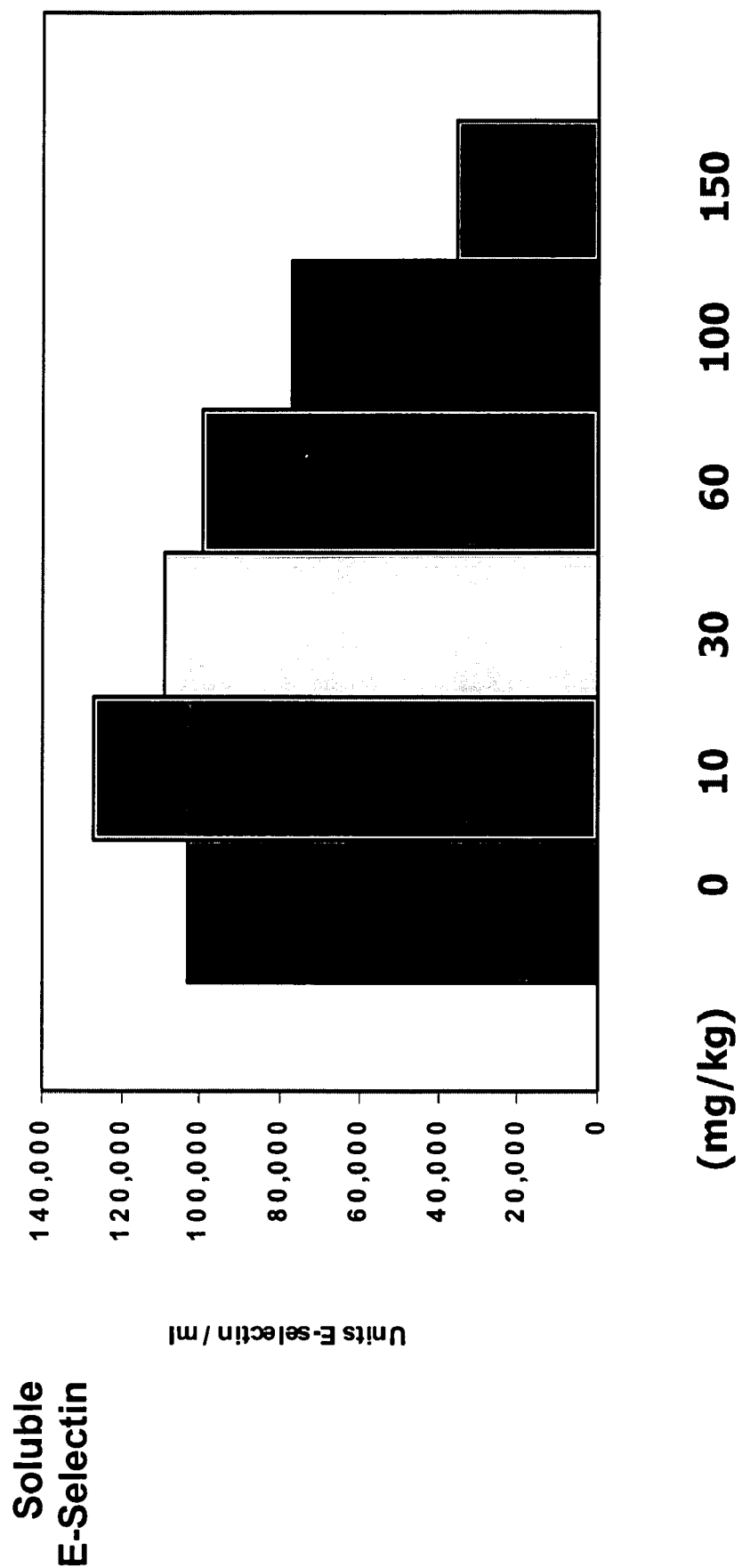
FIG. 3 is a graph showing the dose-dependent inhibition of mouse-specific soluble E-selectin in the serum of 4T1 tumor bearing mice treated with 4-amino-5-fluoro-3-[6-(4-methylpiperazin-1-yl)-1H-benzimidazol-2-yl]quinolin-2(1H)-one.
Figure 4A:
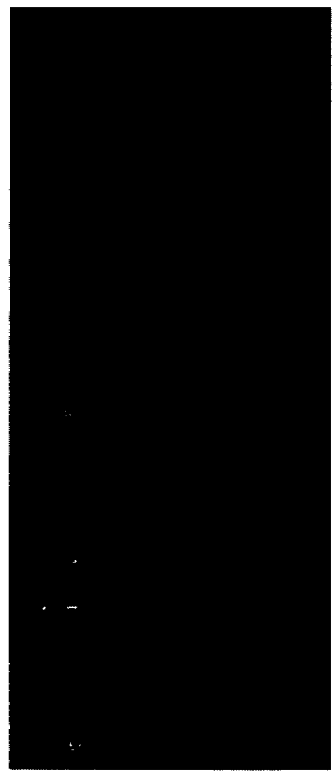
FIGS. 4A, 4B, and 4C are graphs of the Zymography and VEGF ELISA (FIG. 4B) data that show the decrease in MMP9 and VEGF in mice with implanted KM12L4a tumor cells when dosed for 7 days with 100 mg/kg 4-amino-5-fluoro-3-[6-(4-methylpiperazin-1-yl)-1H-benzimidazol-2-yl]quinolin-2(1H)-one.
Figure 4B:
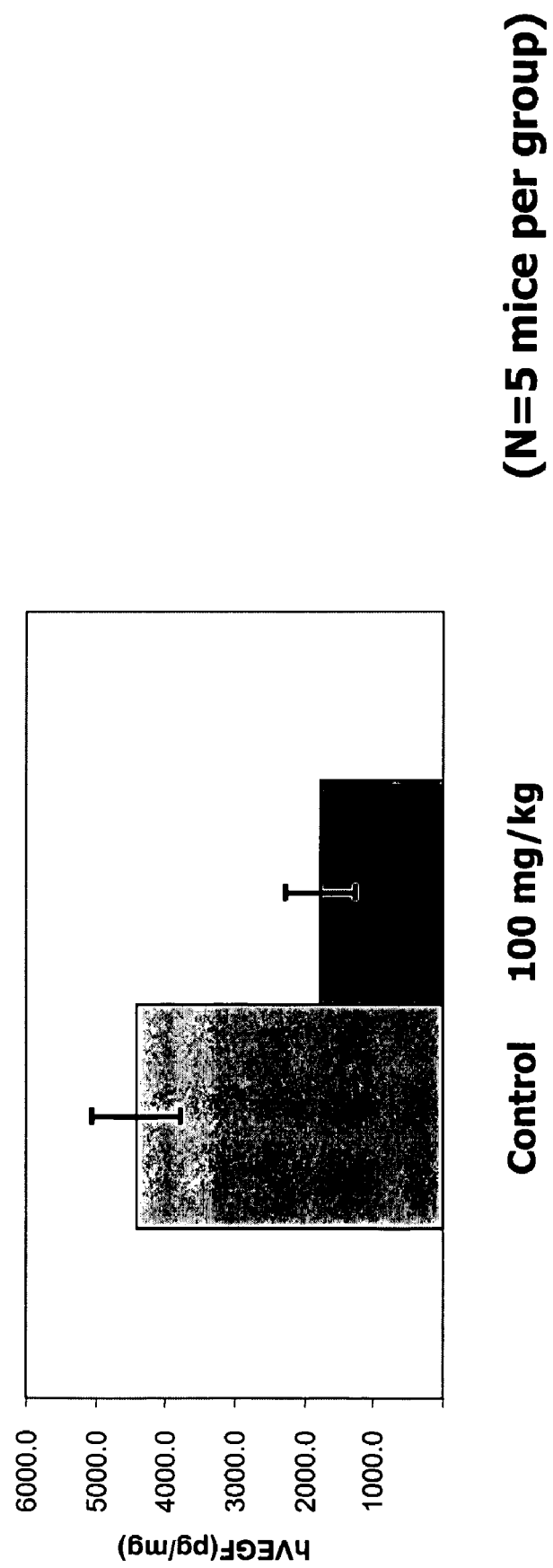
Figure 4C:
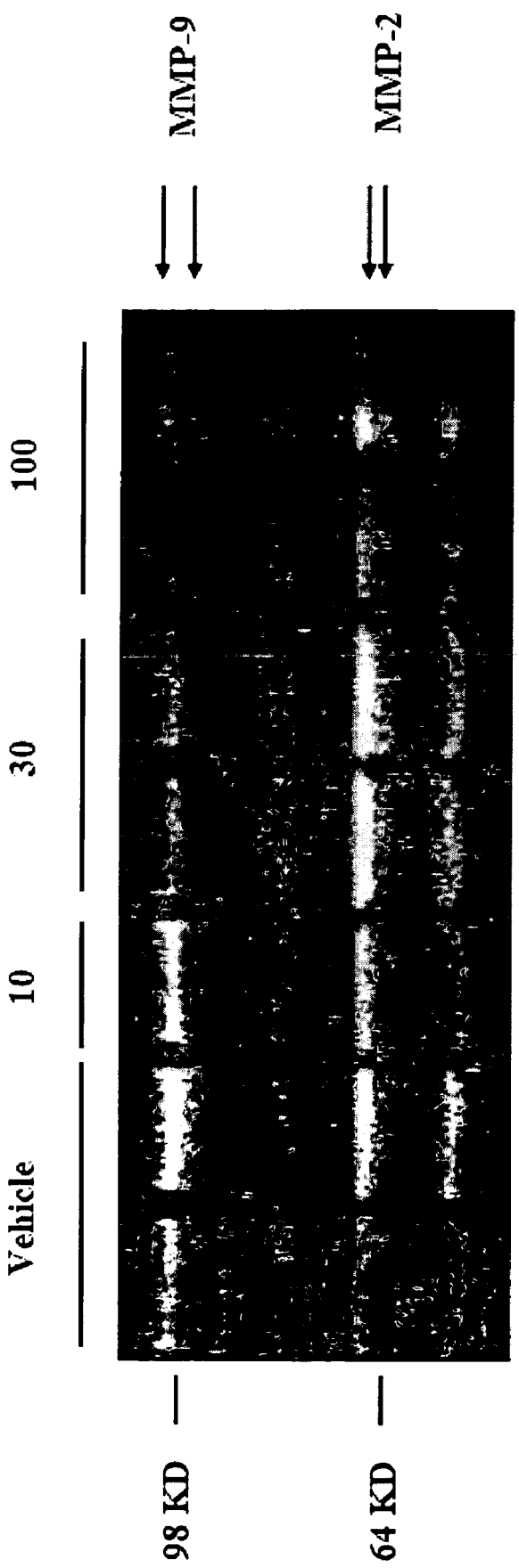
Figure 5:
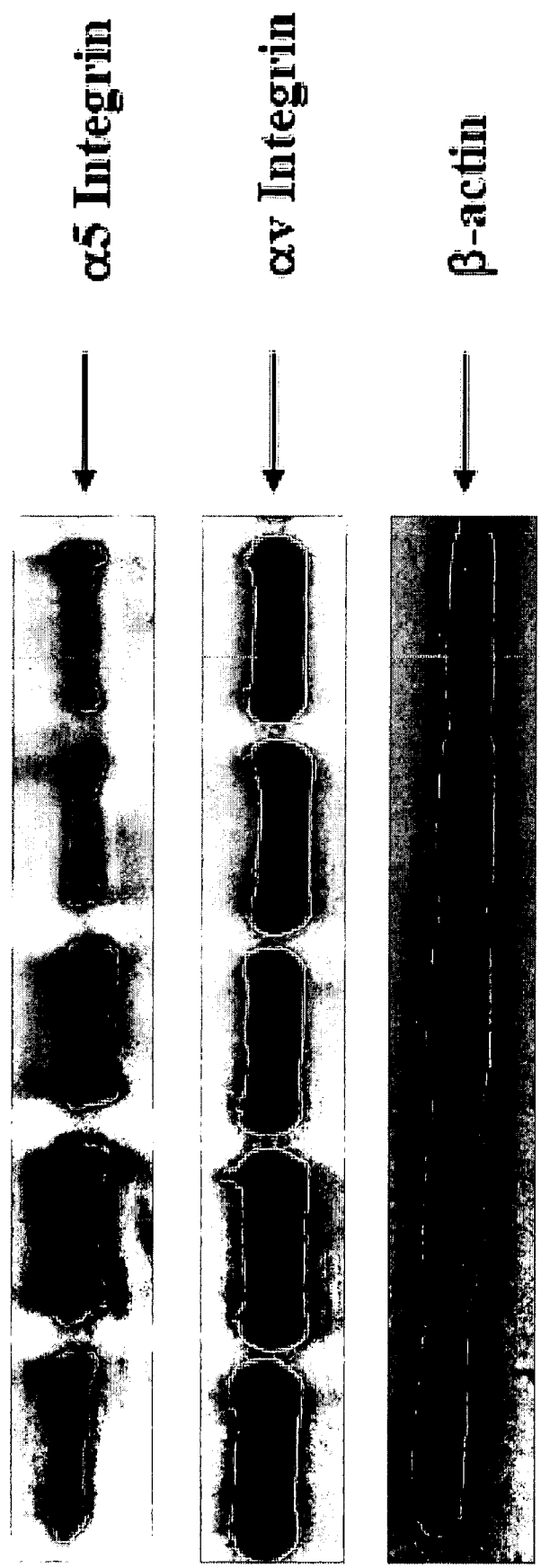
FIG. 5 is a scanned image showing the decrease in the expression of α5 integrin, not αv integrin when HUVECs in culture were treated with 4-amino-5-fluoro-3-[6-(4-methylpiperazin-1-yl)-1H-benzimidazol-2-yl]quinolin-2(1H).

The following abbreviations and definitions are used throughout this application:

The phrase "cellular adhesion" as used herein, refers to cell adhesion. The amount of cellular adhesion in a subject can typically be correlated with the amounts of cell adhesion molecules, such as, but not limited to VCAM, ICAM, and E-Selectin in a subject.

"VCAM" is an abbreviation that stands for vascular cell adhesion molecule.

"ICAM" is an abbreviation that stands for inducible cell adhesion molecule.

"E-Selectin" is also known as endothelial leukocyte adhesion molecule.

"4T1" is a murine breast cell line.

"BALB/C" is a mice strain used in tumor xenograph experiments.

"bFGF" is an abbreviation that stands for basic fibroblast growth factor.

"FGFR1", also referred to as bFGFR, is an abbreviation that stands for a tyrosine kinase that interacts with the fibroblast growth factor FGF.

"FGF" is an abbreviation for the fibroblast growth factor that interacts with FGFR1.

"FGFR3" is an abbreviation that stands for the tyrosine kinase fibroblast growth factor receptor 3 that is often expressed in multiple myeloma-type cancers.

"Flk-1" is an abbreviation that stands for fetal liver tyrosine kinase 1, also known as kinase-insert domain tyrosine kinase or KDR (human), also known as vascular endothelial growth factor receptor-2 or VEGFR2 (KDR (human), Flk-1 (mouse)).

"PDGF" is an abbreviation that stands for platelet derived growth factor. PDGF interacts with tyrosine kinases PDG-FRα and PDGFRβ.

"RTK" is an abbreviation that stands for receptor tyrosine kinase.

"VEGF" is an abbreviation that stands for vascular endothelial growth factor.

"VEGF-RTK" is an abbreviation that stands for vascular endothelial growth factor receptor tyrosine kinase.

"ELISA" is an abbreviation that stands for Enzyme-Linked Immunosorbent Assay.

"MMP-2" is an abbreviation that stands for matrix metalloprotease-2 [includes the 72 KD (pro MMP-2) protein and the 62 KD (active MMP-2) protein]. MMP-2 is also referred to as gelatinase A.

"MMP-9" is an abbreviation that stands for matrix metalloprotease-9 [includes the 105 KD (pro MMP-9) protein and the 92 KD (active MMP-9) protein]. MMP-9 is also referred to as gelatinase B.

"Ki67" is a marker for cellular proliferation.

"Caspase-3" is a apoptosis marker. Activation of caspase-3 requires proteolytic processing of inactive caspase-3 into "cleaved caspase-3" which is 17 KD and 19 KD in size.

"PARP" is an abbreviation that stands for poly ADP-ribose polymerase and is an apoptosis marker. It is a 116 KD protein and is cleaved into a 89 KD protein.

"CD31" is a marker for endothelial cells. Immunostaining with anti-CD31 antibody in tumor section by immunohistochemistry will indicate the number of microvessels (or microvessel density) in tumors.

Generally, reference to a certain element such as hydrogen or H is meant to include all isotopes of that element. For example, if an R group is defined to include hydrogen or H, it also includes deuterium and tritium.

The phrase "unsubstituted alkyl" refers to alkyl groups that do not contain heteroatoms. Thus the phrase includes straight chain alkyl groups such as methyl, ethyl, propyl, butyl, pentyl, hexyl, heptyl, octyl, nonyl, decyl, undecyl, dodecyl and the like. The phrase also includes branched chain isomers of straight chain alkyl groups, including but not limited to, the following which are provided by way of example: —CH(CH$_3$)$_2$, —CH(CH$_3$)(CH$_2$CH$_3$), —CH(CH$_2$CH$_3$)$_2$, —C(CH$_3$)$_3$, —C(CH$_2$CH$_3$)$_3$, —CH$_2$CH(CH$_3$)$_2$, —CH$_2$CH(CH$_3$)(CH$_2$CH$_3$), —CH$_2$CH(CH$_2$CH$_3$)$_2$, —CH$_2$C(CH$_3$)$_3$, —CH$_2$C(CH$_2$CH$_3$)$_3$, —CH(CH$_3$)CH(CH$_3$)(CH$_2$CH$_3$), —CH$_2$CH$_2$CH(CH$_3$)$_2$, —CH$_2$CH$_2$CH(CH$_3$)(CH$_2$CH$_3$), —CH$_2$CH$_2$CH(CH$_2$CH$_3$)$_2$, —CH$_2$CH$_2$C(CH$_3$)$_3$, —CH$_2$CH$_2$C(CH$_2$CH$_3$)$_3$, —CH(CH$_3$)CH$_2$CH(CH$_3$)$_2$, —CH(CH$_3$)CH(CH$_3$)CH(CH$_3$)$_2$, —CH(CH$_2$CH$_3$)CH(CH$_3$)CH(CH$_3$)(CH$_2$CH$_3$), and others. The phrase also includes cyclic alkyl groups such as cycloalkyl groups such as cyclopropyl, cyclobutyl, cyclopentyl, cyclohexyl, cycloheptyl, and cyclooctyl and such rings substituted with straight and branched chain alkyl groups as defined above. The phrase also includes polycyclic alkyl groups such as, but not limited to, adamantyl norbornyl, and bicyclo[2.2.2]octyl and such rings substituted with straight and branched chain alkyl groups as defined above. Thus, the phrase unsubstituted alkyl groups includes primary alkyl groups, secondary alkyl groups, and tertiary alkyl groups. Unsubstituted alkyl groups may be bonded to one or more carbon atom(s), oxygen atom(s), nitrogen atom(s), and/or sulfur atom(s) in the parent compound. Preferred unsubstituted alkyl groups include straight and branched chain alkyl groups and cyclic alkyl groups having 1 to 20 carbon atoms. More preferred such unsubstituted alkyl groups have from 1 to 10 carbon atoms while even more preferred such groups have from 1 to 5 carbon atoms. Most preferred unsubstituted alkyl groups include straight and branched chain alkyl groups having from 1 to 3 carbon atoms and include methyl, ethyl, propyl, and —CH(CH$_3$)$_2$.

The phrase "substituted alkyl" refers to an unsubstituted alkyl group as defined above in which one or more bonds to a carbon(s) or hydrogen(s) are replaced by a bond to non-hydrogen and non-carbon atoms such as, but not limited to, a halogen atom in halides such as F, Cl, Br, and I; an oxygen atom in groups such as hydroxyl groups, alkoxy groups, aryloxy groups, and ester groups; a sulfur atom in groups such as thiol groups, alkyl and aryl sulfide groups, sulfone groups, sulfonyl groups, and sulfoxide groups; a nitrogen atom in groups such as amines, amides, alkylamines, dialkylamines, arylamines, alkylarylamines, diarylamines, N-oxides, imides, and enamines; a silicon atom in groups such as in trialkylsilyl groups, dialkylarylsilyl groups, alkyldiarylsilyl groups, and triarylsilyl groups; and other heteroatoms in various other groups. Substituted alkyl groups also include groups in which one or more bonds to a carbon(s) or hydrogen(s) atom is replaced by a bond to a heteroatom such as oxygen in carbonyl, carboxyl, and ester groups; nitrogen in groups such as imines, oximes, hydrazones, and nitriles. Preferred substituted alkyl groups include, among others, alkyl groups in which one or more bonds to a carbon or hydrogen atom is/are replaced by one or more bonds to fluorine atoms. One example of a substituted alkyl group is the trifluoromethyl group and other alkyl groups that contain the trifluoromethyl group. Other alkyl groups include those in which one or more bonds to a carbon or hydrogen atom is replaced by a bond to an oxygen atom such that the substituted alkyl group contains a hydroxyl, alkoxy, aryloxy group, or heterocyclyloxy group. Still other alkyl groups include alkyl groups that have an amine, alkylamine, dialkylamine, arylamine, (alkyl)(aryl)amine, diarylamine, heterocyclylamine, (alkyl)(heterocyclyl)amine, (aryl)(heterocyclyl)amine, or diheterocyclylamine group.

The phrase "unsubstituted aryl" refers to aryl groups that do not contain heteroatoms. Thus the phrase includes, but is not limited to, groups such as phenyl, biphenyl, anthracenyl, naphthenyl by way of example. Although the phrase "unsubstituted aryl" includes groups containing condensed rings such as naphthalene, it does not include aryl groups that have other groups such as alkyl or halo groups bonded to one of the ring members, as aryl groups such as tolyl are considered herein to be substituted aryl groups as described below. A preferred unsubstituted aryl group is phenyl. Unsubstituted aryl groups may be bonded to one or more carbon atom(s), oxygen atom(s), nitrogen atom(s), and/or sulfur atom(s) in the parent compound, however.

The phrase "substituted aryl group" has the same meaning with respect to unsubstituted aryl groups that substituted alkyl groups had with respect to unsubstituted alkyl groups. However, a substituted aryl group also includes aryl groups in which one of the aromatic carbons is bonded to one of the non-carbon or non-hydrogen atoms described above and also includes aryl groups in which one or more aromatic carbons of the aryl group is bonded to a substituted and/or unsubstituted alkyl, alkenyl, or alkynyl group as defined herein. This includes bonding arrangements in which two carbon atoms of an aryl group are bonded to two atoms of an alkyl, alkenyl, or alkynyl group to define a fused ring system (e.g. dihydronaphthyl or tetrahydronaphthyl). Thus, the phrase "substituted aryl" includes, but is not limited to tolyl, and hydroxyphenyl among others.

The phrase "unsubstituted alkenyl" refers to straight and branched chain and cyclic groups such as those described with respect to unsubstituted alkyl groups as defined above, except that at least one double bond exists between two carbon atoms. Examples include, but are not limited to vinyl, —CH═C(H)(CH$_3$), —CH═C(CH$_3$)$_2$, —C(CH$_3$)═C(H)$_2$, —C(CH$_3$)═C(H)(CH$_3$), —C(CH$_2$CH$_3$)═CH$_2$, cyclohexenyl, cyclopentenyl, cyclohexadienyl, butadienyl, pentadienyl, and hexadienyl among others.

The phrase "substituted alkenyl" has the same meaning with respect to unsubstituted alkenyl groups that substituted alkyl groups had with respect to unsubstituted alkyl groups. A substituted alkenyl group includes alkenyl groups in which a non-carbon or non-hydrogen atom is bonded to a carbon double bonded to another carbon and those in which one of the non-carbon or non-hydrogen atoms is bonded to a carbon not involved in a double bond to another carbon.

The phrase "unsubstituted alkynyl" refers to straight and branched chain groups such as those described with respect to unsubstituted alkyl groups as defined above, except that at least one triple bond exists between two carbon atoms. Examples include, but are not limited to —C≡C(H), —C≡C(CH$_3$), —C≡C(CH$_2$CH$_3$), —C(H$_2$)C≡C(H), —C(H)$_2$C≡C(CH$_3$), and —C(H)$_2$C≡C(CH$_2$CH$_3$) among others.

The phrase "substituted alkynyl" has the same meaning with respect to unsubstituted alkynyl groups that substituted alkyl groups had with respect to unsubstituted alkyl groups. A substituted alkynyl group includes alkynyl groups in which a non-carbon or non-hydrogen atom is bonded to a carbon triple bonded to another carbon and those in which a non-carbon or non-hydrogen atom is bonded to a carbon not involved in a triple bond to another carbon.

The phrase "unsubstituted aralkyl" refers to unsubstituted alkyl groups as defined above in which a hydrogen or carbon bond of the unsubstituted alkyl group is replaced with a bond to an aryl group as defined above. For example, methyl(—CH$_3$) is an unsubstituted alkyl group. If a hydrogen atom of the methyl group is replaced by a bond to a phenyl group, such as if the carbon of the methyl were bonded to a carbon of benzene, then the compound is an unsubstituted aralkyl group (i.e., a benzyl group). Thus the phrase includes, but is not limited to, groups such as benzyl, diphenylmethyl, and 1-phenylethyl(—CH(C$_6$H$_5$)(CH$_3$)) among others.

The phrase "substituted aralkyl" has the same meaning with respect to unsubstituted aralkyl groups that substituted aryl groups had with respect to unsubstituted aryl groups. However, a substituted aralkyl group also includes groups in which a carbon or hydrogen bond of the alkyl part of the group is replaced by a bond to a non-carbon or a non-hydrogen atom. Examples of substituted aralkyl groups include, but are not limited to, —CH$_2$C(═O)(C$_6$H$_5$), and —CH$_2$(2-methylphenyl) among others.

The phrase "unsubstituted heterocyclyl" refers to both aromatic and nonaromatic ring compounds including monocyclic, bicyclic, and polycyclic ring compounds such as, but not limited to, quinuclidyl, containing 3 or more ring members of which one or more is a heteroatom such as, but not limited to, N, O, and S. Although the phrase "unsubstituted heterocyclyl" includes condensed heterocyclic rings such as benzimidazolyl, it does not include heterocyclyl groups that have other groups such as alkyl or halo groups bonded to one of the ring members as compounds such as 2-methylbenzimidazolyl are substituted heterocyclyl groups. Examples of heterocyclyl groups include, but are not limited to: unsaturated 3 to 8 membered rings containing 1 to 4 nitrogen atoms such as, but not limited to pyrrolyl, pyrrolinyl, imidazolyl, pyrazolyl, pyridinyl, dihydropyridinyl, pyrimidyl, pyrazinyl, pyridazinyl, triazolyl (e.g. 4H-1,2,4-triazolyl, 1H-1,2,3-triazolyl, 2H-1,2,3-triazolyl etc.), tetrazolyl, (e.g. 1H-tetrazolyl, 2H tetrazolyl, etc.); saturated 3 to 8 membered rings containing 1 to 4 nitrogen atoms such as, but not limited to, pyrrolidinyl, imidazolidinyl, piperidinyl, piperazinyl; condensed unsaturated heterocyclic groups containing 1 to 4 nitrogen atoms such as, but not limited to, indolyl, isoindolyl, indolinyl, indolizinyl, benzimidazolyl, quinolyl, isoquinolyl, indazolyl, benzotriazolyl; unsaturated 3 to 8 membered rings containing 1 to 2 oxygen atoms and 1 to 3 nitrogen atoms such as, but not limited to, oxazolyl, isoxazolyl, oxadiazolyl (e.g. 1,2,4-oxadiazolyl, 1,3,4-oxadiazolyl, 1,2,5-oxadiazolyl, etc.); saturated 3 to 8 membered rings containing 1 to 2 oxygen atoms and 1 to 3 nitrogen atoms such as, but not limited to, morpholinyl; unsaturated condensed heterocyclic groups containing 1 to 2 oxygen atoms and 1 to 3 nitrogen atoms, for example, benzoxazolyl, benzoxadiazolyl, benzoxazinyl (e.g. 2H-1,4-benzoxazinyl etc.); unsaturated 3 to 8 membered rings containing 1 to 3 sulfur atoms and 1 to 3 nitrogen atoms such as, but not limited to, thiazolyl, isothiazolyl, thiadiazolyl (e.g. 1,2,3-thiadiazolyl, 1,2,4-thiadiazolyl, 1,3,4-thiadiazolyl, 1,2,5-thiadiazolyl, etc.); saturated 3 to 8 membered rings containing 1 to 2 sulfur atoms and 1 to 3 nitrogen atoms such as, but not limited to, thiazolodinyl; saturated and unsaturated 3 to 8 membered rings containing 1 to 2 sulfur atoms such as, but not limited to, thienyl, dihydrodithiinyl, dihydrodithionyl, tetrahydrothiophene, tetrahydrothiopyran; unsaturated condensed heterocyclic rings containing 1 to 2 sulfur atoms and 1 to 3 nitrogen atoms such as, but not limited to, benzothiazolyl, benzothiadiazolyl, benzothiazinyl (e.g. 2H-1,4-benzothiazinyl, etc.), dihydrobenzothiazinyl (e.g., 2H-3,4-dihydrobenzothiazinyl, etc.), unsaturated 3 to 8 membered rings containing oxygen atoms such as, but not limited to furyl; unsaturated condensed heterocyclic rings containing 1 to 2 oxygen atoms such as benzodioxolyl (e.g., 1,3-benzodioxoyl, etc.); unsaturated 3 to 8 membered rings containing an oxygen atom and 1 to 2 sulfur atoms such as, but not limited to, dihydrooxathiinyl; saturated 3 to 8 membered rings containing 1 to 2 oxygen atoms and 1 to 2 sulfur atoms such as 1,4-oxathiane; unsaturated condensed rings containing 1 to 2 sulfur atoms such as benzothienyl, benzodithiinyl; and unsaturated condensed heterocyclic rings containing an oxygen atom and 1 to 2 oxygen atoms such as benzoxathiinyl. Heterocyclyl group also include those described above in which one or more S atoms in the ring is double-bonded to one or two oxygen atoms (sulfoxides and sulfones). For example, heterocyclyl groups include tetrahydrothiophene oxide and tetrahydrothiophene 1,1-dioxide. Preferred heterocyclyl groups contain 5 or 6 ring members. More preferred heterocyclyl groups include morpholine, piperazine, piperidine, pyrrolidine, imidazole, pyrazole, 1,2,3-triazole, 1,2,4-triazole, tetrazole, thiophene, thiomorpholine, thiomorpholine in which the S atom of the thiomorpholine is bonded to one or more O atoms, pyrrole, homopiperazine, oxazolidin-2-one, pyrrolidin-2-one, oxazole, quinuclidine, thiazole, isoxazole, furan, and tetrahydrofuran.

The phrase "substituted heterocyclyl" refers to an unsubstituted heterocyclyl group as defined above in which one or more of the ring members is bonded to a non-hydrogen atom such as described above with respect to substituted alkyl groups and substituted aryl groups. Examples, include, but are not limited to, 2-methylbenzimidazolyl, 5-methylbenzimidazolyl, 5-chlorobenzthiazolyl, N-alkyl piperazinyl groups such as 1-methyl piperazinyl, piperazine-N-oxide, N-alkyl piperazine N-oxides, 2-phenoxy-thiophene, and 2-chloropyridinyl among others. In addition, substituted heterocyclyl groups also include heterocyclyl groups in which the bond to the non-hydrogen atom is a bond to a carbon atom that is part of a substituted and unsubstituted aryl, substituted and unsubstituted aralkyl, or unsubstituted heterocyclyl group. Examples include but are not limited to 1-benzylpiperidinyl, 3-phenylthiomorpholinyl, 3-(pyrrolidin-1-yl)-pyrrolidinyl, and 4-(piperidin-1-yl)-piperidinyl. Groups such as N-alkyl substituted piperazine groups such as N-methyl piperazine, substituted morpholine groups, and piperazine N-oxide groups such as piperazine N-oxide and N-alkyl piperazine N-oxides are examples of some substituted heterocyclyl groups. Groups such as substituted piperazine groups such as N-alkyl substituted piperazine groups such as N-methyl piperazine and the like, substituted morpholine groups, piperazine N-oxide groups, and N-alkyl piperazine N-oxide groups are examples of some substituted heterocyclyl groups that are especially suited as $R^6$ or $R^7$ groups.

The phrase "unsubstituted heterocyclylalkyl" refers to unsubstituted alkyl groups as defined above in which a hydrogen or carbon bond of the unsubstituted alkyl group is replaced with a bond to a heterocyclyl group as defined above. For example, methyl(—$CH_3$) is an unsubstituted alkyl group. If a hydrogen atom of the methyl group is replaced by a bond to a heterocyclyl group, such as if the carbon of the methyl were bonded to carbon 2 of pyridine (one of the carbons bonded to the N of the pyridine) or carbons 3 or 4 of the pyridine, then the compound is an unsubstituted heterocyclylalkyl group.

The phrase "substituted heterocyclylalkyl" has the same meaning with respect to unsubstituted heterocyclylalkyl groups that substituted aralkyl groups had with respect to unsubstituted aralkyl groups. However, a substituted heterocyclylalkyl group also includes groups in which a non-hydrogen atom is bonded to a heteroatom in the heterocyclyl group of the heterocyclylalkyl group such as, but not limited to, a nitrogen atom in the piperidine ring of a piperidinylalkyl group. In addition, a substituted heterocyclylalkyl group also includes groups in which a carbon bond or a hydrogen bond of the alkyl part of the group is replaced by a bond to a substituted and unsubstituted aryl or substituted and unsubstituted aralkyl group. Examples include but are not limited to phenyl-(piperidin-1-yl)-methyl and phenyl-(morpholin-4-yl)-methyl.

The phrase "unsubstituted alkylaminoalkyl" refers to an unsubstituted alkyl group as defined above in which a carbon or hydrogen bond is replaced by a bond to a nitrogen atom that is bonded to a hydrogen atom and an unsubstituted alkyl group as defined above. For example, methyl(—$CH_3$) is an unsubstituted alkyl group. If a hydrogen atom of the methyl group is replaced by a bond to a nitrogen atom that is bonded to a hydrogen atom and an ethyl group, then the resulting compound is —$CH_2$—$N(H)(CH_2CH_3)$ which is an unsubstituted alkylaminoalkyl group.

The phrase "substituted alkylaminoalkyl" refers to an unsubstituted alkylaminoalkyl group as defined above except where one or more bonds to a carbon or hydrogen atom in one or both of the alkyl groups is replaced by a bond to a non-carbon or non-hydrogen atom as described above with respect to substituted alkyl groups except that the bond to the nitrogen atom in all alkylaminoalkyl groups does not by itself qualify all alkylaminoalkyl groups as being substituted. However, substituted alkylaminoalkyl groups does include groups in which the hydrogen bonded to the nitrogen atom of the group is replaced with a non-carbon and non-hydrogen atom.

The phrase "unsubstituted dialkylaminoalkyl" refers to an unsubstituted alkyl group as defined above in which a carbon bond or hydrogen bond is replaced by a bond to a nitrogen atom which is bonded to two other similar or different unsubstituted alkyl groups as defined above.

The phrase "substituted dialkylaminoalkyl" refers to an unsubstituted dialkylaminoalkyl group as defined above in which one or more bonds to a carbon or hydrogen atom in one or more of the alkyl groups is replaced by a bond to a non-carbon and non-hydrogen atom as described with respect to substituted alkyl groups. The bond to the nitrogen atom in all dialkylaminoalkyl groups does not by itself qualify all dialkylaminoalkyl groups as being substituted.

The phrase "unsubstituted alkoxy" refers to a hydroxyl group (—OH) in which the bond to the hydrogen atom is replaced by a bond to a carbon atom of an otherwise unsubstituted alkyl group as defined above.

The phrase "substituted alkoxy" refers to a hydroxyl group (—OH) in which the bond to the hydrogen atom is replaced by a bond to a carbon atom of an otherwise substituted alkyl group as defined above.

The phrase "unsubstituted heterocyclyloxy" refers to a hydroxyl group (—OH) in which the bond to the hydrogen atom is replaced by a bond to a ring atom of an otherwise unsubstituted heterocyclyl group as defined above.

The phrase "substituted heterocyclyloxy" refers to a hydroxyl group (—OH) in which the bond to the hydrogen atom is replaced by a bond to a ring atom of an otherwise substituted heterocyclyl group as defined above.

The phrase "unsubstituted heterocyclyloxyalkyl" refers to an unsubstituted alkyl group as defined above in which a carbon bond or hydrogen bond is replaced by a bond to an oxygen atom which is bonded to an unsubstituted heterocyclyl group as defined above.

The phrase "substituted heterocyclyloxyalkyl" refers to an unsubstituted heterocyclyloxyalkyl group as defined above in which a bond to a carbon or hydrogen group of the alkyl group of the heterocyclyloxyalkyl group is bonded to a non-carbon and non-hydrogen atom as described above with respect to substituted alkyl groups or in which the heterocyclyl group of the heterocyclyloxyalkyl group is a substituted heterocyclyl group as defined above.

The phrase "unsubstituted heterocyclylalkoxy" refers to an unsubstituted alkyl group as defined above in which a carbon bond or hydrogen bond is replaced by a bond to an oxygen atom which is bonded to the parent compound, and in which another carbon or hydrogen bond of the unsubstituted alkyl group is bonded to an unsubstituted heterocyclyl group as defined above.

The phrase "substituted heterocyclylalkoxy" refers to an unsubstituted heterocyclylalkoxy group as defined above in which a bond to a carbon or hydrogen group of the alkyl group of the heterocyclylalkoxy group is bonded to a non-carbon and non-hydrogen atom as described above with respect to substituted alkyl groups or in which the heterocyclyl group of the heterocyclylalkoxy group is a substituted heterocyclyl group as defined above. Further, a substituted heterocyclylalkoxy group also includes groups in which a carbon bond or a hydrogen bond to the alkyl moiety of the group may be substituted with one or more additional substituted and unsubstituted heterocycles. Examples include but are not limited to pyrid-2-ylmorpholin-4-ylmethyl and 2-pyrid-3-yl-2-morpholin-4-ylethyl.

The phrase "unsubstituted arylaminoalkyl" refers to an unsubstituted alkyl group as defined above in which a carbon bond or hydrogen bond is replaced by a bond to a nitrogen atom which is bonded to at least one unsubstituted aryl group as defined above.

The phrase "substituted arylaminoalkyl" refers to an unsubstituted arylaminoalkyl group as defined above except where either the alkyl group of the arylaminoalkyl group is a substituted alkyl group as defined above or the aryl group of the arylaminoalkyl group is a substituted aryl group except that the bonds to the nitrogen atom in all arylaminoalkyl groups does not by itself qualify all arylaminoalkyl groups as being substituted. However, substituted arylaminoalkyl groups does include groups in which the hydrogen bonded to the nitrogen atom of the group is replaced with a non-carbon and non-hydrogen atom.

The phrase "unsubstituted heterocyclylaminoalkyl" refers to an unsubstituted alkyl group as defined above in which a carbon or hydrogen bond is replaced by a bond to a nitrogen atom which is bonded to at least one unsubstituted heterocyclyl group as defined above.

The phrase "substituted heterocyclylaminoalkyl" refers to unsubstituted heterocyclylaminoalkyl groups as defined above in which the heterocyclyl group is a substituted heterocyclyl group as defined above and/or the alkyl group is a substituted alkyl group as defined above. The bonds to the nitrogen atom in all heterocyclylaminoalkyl groups does not by itself qualify all heterocyclylaminoalkyl groups as being substituted. However, substituted heterocyclylaminoalkyl groups do include groups in which the hydrogen bonded to the nitrogen atom of the group is replaced with a non-carbon and non-hydrogen atom.

The phrase "unsubstituted alkylaminoalkoxy" refers to an unsubstituted alkyl group as defined above in which a carbon or hydrogen bond is replaced by a bond to an oxygen atom which is bonded to the parent compound and in which another carbon or hydrogen bond of the unsubstituted alkyl group is bonded to a nitrogen atom which is bonded to a hydrogen atom and an unsubstituted alkyl group as defined above.

The phrase "substituted alkylaminoalkoxy" refers to unsubstituted alkylaminoalkoxy groups as defined above in which a bond to a carbon or hydrogen atom of the alkyl group bonded to the oxygen atom which is bonded to the parent compound is replaced by one or more bonds to a non-carbon and non-hydrogen atoms as discussed above with respect to substituted alkyl groups and/or if the hydrogen bonded to the amino group is bonded to a non-carbon and non-hydrogen atom and/or if the alkyl group bonded to the nitrogen of the amine is bonded to a non-carbon and non-hydrogen atom as described above with respect to substituted alkyl groups. The presence of the amine and alkoxy functionality in all alkylaminoalkoxy groups does not by itself qualify all such groups as substituted alkylaminoalkoxy groups.

The phrase "unsubstituted dialkylaminoalkoxy" refers to an unsubstituted alkyl group as defined above in which a carbon or hydrogen bond is replaced by a bond to an oxygen atom which is bonded to the parent compound and in which another carbon or hydrogen bond of the unsubstituted alkyl group is bonded to a nitrogen atom which is bonded to two other similar or different unsubstituted alkyl groups as defined above.

The phrase "substituted dialkylaminoalkoxy" refers to an unsubstituted dialkylaminoalkoxy group as defined above in which a bond to a carbon or hydrogen atom of the alkyl group bonded to the oxygen atom which is bonded to the parent compound is replaced by one or more bonds to a non-carbon and non-hydrogen atoms as discussed above with respect to substituted alkyl groups and/or if one or more of the alkyl groups bonded to the nitrogen of the amine is bonded to a non-carbon and non-hydrogen atom as described above with respect to substituted alkyl groups. The presence of the amine and alkoxy functionality in all dialkylaminoalkoxy groups does not by itself qualify all such groups as substituted dialkylaminoalkoxy groups.

The term "protected" with respect to hydroxyl groups, amine groups, and sulfhydryl groups refers to forms of these functionalities which are protected from undesirable reaction with a protecting group known to those skilled in the art such as those set forth in Protective Groups in Organic Synthesis, Greene, T. W.; Wuts, P. G. M., John Wiley & Sons, New York, N.Y., (3rd Edition, 1999) which can be added or removed using the procedures set forth therein. Examples of protected hydroxyl groups include, but are not limited to, silyl ethers such as those obtained by reaction of a hydroxyl group with a reagent such as, but not limited to, t-butyldimethyl-chlorosilane, trimethylchlorosilane, triisopropylchlorosilane, triethylchlorosilane; substituted methyl and ethyl ethers such as, but not limited to methoxymethyl ether, methythiomethyl ether, benzyloxymethyl ether, t-butoxymethyl ether, 2-methoxyethoxymethyl ether, tetrahydropyranyl ethers, 1-ethoxyethyl ether, allyl ether, benzyl ether; esters such as, but not limited to, benzoylformate, formate, acetate, trichloroacetate, and trifluoroacetate. Examples of protected amine groups include, but are not limited to, amides such as, formamide, acetamide, trifluoroacetamide, and benzamide; imides, such as phthalimide, and dithiosuccinimide; and others. Examples of protected sulfhydryl groups include, but are not limited to, thioethers such as S-benzyl thioether, and S-4-picolyl thioether; substituted S-methyl derivatives such as hemithio, dithio and aminothio acetals; and others.

A "pharmaceutically acceptable salt" includes a salt with an inorganic base, organic base, inorganic acid, organic acid, or basic or acidic amino acid. As salts of inorganic bases, the invention includes, for example, alkali metals such as sodium or potassium; alkaline earth metals such as calcium and magnesium or aluminum; and ammonia. As salts of organic bases, the invention includes, for example, trimethylamine, triethylamine, pyridine, picoline, ethanolamine, diethanolamine, and triethanolamine. As salts of inorganic acids, the instant invention includes, for example, hydrochloric acid, hydroboric acid, nitric acid, sulfuric acid, and phosphoric acid. As salts of organic acids, the instant invention includes, for example, formic acid, acetic acid, trifluoroacetic acid, fumaric acid, oxalic acid, tartaric acid, lactic acid, maleic acid, citric acid, succinic acid, malic acid, methanesulfonic acid, benzenesulfonic acid, and p-toluenesulfonic acid. As salts of basic amino acids, the instant invention includes, for example, arginine, lysine and ornithine. Acidic amino acids include, for example, aspartic acid and glutamic acid.

In one aspect, the invention provides a method of modulating an inflammatory response and/or reducing cellular adhesion in a subject. Such methods include administering to the subject a compound of Structure I, a tautomer of the compound, a pharmaceutically acceptable salt of the compound, a pharmaceutically acceptable salt of the tautomer, or a mixture thereof. The inflammatory response is modulated in the subject and/or cellular adhesion is reduced in the subject after administration of the compound, the tautomer, the pharmaceutically acceptable salt of the compound, the pharmaceutically acceptable salt of the tautomer, or the mixture thereof.

In one embodiment, the invention provides a method of treating a disorder related to inflammation in a human or animal subject. The method includes administering to the human or animal subject an effective amount of a compound of Structure I, a tautomer of the compound, a pharmaceutically acceptable salt of the compound, a pharmaceutically acceptable salt of the tautomer, or a mixture thereof. Inflammation and inflammatory responses may occur with various biological conditions. Examples of such biological conditions may include cancer, autoimmune diseases, asthma, allergies, eczema, microbial infections, traumatic injuries such as burns or cuts, lupus, arthritis, cardiovascular disease such as, but not limited to, strokes and ischemic injuries, respiratory bacterial and viral infections, and other conditions associated with inflammatory responses.

In another embodiment, the invention provides a method of treating a disorder related to cellular adhesion in a human or animal subject. The method includes administering to the human or animal subject an effective amount of a compound of Structure I, a tautomer of the compound, a pharmaceutically acceptable salt of the compound, a pharmaceutically acceptable salt of the tautomer, or a mixture thereof.

In another embodiment, the invention provides a method of decreasing cellular adhesion molecules such as ICAM, VCAM, E-selectin, MMP-2, or MMP-9 levels in a human or animal subject. The method includes administering to the human or animal subject a compound of Structure I, a tautomer of the compound, a pharmaceutically acceptable salt of the compound, a pharmaceutically acceptable salt of the tautomer, or a mixture thereof. The amount of the cellular adhesion molecule is typically reduced in the subject after administration.

In another embodiment, the invention provides a method of decreasing circulating ICAM, VCAM, E-selectin, MMP-2, or MMP-9 levels in a human or animal subject. The method includes administering to the human or animal subject a compound of Structure I, a tautomer of the compound, a pharmaceutically acceptable salt of the compound, a pharmaceutically acceptable salt of the tautomer, or a mixture thereof.

In another embodiment, the invention provides a method of decreasing circulating cell adhesion molecules in a human or animal subject. The method includes administering to the human or animal subject a compound of Structure I, a tautomer of the compound, a pharmaceutically acceptable salt of the compound, a pharmaceutically acceptable salt of the tautomer, or a mixture thereof.

In yet another embodiment, the invention provides a method of monitoring the progression of a disease or treatment in a human or animal subject. The method includes administering to the human or animal subject a compound of Structure I, a tautomer of the compound, a pharmaceutically acceptable salt of the compound, a pharmaceutically acceptable salt of the tautomer, or a mixture thereof and measuring the amounts of a molecule such as ICAM, VCAM, E-selectin, MMP-2, or MMP-9 levels in the subject.

In another aspect, the invention provides a method of monitoring the progression of a disease or treatment in a human or animal subject. The method includes measuring the amount of at least one cell adhesion molecule in the subject after administration of a compound of Structure I, a tautomer of the compound, a pharmaceutically acceptable salt of the compound, a pharmaceutically acceptable salt of the tautomer, or a mixture thereof to the subject. In some embodiments, the cell adhesion molecule is selected from inducible cell adhesion molecule (ICAM), vascular cell adhesion molecule (VCAM), or endothelial leukocyte adhesion molecule (E-Selectin). Some such methods further include withdrawing a sample of blood from the subject and then measuring the amount of the at least one cell adhesion molecule in at least a portion of the sample.

In another aspect, the invention provides a method of identifying a subject in need of a compound of Structure I, a tautomer of the compound, a pharmaceutically acceptable salt of the compound, a pharmaceutically acceptable salt of the tautomer, or a mixture thereof. The method includes measuring the amount of at least one cell adhesion molecule in the subject before, during, or after administration of the compound of Structure I, the tautomer of the compound, the pharmaceutically acceptable salt of the compound, the pharmaceutically acceptable salt of the tautomer, or the mixture thereof to the subject. In some embodiments, the cell adhesion molecule is selected from inducible cell adhesion molecule, vascular cell adhesion molecule, or endothelial leukocyte adhesion molecule. In some embodiments, the cell adhesion molecule is selected from inducible cell adhesion molecule (ICAM), vascular cell adhesion molecule (VCAM), or endothelial leukocyte adhesion molecule (E-Selectin). Some such methods further include withdrawing a sample of blood from the subject and then measuring the amount of the at least one cell adhesion molecule in at least a portion of the sample.

In some embodiments of any of the methods described herein, the subject is a cancer patient.

Structure I has the following formula:

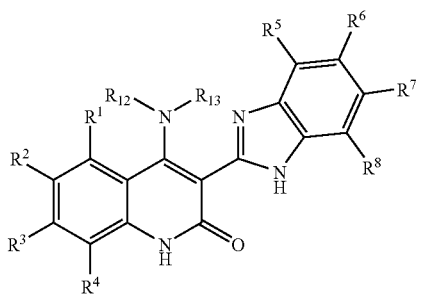

wherein,
- $R^1$, $R^2$, $R^3$, and $R^4$ may be the same or different and are independently selected from the group consisting of H, Cl, Br, F, I, —CN, —NO$_2$, —OH, —OR$^{15}$ groups, —NR$^{16}$R$^{17}$ groups, substituted and unsubstituted amidinyl groups, substituted and unsubstituted guanidinyl groups, substituted and unsubstituted primary, secondary, and tertiary alkyl groups, substituted and unsubstituted aryl groups, substituted and unsubstituted alkenyl groups, substituted and unsubstituted alkynyl groups, substituted and unsubstituted heterocyclyl groups, substituted and unsubstituted aminoalkyl groups, substituted and unsubstituted alkylaminoalkyl groups, substituted and unsubstituted dialkylaminoalkyl groups, substituted and unsubstituted arylaminoalkyl groups, substituted and unsubstituted diarylaminoalkyl groups, substituted and unsubstituted (alkyl)(aryl)aminoalkyl groups, substituted and unsubstituted heterocyclylalkyl groups, and —C(=O)R$^{18}$ groups;
- $R^5$, $R^6$, $R^7$, and $R^8$ may be the same or different and are independently selected from the group consisting of H, Cl, Br, F, I, —NO$_2$, —OH, —OR$^{19}$ groups, —NR$^{20}$R$^{21}$ groups, —SH, —SR$^{22}$ groups, —S(=O)R$^{23}$ groups, —S(=O)$_2$R$^{24}$ groups, —CN, substituted and unsubstituted amidinyl groups, substituted and unsubstituted guanidinyl groups, substituted and unsubstituted primary, secondary, and tertiary alkyl groups, substituted and unsubstituted aryl groups, substituted and unsubstituted alkenyl groups, substituted and unsubstituted alkynyl groups, substituted and unsubstituted heterocyclyl groups, substituted and unsubstituted alkylaminoalkyl groups, substituted and unsubstituted dialkylaminoalkyl groups, substituted and unsubstituted arylaminoalkyl groups, substituted and unsubstituted diarylaminoalkyl groups, substituted and unsubstituted (alkyl)(aryl)aminoalkyl groups, substituted and unsubstituted heterocyclylalkyl groups, —C(=O)R$^{25}$ groups, substituted and unsubstituted aminoalkyl groups, substituted and unsubstituted heterocyclylaminoalkyl groups, substituted and unsubstituted hydroxyalkyl groups, substituted and unsubstituted alkoxyalkyl groups, substituted and unsubstituted aryloxyalkyl groups, and substituted and unsubstituted heterocyclyloxyalkyl groups;
- $R^{12}$ is selected from the group consisting of H, substituted and unsubstituted alkyl groups, substituted and unsubstituted aryl groups, and substituted and unsubstituted heterocyclyl groups;
- $R^{13}$ is selected from the group consisting of H, substituted and unsubstituted alkyl groups, substituted and unsubstituted aryl groups, substituted and unsubstituted heterocyclyl groups, —OH, alkoxy groups, aryloxy groups, —NH$_2$, substituted and unsubstituted heterocyclylalkyl groups, substituted and unsubstituted aminoalkyl groups, substituted and unsubstituted alkylaminoalkyl groups, substituted and unsubstituted dialkylaminoalkyl groups, substituted and unsubstituted arylaminoalkyl groups, substituted and unsubstituted diarylaminoalkyl groups, substituted and unsubstituted (alkyl)(aryl)aminoalkyl groups, substituted and unsubstituted alkylamino groups, substituted and unsubstituted arylamino groups, substituted and unsubstituted dialkylamino groups, substituted and unsubstituted diarylamino groups, substituted and unsubstituted (alkyl)(aryl) amino groups, —C(=O)H, —C(=O)-alkyl groups, —C(=O)-aryl groups, —C(=O)O-alkyl groups, —C(=O)O-aryl groups, —C(=O)NH$_2$, —C(=O)NH(alkyl) groups, —C(=O)NH(aryl) groups, —C(=O)N(alkyl)$_2$ groups, —C(=O)N(aryl)$_2$ groups, —C(=O)N(alkyl)(aryl) groups, —C(=O)-heterocyclyl groups, —C(=O)—O-heterocyclyl groups, —C(=O)NH(heterocyclyl) groups, —C(=O)—N(heterocyclyl)$_2$ groups, —C(=O)—N(alkyl)(heterocyclyl) groups, —C(=O)—N(aryl)(heterocyclyl) groups, substituted and unsubstituted heterocyclylaminoalkyl groups, substituted and unsubstituted hydroxyalkyl groups, substituted and unsubstituted alkoxyalkyl groups, substituted and unsubstituted aryloxyalkyl groups, and substituted and unsubstituted heterocyclyloxyalkyl groups;
- $R^{15}$ and $R^{19}$ may be the same or different and are independently selected from the group consisting of substituted and unsubstituted alkyl groups, substituted and unsubstituted aryl groups, substituted and unsubstituted heterocyclyl groups, substituted and unsubstituted heterocyclylalkyl groups, —C(=O)H, —C(=O)-alkyl groups, —C(=O)-aryl groups, —C(=O)NH$_2$, —C(=O)NH(alkyl) groups, —C(=O)NH(aryl) groups, —C(=O)N(alkyl)$_2$ groups, —C(=O)N(aryl)$_2$ groups, —C(=O)N(alkyl)(aryl) groups, substituted and unsubstituted aminoalkyl groups, substituted and unsubstituted alkylaminoalkyl groups, substituted and unsubstituted dialkylaminoalkyl groups, substituted and unsubstituted arylaminoalkyl groups, substituted and unsubstituted diarylaminoalkyl groups, substituted and unsubstituted (alkyl)(aryl)aminoalkyl groups, substituted and unsubstituted heterocyclylaminoalkyl, substituted and unsubstituted diheterocyclylaminoalkyl, substituted and unsubstituted (heterocyclyl)(alkyl) aminoalkyl, substituted and unsubstituted (heterocyclyl)(aryl)aminoalkyl, substituted and unsubstituted alkoxyalkyl groups, substituted and unsubstituted hydroxyalkyl groups, substituted and unsubstituted aryloxyalkyl groups, and substituted and unsubstituted heterocyclyloxyalkyl groups;
- $R^{16}$ and $R^{20}$ may be the same or different and are independently selected from the group consisting of H, substituted and unsubstituted alkyl groups, substituted and unsubstituted aryl groups, and substituted and unsubstituted heterocyclyl groups;
- $R^{17}$ and $R^{21}$ may be the same or different and are independently selected from the group consisting of H, substituted and unsubstituted alkyl groups, substituted and unsubstituted aryl groups, substituted and unsubstituted heterocyclyl groups, —C(=O)H, —C(=O)-alkyl groups, —C(=O)-aryl groups, —C(=O)NH$_2$, —C(=O)NH(alkyl) groups, —C(=O)NH(aryl) groups, —C(=O)N(alkyl)$_2$ groups, —C(=O)N(aryl)$_2$ groups, —C(=O)N(alkyl)(aryl) groups, —C(=O)O-alkyl groups, —C(=O)O-aryl groups, substituted and unsubstituted heterocyclylalkyl groups, substituted and unsubstituted aminoalkyl groups, substituted and unsubstituted alkylaminoalkyl groups, substituted and unsubstituted dialkylaminoalkyl groups, substituted and unsubstituted arylaminoalkyl groups, substituted and unsubstituted diarylaminoalkyl groups, substituted and unsubstituted (alkyl)(aryl)aminoalkyl groups, —C(=O)-heterocyclyl groups, —C(=O)—O-heterocyclyl groups, —C(=O)NH(heterocyclyl) groups, —C(=O)—N(heterocyclyl)$_2$ groups, —C(=O)—N(alkyl)(heterocyclyl) groups, —C(=O)—N(aryl)(heterocyclyl) groups, substituted and unsubstituted heterocyclylaminoalkyl groups, substituted and unsubstituted hydroxyalkyl groups, substituted and unsubstituted alkoxyalkyl groups, substituted and unsubstituted aryloxyalkyl groups, and substituted and unsubstituted heterocyclyloxyalkyl groups;

$R^{18}$, $R^{23}$, $R^{24}$, and $R^{25}$ may be the same or different and are independently selected from the group consisting of H, —NH$_2$, —NH(alkyl) groups, —NH(aryl) groups, —N(alkyl)$_2$ groups, —N(aryl)$_2$ groups, —N(alkyl)(aryl) groups, —NH(heterocyclyl) groups, —N(heterocyclyl)(alkyl) groups, —N(heterocyclyl)(aryl) groups, —N(heterocyclyl)$_2$ groups, substituted and unsubstituted alkyl groups, substituted and unsubstituted aryl groups, —OH, substituted and unsubstituted alkoxy groups, substituted and unsubstituted aryloxy groups, substituted and unsubstituted heterocyclyl groups, —NHOH, —N(alkyl)OH groups, —N(aryl)OH groups, —N(alkyl)O-alkyl groups, —N(aryl)O-alkyl groups, —N(alkyl)O-aryl groups, and —N(aryl)O-aryl groups; and $R^{22}$ is selected from the group consisting of substituted and unsubstituted alkyl groups, substituted and unsubstituted aryl groups, and substituted and unsubstituted heterocyclyl groups.

In some embodiments of the pharmaceutically acceptable salts of the compounds or the tautomers of the compounds of Structure I, at least one of $R^5$, $R^6$, $R^7$, or $R^8$ is selected from the group consisting of substituted and unsubstituted amidinyl groups, substituted and unsubstituted guanidinyl groups, substituted and unsubstituted saturated heterocyclyl groups, substituted and unsubstituted alkylaminoalkyl groups, substituted and unsubstituted dialkylaminoalkyl groups, substituted and unsubstituted arylaminoalkyl groups, substituted and unsubstituted diarylaminoalkyl groups, substituted and unsubstituted (alkyl)(aryl)aminoalkyl groups, substituted and unsubstituted heterocyclylalkyl groups, substituted and unsubstituted heterocyclylaminoalkyl groups, substituted and unsubstituted hydroxyalkyl groups, substituted and unsubstituted alkoxyalkyl groups, substituted and unsubstituted aryloxyalkyl groups, and substituted and unsubstituted heterocyclyloxyalkyl groups; —OR$^{19}$ groups wherein $R^{19}$ is selected from the group consisting of substituted and unsubstituted aryl groups, substituted and unsubstituted heterocyclyl groups, substituted and unsubstituted heterocyclylalkyl groups, —C(=O)H, —C(=O)-aryl groups, —C(=O)NH$_2$, —C(=O)NH(alkyl) groups, —C(=O)NH(aryl) groups, —C(=O)N(alkyl)$_2$ groups, —C(=O)N(aryl)$_2$ groups, —C(=O)N(alkyl)(aryl) groups, substituted and unsubstituted aminoalkyl groups, substituted and unsubstituted alkylaminoalkyl groups, substituted and unsubstituted dialkylaminoalkyl groups, substituted and unsubstituted arylaminoalkyl groups, substituted and unsubstituted diarylaminoalkyl groups, substituted and unsubstituted (alkyl)(aryl)aminoalkyl groups, substituted and unsubstituted heterocyclylaminoalkyl groups, substituted and unsubstituted diheterocyclylaminoalkyl groups, substituted and unsubstituted (heterocyclyl)(alkyl)aminoalkyl groups, substituted and unsubstituted (heterocyclyl)(aryl)aminoalkyl groups, substituted and unsubstituted hydroxyalkyl groups, substituted and unsubstituted alkoxyalkyl groups, substituted and unsubstituted aryloxyalkyl groups, and substituted and unsubstituted heterocyclyloxyalkyl groups; —NR$^{20}$R$^{21}$ groups wherein $R^{20}$ is selected from the group consisting of substituted and unsubstituted heterocyclyl groups; —NR$^{20}$R$^{21}$ groups wherein $R^{21}$ is selected from the group consisting of substituted and unsubstituted heterocyclyl groups, —C(=O)H, —C(=O)-aryl groups, —C(=O)NH$_2$, —C(=O)NH(alkyl) groups, —C(=O)NH(aryl) groups, —C(=O)N(alkyl)$_2$ groups, —C(=O)N(aryl)$_2$ groups, —C(=O)N(alkyl)(aryl) groups, —C(=O)O-alkyl groups, —C(=O)O-aryl groups, substituted and unsubstituted aminoalkyl groups, substituted and unsubstituted alkylaminoalkyl groups, substituted and unsubstituted dialkylaminoalkyl groups, substituted and unsubstituted arylaminoalkyl groups, substituted and unsubstituted diarylaminoalkyl groups, substituted and unsubstituted (alkyl)(aryl)aminoalkyl groups, substituted and unsubstituted heterocyclylaminoalkyl groups, substituted and unsubstituted hydroxyalkyl groups, substituted and unsubstituted alkoxyalkyl groups, substituted and unsubstituted aryloxyalkyl groups, substituted and unsubstituted heterocyclylalkyl groups, and substituted and unsubstituted heterocyclyloxyalkyl groups; and —C(=O)R$^{25}$ groups wherein $R^{25}$ is selected from the group consisting of H, —NH$_2$, —NH(alkyl) groups, —NH(aryl) groups, —N(alkyl)$_2$ groups, —N(aryl)$_2$ groups, —N(alkyl)(aryl) groups, —NH(heterocyclyl) groups, —N(heterocyclyl)(alkyl) groups, —N(heterocyclyl)(aryl) groups, —N(heterocyclyl)$_2$ groups, substituted and unsubstituted aryl groups, substituted and unsubstituted aryloxy groups, and substituted and unsubstituted heterocyclyl groups.

In one embodiment, the invention relates to a pharmaceutically acceptable salt of 4-amino-5-fluoro-3-[6-(4-methylpiperazin-1-yl)-1H-benzimidazol-2-yl]quinolin-2(1H)-one (Compound 1) or a tautomer thereof. In some such embodiments, the salt is selected from the group consisting of tartrate, malate, lactate, bis-acetate, citrate, mesylate, bismesylate and bishydrochloride.

In some specific embodiments, the compound of structure I is a lactate salt of 4-amino-5-fluoro-3-[6-(4-methylpiperazin-1-yl)-1H-benzimidazol-2-yl]quinolin-2(1H)-one or a tautomer thereof.

In some specific embodiments, the pharmaceutically acceptable salt of the compound of Structure I, the pharmaceutically acceptable salt of the tautomer, or the mixture thereof is administered to the subject, and the salt is a lactate salt.

In some embodiments, at least one of $R^{12}$ and $R^{13}$ is H, and in other embodiments, both $R^{12}$ and $R^{13}$ are H.

In a some embodiments, $R^1$ is selected from the group consisting of F, Cl, substituted and unsubstituted alkoxy groups, substituted and unsubstituted heterocyclylalkoxy groups, substituted and unsubstituted heterocyclyl groups, substituted and unsubstituted alkylaminoalkoxy groups, substituted and unsubstituted arylaminoalkoxy groups, substituted and unsubstituted dialkylaminoalkoxy groups, substituted and unsubstituted diarylaminoalkoxy groups, and substituted and unsubstituted (alkyl)(aryl)aminoalkoxy groups.

In some embodiments, $R^1$ is F and $R^2$, $R^3$, $R^3$, $R^4$, $R^5$, and $R^8$ are all H, and one of $R^6$ or $R^7$ is H.

In some other embodiments, at least one of $R^5$, $R^6$, $R^7$, and $R^8$ is a substituted or unsubstituted heterocyclyl group.

In still other embodiments, at least one of $R^5$, $R^6$, $R^7$, and $R^8$ is a substituted or unsubstituted heterocyclyl group comprising at least one O or N atom.

In yet other embodiments, at least one of $R^5$, $R^6$, $R^7$, and $R^8$ is a substituted or unsubstituted heterocyclyl group and the heterocyclyl group is selected from the group consisting of morpholine, piperazine, piperidine, pyrrolidine, thiomorpholine, homopiperazine, tetrahydrothiophene, tetrahydrofuran, and tetrahydropyran.

In yet other embodiments, at least one of $R^6$ or $R^7$ is a substituted or unsubstituted heterocyclyl group.

In yet other embodiments, at least one of $R^6$ or $R^7$ is a substituted or unsubstituted heterocyclyl group comprising at least one O or N atom.

In yet other embodiments, one of $R^6$ or $R^7$ is a substituted or unsubstituted heterocyclyl group and the heterocyclyl group is selected from the group consisting of morpholine, piperazine, piperidine, pyrrolidine, thiomorpholine, homopiperazine, tetrahydrothiophene, tetrahydrofuran, and tetrahydropyran.

In still other particular embodiments, one of $R^6$ or $R^7$ is selected from the group consisting of substituted and unsubstituted morpholine groups, and substituted and unsubstituted piperazine groups. In some such embodiments, one of $R^6$ or $R^7$ is a piperazine N-oxide or is an N-alkyl substituted piperazine.

In yet other embodiments, at least one of and in some embodiments one of $R^6$ or $R^7$ is selected from the group consisting of —$NR^{20}R^{21}$ groups wherein $R^{20}$ is selected from the group consisting of substituted and unsubstituted heterocyclyl groups; and —$NR^{20}R^{21}$ groups wherein $R^{21}$ is selected from the group consisting of substituted and unsubstituted heterocyclyl groups, groups, substituted and unsubstituted aminoalkyl groups, substituted and unsubstituted alkylaminoalkyl groups, substituted and unsubstituted dialkylaminoalkyl groups, substituted and unsubstituted arylaminoalkyl groups, substituted and unsubstituted diarylaminoalkyl groups, substituted and unsubstituted (alkyl)(aryl)aminoalkyl groups, substituted and unsubstituted heterocyclylaminoalkyl groups, substituted and unsubstituted hydroxyalkyl groups, substituted and unsubstituted alkoxyalkyl groups, substituted and unsubstituted aryloxyalkyl groups, substituted and unsubstituted heterocyclylalkyl groups, and substituted and unsubstituted heterocyclyloxyalkyl groups.

In yet another embodiment, $R^1$ is selected from the group consisting of H and F.

In yet another embodiment, the compounds and their corresponding salts and tautomers are provided in the following two tables below. The synthesis of these compounds is described in U.S. Pat. No. 6,605,617, published U.S. Patent Application No. 2004/0092535, published U.S. Patent Application No. 2004/0220196 as are various kinase assay procedures. Each of these references is, therefore, hereby incorporated by reference in its entirety and for all purposes as if set forth in its entirety.

TABLE of Exemplary Compounds

| Example | Name | LC/MS m/z (MH+) |
|---|---|---|
| 1 | 4-amino-3-{5-[(3S)-3-(dimethylamino)pyrrolidin-1-yl]-1H-benzimidazol-2-yl}quinolin-2(1H)-one | 389.4 |
| 2 | 4-[(3S)-1-azabicyclo[2.2.2]oct-3-ylamino]-3-(1H-benzimidazol-2-yl)-6-chloroquinolin-2(1H)-one | 420 |
| 3 | 4-[(3R)-1-azabicyclo[2.2.2]oct-3-ylamino]-3-(1H-benzimidazol-2-yl)-6-chloroquinolin-2(1H)-one | 420 |
| 4 | 3-(1H-benzimidazol-2-yl)-4-[(3R)-3-(dimethylamino)pyrrolidin-1-yl]quinolin-2(1H)-one | 374.2 |
| 5 | 3-(1H-benzimidazol-2-yl)-6-chloro-4-[(3R)-3-(dimethylamino)pyrrolidin-1-yl]quinolin-2(1H)-one | 408.1 |
| 6 | 4-amino-3-[5-(4-ethylpiperazin-1-yl)-1H-benzimidazol-2-yl]-1-methylquinolin-2(1H)-one | 403.2 |
| 7 | 4-amino-3-(6-piperazin-1-yl-1H-benzimidazol-2-yl)quinolin-2(1H)-one | 361.2 |
| 8 | 4-amino-3-[6-(pyridin-4-ylmethyl)-1H-benzimidazol-2-yl]quinolin-2(1H)-one | 368.2 |
| 9 | 4-amino-3-{5-[(3R,5S)-3,5-dimethylpiperazin-1-yl]-1H-benzimidazol-2-yl}quinolin-2(1H)-one | 389.4 |
| 10 | 4-amino-3-[5-(4-methylpiperazin-1-yl)-1H-benzimidazol-2-yl]quinolin-2(1H)-one | 375.2 |
| 11 | 4-amino-3-(6-methyl-5-morpholin-4-yl-1H-benzimidazol-2-yl)quinolin-2(1H)-one | 376 |
| 12 | 4-amino-3-{5-[(1-methylpiperidin-3-yl)oxy]-1H-benzimidazol-2-yl}quinolin-2(1H)-one | 390.1 |
| 13 | 4-amino-3-{5-[(2R,6S)-2,6-dimethylmorpholin-4-yl]-6-fluoro-1H-benzimidazol-2-yl}quinolin-2(1H)-one | 408.2 |
| 14 | 4-amino-3-{5-[(1-methylpyrrolidin-3-yl)oxy]-1H-benzimidazol-2-yl}quinolin-2(1H)-one | 376.2 |
| 15 | 4-amino-3-[5-(4-methyl-1,4-diazepan-1-yl)-1H-benzimidazol-2-yl]quinolin-2(1H)-one | 389.2 |
| 16 | 4-amino-3-{5-[(3R)-3-(dimethylamino)pyrrolidin-1-yl]-1H-benzimidazol-2-yl}quinolin-2(1H)-one | 389.2 |
| 17 | 4-amino-6-chloro-3-{5-[(3R)-3-(dimethylamino)pyrrolidin-1-yl]-1H-benzimidazol-2-yl}quinolin-2(1H)-one | 423 |
| 18 | ethyl {4-[2-(4-amino-2-oxo-1,2-dihydroquinolin-3-yl)-1H-benzimidazol-6-yl]piperazin-1-yl}acetate | 447.2 |

-continued

TABLE of Exemplary Compounds

| Example | Name | LC/MS m/z (MH+) |
|---|---|---|
| 19 | 4-amino-3-{6-[methyl(1-methylpiperidin-4-yl)amino]-1H-benzimidazol-2-yl}quinolin-2(1H)-one | 403.1 |
| 20 | 3-[6-(4-acetylpiperazin-1-yl)-1H-benzimidazol-2-yl]-4-aminoquinolin-2(1H)-one | 403.3 |
| 21 | 4-amino-3-[6-(1,4'-bipiperidin-1'-yl)-1H-benzimidazol-2-yl]quinolin-2(1H)-one | 443.3 |
| 22 | 2-(4-amino-2-oxo-1,2-dihydroquinolin-3-yl)-1H-be-nzimidazole-6-carboxylic acid | 321.2 |
| 23 | 4-amino-5-(methyloxy)-3-[6-(4-methylpiperazin-1-yl)-1H-benzimidazol-2-yl]quinolin-2(1H)-one | 405.3 |
| 24 | 4-amino-3-{6-[4-(1-methylethyl)piperazin-1-yl]-1H-benzimidazol-2-yl}quinolin-2(1H)-one | 403.3 |
| 25 | {4-[2-(4-amino-2-oxo-1,2-dihydroquinolin-3-yl)-1H-benzimidazol-6-yl]piperazin-1-yl}acetic acid | 419.2 |
| 26 | 4-[(3S)-1-azabicyclo[2.2.2]oct-3-ylamino]-3-(1H-benzimidazol-2-yl)quinolin-2(1H)-one | 386.1 |
| 27 | 4-[(3R)-1-azabicyclo[2.2.2]oct-3-ylamino]-3-(1H-benzimidazol-2-yl)quinolin-2(1H)-one | 386.1 |
| 28 | 4-amino-3-[5-(4-ethylpiperazin-1-yl)-1H-benzimidazol-2-yl]quinolin-2(1H)-one | 389.1 |
| 29 | 4-amino-3-(5-{(2S,5S)-2-[(dimethylamino)methyl]-5-methylmorpholin-4-yl}-1H-benzimidazol-2-yl)quinolin-2(1H)-one | 433.3 |
| 30 | 4-amino-6-chloro-3-[5-(4-methylpiperazin-1-yl)-1H-benzimidazol-2-yl]quinolin-2(1H)-one | 409.2 |
| 31 | 4-amino-6-chloro-3-{5-[(3S)-3-(dimethylamino)pyrrolidin-1-yl]-1H-benzimidazol-2-yl}quinolin-2(1H)-one | 423.1 |
| 32 | 4-amino-5,6-dichloro-3-{5-[(3S)-3-(dimethylamino)pyrrolidin-1-yl]-1H-benzimidazol-2-yl}quinolin-2(1H)-one | 457.2 |
| 33 | 4-amino-5,6-dichloro-3-{5-(4-methylpiperazin-1-yl)-1H-benzimidazol-2-yl]quinolin-2(1H)-one | 443.2 |
| 34 | 4-amino-3-(1H-benzimidazol-2-yl)-6-[(pyridin-2-ylmethyl)oxy]quinolin-2(1H)-one | 384.2 |
| 35 | 4-amino-3-(1H-benzimidazol-2-yl)-6-[(2R,6S)-2,6-dimethylmorpholin-4-yl]quinolin-2(1H)-one | 390.1 |
| 36 | 4-amino-3-(1H-benzimidazol-2-yl)-6-morpholin-4-ylquinolin-2(1H)-one | 362.2 |
| 37 | 4-amino-3-(1H-benzimidazol-2-yl)-5-[(1-methylpiperidin-3-yl)oxy]quinolin-2(1H)-one | 390.2 |
| 38 | 4-amino-3-(1H-benzimidazol-2-yl)-5-[(pyridin-2-ylmethyl)oxy]quinolin-2(1H)-one | 384.1 |
| 39 | 4-amino-3-(5-morpholin-4-yl-1H-benzimidazol-2-yl)-5-[(pyridin-4-ylmethyl)oxy]quinolin-2(1H)-one | 469.2 |
| 40 | 4-amino-3-(1H-benzimidazol-2-yl)-5-(methyloxy)quinolin-2(1H)-one | 307.1 |
| 41 | 4-amino-3-(5-methyl-1H-benzimidazol-2-yl)-5-(methyloxy)quinolin-2(1H)-one | 321.1 |
| 42 | 4-amino-3-{5-[(2R,6S)-2,6-dimethylmorpholin-4-yl]-1H-benzimidazol-2-yl}-5-(methyloxy)quinolin-2(1H)-one | 420.2 |
| 43 | 4-amino-3-(1H-benzimidazol-2-yl)-5-morpholin-4-ylquinolin-2(1H)-one | 362.2 |
| 44 | 4-amino-3-(1H-benzimidazol-2-yl)-5-[(2R,6S)-2,6-dimethylmorpholin-4-yl]quinolin-2(1H)-one | 390.2 |
| 45 | 4-amino-3-(1H-benzimidazol-2-yl)-5-(4-methylpiperazin-1-yl)quinolin-2(1H)-one | 375.1 |
| 46 | 4-amino-5,6-dichloro-3-(5-morpholin-4-yl-1H-benzimidazol-2-yl)quinolin-2(1H)-one | 430 |
| 47 | 3-{5-[(2-morpholin-4-ylethyl)oxy]-1H-benzimidazol-2-yl}quinolin-2(1H)-one | 391.3 |
| 48 | 4-amino-3-{5-[(3-pyrrolidin-1-ylpropyl)oxy]-1H-benzimidazol-2-yl}quinolin-2(1H)-one | 404 |
| 49 | 4-amino-3-{5-[(3-morpholin-4-ylpropyl)oxy]-1H-benzimidazol-2-yl}quinolin-2(1H)-one | 420.4 |
| 50 | 4-amino-6-fluoro-3-(5-morpholin-4-yl-1H-benzimidazol-2-yl)quinolin-2(1H)-one | 380 |
| 51 | 4-amino-3-{5-[3-(dimethylamino)pyrrolidin-1-yl]-1H-benzimidazol-2-yl}-6-fluoroquinolin-2(1H)-one | 407 |
| 52 | 4-amino-3-(1H-benzimidazol-2-yl)-6-fluoroquinolin-2(1H)-one | 295 |
| 53 | 4-amino-3-(6-fluoro-5-morpholin-4-yl-1H-benzimidazol-2-yl)quinolin-2(1H)-one | 380 |
| 54 | 4-amino-3-{5-[(tetrahydrofuran-2-ylmethyl)oxy]-1H-benzimidazol-2-yl}quinolin-2(1H)-one | 377 |
| 55 | 4-amino-6-fluoro-3-(6-fluoro-5-morpholin-4-yl-1H-benzimidazol-2-yl)quinolin-2(1H)-one | 398 |

-continued

TABLE of Exemplary Compounds

| Example | Name | LC/MS m/z (MH+) |
|---|---|---|
| 56 | 4-amino-3-[6-fluoro-5-(4-methylpiperazin-1-yl)-1H-benzimidazol-2-yl]quinolin-2(1H)-one | 393 |
| 57 | 4-amino-3-(5-{[2-(methyloxy)ethyl]oxy}-1H-benzimidazol-2-yl)quinolin-2(1H)-one | 351 |
| 58 | 4-amino-3-[4,6-difluoro-5-(4-methylpiperazin-1-yl)-1H-benzimidazol-2-yl]quinolin-2(1H)-one | 411 |
| 59 | 4-amino-3-{5-[3-(dimethylamino)pyrrolidin-1-yl]-1H-benzimidazol-2-yl}-5-fluoroquinolin-2(1H)-one | 407.1 |
| 60 | 4-amino-5-fluoro-3-[5-(4-methylpiperazin-1-yl)-1H-benzimidazol-2-yl]quinolin-2(1H)-one | 393.1 |
| 61 | 4-amino-5-chloro-3-[5-(4-methylpiperazin-1-yl)-1H-benzimidazol-2-yl]quinolin-2(1H)-one | 409.1 |
| 62 | 4-amino-3-{5-[3-(dimethylamino)pyrrolidin-1-yl]-6-fluoro-1H-benzimidazol-2-yl}quinolin-2(1H)-one | 407.1 |
| 63 | 4-amino-5-chloro-3-{5-[3-(dimethylamino)pyrrolidin-1-yl]-1H-benzimidazol-2-yl}quinolin-2(1H)-one | 423.1 |
| 64 | 4-amino-6-chloro-3-{5-[3-(dimethylamino)pyrrolidin-1-yl]-6-fluoro-1H-benzimidazol-2-yl}quinolin-2(1H)-one | 441 |
| 65 | 4-amino-5-[(2R,6S)-2,6-dimethylmorpholin-4-yl]-3-(3H-imidazo[4,5-b]pyridin-2-yl)quinolin-2(1H)-one | 391.2 |
| 66 | 4-amino-3-(6-thiomorpholin-4-yl-1H-benzimidazol-2-yl)quinolin-2(1H)-one | 378.4 |
| 67 | 4-amino-3-[5-(4-cyclohexylpiperazin-1-yl)-1H-benzimidazol-2-yl]quinolin-2(1H)-one | 443.1 |
| 68 | 4-amino-3-{6-[3-(diethylamino)pyrrolidin-1-yl]-1H-benzimidazol-2-yl}quinolin-2(1H)-one | 417.1 |
| 69 | 4-amino-3-[6-(4-pyridin-2-ylpiperazin-1-yl)-1H-benzimidazol-2-yl]quinolin-2(1H)-one | 438.3 |
| 70 | 4-amino-3-[5-(4-methylpiperazin-1-yl)-3H-imidazo[4,5-b]pyridin-2-yl]quinolin-2(1H)-one | 376.3 |
| 71 | 4-amino-6-chloro-3-[5-(4-methylpiperazin-1-yl)-1H-imidazo[4,5-b]pyridin-2-yl]quinolin-2(1H)-one | 410.2 |
| 72 | 2-(4-amino-2-oxo-1,2-dihydroquinolin-3-yl)-N-methyl-N-(1-methylpiperidin-4-yl)-1H-benzimidazole-5-carboxamide | 431.3 |
| 73 | 4-amino-3-(5-{[4-(1-methylethyl)piperazin-1-yl]carbonyl}-1H-benzimidazol-2-yl)quinolin-2(1H)-one | 431.3 |
| 74 | 4-amino-3-[5-(4-methylpiperazin-1-yl)-1H-benzimidazol-2-yl]-6-nitroquinolin-2(1H)-one | 420.2 |
| 75 | 4-amino-3-[5-(1,4'-bipiperidin-1'-ylcarbonyl)-1H-benzimidazol-2-yl]quinolin-2(1H)-one | 471.1 |
| 76 | 4-amino-3-{5-[(4-methylpiperazin-1-yl)carbonyl]-1H-benzimidazol-2-yl}quinolin-2(1H)-one | 403.3 |
| 77 | 4-amino-3-[5-(1-oxidothiomorpholin-4-yl)-1H-benzimidazol-2-yl]quinolin-2(1H)-one | 394.5 |
| 78 | 3-{5-[(4-acetylpiperazin-1-yl)carbonyl]-1H-benzimidazol-2-yl}-4-aminoquinolin-2(1H)-one | 431.3 |
| 79 | 4-amino-3-(5-{[(3R)-3-(dimethylamino)pyrrolidin-1-yl]carbonyl}-1H-benzimidazol-2-yl)quinolin-2(1H)-one | 417.4 |
| 80 | 4-amino-3-(5-{[(3S)-3-(dimethylamino)pyrrolidin-1-yl]carbonyl}-1H-benzimidazol-2-yl)quinolin-2(1H)-one | 417.4 |
| 81 | 4-amino-3-(5-{[4-(dimethylamino)piperidin-1-yl]carbonyl}-1H-benzimidazol-2-yl)quinolin-2(1H)-one | 431.4 |
| 82 | methyl 2-(4-amino-5-fluoro-2-oxo-1,2-dihydroquinolin-3-yl)-1H-benzimidazole-6-carboxylate | 353.2 |
| 83 | 4-amino-3-[5-(1,3'-bipyrrolidin-1'-yl)-1H-benzimidazol-2-yl]quinolin-2(1H)-one | 415.5 |
| 84 | 4-amino-3-[5-(pyridin-3-yloxy)-1H-benzimidazol-2-yl]quinolin-2(1H)-one | 370.2 |
| 85 | 4-amino-5,6-bis(methyloxy)-3-[5-(4-methylpiperazin-1-yl)-1H-benzimidazol-2-yl]quinolin-2(1H)-one | 435.5 |
| 86 | 2-(4-amino-2-oxo-1,2-dihydroquinolin-3-yl)-N-[2-(dimethylamino)ethyl]-N-methyl-1H-benzimidazole-5-carboxamide | 405.3 |
| 87 | 2-(4-amino-2-oxo-1,2-dihydroquinolin-3-yl)-N-methyl-N-(1-methylpyrrolidin-3-yl)-1H-benzimidazole-5-carboxamide | 417.2 |
| 88 | 4-amino-3-{5-[(5-methyl-2,5-diazabicyclo[2.2.1]hept-2-yl)carbonyl]-1H-benzimidazol-2-yl}quinolin-2(1H)-one | 415.2 |
| 89 | 4-amino-3-{5-[(4-cyclohexylpiperazin-1-yl)carbonyl]-1H-benzimidazol-2-yl}quinolin-2(1H)-one | 471.6 |
| 90 | 4-amino-3-{5-[(2-piperidin-1-ylethyl)amino]-1H-benzimidazol-2-yl}quinolin-2(1H)-one | 403.2 |
| 91 | ethyl 4-{[2-(4-amino-2-oxo-1,2-dihydroquinolin-3-yl)-1H-benzimidazol-5-yl]amino}piperidine-1-carboxylate | 447.3 |

-continued

TABLE of Exemplary Compounds

| Example | Name | LC/MS m/z (MH+) |
|---|---|---|
| 92 | 4-amino-3-[5-({(5R)-5-[(methyloxy)methyl]pyrrolidin-3-yl}amino)-1H-benzimidazol-2-yl]quinolin-2(1H)-one | 405.2 |
| 93 | 4-amino-3-{5-[(pyridin-2-ylmethyl)amino]-1H-benzimidazol-2-yl}quinolin-2(1H)-one | 383.3 |
| 94 | 4-amino-3-[5-(piperidin-3-ylamino)-1H-benzimidazol-2-yl]quinolin-2(1H)-one | 375.2 |
| 95 | 4-amino-5-fluoro-3-{5-[(pyridin-2-ylmethyl)amino]-1H-benzimidazol-2-yl}quinolin-2(1H)-one | 401.3 |
| 96 | ethyl 4-{[2-(4-amino-5-fluoro-2-oxo-1,2-dihydroquinolin-3-yl)-1H-benzimidazol-5-yl]amino}piperidine-1-carboxylate | 465.5 |
| 97 | 4-amino-5-fluoro-3-[5-(piperidin-3-ylamino)-1H-benzimidazol-2-yl]quinolin-2(1H)-one | 393.3 |
| 98 | 4-amino-3-(1H-benzimidazol-2-yl)-6-bromoquinolin-2(1H)-one | 357.1 |
| 99 | 4-amino-3-(1H-benzimidazol-2-yl)-7-bromoquinolin-2(1H)-one | 357.1 |
| 100 | 4-amino-3-(5-bromo-1H-benzimidazol-2-yl)quinolin-2(1H)-one | 357.1 |
| 101 | N,N-dimethyl-2-(2-oxo-1,2-dihydroquinolin-3-yl)-1H-benzimidazole-5-carboxamide | 333.1 |
| 102 | 4-amino-3-(5-thien-2-yl-1H-benzimidazol-2-yl)quinolin-2(1H)-one | 359.2 |
| 103 | 2-(4-amino-2-oxo-1,2-dihydroquinolin-3-yl)-N,N-dimethyl-1H-benzimidazole-5-sulfonamide | 384.1 |
| 104 | 4-amino-6-iodo-3-[5-(4-methylpiperazin-1-yl)-1H-benzimidazol-2-yl]quinolin-2(1H)-one | 501.1 |
| 105 | 4-amino-3-(5-{2-[(dimethylamino)methyl]-morpholin-4-yl}-1H-benzimidazol-2-yl)quinolin-2(1H)-one | 419.2 |
| 106 | 4-[(3R)-1-azabicyclo[2.2.2]oct-3-ylamino]-3-(1H-benzimidazol-2-yl)-7-chloro-6-iodoquinolin-2(1H)-one | 547 |
| 107 | 4-[(3R)-1-azabicyclo[2.2.2]oct-3-ylamino]-3-(1H-benzimidazol-2-yl)-6-nitroquinolin-2(1H)-one | 431 |
| 108 | 4-[(3R)-1-azabicyclo[2.2.2]oct-3-ylamino]-3-(1H-benzimidazol-2-yl)-6-methylquinolin-2(1H)-one | 401 |
| 109 | 4-[(3R)-1-azabicyclo[2.2.2]oct-3-ylamino]-3-(1H-benzimidazol-2-yl)-6,7-difluoroquinolin-2(1H)-one | 422 |
| 110 | 4-[(3S)-1-azabicyclo[2.2.2]oct-3-ylamino]-3-(1H-benzimidazol-2-yl)-7-chloroquinolin-2(1H)-one | 421 |
| 111 | 4-[(3R)-1-azabicyclo[2.2.2]oct-3-ylamino]-3-(1H-benzimidazol-2-yl)-6-bromoquinolin-2(1H)-one | 465 |
| 112 | 4-[(3R)-1-azabicyclo[2.2.2]oct-3-ylamino]-3-(1H-benzimidazol-2-yl)-2-oxo-1,2-dihydroquinoline-6-carbonitrile | 411 |
| 113 | 4-[(3R)-1-azabicyclo[2.2.2]oct-3-ylamino]-3-(1H-benzimidazol-2-yl)-6-fluoroquinolin-2(1H)-one | 404 |
| 114 | 4-[(3S)-1-azabicyclo[2.2.2]oct-3-ylamino]-3-(1H-benzimidazol-2-yl)-6,7-bis(methyloxy)quinolin-2(1H)-one | 447 |
| 115 | 4-[(3R)-1-azabicyclo[2.2.2]oct-3-ylamino]-3-(1H-benzimidazol-2-yl)-6,7-dichloroquinolin-2(1H)-one | 455 |
| 116 | 1-[4-[(3S)-1-azabicyclo[2.2.2]oct-3-ylamino]-3-(1H-benzimidazol-2-yl)-6-fluoro-2-oxo-1,2-dihydroquinolin-7-yl]piperidine-4-carboxamide | 531 |
| 117 | 4-[(3S)-1-azabicyclo[2.2.2]oct-3-ylamino]-3-(1H-benzimidazol-2-yl)-6-fluoro-7-[(3-hydroxypropyl)amino]quinolin-2(1H)-one | 478 |
| 118 | 4-[(3S)-1-azabicyclo[2.2.2]oct-3-ylamino]-3-(1H-benzimidazol-2-yl)-7-(dimethylamino)-6-fluoroquinolin-2(1H)-one | 448 |
| 119 | 4-[(3R)-1-azabicyclo[2.2.2]oct-3-ylamino]-3-(1H-benzimidazol-2-yl)-5-fluoroquinolin-2(1H)-one | 404 |
| 120 | 4-[(3R)-1-azabicyclo[2.2.2]oct-3-ylamino]-3-(1H-benzimidazol-2-yl)-6-(4-nitrophenyl)quinolin-2(1H)-one | 508 |
| 121 | 4-[(3S)-1-azabicyclo[2.2.2]oct-3-ylamino]-3-(1H-benzimidazol-2-yl)-7-{[2-(dimethylamino)ethyl]amino}-6-fluoroquinolin-2(1H)-one | 491 |
| 122 | 4-[(3S)-1-azabicyclo[2.2.2]oct-3-ylamino]-3-(1H-benzimidazol-2-yl)-6-fluoro-7-(1H-imidazol-1-yl)quinolin-2(1H)-one | 471 |
| 123 | 4-[(3R)-1-azabicyclo[2.2.2]oct-3-ylamino]-3-(1H-benzimidazol-2-yl)-6-[4-(methyloxy)phenyl]quinolin-2(1H)-one | 493 |
| 124 | 4-[(3S)-1-azabicyclo[2.2.2]oct-3-ylamino]-3-(1H-benzimidazol-2-yl)-6-fluoro-7-morpholin-4-ylquinolin-2(1H)-one | 490 |
| 125 | 4-[(3R)-1-azabicyclo[2.2.2]oct-3-ylamino]-6,7-difluoro-3-(3H-imidazo[4,5-b]pyridin-2-yl)quinolin-2(1H)-one | 423 |
| 126 | 4-[(3R)-1-azabicyclo[2.2.2]oct-3-ylamino]-3-(1H-benzimidazol-2-yl)-6-(3-nitrophenyl)quinolin-2(1H)-one | 508 |
| 127 | 1-[4-[(3S)-1-azabicyclo[2.2.2]oct-3-ylamino]-3-(1H-benzimidazol-2-yl)-6-fluoro-2-oxo-1,2-dihydroquinolin-7-yl]piperidine-3-carboxamide | 531 |
| 128 | 4-[(3S)-1-azabicyclo[2.2.2]oct-3-ylamino]-3-(1H-benzimidazol-2-yl)-5-methylquinolin-2(1H)-one | 401 |

-continued

TABLE of Exemplary Compounds

| Example | Name | LC/MS m/z (MH+) |
|---|---|---|
| 129 | 6-(3-acetylphenyl)-4-[(3R)-1-azabicyclo[2.2.2]oct-3-ylamino]-3-(3H-imidazo[4,5-b]pyridin-2-yl)quinolin-2(1H)-one | 506 |
| 130 | 4-[(3S)-1-azabicyclo[2.2.2]oct-3-ylamino]-3-(1H-benzimidazol-2-yl)-5-chloroquinolin-2(1H)-one | 421 |
| 131 | 4-[(3R)-1-azabicyclo[2.2.2]oct-3-ylamino]-6-fluoro-3-(3H-imidazo[4,5-b]pyridin-2-yl)-7-morpholin-4-ylquinolin-2(1H)-one | 491 |
| 132 | 4-[(3S)-1-azabicyclo[2.2.2]oct-3-ylamino]-3-(1H-benzimidazol-2-yl)-7-(cyclopropylamino)-6-fluoroquinolin-2(1H)-one | 460 |
| 133 | N-{3-[4-[(3R)-1-azabicyclo[2.2.2]oct-3-ylamino]-3-(3H-imidazo[4,5-b]pyridin-2-yl)-2-oxo-1,2-dihydroquinolin-6-yl]phenyl}acetamide | 521 |
| 134 | 4-[(3S)-1-azabicyclo[2.2.2]oct-3-ylamino]-3-(1H-benzimidazol-2-yl)-6-fluoro-7-(4-methylpiperazin-1-yl)quinolin-2(1H)-one | 503 |
| 135 | 4-[(3R)-1-azabicyclo[2.2.2]oct-3-ylamino]-6-fluoro-7-(1H-imidazol-1-yl)-3-(3H-imidazo[4,5-b]pyridin-2-yl)quinolin-2(1H)-one | 472 |
| 136 | 4-[(3S)-1-azabicyclo[2.2.2]oct-3-ylamino]-3-(1H-benzimidazol-2-yl)-6-fluoro-7-[(2-pyridin-2-ylethyl)amino]quinolin-2(1H)-one | 525 |
| 137 | 4-[(3S)-1-azabicyclo[2.2.2]oct-3-ylamino]-3-(1H-benzimidazol-2-yl)-6-fluoro-7-piperidin-1-ylquinolin-2(1H)-one | 488 |
| 138 | 6-chloro-3-(3H-imidazo[4,5-b]pyridin-2-yl)quinolin-2(1H)-one | 298 |
| 139 | ethyl 1-[4-[(3S)-1-azabicyclo[2.2.2]oct-3-ylamino]-3-(1H-benzimidazol-2-yl)-6-fluoro-2-oxo-1,2-dihydroquinolin-7-yl]piperidine-4-carboxylate | 560 |
| 140 | 4-[(3R)-1-azabicyclo[2.2.2]oct-3-ylamino]-3-(1H-benzimidazol-2-yl)-6-(1-benzothien-2-yl)quinolin-2(1H)-one | 519 |
| 141 | 4-[(3S)-1-azabicyclo[2.2.2]oct-3-ylamino]-3-(1H-benzimidazol-2-yl)-6-fluoro-7-pyrrolidin-1-ylquinolin-2(1H)-one | 474 |
| 142 | 4-[(3R)-1-azabicyclo[2.2.2]oct-3-ylamino]-3-(3H-imidazo[4,5-b]pyridin-2-yl)-6-[2-(trifluoromethyl)phenyl]quinolin-2(1H)-one | 532 |
| 143 | 4-[(3R)-1-azabicyclo[2.2.2]oct-3-ylamino]-3-(3H-imidazo[4,5-b]pyridin-2-yl)-6-[2-(methyloxy)phenyl]quinolin-2(1H)-one | 494 |
| 144 | ethyl 1-[4-[(3S)-1-azabicyclo[2.2.2]oct-3-ylamino]-3-(1H-benzimidazol-2-yl)-6-fluoro-2-oxo-1,2-dihydroquinolin-7-yl]piperidine-3-carboxylate | 560 |
| 145 | 4-[(3R)-1-azabicyclo[2.2.2]oct-3-ylamino]-3-(1H-benzimidazol-2-yl)-6-(4-ethylphenyl)quinolin-2(1H)-one | 491 |
| 146 | 4-[(3S)-1-azabicyclo[2.2.2]oct-3-ylamino]-3-(1H-benzimidazol-2-yl)-6-fluoro-7-[(2-methylpropyl)amino]quinolin-2(1H)-one | 476 |
| 147 | 4-[(3R)-1-azabicyclo[2.2.2]oct-3-ylamino]-3-(1H-benzimidazol-2-yl)-5-methylquinolin-2(1H)-one | 401 |
| 148 | 4-[(3R)-1-azabicyclo[2.2.2]oct-3-ylamino]-6-(2,4-dichlorophenyl)-3-(3H-imidazo[4,5-b]pyridin-2-yl)quinolin-2(1H)-one | 532 |
| 149 | 4-[(3R)-1-azabicyclo[2.2.2]oct-3-ylamino]-3-(1H-benzimidazol-2-yl)-6-[3-(trifluoromethyl)phenyl]quinolin-2(1H)-one | 531 |
| 150 | 3-(1H-benzimidazol-2-yl)-4-(dimethylamino)quinoline-2(1H)-one | 305 |
| 151 | 4-hydroxy-3-(1H-imidazo[4,5-f]quinolin-2-yl)quinolin-2(1H)-one | 329 |
| 152 | 4-hydroxy-3-(1H-imidazo[4,5-b]pyridin-2-yl)quinolin-2(1H)-one | 279 |
| 153 | 4-[4-[(3R)-1-azabicyclo[2.2.2]oct-3-ylamino]-3-(1H-benzimidazol-2-yl)-5-fluoro-2-oxo-1,2-dihydroquinolin-6-yl]benzoic acid | 525 |
| 154 | 4-[4-[(3R)-1-azabicyclo[2.2.2]oct-3-ylamino]-3-(1H-benzimidazol-2-yl)-5-fluoro-2-oxo-1,2-dihydroquinolin-6-yl]benzamide | 524 |
| 155 | N-{3-[4-[(3R)-1-azabicyclo[2.2.2]oct-3-ylamino]-3-(1H-benzimidazol-2-yl)-5-fluoro-2-oxo-1,2-dihydroquinolin-6-yl]phenyl}acetamide | 538 |
| 156 | 3-[4-[(3R)-1-azabicyclo[2.2.2]oct-3-ylamino]-3-(1H-benzimidazol-2-yl)-5-fluoro-2-oxo-1,2-dihydroquinolin-6-yl]benzoic acid | 525 |
| 157 | 4-[4-[(3R)-1-azabicyclo[2.2.2]oct-3-ylamino]-3-(1H-benzimidazol-2-yl)-7-fluoro-2-oxo-1,2-dihydroquinolin-6-yl]benzoic acid | 525 |
| 158 | N-{3-[4-[(3R)-1-azabicyclo[2.2.2]oct-3-ylamino]-3-(1H benzimidazol-2-yl)-7-fluoro-2-oxo-1,2-dihydroquinolin-6-yl]phenyl}acetamide | 538 |
| 159 | 4-[(3R)-1-azabicyclo[2.2.2]oct-3-ylamino]-3-(1H-benzimidazol-2-yl)-7-chloro-6-(2-methylphenyl)quinolin-2(1H)-one | 511 |
| 160 | 4-[(3R)-1-azabicyclo[2.2.2]oct-3-ylamino]-3-(1H-benzimidazol-2-yl)-2-oxo-1,2-dihydroquinoline-7-carbonitrile | 411 |
| 161 | 4-[(3R)-1-azabicyclo[2.2.2]oct-3-ylamino]-3-(1H-benzimidazol-2-yl)-7-(methyloxy)quinolin-2(1H)-one | 417 |
| 162 | 4-[4-[(3R)-1-azabicyclo[2.2.2]oct-3-ylamino]-3-(1H-benzimidazol-2-yl)-2-oxo-1,2-dihydroquinolin-7-yl]benzamide | 506 |

-continued

TABLE of Exemplary Compounds

| Example | Name | LC/MS m/z (MH+) |
|---|---|---|
| 163 | 4-[(3R)-1-azabicyclo[2.2.2]oct-3-ylamino]-3-(1H-benzimidazol-2-yl)-6-fluoro-7-(methyloxy)quinolin-2(1H)-one | 434 |
| 164 | 4-[(3R)-1-azabicyclo[2.2.2]oct-3-ylamino]-3-(1H-benzimidazol-2-yl)-6-chloro-7-(dimethylamino)quinolin-2(1H)-one | 464 |
| 165 | 4-[(3R)-1-azabicyclo[2.2.2]oct-3-ylamino]-3-(1H-benzimidazol-2-yl)-7-(dimethylamino)-6-iodoquinolin-2(1H)-one | 555 |
| 166 | 3-[4-[(3R)-1-azabicyclo[2.2.2]oct-3-ylamino]-3-(1H-benzimidazol-2-yl)-7-(1H-imidazol-1-yl)-2-oxo-1,2-dihydroquinolin-6-yl]benzoic acid | 573 |
| 167 | 4-[4-[(3R)-1-azabicyclo[2.2.2]oct-3-ylamino]-3-(1H-benzimidazol-2-yl)-2-oxo-7-piperidin-1-yl-1,2-dihydroquinolin-6-yl]benzoic acid | 590 |
| 168 | 4-[(3R)-1-azabicyclo[2.2.2]oct-3-ylamino]-3-(1H-benzimidazol-2-yl)-7-(methyloxy)-6-[4-(methylsulfonyl)phenyl]quinolin-2(1H)-one | 571 |
| 169 | 4-[(3R)-1-azabicyclo[2.2.2]oct-3-ylamino]-3-(1H-benzimidazol-2-yl)-8-methylquinolin-2(1H)-one | 401 |
| 170 | 4-[(3S)-1-azabicyclo[2.2.2]oct-3-ylamino]-3-(1H-benzimidazol-2-yl)-6,7-difluoroquinolin-2(1H)-one | 422 |
| 171 | 3-(1H-benzimidazol-2-yl)-6-methyl-4-(piperidin-3-ylamino)quinolin-2(1H)-one | 374 |
| 172 | 4-[(3S)-1-azabicyclo[2.2.2]oct-3-ylamino]-3-(1H-benzimidazol-2-yl)-6-[2-(methyloxy)phenyl]quinolin-2(1H)-one | 493 |
| 173 | 4-[(3S)-1-azabicyclo[2.2.2]oct-3-ylamino]-3-(1H-benzimidazol-2-yl)-6-[3-(methyloxy)phenyl]quinolin-2(1H)-one | 493 |
| 174 | 3-(1H-benzimidazol-2-yl)-6,7-difluoro-4-(piperidin-4-ylamino)quinolin-2(1H)-one | 396 |
| 175 | 3-(1H-benzimidazol-2-yl)-6,7-difluoro-4-(pyrrolidin-3-ylamino)quinolin-2(1H)-one | 382 |
| 176 | 3-(1H-benzimidazol-2-yl)-6-chloro-4-[(3-morpholin-4-ylpropyl)amino]quinolin-2(1H)-one | 439 |
| 177 | 6-chloro-3-(5-morpholin-4-yl-1H-benzimidazol-2-yl)-4-(piperidin-4-ylamino)quinolin-2(1H)-one | 480 |
| 178 | 6-chloro-3-(5-morpholin-4-yl-1H-benzimidazol-2-yl)-4-[(piperidin-2-ylmethyl)amino]quinolin-2(1H)-one | 494 |
| 179 | 4-[(3S)-1-azabicyclo[2.2.2]oct-3-ylamino]-6-chloro-3-(5-morpholin-4-yl-1H-benzimidazol-2-yl)quinolin-2(1H)-one | 506 |
| 180 | 6-chloro-3-(5-morpholin-4-yl-1H-benzimidazol-2-yl)-4-(piperidin-3-ylamino)quinolin-2(1H)-one | 480 |
| 181 | 6-chloro-4-{[2-(dimethylamino)ethyl]amino}-3-(5-morpholin-4-yl-1H-benzimidazol-2-yl)quinolin-2(1H)-one | 468 |
| 182 | 4-[(3R)-1-azabicyclo[2.2.2]oct-3-ylamino]-6-chloro-3-(5-morpholin-4-yl-1H-benzimidazol-2-yl)quinolin-2(1H)-one | 506 |
| 183 | 6-chloro-3-(5-morpholin-4-yl-1H-benzimidazol-2-yl)-4-[(piperidin-3-ylmethyl)amino]quinolin-2(1H)-one | 494 |
| 184 | 6-chloro-3-(5-morpholin-4-yl-1H-benzimidazol-2-yl)-4-[(piperidin-4-ylmethyl)amino]quinolin-2(1H)-one | 494 |
| 185 | 4-{[(1R,2R)-2-aminocyclohexyl]amino}-6-chloro-3-(5-morpholin-4-yl-1H-benzimidazol-2-yl)quinolin-2(1H)-one | 494 |
| 186 | 4-[(4-aminocyclohexyl)amino]-6-chloro-3-(5-morpholin-4-yl-1H-benzimidazol-2-yl)quinolin-2(1H)-one | 494 |
| 187 | 4-{[(2S)-2-amino-3-methylbutyl]amino}-6-chloro-3-(5-morpholin-4-yl-1H-benzimidazol-2-yl)quinolin-2(1H)-one | 482 |
| 188 | 4-({[4-(aminomethyl)phenyl]methyl}amino)-6-chloro-3-(5-morpholin-4-yl-1H-benzimidazol-2-yl)quinolin-2(1H)-one | 516 |
| 189 | 6-chloro-3-(5-morpholin-4-yl-1H-benzimidazol-2-yl)-4-[(pyrrolidin-2-ylmethyl)amino]quinolin-2(1H)-one | 480 |
| 190 | 4-{[(1R)-1-(aminomethyl)propyl]amino}-6-chloro-3-(5-morpholin-4-yl-1H-benzimidazol-2-yl)quinolin-2(1H)-one | 468 |
| 191 | 4-{[(1S)-2-amino-1-(phenylmethyl)ethyl]amino}-6-chloro-3-(5-morpholin-4-yl-1H-benzimidazol-2-yl)quinolin-2(1H)-one | 530 |
| 192 | 6-chloro-4-{[3-(4-methylpiperazin-1-yl)propyl]amino}-3-(5-morpholin-4-yl-1H-benzimidazol-2-yl)quinolin-2(1H)-one | 537 |
| 193 | 6-chloro-3-(5-morpholin-4-yl-1H-benzimidazol-2-yl)-4-{[1-(phenylmethyl)piperidin-4-yl]amino}quinolin-2(1H)-one | 570 |
| 194 | 6-chloro-3-(5-morpholin-4-yl-1H-benzimidazol-2-yl)-4-[(3-morpholin-4-ylpropyl)amino]quinolin-2(1H)-one | 524 |
| 195 | 6-chloro-3-(5-morpholin-4-yl-1H-benzimidazol-2-yl)-4-[(2-piperidin-1-ylethyl)amino]quinolin-2(1H)-one | 508 |
| 196 | 6-chloro-3-(5-morpholin-4-yl-1H-benzimidazol-2-yl)-4-[(pyridin-3-ylmethyl)amino]quinolin-2(1H)-one | 488 |
| 197 | 6-chloro-4-{[3-(1H-imidazol-1-yl)propyl]amino}-3-(5-morpholin-4-yl-1H-benzimidazol-2-yl)quinolin-2(1H)-one | 505 |

-continued

TABLE of Exemplary Compounds

| Example | Name | LC/MS m/z (MH+) |
|---|---|---|
| 198 | 6-chloro-3-(5-morpholin-4-yl-1H-benzimidazol-2-yl)-4-[(pyridin-4-ylmethyl)amino]quinolin-2(1H)-one | 488 |
| 199 | 6-chloro-4-{[2-(methylamino)ethyl]amino}-3-(5-morpholin-4-yl-1H-benzimidazol-2-yl)quinolin-2(1H)-one | 454 |
| 200 | 6-chloro-4-{[(2-methyl-1-piperidin-4-yl-1H-benzimidazol-5-yl)methyl]amino}-3-(5-morpholin-4-yl-1H-benzimidazol-2-yl)quinolin-2(1H)-one | 624 |
| 201 | 6-chloro-3-(5-morpholin-4-yl-1H-benzimidazol-2-yl)-4-[(2-pyrrolidin-1-ylethyl)amino]quinolin-2(1H)-one | 494 |
| 202 | 6-chloro-3-(5-morpholin-4-yl-1H-benzimidazol-2-yl)-4-(pyrrolidin-3-ylamino)quinolin-2(1H)-one | 466 |
| 203 | 4-{[(1R,2R)-2-aminocyclohexyl]amino}-6-chloro-3-[5-(4-methylpiperazin-1-yl)-1H-benzimidazol-2-yl]quinolin-2(1H)-one | 507 |
| 204 | 4-[(4-aminocyclohexyl)amino]-6-chloro-3-[5-(4-methylpiperazin-1-yl)-1H-benzimidazol-2-yl]quinolin-2(1H)-one | 507 |
| 205 | 4-({[4-(aminomethyl)phenyl]methyl}amino)-6-chloro-3-[5-(4-methylpiperazin-1-yl)-1H-benzimidazol-2-yl]quinolin-2(1H)-one | 529 |
| 206 | 6-chloro-4-{[2-(methylamino)ethyl]amino}-3-[5-(4-methylpiperazin-1-yl)-1H-benzimidazol-2-yl]quinolin-2(1H)-one | 467 |
| 207 | 6-chloro-3-[5-(4-methylpiperazin-1-yl)-1H-benzimidazol-2-yl]-4-{[3-(4-methylpiperazin-1-yl)propyl]amino}quinolin-2(1H)-one | 550 |
| 208 | 6-chloro-3-[5-(4-methylpiperazin-1-yl)-1H-benzimidazol-2-yl]-4-{[1-(phenylmethyl)piperidin-4-yl]amino}quinolin-2(1H)-one | 583 |
| 209 | 6-chloro-3-[5-(4-methylpiperazin-1-yl)-1H-benzimidazol-2-yl]-4-[(2-pyrrolidin-1-ylethyl)amino]quinolin-2(1H)-one | 507 |
| 210 | 6-chloro-3-[5-(4-methylpiperazin-1-yl)-1H-benzimidazol-2-yl]-4-(pyrrolidin-3-ylamino)quinolin-2(1H)-one | 479 |
| 211 | 6-chloro-3-[5-(4-methylpiperazin-1-yl)-1H-benzimidazol-2-yl]-4-(piperidin-4-ylamino)quinolin-2(1H)-one | 493 |
| 212 | 6-chloro-3-(5-morpholin-4-yl-1H-benzimidazol-2-yl)-4-[(2-piperidin-2-ylethyl)amino]quinolin-2(1H)-one | 508 |
| 213 | 4-[(3S)-1-azabicyclo[2.2.2]oct-3-ylamino]-7-chloro-3-(5-morpholin-4-yl-1H-benzimidazol-2-yl)quinolin-2(1H)-one | 506 |
| 214 | 7-chloro-3-(5-morpholin-4-yl-1H-benzimidazol-2-yl)-4-(piperidin-3-ylamino)quinolin-2(1H)-one | 480 |
| 215 | 6-chloro-3-[5-(4-methylpiperazin-1-yl)-1H-benzimidazol-2-yl]-4-[(piperidin-2-ylmethyl)amino]quinolin-2(1H)-one | 507 |
| 216 | 6-chloro-3-[5-(4-methylpiperazin-1-yl)-1H-benzimidazol-2-yl]-4-{[(2S)-pyrrolidin-2-ylmethyl]amino}quinolin-2(1H)-one | 493 |
| 217 | 6-chloro-3-[5-(4-methylpiperazin-1-yl)-1H-benzimidazol-2-yl]-4-{[(2R)-pyrrolidin-2-ylmethyl]amino}quinolin-2(1H)-one | 493 |
| 218 | 6-chloro-4-({[(2S)-1-ethylpyrrolidin-2-yl]methyl}amino)-3-[5-(4-methylpiperazin-1-yl)-1H-benzimidazol-2-yl]quinolin-2(1H)-one | 521 |
| 219 | 6-chloro-4-({[(2R)-1-ethylpyrrolidin-2-yl]methyl}amino)-3-[5-(4-methylpiperazin-1-yl)-1H-benzimidazol-2-yl]quinolin-2(1H)-one | 521 |
| 220 | 4-[(3S)-1-azabicyclo[2.2.2]oct-3-ylamino]-3-(1H-benzimidazol-2-yl)-6-[4-(methyloxy)phenyl]quinolin-2(1H)-one | 493 |
| 221 | 6-(3-aminophenyl)-4-[(3S)-1-azabicyclo[2.2.2]oct-3-ylamino]-3-(1H-benzimidazol-2-yl)quinolin-2(1H)-one | 478 |

TABLE of Additional Exemplary Compounds

| Example | Name | LC/MS m/z (MH$^+$) |
|---|---|---|
| 222 | 4-amino-3-(1H-benzimidazol-2-yl)quinolin-2(1H)-one | 277.3 |
| 223 | 4-amino-3-(1H-benzimidazol-2-yl)-6,7-dimethoxyquinolin-2(1H)-one | 337.3 |
| 224 | 3-(1H-benzimidazol-2-yl)-4-(dimethylamino)-1-methylquinolin-2(1H)-one | 319.4 |
| 225 | 3-(1H-benzimidazol-2-yl)-4-{[2-(dimethylamino)ethyl]amino}-1-methylquinolin-2(1H)-one | 362.4 |
| 226 | 4-amino-3-(1H-benzimidazol-2-yl)-1-methylquinolin-2(1H)-one | 291.3 |
| 227 | 4-amino-3-(6-methyl-1H-benzimidazol-2-yl)quinolin-2(1H)-one | 291.3 |
| 228 | 3-(1H-benzimidazol-2-yl)-4-{[3-(1H-imidazol-1-yl)propyl]amino}quinolin-2(1H)-one | 385.4 |
| 229 | 3-(1H-benzimidazol-2-yl)-4-[(pyridin-3-ylmethyl)amino]quinolin-2(1H)-one | 368.4 |

-continued

TABLE of Additional Exemplary Compounds

| Example | Name | LC/MS m/z (MH+) |
|---|---|---|
| 230 | 4-amino-3-(1H-benzimidazol-2-yl)-5-fluoroquinolin-2(1H)-one | 295.3 |
| 231 | 3-(1H-benzimidazol-2-yl)-4-pyrrolidin-1-ylquinolin-2(1H)-one | 331.4 |
| 232 | 3-(1H-benzimidazol-2-yl)-4-[(pyridin-4-ylmethyl)amino]quinolin-2(1H)-one | 368.4 |
| 233 | 3-(1H-benzimidazol-2-yl)-4-{[2-(1-methylpyrrolidin-2-yl)ethyl]amino}quinolin-2(1H)-one | 388.5 |
| 234 | 4-amino-3-(1H-benzimidazol-2-yl)-7-methylquinolin-2(1H)-one | 291.3 |
| 235 | 4-amino-3-(1H-benzimidazol-2-yl)-7-chloroquinolin-2(1H)-one | 311.7 |
| 236 | 4-amino-3-(1H-benzimidazol-2-yl)-6-chloroquinolin-2(1H)-one | 311.7 |
| 237 | 4-amino-3-[6-(3-aminopyrrolidin-1-yl)-1H-benzimidazol-2-yl]quinolin-2(1H)-one | 361.4 |
| 238 | 3-(1H-benzimidazol-2-yl)-4-(diethylamino)quinolin-2(1H)-one | 333.4 |
| 239 | 3-(1H-benzimidazol-2-yl)-4-(1,2-dimethylhydrazino)quinolin-2(1H)-one | 320.4 |
| 240 | 4-amino-3-[5-(trifluoromethyl)-1H-benzimidazol-2-yl]quinolin-2(1H)-one | 345.3 |
| 241 | 4-amino-3-(5,6-dichloro-1H-benzimidazol-2-yl)quinolin-2(1H)-one | 346.2 |
| 242 | 4-(3-aminopyrrolidin-1-yl)-3-(5-morpholin-4-yl-1H-benzimidazol-2-yl)quinolin-2(1H)-one | 431.5 |
| 243 | 4-amino-5-fluoro-3-(5-methyl-1H-benzimidazol-2-yl)quinolin-2(1H)-one | 309.3 |
| 244 | 4-amino-3-(1H-benzimidazol-2-yl)-6-nitroquinolin-2(1H)-one | 322.3 |
| 245 | 4-amino-3-(4-methyl-1H-benzimidazol-2-yl)quinolin-2(1H)-one | 291.3 |
| 246 | 4-amino-3-(6-ethoxy-1H-benzimidazol-2-yl)quinolin-2(1H)-one | 321.4 |
| 247 | 4-amino-3-(7-hydroxy-1H-benzimidazol-2-yl)quinolin-2(1H)-one | 293.3 |
| 248 | 4-amino-3-(6-tert-butyl-1H-benzimidazol-2-yl)quinolin-2(1H)-one | 333.4 |
| 249 | 2-(4-amino-2-oxo-1,2-dihydroquinolin-3-yl)-1H-benzimidazole-5-carbonitrile | 302.3 |
| 250 | 4-amino-3-(5,6-dimethyl-1H-benzimidazol-2-yl)quinolin-2(1H)-one | 305.4 |
| 251 | 4-amino-3-(4,5-dimethyl-1H-benzimidazol-2-yl)quinolin-2(1H)-one | 305.4 |
| 252 | 4-amino-6-chloro-3-(5-methyl-1H-benzimidazol-2-yl)quinolin-2(1H)-one | 325.8 |
| 253 | 4-amino-3-(1H-benzimidazol-2-yl)-6,8-dichloroquinolin-2(1H)-one | 346.2 |
| 254 | 4-amino-3-(1H-benzimidazol-2-yl)-5-chloroquinolin-2(1H)-one | 311.7 |
| 255 | 2-(4-amino-2-oxo-1,2-dihydroquinolin-3-yl)-N,N-dimethyl-1H-benzimidazole-5-carboxamide | 348.4 |
| 256 | 4-amino-3-{5-[3-(dimethylamino)pyrrolidin-1-yl]-1H-benzimidazol-2-yl}quinolin-2(1H)-one | 389.5 |
| 257 | 4-amino-3-(6-methoxy-5-methyl-1H-benzimidazol-2-yl)quinolin-2(1H)-one | 321.4 |
| 258 | 2-(4-amino-2-oxo-1,2-dihydroquinolin-3-yl)-1H-benzimidazole-6-carboximidamide | 319.3 |
| 259 | 4-amino-7-(3-aminophenyl)-3-(1H-benzimidazol-2-yl)quinolin-2(1H)-one | 368.4 |
| 260 | 4-amino-3-(1H-benzimidazol-2-yl)-7-thien-2-ylquinolin-2(1H)-one | 359.4 |
| 261 | 4-amino-3-(5-thien-3-yl-1H-benzimidazol-2-yl)quinolin-2(1H)-one | 359.4 |
| 262 | 4-amino-3-(1H-benzimidazol-2-yl)-7-thien-3-ylquinolin-2(1H)-one | 359.4 |
| 263 | 4-{[(1S,2R)-2-aminocyclohexyl]amino}-3-(5-morpholin-4-yl-1H-benzimidazol-2-yl)quinolin-2(1H)-one | 459.6 |
| 264 | 4-{[(1R,2R)-2-aminocyclohexyl]amino}-3-(5-morpholin-4-yl-1H-benzimidazol-2-yl)quinolin-2(1H)-one | 459.6 |
| 265 | 4-{[(1S,2S)-2-aminocyclohexyl]amino}-3-(5-morpholin-4-yl-1H-benzimidazol-2-yl)quinolin-2(1H)-one | 459.6 |
| 266 | 4-amino-3-{5-[(2R,6S)-2,6-dimethylmorpholin-4-yl]-1H-benzimidazol-2-yl}quinolin-2(1H)-one | 390.5 |
| 267 | 3-(1H-benzimidazol-2-yl)-4-morpholin-4-ylquinolin-2(1H)-one- | 347.4 |
| 268 | 3-(1H-benzimidazol-2-yl)-4-(piperidin-3-ylamino)quinolin-2(1H)-one | 360.4 |
| 269 | 4-(1-azabicyclo[2.2.2]oct-3-ylamino)-3-(5-chloro-1H-benzimidazol-2-yl)quinolin-2(1H)-one | 420.9 |
| 270 | 4-[(3R)-1-azabicyclo[2.2.2]oct-3-ylamino]-6-chloro-3-(5-methyl-1H-benzimidazol-2-yl)quinolin-2(1H)-one | 434.9 |
| 271 | 6-chloro-3-(5-methyl-1H-benzimidazol-2-yl)-4-(piperidin-3-ylamino)quinolin-2(1H)-one | 408.9 |

-continued

TABLE of Additional Exemplary Compounds

| Example | Name | LC/MS m/z (MH+) |
|---|---|---|
| 272 | 3-(1H-benzimidazol-2-yl)-4-[(2-hydroxyethyl)amino]quinolin-2(1H)-one | 321.4 |
| 273 | 3-(1H-benzimidazol-2-yl)-6-chloro-4-(piperidin-3-ylamino)quinolin-2(1H)-one | 394.9 |
| 274 | 3-(1H-benzimidazol-2-yl)-6-chloro-4-{[(1S)-1-cyclohexylethyl]amino}quinolin-2(1H)-one | 421.9 |
| 275 | 3-(1H-benzimidazol-2-yl)-6-chloro-4-[(piperidin-3-ylmethyl)amino]quinolin-2(1H)-one | 408.9 |
| 276 | 3-(1H-benzimidazol-2-yl)-6-chloro-4-(pyridin-4-ylamino)quinolin-2(1H)-one | 388.8 |
| 277 | 3-(1H-benzimidazol-2-yl)-6-chloro-4-[(piperidin-4-ylethyl)amino]quinolin-2(1H)-one | 408.9 |
| 278 | 3-(1H-benzimidazol-2-yl)-6-chloro-4-[(2-morpholin-4-ylethyl)amino]quinolin-2(1H)-one | 424.9 |
| 279 | 3-(1H-benzimidazol-2-yl)-6-chloro-4-(cyclohexylamino)quinolin-2(1H)-one | 393.9 |
| 280 | 3-(1H-benzimidazol-2-yl)-6-chloro-4-{[3-(1H-imidazol-1-yl)propyl]amino}quinolin-2(1H)-one | 419.9 |
| 281 | 3-(1H-benzimidazol-2-yl)-6-chloro-4-{[2-(dimethylamino)ethyl]amino}quinolin-2(1H)-one | 382.9 |
| 282 | 3-(1H-benzimidazol-2-yl)-6-chloro-4-[(cyclohexylmethyl)amino]quinolin-2(1H)-one | 407.9 |
| 283 | 3-(1H-benzimidazol-2-yl)-6-chloro-4-[(tetrahydrofuran-2-ylmethyl)amino]quinolin-2(1H)-one | 395.9 |
| 284 | 3-(1H-benzimidazol-2-yl)-6-chloro-4-[(pyridin-4-ylmethyl)amino]quinolin-2(1H)-one | 402.9 |
| 285 | 3-(1H-benzimidazol-2-yl)-6,7-difluoro-4-(piperidin-3-ylamino)quinolin-2(1H)-one | 396.4 |
| 286 | 4-[(3S)-1-azabicyclo[2.2.2]oct-3-ylamino]-3-(1H-benzimidazol-2-yl)-6-bromoquinolin-2(1H)-one | 465.4 |
| 287 | 3-(1H-benzimidazol-2-yl)-6-fluoro-4-(piperidin-3-ylamino)quinolin-2(1H)-one | 378.4 |
| 288 | 4-[(3S)-1-azabicyclo[2.2.2]oct-3-ylamino]-3-(1H-benzimidazol-2-yl)-6-methylquinolin-2(1H)-one | 400.5 |
| 289 | 4-[(3S)-1-azabicyclo[2.2.2]oct-3-ylamino]-3-(1H-benzimidazol-2-yl)-6-fluoroquinolin-2(1H)-one | 404.5 |
| 290 | 4-amino-3-[6-(4-methylpiperazin-1-yl)-1H-benzimidazol-2-yl]-1-propylquinolin-2(1H)-one | 417.5 |
| 291 | 3-(1H-benzimidazol-2-yl)-6-chloro-4-{[(1-ethylpyrrolidin-2-yl)methyl]amino}quinolin-2(1H)-one | 422.9 |
| 292 | 3-(1H-benzimidazol-2-yl)-6-chloro-4-{[3-(2-oxopyrrolidin-1-yl)propyl]amino}quinolin-2(1H)-one | 436.9 |
| 293 | 3-(1H-benzimidazol-2-yl)-6-chloro-4-[(piperidin-2-ylmethyl)amino]quinolin-2(1H)-one | 408.9 |
| 294 | 3-(1H-benzimidazol-2-yl)-6-chloro-4-(4-methyl-1,4-diazepan-1-yl)quinolin-2(1H)-one | 408.9 |
| 295 | 3-(1H-benzimidazol-2-yl)-6-chloro-4-[(pyridin-3-ylmethyl)amino]quinolin-2(1H)-one | 402.9 |
| 296 | 4-anilino-3-(1H-benzimidazol-2-yl)-6-chloroquinolin-2(1H)-one | 387.8 |
| 297 | 3-(1H-benzimidazol-2-yl)-6-chloro-4-{[(5-methylpyrazin-2-yl)methyl]amino}quinolin-2(1H)-one | 417.9 |
| 298 | 3-(1H-benzimidazol-2-yl)-6-chloro-4-(piperidin-4-ylamino)quinolin-2(1H)-one | 402.9 |
| 299 | 3-(1H-benzimidazol-2-yl)-6-chloro-4-{[2-(1-methylpyrrolidin-2-yl)ethyl]amino}quinolin-2(1H)-one | 422.9 |
| 300 | 3-(1H-benzimidazol-2-yl)-4-[(1H-benzimidazol-5-ylmethyl)amino]-6-chloroquinolin-2(1H)-one | 441.9 |
| 301 | 3-(1H-benzimidazol-2-yl)-6-chloro-4-(piperidin-4-ylamino)quinolin-2(1H)-one | 394.9 |
| 302 | 3-(1H-benzimidazol-2-yl)-6-chloro-4-[(4-hydroxycyclohexyl)amino]quinolin-2(1H)-one | 409.9 |
| 303 | 4-[(3S)-1-azabicyclo[2.2.2]oct-3-ylamino]-3-(1H-benzimidazol-2-yl)-5-fluoroquinolin-2(1H)-one | 404.5 |
| 304 | 3-(1H-benzimidazol-2-yl)-6,8-dimethyl-4-(piperidin-3-ylamino)quinolin-2(1H)-one | 388.5 |
| 305 | 3-(1H-benzimidazol-2-yl)-5-fluoro-4-(piperidin-3-ylamino)quinolin-2(1H)-one | 378.4 |
| 306 | 4-[(3R)-1-azabicyclo[2.2.2]oct-3-ylamino]-3-(1H-benzimidazol-2-yl)-6,8-dimethylquinolin-2(1H)-one | 414.5 |
| 307 | 4-[(3S)-1-azabicyclo[2.2.2]oct-3-ylamino]-3-(1H-benzimidazol-2-yl)-6,8-dimethylquinolin-2(1H)-one | 414.5 |
| 308 | 4-[(3R)-1-azabicyclo[2.2.2]oct-3-ylamino]-3-(1H-benzimidazol-2-yl)-7-chloroquinolin-2(1H)-one | 420.9 |

-continued

TABLE of Additional Exemplary Compounds

| Example | Name | LC/MS m/z (MH+) |
|---|---|---|
| 309 | 3-(1H-benzimidazol-2-yl)-6-chloro-4-[(2-piperidin-1-ylethyl)amino]quinolin-2(1H)-one | 422.9 |
| 310 | 4-({2-[(4-amino-5-nitropyridin-2-yl)amino]ethyl}amino)-3-(1H-benzimidazol-2-yl)-6-chloroquinolin-2(1H)-one | 491.9 |
| 311 | 3-(1H-benzimidazol-2-yl)-6-chloro-4-({2-[(5-nitropyridin-2-yl)amino]ethyl}amino)quinolin-2(1H)-one | 476.9 |
| 312 | 3-(1H-benzimidazol-2-yl)-4-[(1H-benzimidazol-2-ylmethyl)amino]-6-chloroquinolin-2(1H)-one | 441.9 |
| 313 | 3-(1H-benzimidazol-2-yl)-6-chloro-4-(2,5-diazabicyclo[2.2.1]hept-2-yl)quinolin-2(1H)-one | 392.9 |
| 314 | 3-(1H-benzimidazol-2-yl)-6-chloro-4-[(2-{[5-(trifluoromethyl)pyridin-2-yl]amino}ethyl)amino]quinolin-2(1H)-one | 499.9 |
| 315 | 4-[(3S)-1-azabicyclo[2.2.2]oct-3-ylamino]-3-(1H-benzimidazol-2-yl)-7-methylquinolin-2(1H)-one | 400.5 |
| 316 | 4-[(3R)-1-azabicyclo[2.2.2]oct-3-ylamino]-3-(1H-benzimidazol-2-yl)-7-methylquinolin-2(1H)-one | 400.5 |
| 317 | 3-(1H-benzimidazol-2-yl)-7-chloro-4-{[(2R)-pyrrolidin-2-ylmethyl]amino}quinolin-2(1H)-one | 394.9 |
| 318 | 3-(1H-benzimidazol-2-yl)-6-chloro-4-[(pyrrolidin-2-ylmethyl)amino]quinolin-2(1H)-one | 394.9 |
| 319 | 6-[(2-{[3-(1H-benzimidazol-2-yl)-6-chloro-2-oxo-1,2-dihydroquinolin-4-yl]amino}ethyl)amino]nicotinamide | 474.9 |
| 320 | 3-(1H-benzimidazol-2-yl)-6-chloro-4-(pyrrolidin-3-ylamino)quinolin-2(1H)-one | 380.8 |
| 321 | 4-{[(2R)-2-aminobutyl]amino}-3-(1H-benzimidazol-2-yl)-6-chloroquinolin-2(1H)-one | 382.9 |
| 322 | 4-{[(2S)-2-amino-3-phenylpropyl]amino}-3-(1H-benzimidazol-2-yl)-6-chloroquinolin-2(1H)-one | 444.9 |
| 323 | 4-[(4-aminocyclohexyl)amino]-3-(1H-benzimidazol-2-yl)-6-chloroquinolin-2(1H)-one | 408.9 |
| 324 | 4-[(3R)-1-azabicyclo[2.2.2]oct-3-ylamino]-3-(1H-benzimidazol-2-yl)-6-iodoquinolin-2(1H)-one | 512.4 |
| 325 | 4-[(3S)-1-azabicyclo[2.2.2]oct-3-ylamino]-3-(1H-benzimidazol-2-yl)-6-iodoquinolin-2(1H)-one | 512.4 |
| 326 | 3-(1H-benzimidazol-2-yl)-6,7-dimethoxy-4-(piperidin-3-ylamino)quinolin-2(1H)-one | 420.5 |
| 327 | 4-[(3R)-1-azabicyclo[2.2.2]oct-3-ylamino]-3-(1H-benzimidazol-2-yl)-6,7-dimethoxyquinolin-2(1H)-one | 446.5 |
| 328 | 4-[(3S)-1-azabicyclo[2.2.2]oct-3-ylamino]-3-(1H-benzimidazol-2-yl)-6-nitroquinolin-2(1H)-one | 431.5 |
| 329 | 3-(1H-benzimidazol-2-yl)-6-iodo-4-(piperidin-3-ylamino)quinolin-2(1H)-one | 486.3 |
| 330 | 4-[(3R)-1-azabicyclo[2.2.2]oct-3-ylamino]-3-(1H-benzimidazol-2-yl)-5-chloroquinolin-2(1H)-one | 420.9 |
| 331 | 3-(1H-benzimidazol-2-yl)-6-chloro-4-{[(1-piperidin-4-yl-1H-benzimidazol-6-yl)methyl]amino}quinolin-2(1H)-one | 525.0 |
| 332 | 3-(1H-benzimidazol-2-yl)-6-methyl-4-[(piperidin-3-ylmethyl)amino]quinolin-2(1H)-one | 388.5 |
| 333 | 3-(1H-benzimidazol-2-yl)-6-methyl-4-(piperidin-4-ylamino)quinolin-2(1H)-one | 374.5 |
| 334 | 3-(1H-benzimidazol-2-yl)-6-methyl-4-[(piperidin-4-ylmethyl)amino]quinolin-2(1H)-one | 388.5 |
| 335 | 3-(1H-benzimidazol-2-yl)-6-methyl-4-[(piperidin-2-ylmethyl)amino]quinolin-2(1H)-one | 388.5 |
| 336 | 4-{[4-(2-aminoethoxy)benzyl]amino}-3-(1H-benzimidazol-2-yl)-6-chloroquinolin-2(1H)-one | 460.9 |
| 337 | 4-{[2-(2-aminoethoxy)benzyl]amino}-3-(1H-benzimidazol-2-yl)-6-chloroquinolin-2(1H)-one | 460.9 |
| 338 | 4-(1-azabicyclo[2.2.2]oct-3-ylamino)-3-(5-hydroxy-1H-benzimidazol-2-yl)quinolin-2(1H)-one | 402.5 |
| 339 | 4-[(3S)-1-azabicyclo[2.2.2]oct-3-ylamino]-3-(1H-benzimidazol-2-yl)-2-oxo-1,2-dihydroquinoline-6-carbonitrile | 411.5 |
| 340 | 4-[(3R)-1-azabicyclo[2.2.2]oct-3-ylamino]-3-(1H-benzimidazol-2-yl)-6,7-dihydroxyquinolin-2(1H)-one | 418.5 |
| 341 | 4-[(3S)-1-azabicyclo[2.2.2]oct-3-ylamino]-3-(1H-benzimidazol-2-yl)-6,7-dihydroxyquinolin-2(1H)-one | 418.5 |
| 342 | 4-[(3R)-1-azabicyclo[2.2.2]oct-3-ylamino]-3-(1H-benzimidazol-2-yl)-2-oxo-1,2-dihydroquinoline-6-carboxylic acid | 430.5 |
| 343 | 4-[(3R)-1-azabicyclo[2.2.2]oct-3-ylamino]-3-(1H-benzimidazol-2-yl)-7-fluoroquinolin-2(1H)-one | 404.5 |
| 344 | 4-[(3S)-1-azabicyclo[2.2.2]oct-3-ylamino]-3-(1H-benzimidazol-2-yl)-7-fluoroquinolin-2(1H)-one | 404.5 |

-continued

TABLE of Additional Exemplary Compounds

| Example | Name | LC/MS m/z (MH+) |
|---|---|---|
| 345 | 2-(4-amino-2-oxo-1-propyl-1,2-dihydroquinolin-3-yl)-1H-benzimidazole-6-carbonitrile | 344.4 |
| 346 | tert-butyl 4-[4-[(3R)-1-azabicyclo[2.2.2]oct-3-ylamino]-3-(1H-benzimidazol-2-yl)-2-oxo-1,2-dihydroquinolin-6-yl]-3,6-dihydropyridine-1(2H)-carboxylate | 567.7 |
| 347 | tert-butyl 4-[4-[(3S)-1-azabicyclo[2.2.2]oct-3-ylamino]-3-(1H-benzimidazol-2-yl)-2-oxo-1,2-dihydroquinolin-6-yl]-3,6-dihydropyridine-1(2H)-carboxylate | 567.7 |
| 348 | 4-[(3R)-1-azabicyclo[2.2.2]oct-3-ylamino]-3-(1H-benzimidazol-2-yl)-6-(1,2,3,6-tetrahydropyridin-4-yl)quinolin-2(1H)-one | 467.6 |
| 349 | 4-[(3S)-1-azabicyclo[2.2.2]oct-3-ylamino]-3-(1H-benzimidazol-2-yl)-6-thien-2-ylquinolin-2(1H)-one | 468.6 |
| 350 | 4-[(3S)-1-azabicyclo[2.2.2]oct-3-ylamino]-3-(1H-benzimidazol-2-yl)-6-(1,2,3,6-tetrahydropyridin-4-yl)quinolin-2(1H)-one | 467.6 |
| 351 | 4-[(3S)-1-azabicyclo[2.2.2]oct-3-ylamino]-3-(1H-benzimidazol-2-yl)-6-(2,4-difluorophenyl)quinolin-2(1H)-one | 498.5 |
| 352 | tert-butyl 2-[4-[(3S)-1-azabicyclo[2.2.2]oct-3-ylamino]-3-(1H-benzimidazol-2-yl)-2-oxo-1,2-dihydroquinolin-6-yl]-1H-pyrrole-1-carboxylate | 551.7 |
| 353 | tert-butyl 2-[4-[(3R)-1-azabicyclo[2.2.2]oct-3-ylamino]-3-(1H-benzimidazol-2-yl)-2-oxo-1,2-dihydroquinolin-6-yl]-1H-pyrrole-1-carboxylate | 551.7 |
| 354 | 4-[(3S)-1-azabicyclo[2.2.2]oct-3-ylamino]-3-(1H-benzimidazol-2-yl)-6-pyridin-2-ylquinolin-2(1H)-one | 463.6 |
| 355 | 4-[(3R)-1-azabicyclo[2.2.2]oct-3-ylamino]-3-(1H-benzimidazol-2-yl)-6-thien-2-ylquinolin-2(1H)-one | 468.6 |
| 356 | 4-[(3R)-1-azabicyclo[2.2.2]oct-3-ylamino]-3-(1H-benzimidazol-2-yl)-6-(2,4-difluorophenyl)quinolin-2(1H)-one | 498.5 |
| 357 | 4-[(3R)-1-azabicyclo[2.2.2]oct-3-ylamino]-3-(1H-benzimidazol-2-yl)-6-thien-3-ylquinolin-2(1H)-one | 468.6 |
| 358 | 4-[4-[(3S)-1-azabicyclo[2.2.2]oct-3-ylamino]-3-(1H-benzimidazol-2-yl)-2-oxo-1,2-dihydroquinolin-6-yl]benzonitrile | 487.6 |
| 359 | 4-[(3R)-1-azabicyclo[2.2.2]oct-3-ylamino]-3-(1H-benzimidazol-2-yl)-6-(2-chlorophenyl)quinolin-2(1H)-one | 497.0 |
| 360 | 4-[(3R)-1-azabicyclo[2.2.2]oct-3-ylamino]-3-(1H-benzimidazol-2-yl)-6-[2-(trifluoromethyl)phenyl]quinolin-2(1H)-one | 530.6 |
| 361 | 4-[(3R)-1-azabicyclo[2.2.2]oct-3-ylamino]-3-(1H-benzimidazol-2-yl)-6-(3-methoxyphenyl)quinolin-2(1H)-one | 492.6 |
| 362 | 4-[(3S)-1-azabicyclo[2.2.2]oct-3-ylamino]-3-(1H-benzimidazol-2-yl)-6-pyridin-3-ylquinolin-2(1H)-one | 463.6 |
| 363 | 4-[(3S)-1-azabicyclo[2.2.2]oct-3-ylamino]-3-(1H-benzimidazol-2-yl)-6-pyridin-4-ylquinolin-2(1H)-one | 463.6 |
| 364 | 4-[(3S)-1-azabicyclo[2.2.2]oct-3-ylamino]-3-(1H-benzimidazol-2-yl)-2-oxo-1,2-dihydroquinoline-6-carboxylic acid | 430.5 |
| 365 | 3-(5-hydroxy-1H-benzimidazol-2-yl)-4-(piperidin-3-ylamino)quinolin-2(1H)-one | 376.4 |
| 366 | 4-[(3S)-1-azabicyclo[2.2.2]oct-3-ylamino]-3-(1H-benzimidazol-2-yl)-8-methylquinolin-2(1H)-one | 400.5 |
| 367 | 4-[(3S)-1-azabicyclo[2.2.2]oct-3-ylamino]-3-(1H-benzimidazol-2-yl)-6-(2-chlorophenyl)quinolin-2(1H)-one | 497.0 |
| 368 | 4-[(3S)-1-azabicyclo[2.2.2]oct-3-ylamino]-3-(1H-benzimidazol-2-yl)-6-[2-(trifluoromethyl)phenyl]quinolin-2(1H)-one | 530.6 |
| 369 | 4-[4-[(3S)-1-azabicyclo[2.2.2]oct-3-ylamino]-3-(1H-benzimidazol-2-yl)-2-oxo-1,2-dihydroquinolin-6-yl]benzonitrile | 487.6 |
| 370 | 4-[(3S)-1-azabicyclo[2.2.2]oct-3-ylamino]-3-(1H-benzimidazol-2-yl)-6-thien-3-ylquinolin-2(1H)-one | 468.6 |
| 371 | 4-[(3R)-1-azabicyclo[2.2.2]oct-3-ylamino]-3-(1H-benzimidazol-2-yl)-6-pyridin-4-ylquinolin-2(1H)-one | 463.6 |
| 372 | 4-[(3R)-1-azabicyclo[2.2.2]oct-3-ylamino]-3-(1H-benzimidazol-2-yl)-6-(2-methoxyphenyl)quinolin-2(1H)-one | 492.6 |
| 373 | 4-[(3R)-1-azabicyclo[2.2.2]oct-3-ylamino]-3-(1H-benzimidazol-2-yl)-6-(2-methylphenyl)quinolin-2(1H)-one | 476.6 |
| 374 | 6-(3-acetylphenyl)-4-[(3R)-1-azabicyclo[2.2.2]oct-3-ylamino]-3-(1H-benzimidazol-2-yl)quinolin-2(1H)-one | 504.6 |
| 375 | 6-(4-acetylphenyl)-4-[(3R)-1-azabicyclo[2.2.2]oct-3-ylamino]-3-(1H-benzimidazol-2-yl)quinolin-2(1H)-one | 504.6 |
| 376 | 4-[4-[(3R)-1-azabicyclo[2.2.2]oct-3-ylamino]-3-(1H-benzimidazol-2-yl)-2-oxo-1,2-dihydroquinolin-6-yl]benzoic acid | 506.6 |
| 377 | N-{3-[4-[(3R)-1-azabicyclo[2.2.2]oct-3-ylamino]-3-(1H-benzimidazol-2-yl)-2-oxo-1,2-dihydroquinolin-6-yl]phenyl}acetamide | 519.6 |
| 378 | 4-[(3R)-1-azabicyclo[2.2.2]oct-3-ylamino]-3-(1H-benzimidazol-2-yl)-6-(2,6-difluorophenyl)quinolin-2(1H)-one | 498.5 |

-continued

TABLE of Additional Exemplary Compounds

| Example | Name | LC/MS m/z (MH⁺) |
|---|---|---|
| 379 | 4-[(3R)-1-azabicyclo[2.2.2]oct-3-ylamino]-3-(1H-benzimidazol-2-yl)-6-(1,3-benzodioxol-5-yl)quinolin-2(1H)-one | 506.6 |
| 380 | 4-[(3R)-1-azabicyclo[2.2.2]oct-3-ylamino]-3-(1H-benzimidazol-2-yl)-6-(4-chlorophenyl)quinolin-2(1H)-one | 497.0 |
| 381 | 4-[4-[(3R)-1-azabicyclo[2.2.2]oct-3-ylamino]-3-(1H-benzimidazol-2-yl)-2-oxo-1,2-dihydroquinolin-6-yl]benzaldehyde | 490.6 |
| 382 | 4-[(3R)-1-azabicyclo[2.2.2]oct-3-ylamino]-3-(1H-benzimidazol-2-yl)-6-[4-(methylthio)phenyl]quinolin-2(1H)-one | 508.7 |
| 383 | 4-[(3R)-1-azabicyclo[2.2.2]oct-3-ylamino]-3-(1H-benzimidazol-2-yl)-6-[4-(dimethylamino)phenyl]quinolin-2(1H)-one | 505.6 |
| 384 | 4-[(3R)-1-azabicyclo[2.2.2]oct-3-ylamino]-3-(1H-benzimidazol-2-yl)-6-(4-chloro-2-fluorophenyl)quinolin-2(1H)-one | 515.0 |
| 385 | 4-[(3R)-1-azabicyclo[2.2.2]oct-3-ylamino]-3-(1H-benzimidazol-2-yl)-6-(2,4-dichlorophenyl)quinolin-2(1H)-one | 531.5 |
| 386 | 4-[(3R)-1-azabicyclo[2.2.2]oct-3-ylamino]-3-(1H-benzimidazol-2-yl)-6-phenylquinolin-2(1H)-one | 462.6 |
| 387 | 3-(1H-benzimidazol-2-yl)-6-chloro-4-[(1-ethylpiperidin-3-yl)amino]quinolin-2(1H)-one | 422.9 |
| 388 | 1-[4-[(3R)-1-azabicyclo[2.2.2]oct-3-ylamino]-3-(1H-benzimidazol-2-yl)-6-fluoro-2-oxo-1,2-dihydroquinolin-7-yl]piperidine-4-carboxamide | 530.6 |
| 389 | ethyl 1-[4-[(3R)-1-azabicyclo[2.2.2]oct-3-ylamino]-3-(1H-benzimidazol-2-yl)-6-fluoro-2-oxo-1,2-dihydroquinolin-7-yl]piperidine-4-carboxylate | 559.7 |
| 390 | 1-[4-[(3R)-1-azabicyclo[2.2.2]oct-3-ylamino]-3-(1H-benzimidazol-2-yl)-6-fluoro-2-oxo-1,2-dihydroquinolin-7-yl]piperidine-3-carboxamide | 530.6 |
| 391 | ethyl 1-[4-[(3R)-1-azabicyclo[2.2.2]oct-3-ylamino]-3-(1H-benzimidazol-2-yl)-6-fluoro-2-oxo-1,2-dihydroquinolin-7-yl]piperidine-3-carboxylate | 559.7 |
| 392 | 4-[(3R)-1-azabicyclo[2.2.2]oct-3-ylamino]-3-(1H-benzimidazol-2-yl)-6-fluoro-7-(1H-imidazol-1-yl)quinolin-2(1H)-one | 470.5 |
| 393 | 4-[(3R)-1-azabicyclo[2.2.2]oct-3-ylamino]-3-(1H-benzimidazol-2-yl)-7-{[2-(dimethylamino)ethyl]amino}-6-fluoroquinolin-2(1H)-one | 490.6 |
| 394 | 4-[(3R)-1-azabicyclo[2.2.2]oct-3-ylamino]-3-(1H-benzimidazol-2-yl)-6-fluoro-7-morpholin-4-ylquinolin-2(1H)-one | 489.6 |
| 395 | 4-[(3R)-1-azabicyclo[2.2.2]oct-3-ylamino]-3-(1H-benzimidazol-2-yl)-7-(dimethylamino)-6-fluoroquinolin-2(1H)-one | 447.5 |
| 396 | 4-[(3R)-1-azabicyclo[2.2.2]oct-3-ylamino]-3-(1H-benzimidazol-2-yl)-7-bromoquinolin-2(1H)-one | 465.4 |
| 397 | 1-[4-[(3R)-1-azabicyclo[2.2.2]oct-3-ylamino]-3-(1H-benzimidazol-2-yl)-6-fluoro-2-oxo-1,2-dihydroquinolin-7-yl]piperidine-4-carboxylic acid | 531.6 |
| 398 | 1-[4-[(3R)-1-azabicyclo[2.2.2]oct-3-ylamino]-3-(1H-benzimidazol-2-yl)-6-fluoro-2-oxo-1,2-dihydroquinolin-7-yl]piperidine-3-carboxylic acid | 531.6 |
| 399 | methyl 4-[4-[(3R)-1-azabicyclo[2.2.2]oct-3-ylamino]-3-(1H-benzimidazol-2-yl)-2-oxo-1,2-dihydroquinolin-6-yl]benzoate | 520.6 |
| 400 | 4-[4-[(3R)-1-azabicyclo[2.2.2]oct-3-ylamino]-3-(1H-benzimidazol-2-yl)-7-chloro-2-oxo-1,2-dihydroquinolin-6-yl]benzamide | 505.6 |
| 401 | 4-[(3R)-1-azabicyclo[2.2.2]oct-3-ylamino]-3-(1H-benzimidazol-2-yl)-6-[4-(methylsulfonyl)phenyl]quinolin-2(1H)-one | 540.7 |
| 402 | methyl 3-amino-4-[4-[(3R)-1-azabicyclo[2.2.2]oct-3-ylamino]-3-(1H-benzimidazol-2-yl)-2-oxo-1,2-dihydroquinolin-6-yl]benzoate | 535.6 |
| 403 | 4-[4-[(3R)-1-azabicyclo[2.2.2]oct-3-ylamino]-3-(1H-benzimidazol-2-yl)-7-chloro-2-oxo-1,2-dihydroquinolin-6-yl]benzoic acid | 541.0 |
| 404 | N-{3-[4-[(3R)-1-azabicyclo[2.2.2]oct-3-ylamino]-3-(1H-benzimidazol-2-yl)-7-chloro-2-oxo-1,2-dihydroquinolin-6-yl]phenyl}acetamide | 554.1 |
| 405 | 6-(3-acetylphenyl)-4-[(3R)-1-azabicyclo[2.2.2]oct-3-ylamino]-3-(1H-benzimidazol-2-yl)-7-chloroquinolin-2(1H)-one | 539.0 |
| 406 | 4-[(3R)-1-azabicyclo[2.2.2]oct-3-ylamino]-3-(1H-benzimidazol-2-yl)-7-chloro-6-(2-methoxyphenyl)quinolin-2(1H)-one | 527.0 |
| 407 | 4-[(3R)-1-azabicyclo[2.2.2]oct-3-ylamino]-3-(1H-benzimidazol-2-yl)-7-chloro-6-(2,4-dichlorophenyl)quinolin-2(1H)-one | 565.9 |
| 408 | 6-(4-acetylphenyl)-4-[(3R)-1-azabicyclo[2.2.2]oct-3-ylamino]-3-(1H-benzimidazol-2-yl)-7-chloroquinolin-2(1H)-one | 539.0 |

-continued

TABLE of Additional Exemplary Compounds

| Example | Name | LC/MS m/z (MH+) |
|---|---|---|
| 409 | 4-[4-[(3R)-1-azabicyclo[2.2.2]oct-3-ylamino]-3-(1H-benzimidazol-2-yl)-7-chloro-2-oxo-1,2-dihydroquinolin-6-yl]benzamide | 540.0 |
| 410 | methyl 4-[4-[(3R)-1-azabicyclo[2.2.2]oct-3-ylamino]-3-(1H-benzimidazol-2-yl)-7-chloro-2-oxo-1,2-dihydroquinolin-6-yl]benzoate | 555.0 |
| 411 | 4-[(3R)-1-azabicyclo[2.2.2]oct-3-ylamino]-3-(1H-benzimidazol-2-yl)-7-[[2-(dimethylamino)ethyl](methyl)amino]-6-fluoroquinolin-2(1H)-one | 504.6 |
| 412 | 4-[(3R)-1-azabicyclo[2.2.2]oct-3-ylamino]-3-(1H-benzimidazol-2-yl)-6-fluoro-7-[(3-methoxypropyl)amino]quinolin-2(1H)-one | 491.6 |
| 413 | N-{(3R)-1-[4-[(3R)-1-azabicyclo[2.2.2]oct-3-ylamino]-3-(1H-benzimidazol-2-yl)-6-fluoro-2-oxo-1,2-dihydroquinolin-7-yl]pyrrolidin-3-yl}acetamide | 530.6 |
| 414 | 4-[(3R)-1-azabicyclo[2.2.2]oct-3-ylamino]-3-(1H-benzimidazol-2-yl)-6-fluoro-7-{[3-(2-oxopyrrolidin-1-yl)propyl]amino}quinolin-2(1H)-one | 544.6 |
| 415 | 4-[(3R)-1-azabicyclo[2.2.2]oct-3-ylamino]-7-azepan-1-yl-3-(1H-benzimidazol-2-yl)-6-fluoroquinolin-2(1H)-one | 501.6 |
| 416 | 4-[(3R)-1-azabicyclo[2.2.2]oct-3-ylamino]-3-(1H-benzimidazol-2-yl)-6-fluoro-7-(1H-pyrrol-1-yl)quinolin-2(1H)-one | 469.5 |
| 417 | 4-[(3R)-1-azabicyclo[2.2.2]oct-3-ylamino]-3-(1H-benzimidazol-2-yl)-6-fluoro-7-(2-methyl-1H-imidazol-1-yl)quinolin-2(1H)-one | 484.5 |
| 418 | 4-[(3R)-1-azabicyclo[2.2.2]oct-3-ylamino]-3-(1H-benzimidazol-2-yl)-6-fluoro-7-pyrrolidin-1-ylquinolin-2(1H)-one | 473.6 |
| 419 | 4-[(3R)-1-azabicyclo[2.2.2]oct-3-ylamino]-3-(1H-benzimidazol-2-yl)-6-fluoro-7-piperidin-1-ylquinolin-2(1H)-one | 487.6 |
| 420 | 4-[(3R)-1-azabicyclo[2.2.2]oct-3-ylamino]-3-(1H-benzimidazol-2-yl)-6-fluoro-7-(4-methylpiperazin-1-yl)quinolin-2(1H)-one | 502.6 |
| 421 | 4-[(3R)-1-azabicyclo[2.2.2]oct-3-ylamino]-3-(1H-benzimidazol-2-yl)-6-fluoro-7-[(3-hydroxypropyl)amino]quinolin-2(1H)-one | 477.6 |
| 422 | 4-[(3R)-1-azabicyclo[2.2.2]oct-3-ylamino]-3-(1H-benzimidazol-2-yl)-6-chloro-7-morpholin-4-ylquinolin-2(1H)-one | 506.0 |
| 423 | 4-[(3R)-1-azabicyclo[2.2.2]oct-3-ylamino]-3-(1H-benzimidazol-2-yl)-6-chloro-7-(4-methylpiperazin-1-yl)quinolin-2(1H)-one | 519.1 |
| 424 | 4-[(3R)-1-azabicyclo[2.2.2]oct-3-ylamino]-3-(1H-benzimidazol-2-yl)-6-chloro-7-piperidin-1-ylquinolin-2(1H)-one | 504.0 |
| 425 | 4-[4-[(3R)-1-azabicyclo[2.2.2]oct-3-ylamino]-3-(1H-benzimidazol-2-yl)-2-oxo-1,2-dihydroquinolin-7-yl]benzoic acid | 506.6 |
| 426 | 4-[(3R)-1-azabicyclo[2.2.2]oct-3-ylamino]-3-(1H-benzimidazol-2-yl)-7-(2,4-dichlorophenyl)quinolin-2(1H)-one | 531.5 |
| 427 | 4-[(3R)-1-azabicyclo[2.2.2]oct-3-ylamino]-3-(1H-benzimidazol-2-yl)-7-(dimethylamino)quinolin-2(1H)-one | 429.5 |
| 428 | 7-(4-acetylphenyl)-4-[(3R)-1-azabicyclo[2.2.2]oct-3-ylamino]-3-(1H-benzimidazol-2-yl)quinolin-2(1H)-one | 504.6 |
| 429 | 4-[(3R)-1-azabicyclo[2.2.2]oct-3-ylamino]-3-(1H-benzimidazol-2-yl)-7-(2-methylphenyl)quinolin-2(1H)-one | 476.6 |
| 430 | 7-(3-acetylphenyl)-4-[(3R)-1-azabicyclo[2.2.2]oct-3-ylamino]-3-(1H-benzimidazol-2-yl)quinolin-2(1H)-one | 504.6 |
| 431 | 4-[(3R)-1-azabicyclo[2.2.2]oct-3-ylamino]-3-(1H-benzimidazol-2-yl)-7-(2-methoxyphenyl)quinolin-2(1H)-one | 492.6 |
| 432 | 3-(1H-benzimidazol-2-yl)-6,7-difluoro-4-[(piperidin-2-ylmethyl)amino]quinolin-2(1H)-one | 410.4 |
| 433 | N-[3-(1H-benzimidazol-2-yl)-6,7-difluoro-2-oxo-1,2-dihydroquinolin-4-yl]glycine | 371.3 |
| 434 | N-[3-(1H-benzimidazol-2-yl)-6,7-difluoro-2-oxo-1,2-dihydroquinolin-4-yl]-beta-alanine | 385.3 |
| 435 | 4-[(3S)-1-azabicyclo[2.2.2]oct-3-ylamino]-3-(6-fluoro-1H-benzimidazol-2-yl)-6,7-dimethoxyquinolin-2(1H)-one | 464.5 |
| 436 | 3-(6-fluoro-1H-benzimidazol-2-yl)-6,7-dimethoxy-4-(piperidin-3-ylamino)quinolin-2(1H)-one | 438.5 |
| 437 | 3-(6-fluoro-1H-benzimidazol-2-yl)-6,7-dimethoxy-4-(pyrrolidin-3-ylamino)quinolin-2(1H)-one | 424.4 |
| 438 | 4-[(4-aminocyclohexyl)amino]-3-(6-fluoro-1H-benzimidazol-2-yl)-6,7-dimethoxyquinolin-2(1H)-one | 452.5 |
| 439 | 4-[(3R)-1-azabicyclo[2.2.2]oct-3-ylamino]-3-(6-fluoro-1H-benzimidazol-2-yl)-6,7-dimethoxyquinolin-2(1H)-one | 464.5 |
| 440 | 4-[(3R)-1-azabicyclo[2.2.2]oct-3-ylamino]-3-(1H-benzimidazol-2-yl)-7-[ethyl(methyl)amino]-6-fluoroquinolin-2(1H)-one | 461.6 |
| 441 | 4-[(3R)-1-azabicyclo[2.2.2]oct-3-ylamino]-3-(1H-benzimidazol-2-yl)-7-(diethylamino)-6-fluoroquinolin-2(1H)-one | 475.6 |
| 442 | 4-[(3R)-1-azabicyclo[2.2.2]oct-3-ylamino]-3-(1H-benzimidazol-2-yl)-7-[(3R)-3-(dimethylamino)pyrrolidin-1-yl]-6-fluoroquinolin-2(1H)-one | 516.6 |

-continued

TABLE of Additional Exemplary Compounds

| Example | Name | LC/MS m/z (MH+) |
|---|---|---|
| 443 | 7-(3-acetyl-1H-pyrrol-1-yl)-4-[(3R)-1-azabicyclo[2.2.2]oct-3-ylamino]-3-(1H-benzimidazol-2-yl)-6-fluoroquinolin-2(1H)-one | 511.6 |
| 444 | ethyl 4-[4-[(3R)-1-azabicyclo[2.2.2]oct-3-ylamino]-3-(1H-benzimidazol-2-yl)-2-oxo-1,2-dihydroquinolin-6-yl]benzoate | 534.6 |
| 445 | methyl 3-[4-[(3R)-1-azabicyclo[2.2.2]oct-3-ylamino]-3-(1H-benzimidazol-2-yl)-2-oxo-1,2-dihydroquinolin-6-yl]benzoate | 520.6 |
| 446 | 4-[(3R)-1-azabicyclo[2.2.2]oct-3-ylamino]-3-(1H-benzimidazol-2-yl)-7-{[2-(diethylamino)ethyl]amino}-6-fluoroquinolin-2(1H)-one | 518.6 |
| 447 | 4-[(3R)-1-azabicyclo[2.2.2]oct-3-ylamino]-3-(1H-benzimidazol-2-yl)-6-fluoro-7-[(2-pyrrolidin-1-ylethyl)amino]quinolin-2(1H)-one | 516.6 |
| 448 | 4-[(3R)-1-azabicyclo[2.2.2]oct-3-ylamino]-3-(1H-benzimidazol-2-yl)-6-fluoro-7-[(2-piperidin-1-ylethyl)amino]quinolin-2(1H)-one | 530.7 |
| 449 | 4-[(3R)-1-azabicyclo[2.2.2]oct-3-ylamino]-3-(1H-benzimidazol-2-yl)-7-{[3-(dimethylamino)propyl]amino}-6-fluoroquinolin-2(1H)-one | 504.6 |
| 450 | N-(2-{[4-[(3R)-1-azabicyclo[2.2.2]oct-3-ylamino]-3-(1H-benzimidazol-2-yl)-6-fluoro-2-oxo-1,2-dihydroquinolin-7-yl]amino}ethyl)acetamide | 504.6 |
| 451 | N-{1-[4-[(3R)-1-azabicyclo[2.2.2]oct-3-ylamino]-3-(1H-benzimidazol-2-yl)-6-fluoro-2-oxo-1,2-dihydroquinolin-7-yl]pyrrolidin-3-yl}-2,2,2-trifluoroacetamide | 584.6 |
| 452 | 3-{[4-[(3R)-1-azabicyclo[2.2.2]oct-3-ylamino]-3-(1H-benzimidazol-2-yl)-6-fluoro-2-oxo-1,2-dihydroquinolin-7-yl]amino}propanenitrile | 472.5 |
| 453 | 4-[(3R)-1-azabicyclo[2.2.2]oct-3-ylamino]-3-(1H-benzimidazol-2-yl)-6-fluoro-7-[(2-hydroxyethyl)amino]quinolin-2(1H)-one | 463.5 |
| 454 | 4-[(3R)-1-azabicyclo[2.2.2]oct-3-ylamino]-3-(1H-benzimidazol-2-yl)-6-fluoro-7-[(2-methoxyethyl)amino]quinolin-2(1H)-one | 477.6 |
| 455 | 4-[(3R)-1-azabicyclo[2.2.2]oct-3-ylamino]-3-(1H-benzimidazol-2-yl)-6-fluoro-7-(3-hydroxypiperidin-1-yl)quinolin-2(1H)-one | 503.6 |
| 456 | 4-[(3S)-1-azabicyclo[2.2.2]oct-3-ylamino]-3-(1H-benzimidazol-2-yl)-7-[[2-(dimethylamino)ethyl](methyl)amino]-6-fluoroquinolin-2(1H)-one | 504.6 |
| 457 | 4-[(3S)-1-azabicyclo[2.2.2]oct-3-ylamino]-3-(1H-benzimidazol-2-yl)-7-{[3-(dimethylamino)propyl]amino}-6-fluoroquinolin-2(1H)-one | 504.6 |
| 458 | 4-[(3S)-1-azabicyclo[2.2.2]oct-3-ylamino]-3-(1H-benzimidazol-2-yl)-7-{[2-(diethylamino)ethyl]amino}-6-fluoroquinolin-2(1H)-one | 518.6 |
| 459 | 4-[(3S)-1-azabicyclo[2.2.2]oct-3-ylamino]-3-(1H-benzimidazol-2-yl)-6-fluoro-7-[(2-pyrrolidin-1-ylethyl)amino]quinolin-2(1H)-one | 516.6 |
| 460 | 4-[(3S)-1-azabicyclo[2.2.2]oct-3-ylamino]-3-(1H-benzimidazol-2-yl)-6-fluoro-7-(3-hydroxypiperidin-1-yl)quinolin-2(1H)-one | 530.7 |
| 461 | 4-[(3S)-1-azabicyclo[2.2.2]oct-3-ylamino]-3-(1H-benzimidazol-2-yl)-6-fluoro-7-{[3-(2-oxopyrrolidin-1-yl)propyl]amino}quinolin-2(1H)-one | 544.6 |
| 462 | N-(2-{[4-[(3S)-1-azabicyclo[2.2.2]oct-3-ylamino]-3-(1H-benzimidazol-2-yl)-6-fluoro-2-oxo-1,2-dihydroquinolin-7-yl]amino}ethyl)acetamide | 504.6 |
| 463 | 4-[(3S)-1-azabicyclo[2.2.2]oct-3-ylamino]-3-(1H-benzimidazol-2-yl)-6-fluoro-7-[(3-methoxypropyl)amino]quinolin-2(1H)-one | 491.6 |
| 464 | 4-[(3S)-1-azabicyclo[2.2.2]oct-3-ylamino]-3-(1H-benzimidazol-2-yl)-6-fluoro-7-[(2-methoxyethyl)amino]quinolin-2(1H)-one | 477.6 |
| 465 | 4-[(3S)-1-azabicyclo[2.2.2]oct-3-ylamino]-3-(1H-benzimidazol-2-yl)-6-fluoro-7-[(2-hydroxyethyl)amino]quinolin-2(1H)-one | 463.5 |
| 466 | 4-[(3S)-1-azabicyclo[2.2.2]oct-3-ylamino]-3-(1H-benzimidazol-2-yl)-7-[ethyl(methyl)amino]-6-fluoroquinolin-2(1H)-one | 461.6 |
| 467 | 4-[(3S)-1-azabicyclo[2.2.2]oct-3-ylamino]-3-(1H-benzimidazol-2-yl)-7-(diethylamino)-6-fluoroquinolin-2(1H)-one | 475.6 |
| 468 | N-{(3R)-1-[4-[(3S)-1-azabicyclo[2.2.2]oct-3-ylamino]-3-(1H-benzimidazol-2-yl)-6-fluoro-2-oxo-1,2-dihydroquinolin-7-yl]pyrrolidin-3-yl}acetamide | 530.6 |
| 469 | N-{(3S)-1-[4-[(3S)-1-azabicyclo[2.2.2]oct-3-ylamino]-3-(1H-benzimidazol-2-yl)-6-fluoro-2-oxo-1,2-dihydroquinolin-7-yl]pyrrolidin-3-yl}acetamide | 530.6 |
| 470 | 4-[(3S)-1-azabicyclo[2.2.2]oct-3-ylamino]-3-(1H-benzimidazol-2-yl)-7-[(3R)-3-(dimethylamino)pyrrolidin-1-yl]-6-fluoroquinolin-2(1H)-one | 516.6 |

-continued

TABLE of Additional Exemplary Compounds

| Example | Name | LC/MS m/z (MH+) |
|---|---|---|
| 471 | N-{1-[4-[(3S)-1-azabicyclo[2.2.2]oct-3-ylamino]-3-(1H-benzimidazol-2-yl)-6-fluoro-2-oxo-1,2-dihydroquinolin-7-yl]pyrrolidin-3-yl}-2,2,2-trifluoroacetamide | 584.6 |
| 472 | 4-[(3S)-1-azabicyclo[2.2.2]oct-3-ylamino]-7-azepan-1-yl-3-(1H-benzimidazol-2-yl)-6-fluoroquinolin-2(1H)-one | 501.6 |
| 473 | 4-[(3S)-1-azabicyclo[2.2.2]oct-3-ylamino]-3-(1H-benzimidazol-2-yl)-6-fluoro-7-(3-hydroxypiperidin-1-yl)quinolin-2(1H)-one | 503.6 |
| 474 | 3-{[4-[(3S)-1-azabicyclo[2.2.2]oct-3-ylamino]-3-(1H-benzimidazol-2-yl)-6-fluoro-2-oxo-1,2-dihydroquinolin-7-yl]amino}propanenitrile | 472.5 |
| 475 | 4-[(3S)-1-azabicyclo[2.2.2]oct-3-ylamino]-3-(1H-benzimidazol-2-yl)-6-fluoro-7-(1H-pyrrol-1-yl)quinolin-2(1H)-one | 469.5 |
| 476 | 7-(3-acetyl-1H-pyrrol-1-yl)-4-[(3S)-1-azabicyclo[2.2.2]oct-3-ylamino]-3-(1H-benzimidazol-2-yl)-6-fluoroquinolin-2(1H)-one | 511.6 |
| 477 | 4-[(3S)-1-azabicyclo[2.2.2]oct-3-ylamino]-3-(1H-benzimidazol-2-yl)-6-fluoro-7-(2-methyl-1H-imidazol-1-yl)quinolin-2(1H)-one | 484.5 |
| 478 | 4-[(3S)-1-azabicyclo[2.2.2]oct-3-ylamino]-3-(1H-benzimidazol-2-yl)-7-[(3S)-3-(dimethylamino)pyrrolidin-1-yl]-6-fluoroquinolin-2(1H)-one | 516.6 |
| 479 | 4-[(3S)-1-azabicyclo[2.2.2]oct-3-ylamino]-3-(1H-benzimidazol-2-yl)-6-fluoro-7-methoxyquinolin-2(1H)-one | 434.5 |
| 480 | 4-[(3R)-1-azabicyclo[2.2.2]oct-3-ylamino]-3-(1H-benzimidazol-2-yl)-7-[(3S)-3-(dimethylamino)pyrrolidin-1-yl]-6-fluoroquinolin-2(1H)-one | 516.6 |
| 481 | N-{(3S)-1-[4-[(3R)-1-azabicyclo[2.2.2]oct-3-ylamino]-3-(1H-benzimidazol-2-yl)-6-fluoro-2-oxo-1,2-dihydroquinolin-7-yl]pyrrolidin-3-yl}acetamide | 530.6 |
| 482 | 4-[(3R)-1-azabicyclo[2.2.2]oct-3-ylamino]-3-(1H-benzimidazol-2-yl)-6-fluoro-7-[(2-pyridin-2-ylethyl)amino]quinolin-2(1H)-one | 524.6 |
| 483 | 4-[(3R)-1-azabicyclo[2.2.2]oct-3-ylamino]-3-(1H-benzimidazol-2-yl)-6-fluoro-7-(isobutylamino)quinolin-2(1H)-one | 475.6 |
| 484 | methyl 3-amino-4-[4-[(3R)-1-azabicyclo[2.2.2]oct-3-ylamino]-3-(1H-benzimidazol-2-yl)-7-chloro-2-oxo-1,2-dihydroquinolin-6-yl]benzoate | 570.1 |
| 485 | 4-[(3R)-1-azabicyclo[2.2.2]oct-3-ylamino]-3-(1H-benzimidazol-2-yl)-7-chloro-6-[4-(methylsulfonyl)phenyl]quinolin-2(1H)-one | 575.1 |
| 486 | methyl 3-[4-[(3R)-1-azabicyclo[2.2.2]oct-3-ylamino]-3-(1H-benzimidazol-2-yl)-7-chloro-2-oxo-1,2-dihydroquinolin-6-yl]benzoate | 555.0 |
| 487 | 1-[4-[(3S)-1-azabicyclo[2.2.2]oct-3-ylamino]-3-(1H-benzimidazol-2-yl)-6-fluoro-2-oxo-1,2-dihydroquinolin-7-yl]piperidine-4-carboxylic acid | 531.6 |
| 488 | 1-[4-[(3S)-1-azabicyclo[2.2.2]oct-3-ylamino]-3-(1H-benzimidazol-2-yl)-6-fluoro-2-oxo-1,2-dihydroquinolin-7-yl]piperidine-3-carboxylic acid | 531.6 |
| 489 | 4-[(4-aminobenzyl)amino]-3-(1H-benzimidazol-2-yl)-6,7-dimethoxyquinolin-2(1H)-one | 442.5 |
| 490 | 4-(2-{[3-(1H-benzimidazol-2-yl)-6,7-dimethoxy-2-oxo-1,2-dihydroquinolin-4-yl]amino}ethyl)benzenesulfonamide | 520.6 |
| 491 | 4-[(3-aminopropyl)amino]-3-(1H-benzimidazol-2-yl)-6,7-dimethoxyquinolin-2(1H)-one | 394.4 |
| 492 | 4-[(2-aminoethyl)amino]-3-(1H-benzimidazol-2-yl)-6,7-dimethoxyquinolin-2(1H)-one | 380.4 |
| 493 | 3-(1H-benzimidazol-2-yl)-4-{[2-(1H-imidazol-5-yl)ethyl]amino}-6,7-dimethoxyquinolin-2(1H)-one | 431.5 |
| 494 | 3-(1H-benzimidazol-2-yl)-4-{[2-(1H-benzimidazol-2-yl)ethyl]amino}-6,7-dimethoxyquinolin-2(1H)-one | 481.5 |
| 495 | 4-{[(4-amino-2-methylpyrimidin-5-yl)methyl]amino}-3-(1H-benzimidazol-2-yl)-6,7-dimethoxyquinoln-2(1H)-one | 458.5 |
| 496 | 3-(1H-benzimidazol-2-yl)-4-{[2-(5-fluoro-1H-indol-3-yl)ethyl]amino}-6,7-dimethoxyquinolin-2(1H)-one | 498.5 |
| 497 | 4-{[2-(4-aminophenyl)ethyl]amino}-3-(1H-benzimidazol-2-yl)-6,7-dimethoxyquinolin-2(1H)-one | 456.5 |
| 498 | 4-[(3R)-1-azabicyclo[2.2.2]oct-3-ylamino]-3-(1H-benzimidazol-2yl)-7-morpholin-4-ylquinolin-2(1H)-one | 471.6 |
| 499 | 4-[(3R)-1-azabicyclo[2.2.2]oct-3-ylamino]-3-(5,6-difluoro-1H-benzimidazol-2-yl)-6,7-dimethoxyquinolin-2(1H)-one | 430.5 |
| 500 | methyl 3-amino-4-[4-[(3R)-1-azabicyclo[2.2.2]oct-3-ylamino]-3-(1H-benzimidazol-2-yl)-2-oxo-1,2-dihydroquinolin-7-yl]benzoate | 535.6 |
| 501 | 4-[(3R)-1-azabicyclo[2.2.2]oct-3-ylamino]-3-(1H-benzimidazol-2-yl)-7-[4-(methylsulfonyl)phenyl]quinolin-2(1H)-one | 540.7 |
| 502 | methyl 4-[4-[(3R)-1-azabicyclo[2.2.2]oct-3-ylamino]-3-(1H-benzimidazol-2-yl)-2-oxo-1,2-dihydroquinolin-7-yl]benzoate | 520.6 |

-continued

TABLE of Additional Exemplary Compounds

| Example | Name | LC/MS m/z (MH+) |
|---|---|---|
| 503 | methyl 3-[4-[(3R)-1-azabicyclo[2.2.2]oct-3-ylamino]-3-(1H-benzimidazol-2-yl)-2-oxo-1,2-dihydroquinolin-7-yl]benzoate | 520.6 |
| 504 | N-{3-[4-[(3R)-1-azabicyclo[2.2.2]oct-3-ylamino]-3-(1H-benzimidazol-2-yl)-2-oxo-1,2-dihydroquinolin-7-yl]phenyl}acetamide | 519.6 |
| 505 | 4-[(3R)-1-azabicyclo[2.2.2]oct-3-ylamino]-3-(5,6-difluoro-1H-benzimidazol-2-yl)-6,7-dimethoxyquinolin-2(1H)-one | 482.5 |
| 506 | 3-(5,6-difluoro-1H-benzimidazol-2-yl)-6,7-dimethoxy-4-(piperidin-3-ylamino)quinolin-2(1H)-one | 456.5 |
| 507 | 4-[(4-aminocyclohexyl)amino]-3-(5,6-difluoro-1H-benzimidazol-2-yl)-6,7-dimethoxyquinolin-2(1H)-one | 470.5 |
| 508 | 3-(5,6-difluoro-1H-benzimidazol-2-yl)-6,7-dimethoxy-4-(pyrrolidin-3-ylamino)quinolin-2(1H)-one | 442.4 |
| 509 | 4-[(3R)-1-azabicyclo[2.2.2]oct-3-ylamino]-3-(1H-benzimidazol-2-yl)-6-chloro-7-(1H-imidazol-1-yl)quinolin-2(1H)-one | 487.0 |
| 510 | 4-[(3R)-1-azabicyclo[2.2.2]oct-3-ylamino]-3-(1H-benzimidazol-2-yl)-7-[(3-hydroxypropyl)amino]quinolin-2(1H)-one | 459.6 |
| 511 | 4-[(3R)-1-azabicyclo[2.2.2]oct-3-ylamino]-3-(1H-benzimidazol-2-yl)-7-{[3-(2-oxopyrrolidin-1-yl)propyl]amino}quinolin-2(1H)-one | 526.7 |
| 512 | 4-[(3R)-1-azabicyclo[2.2.2]oct-3-ylamino]-3-(1H-benzimidazol-2-yl)-7-(4-methylpiperazin-1-yl)quinolin-2(1H)-one | 484.6 |
| 513 | 4-[4-[(3R)-1-azabicyclo[2.2.2]oct-3-ylamino]-3-(1H-benzimidazol-2-yl)-2-oxo-1,2-dihydroquinolin-7-yl]benzonitrile | 487.6 |
| 514 | 4-[(3R)-1-azabicyclo[2.2.2]oct-3-ylamino]-3-(1H-benzimidazol-2-yl)-7-[2-(trifluoromethyl)phenyl]quinolin-2(1H)-one | 530.6 |
| 515 | 4-[(3R)-1-azabicyclo[2.2.2]oct-3-ylamino]-3-(1H-benzimidazol-2-yl)-7-(1,3-benzodioxol-5-yl)quinolin-2(1H)-one | 506.6 |
| 516 | 4-[(3R)-1-azabicyclo[2.2.2]oct-3-ylamino]-3-(1H-benzimidazol-2-yl)-7-(morpholin-4-ylcarbonyl)quinolin-2(1H)-one | 499.6 |
| 517 | 4-[(3R)-1-azabicyclo[2.2.2]oct-3-ylamino]-3-(1H-benzimidazol-2-yl)-N,N-dimethyl-2-oxo-1,2-dihydroquinoline-7-carboxamide | 457.5 |
| 518 | 4-[(3R)-1-azabicyclo[2.2.2]oct-3-ylamino]-3-(1H-benzimidazol-2-yl)-2-oxo-1,2-dihydroquinoline-7-carboxamide | 429.5 |
| 519 | 3-[4-[(3R)-1-azabicyclo[2.2.2]oct-3-ylamino]-3-(1H-benzimidazol-2-yl)-2-oxo-1,2-dihydroquinolin-7-yl]benzoic acid | 506.6 |
| 520 | 4-[(3S)-1-azabicyclo[2.2.2]oct-3-ylamino]-3-(1H-benzimidazol-2-yl)-7-bromoquinolin-2(1H)-one | 465.4 |
| 521 | 4-{4-[(3R)-1-azabicyclo[2.2.2]oct-3-ylamino]-3-(1H-benzimidazol-2-yl)-7-[4-(ethoxycarbonyl)piperidin-1-yl]-2-oxo-1,2-dihydroquinolin-6-yl}benzoic acid | 661.8 |
| 522 | 4-[7-(3-acetyl-1H-pyrrol-1-yl)-4-[(3R)-1-azabicyclo[2.2.2]oct-3-ylamino]-3-(1H-benzimidazol-2-yl)-2-oxo-1,2-dihydroquinolin-6-yl]benzoic acid | 613.7 |
| 523 | 4-[4-[(3R)-1-azabicyclo[2.2.2]oct-3-ylamino]-3-(1H-benzimidazol-2-yl)-7-(dimethylamino)-2-oxo-1,2-dihydroquinolin-6-yl]benzoic acid | 549.6 |
| 524 | 4-[4-[(3R)-1-azabicyclo[2.2.2]oct-3-ylamino]-3-(1H-benzimidazol-2-yl)-7-(1H-imidazol-1-yl)-2-oxo-1,2-dihydroquinolin-6-yl]benzoic acid | 572.6 |
| 525 | 4-[(3R)-1-azabicyclo[2.2.2]oct-3-ylamino]-3-(1H-benzimidazol-2-yl)-7-fluoro-6-iodoquinolin-2(1H)-one | 530.4 |
| 526 | 4-[(3R)-1-azabicyclo[2.2.2]oct-3-ylamino]-3-(1H-benzimidazol-2-yl)-7-fluoro-6-[4-(methylsulfonyl)phenyl]quinolin-2(1H)-one | 558.6 |
| 527 | 4-[4-[(3R)-1-azabicyclo[2.2.2]oct-3-ylamino]-3-(1H-benzimidazol-2-yl)-7-fluoro-2-oxo-1,2-dihydroquinolin-6-yl]benzamide | 523.6 |
| 528 | 6-(4-acetylphenyl)-4-[(3R)-1-azabicyclo[2.2.2]oct-3-ylamino]-3-(1H-benzimidazol-2-yl)-7-fluoroquinolin-2(1H)-one | 522.6 |
| 529 | methyl 4-[4-[(3R)-1-azabicyclo[2.2.2]oct-3-ylamino]-3-(1H-benzimidazol-2-yl)-7-fluoro-2-oxo-1,2-dihydroquinolin-6-yl]benzoate | 538.6 |
| 530 | methyl 3-amino-4-[4-[(3R)-1-azabicyclo[2.2.2]oct-3-ylamino]-3-(1H-benzimidazol-2-yl)-7-fluoro-2-oxo-1,2-dihydroquinolin-6-yl]benzoate | 553.6 |
| 531 | 6-(3-acetylphenyl)-4-[(3R)-1-azabicyclo[2.2.2]oct-3-ylamino]-3-(1H-benzimidazol-2-yl)-7-fluoroquinolin-2(1H)-one | 522.6 |
| 532 | methyl 3-[4-[(3R)-1-azabicyclo[2.2.2]oct-3-ylamino]-3-(1H-benzimidazol-2-yl)-7-fluoro-2-oxo-1,2-dihydroquinolin-6-yl]benzoate | 538.6 |
| 533 | 4-[(3R)-1-azabicyclo[2.2.2]oct-3-ylamino]-3-(1H-benzimidazol-2-yl)-7-fluoro-6-(2-methylphenyl)quinolin-2(1H)-one | 494.6 |
| 534 | 4-[(3R)-1-azabicyclo[2.2.2]oct-3-ylamino]-3-(1H-benzimidazol-2-yl)-7-fluoro-6-(2-methoxyphenyl)quinolin-2(1H)-one | 510.6 |

-continued

TABLE of Additional Exemplary Compounds

| Example | Name | LC/MS m/z (MH+) |
|---|---|---|
| 535 | 4-[(3R)-1-azabicyclo[2.2.2]oct-3-ylamino]-3-(1H-benzimidazol-2-yl)-6-(2,4-dichlorophenyl)-7-fluoroquinolin-2(1H)-one | 549.4 |
| 536 | ethyl 1-[4-[(3R)-1-azabicyclo[2.2.2]oct-3-ylamino]-3-(1H-benzimidazol-2-yl)-6-iodo-2-oxo-1,2-dihydroquinolin-7-yl]piperidine-4-carboxylate | 667.6 |
| 537 | 4-[(3R)-1-azabicyclo[2.2.2]oct-3-ylamino]-3-(1H-benzimidazol-2-yl)-7-(1H-imidazol-1-yl)-6-iodoquinolin-2(1H)-one | 578.4 |
| 538 | 4-[(3R)-1-azabicyclo[2.2.2]oct-3-ylamino]-3-(1H-benzimidazol-2-yl)-6-(2-ethylphenyl)-7-(1H-imidazol-1-yl)quinolin-2(1H)-one | 556.7 |
| 539 | 4-[4-[(3R)-1-azabicyclo[2.2.2]oct-3-ylamino]-3-(1H-benzimidazol-2-yl)-7-(1H-imidazol-1-yl)-2-oxo-1,2-dihydroquinolin-6-yl]benzamide | 571.7 |
| 540 | 6-(4-acetylphenyl)-4-[(3R)-1-azabicyclo[2.2.2]oct-3-ylamino]-3-(1H-benzimidazol-2-yl)-7-(1H-imidazol-1-yl)quinolin-2(1H)-one | 570.7 |
| 541 | 6-(3-acetylphenyl)-4-[(3R)-1-azabicyclo[2.2.2]oct-3-ylamino]-3-(1H-benzimidazol-2-yl)-7-(1H-imidazol-1-yl)quinolin-2(1H)-one | 587.7 |
| 542 | N-{3-[4-[(3R)-1-azabicyclo[2.2.2]oct-3-ylamino]-3-(1H-benzimidazol-2-yl)-7-(1H-imidazol-1-yl)-2-oxo-1,2-dihydroquinolin-6-yl]phenyl}acetamide | 585.7 |
| 543 | 6-(3-acetylphenyl)-4-[(3R)-1-azabicyclo[2.2.2]oct-3-ylamino]-3-(1H-benzimidazol-2-yl)-7-(1H-imidazol-1-yl)quinolin-2(1H)-one | 570.7 |
| 544 | 4-[(3R)-1-azabicyclo[2.2.2]oct-3-ylamino]-3-(1H-benzimidazol-2-yl)-7-(1H-imidazol-1-yl)-6-(2-methylphenyl)quinolin-2(1H)-one | 542.7 |
| 545 | 4-[(3R)-1-azabicyclo[2.2.2]oct-3-ylamino]-3-(1H-benzimidazol-2-yl)-7-(1H-imidazol-1-yl)-6-(2-methoxyphenyl)quinolin-2(1H)-one | 558.7 |
| 546 | 4-[(3R)-1-azabicyclo[2.2.2]oct-3-ylamino]-3-(1H-benzimidazol-2-yl)-6-(2,4-dichlorophenyl)-7-(1H-imidazol-1-yl)quinolin-2(1H)-one | 597.5 |
| 547 | 4-[(3R)-1-azabicyclo[2.2.2]oct-3-ylamino]-3-(1H-benzimidazol-2-yl)-6-(2-ethylphenyl)quinolin-2(1H)-one | 490.6 |
| 548 | 4-[(3R)-1-azabicyclo[2.2.2]oct-3-ylamino]-3-(1H-benzimidazol-2-yl)-6-(2-ethylphenyl)-7-fluoroquinolin-2(1H)-one | 508.6 |
| 549 | 3-[4-[(3R)-1-azabicyclo[2.2.2]oct-3-ylamino]-3-(1H-benzimidazol-2-yl)-2-oxo-1,2-dihydroquinolin-6-yl]benzoic acid | 506.6 |
| 550 | 3-amino-4-[4-[(3R)-1-azabicyclo[2.2.2]oct-3-ylamino]-3-(1H-benzimidazol-2-yl)-7-chloro-2-oxo-1,2-dihydroquinolin-6-yl]benzoic acid | 556.0 |
| 551 | 3-[4-[(3R)-1-azabicyclo[2.2.2]oct-3-ylamino]-3-(1H-benzimidazol-2-yl)-7-chloro-2-oxo-1,2-dihydroquinolin-6-yl]benzoic acid | 541.0 |
| 552 | 4-[(3R)-1-azabicyclo[2.2.2]oct-3-ylamino]-3-(1H-benzimidazol-2-yl)-6-fluoro-7-[(pyridin-2-ylmethyl)amino]quinolin-2(1H)-one | 510.6 |
| 553 | 4-[(3R)-1-azabicyclo[2.2.2]oct-3-ylamino]-3-(1H-benzimidazol-2-yl)-6-fluoro-7-[(3-pyrrolidin-1-ylpropyl)amino]quinolin-2(1H)-one | 527.6 |
| 554 | 4-[(3R)-1-azabicyclo[2.2.2]oct-3-ylamino]-3-(1H-benzimidazol-2-yl)-6-fluoro-7-[(pyridin-3-ylmethyl)amino]quinolin-2(1H)-one | 510.6 |
| 555 | 4-[(3R)-1-azabicyclo[2.2.2]oct-3-ylamino]-3-(1H-benzimidazol-2-yl)-6-fluoro-7-[(3-pyrrolidin-1-ylpropyl)amino]quinolin-2(1H)-one | 530.7 |
| 556 | 4-[(3R)-1-azabicyclo[2.2.2]oct-3-ylamino]-3-(1H-benzimidazol-2-yl)-6-fluoro-7-[(3R)-3-hydroxypyrrolidin-1-yl]quinolin-2(1H)-one | 489.6 |
| 557 | 4-[(3R)-1-azabicyclo[2.2.2]oct-3-ylamino]-3-(1H-benzimidazol-2-yl)-6-fluoro-7-{[2-(1-methylpyrrolidin-2-yl)ethyl]amino}quinolin-2(1H)-one | 530.7 |
| 558 | 4-[(3R)-1-azabicyclo[2.2.2]oct-3-ylamino]-3-(1H-benzimidazol-2-yl)-6-fluoro-7-[(pyridin-4-ylmethyl)amino]quinolin-2(1H)-one | 510.6 |
| 559 | 4-[(3R)-1-azabicyclo[2.2.2]oct-3-ylamino]-3-(1H-benzimidazol-2-yl)-6-fluoro-7-[3-(methylsulfonyl)pyrrolidin-1-yl]quinolin-2(1H)-one | 551.7 |
| 560 | 4-[(3R)-1-azabicyclo[2.2.2]oct-3-ylamino]-3-(1H-benzimidazol-2-yl)-6-fluoro-7-(3-pyridin-4-ylpyrrolidin-1-yl)quinolin-2(1H)-one | 550.7 |
| 561 | 4-[(3R)-1-azabicyclo[2.2.2]oct-3-ylamino]-3-(1H-benzimidazol-2-yl)-6-fluoro-7-[(2-morpholin-4-ylethyl)amino]quinolin-2(1H)-one | 532.6 |
| 562 | 4-[(3R)-1-azabicyclo[2.2.2]oct-3-ylamino]-3-(1H-benzimidazol-2-yl)-6-fluoro-7-[4-(pyridin-4-ylmethyl)piperazin-1-yl]quinolin-2(1H)-one | 579.7 |
| 563 | 4-[(3R)-1-azabicyclo[2.2.2]oct-3-ylamino]-3-(1H-benzimidazol-2-yl)-7-(benzylamino)-6-fluoroquinolin-2(1H)-one | 509.6 |

-continued

TABLE of Additional Exemplary Compounds

| Example | Name | LC/MS m/z (MH+) |
|---|---|---|
| 564 | 4-[(3R)-1-azabicyclo[2.2.2]oct-3-ylamino]-3-(1H-benzimidazol-2-yl)-6-fluoro-7-(2-pyridin-3-ylpyrrolidin-1-yl)quinolin-2(1H)-one | 550.7 |
| 565 | 4-[(3R)-1-azabicyclo[2.2.2]oct-3-ylamino]-3-(1H-benzimidazol-2-yl)-6-fluoro-7-[(2-pyridin-4-ylethyl)amino]quinolin-2(1H)-one | 524.6 |
| 566 | 4-[(3R)-1-azabicyclo[2.2.2]oct-3-ylamino]-3-(1H-benzimidazol-2-yl)-6-fluoro-7-[(3-morpholin-4-ylpropyl)amino]quinolin-2(1H)-one | 546.7 |
| 567 | 4-[(3R)-1-azabicyclo[2.2.2]oct-3-ylamino]-3-(1H-benzimidazol-2-yl)-6-fluoro-7-[(4-hydroxycyclohexyl)amino]quinolin-2(1H)-one | 524.6 |
| 568 | 7-{[2-(4-aminophenyl)ethyl]amino}-4-[(3R)-1-azabicyclo[2.2.2]oct-3-ylamino]-3-(1H-benzimidazol-2-yl)-6-fluoroquinolin-2(1H)-one | 538.6 |
| 569 | 4-[(3R)-1-azabicyclo[2.2.2]oct-3-ylamino]-3-(1H-benzimidazol-2-yl)-6-fluoro-7-[(4-hydroxycyclohexyl)amino]quinolin-2(1H)-one | 517.6 |
| 570 | 4-(1-azabicyclo[2.2.2]oct-3-ylamino)-3-(1H-benzimidazol-2-yl)-6-fluoro-7-[(piperidin-3-ylmethyl)amino]quinolin-2(1H)-one | 516.6 |
| 571 | 4-(1-azabicyclo[2.2.2]oct-3-ylamino)-3-(1H-benzimidazol-2-yl)-6-fluoro-7-(pyrrolidin-3-ylamino)quinolin-2(1H)-one | 488.6 |
| 572 | 4-[4-[(3R)-1-azabicyclo[2.2.2]oct-3-ylamino]-3-(1H-benzimidazol-2-yl)-7-(2-methyl-1H-imidazol-1-yl)-2-oxo-1,2-dihydroquinolin-6-yl]benzoic acid | 586.7 |
| 573 | 1-[4-[(3R)-1-azabicyclo[2.2.2]oct-3-ylamino]-3-(1H-benzimidazol-2-yl)-6-chloro-2-oxo-1,2-dihydroquinolin-7-yl]piperidine-4-carboxamide | 547.1 |
| 574 | ethyl 1-[4-[(3R)-1-azabicyclo[2.2.2]oct-3-ylamino]-3-(1H-benzimidazol-2-yl)-6-chloro-2-oxo-1,2-dihydroquinolin-7-yl]piperidine-4-carboxylate | 576.1 |
| 575 | 4-[(3R)-1-azabicyclo[2.2.2]oct-3-ylamino]-3-(1H-benzimidazol-2-yl)-7-(1H-imidazol-1-yl)quinolin-2(1H)-one | 452.5 |
| 576 | 4-[(3R)-1-azabicyclo[2.2.2]oct-3-ylamino]-3-(1H-benzimidazol-2-yl)-7-(2-methyl-1H-imidazol-1-yl)quinolin-2(1H)-one | 466.6 |
| 577 | ethyl 1-[4-[(3R)-1-azabicyclo[2.2.2]oct-3-ylamino]-3-(1H-benzimidazol-2-yl)-2-oxo-1,2-dihydroquinolin-7-yl]piperidine-4-carboxylate | 541.7 |
| 578 | 1-[4-[(3R)-1-azabicyclo[2.2.2]oct-3-ylamino]-3-(1H-benzimidazol-2-yl)-2-oxo-1,2-dihydroquinolin-7-yl]piperidine-4-carboxamide | 512.6 |
| 579 | 4-[(3R)-1-azabicyclo[2.2.2]oct-3-ylamino]-3-(1H-benzimidazol-2-yl)-6-fluoro-7-[(2-mercaptoethyl)amino]quinolin-2(1H)-one | 479.6 |
| 580 | 4-[(3R)-1-azabicyclo[2.2.2]oct-3-ylamino]-3-(1H-benzimidazol-2-yl)-6-fluoro-7-[4-(pyridin-3-ylmethyl)piperazin-1-yl]quinolin-2(1H)-one | 579.7 |
| 581 | 3-(1H-benzimidazol-2-yl)-4-[(2-hydroxyethyl)amino]-6,7-dimethoxyquinolin-2(1H)-one | 381.4 |
| 582 | 3-(1H-benzimidazol-2-yl)-4-[(3-hydroxypropyl)amino]-6,7-dimethoxyquinolin-2(1H)-one | 395.4 |
| 583 | 4-[(3R)-1-azabicyclo[2.2.2]oct-3-ylamino]-3-(1H-benzimidazol-2-yl)-6-fluoro-7-{[(1-hydroxycyclohexyl)methyl]amino}quinolin-2(1H)-one | 531.6 |
| 584 | 3-(1H-benzimidazol-2-yl)-6,7-dimethoxy-4-[(3-pyrrolidin-1-ylpropyl)amino]quinolin-2(1H)-one | 448.5 |
| 585 | 4[(3S)-1-azabicyclo[2.2.2]oct-3-ylamino]-3-(1H-benzimidazol-2-yl)-2-oxo-1,2-dihydroquinoline-7-carbonitrile | 411.5 |
| 586 | 3-(1H-benzimidazol-2-yl)-6-chloro-4-(pyridine-3-ylamino)quinolin-2(1H)-one | 388.8 |
| 587 | 3-(1H-benzimidazol-2-yl)-4-[(1-benzylpiperidin-4-yl)amino]-6-chloroquinolin-2(1H)-one | 485.0 |
| 588 | 4-[(3S)-1-azabicyclo[2.2.2]oct-3-ylamino]-3-(1H-benzimidazol-2-yl)-7-methoxyquinolin-2(1H)-one | 416.5 |
| 589 | 4-[(3R)-1-azabicyclo[2.2.2]oct-3-ylamino]-3-(1H-benzimidazol-2-yl)-6-bromo-7-methoxyquinolin-2(1H)-one | 495.4 |
| 590 | 3-(1H-benzimidazol-2-yl)-6,7-dimethoxy-4-{[(5-methylpyrazin-2-yl)methyl]amino}quinolin-2(1H)-one | 443.5 |
| 591 | 4-[(3-amino-2-hydroxypropyl)amino]-3-(1H-benzimidazol-2-yl)-6,7-dimethoxyquinolin-2(1H)-one | 410.4 |
| 592 | 3-(1H-benzimidazol-2-yl)-6,7-dimethoxy-4-[(2-methoxyethyl)amino]quinolin-2(1H)-one | 395.4 |
| 593 | {3-(1H-benzimidazol-2-yl)-6,7-dimethoxy-2-oxo-1,2-dihydroquinolin-4-yl]amino}acetonitrile | 376.4 |
| 594 | 3-(1H-benzimidazol-2-yl)-4-{[2-(2-hydroxyethoxy)ethyl]amino}-6,7-dimethoxyquinolin-2(1H)-one | 425.5 |

-continued

TABLE of Additional Exemplary Compounds

| Example | Name | LC/MS m/z (MH+) |
|---|---|---|
| 595 | 3-(1H-benzimidazol-2-yl)-4-[(3R)-3-hydroxypyrrolidin-1-yl]-6,7-dimethoxyquinolin-2(1H)-one | 407.4 |
| 596 | 4-[4-[(3S)-1-azabicyclo[2.2.2]oct-3-ylamino]-3-(1H-benzimidazol-2-yl)-2-oxo-1,2-dihydroquinolin-7-yl]benzonitrile | 487.6 |
| 597 | 4-[4-[(3S)-1-azabicyclo[2.2.2]oct-3-ylamino]-3-(1H-benzimidazol-2-yl)-2-oxo-1,2-dihydroquinolin-7-yl]benzoic acid | 506.6 |
| 598 | 4-[4-[(3S)-1-azabicyclo[2.2.2]oct-3-ylamino]-3-(1H-benzimidazol-2-yl)-2-oxo-1,2-dihydroquinolin-7-yl]benzamide | 505.6 |
| 599 | methyl 3-[4-[(3S)-1-azabicyclo[2.2.2]oct-3-ylamino]-3-(1H-benzimidazol-2-yl)-2-oxo-1,2-dihydroquinolin-7-yl]benzoate | 520.6 |
| 600 | 6-chloro-3-(5-morpholin-4-yl-1H-benzimidazol-2-yl)-4-({[6-(piperidin-3-yloxy)pyridin-3-yl]methyl}amino)quinolin-2(1H)-one | 587.1 |
| 601 | 6-chloro-3-(5-morpholin-4-yl-1H-benzimidazol-2-yl)-4-{[3-(2-oxopyrrolidin-1-yl)propyl]amino}quinolin-2(1H)-one | 488.0 |
| 602 | 6-chloro-3-(5-morpholin-4-yl-1H-benzimidazol-2-yl)-4-[(2-pyridin-2-ylethyl)amino]quinolin-2(1H)-one | 502.0 |
| 603 | 6-chloro-3-(5-morpholin-4-yl-1H-benzimidazol-2-yl)-4-{[3-(2-oxopyrrolidin-1-yl)propyl]amino}quinolin-2(1H)-one | 522.0 |
| 604 | 6-chloro-4-[(6-methoxypyridin-3-yl)amino]-3-(5-morpholin-4-yl-1H-benzimidazol-2-yl)quinolin-2(1H)-one | 504.0 |
| 605 | 6-chloro-3-(5-morpholin-4-yl-1H-benzimidazol-2-yl)-4-[(3-pyridin-2-ylpropyl)amino]quinolin-2(1H)-one | 516.0 |
| 606 | 6-chloro-3-(5-morpholin-4-yl-1H-benzimidazol-2-yl)-4-(pyridin-4-ylamino)quinolin-2(1H)-one | 473.9 |
| 607 | 6-chloro-3-(5-morpholin-4-yl-1H-benzimidazol-2-yl)-4-({[6-(piperidin-3-ylmethoxy)pyridin-3-yl]methyl}amino)quinolin-2(1H)-one | 601.1 |
| 608 | 6-chloro-3-(5-morpholin-4-yl-1H-benzimidazol-2-yl)-4-(pyridin-2-ylamino)quinolin-2(1H)-one | 473.9 |
| 609 | 1-[4-[(3R)-1-azabicyclo[2.2.2]oct-3-ylamino]-3-(1H-benzimidazol-2-yl)-6-chloro-2-oxo-1,2-dihydroquinolin-7-yl]piperidine-4-carboxylic acid | 548.1 |
| 610 | 1-[4-[(3R)-1-azabicyclo[2.2.2]oct-3-ylamino]-3-(1H-benzimidazol-2-yl)-2-oxo-1,2-dihydroquinolin-7-yl]piperidine-4-carboxylic acid | 513.6 |
| 611 | 3-[4-[(3S)-1-azabicyclo[2.2.2]oct-3-ylamino]-3-(1H-benzimidazol-2-yl)-2-oxo-1,2-dihydroquinolin-7-yl]benzoic acid | 506.6 |
| 612 | 6-chloro-3-(5-morpholin-4-yl-1H-benzimidazol-2-yl)-4-({[2-(piperidin-4-yloxy)pyridin-3-yl]methyl}amino)quinolin-2(1H)-one | 430.5 |
| 613 | 4-[(3S)-1-azabicyclo[2.2.2]oct-3-ylamino]-3-(1H-benzimidazol-2-yl)-6,7-dichloroquinolin-2(1H)-one | 455.4 |
| 614 | 6-chloro-3-(5-morpholin-4-yl-1H-benzimidazol-2-yl)-4-({[2-(piperidin-4-yloxy)pyridin-3-yl]methyl}amino)quinolin-2(1H)-one | 587.1 |
| 615 | 6-chloro-3-(5-morpholin-4-yl-1H-benzimidazol-2-yl)-4-(pyrazin-2-ylamino)quinolin-2(1H)-one | 474.9 |
| 616 | 4-amino-3-(6-thiomorpholin-4-yl-1H-benzimidazol-2-yl)quinolin-2(1H)-one | 378.5 |
| 617 | 4-[(3R)-1-azabicyclo[2.2.2]oct-3-ylamino]-3-(1H-benzimidazol-2-yl)-6-fluoro-7-(3-pyridin-3-ylpyrrolidin-1-yl)quinolin-2(1H)-one | 550.7 |
| 618 | 4-[(3R)-1-azabicyclo[2.2.2]oct-3-ylamino]-3-(1H-benzimidazol-2-yl)-5-fluoro-6-[4-(methylsulfonyl)phenyl]quinolin-2(1H)-one | 558.6 |
| 619 | 6-(4-acetylphenyl)-4-[(3R)-1-azabicyclo[2.2.2]oct-3-ylamino]-3-(1H-benzimidazol-2-yl)-5-fluoroquinolin-2(1H)-one | 522.6 |
| 620 | methyl 4-[4-[(3R)-1-azabicyclo[2.2.2]oct-3-ylamino]-3-(1H-benzimidazol-2-yl)-5-fluoro-2-oxo-1,2-dihydroquinolin-6-yl]benzoate | 538.6 |
| 621 | methyl 3-amino-4-[4-[(3R)-1-azabicyclo[2.2.2]oct-3-ylamino]-3-(1H-benzimidazol-2-yl)-5-fluoro-2-oxo-1,2-dihydroquinolin-6-yl]benzoate | 553.6 |
| 622 | methyl 3-[4-[(3R)-1-azabicyclo[2.2.2]oct-3-ylamino]-3-(1H-benzimidazol-2-yl)-5-fluoro-2-oxo-1,2-dihydroquinolin-6-yl]benzoate | 538.6 |
| 623 | 4-[(3R)-1-azabicyclo[2.2.2]oct-3-ylamino]-3-(1H-benzimidazol-2-yl)-5-fluoro-6-(2-methylphenyl)quinolin-2(1H)-one | 494.6 |
| 624 | 4-[(3R)-1-azabicyclo[2.2.2]oct-3-ylamino]-3-(1H-benzimidazol-2-yl)-6-(2-ethylphenyl)-5-fluoroquinolin-2(1H)-one | 508.6 |
| 625 | 4-[(3R)-1-azabicyclo[2.2.2]oct-3-ylamino]-3-(1H-benzimidazol-2-yl)-5-fluoro-6-(2-methoxyphenyl)quinolin-2(1H)-one | 510.6 |
| 626 | 4-[(3R)-1-azabicyclo[2.2.2]oct-3-ylamino]-3-(1H-benzimidazol-2-yl)-6-(2,4-dichlorophenyl)-5-fluoroquinolin-2(1H)-one | 549.4 |

-continued

TABLE of Additional Exemplary Compounds

| Example | Name | LC/MS m/z (MH+) |
|---|---|---|
| 627 | 4-[4-[(3S)-1-azabicyclo[2.2.2]oct-3-ylamino]-3-(1H-benzimidazol-2-yl)-7-fluoro-2-oxo-1,2-dihydroquinolin-6-yl]benzoic acid | 524.6 |
| 628 | 4-[4-[(3S)-1-azabicyclo[2.2.2]oct-3-ylamino]-3-(1H-benzimidazol-2-yl)-7-fluoro-2-oxo-1,2-dihydroquinolin-6-yl]benzamide | 523.6 |
| 629 | N-{3-[4-[(3S)-1-azabicyclo[2.2.2]oct-3-ylamino]-3-(1H-benzimidazol-2-yl)-7-fluoro-2-oxo-1,2-dihydroquinolin-6-yl]phenyl}acetamide | 537.6 |
| 630 | 3-[4-[(3S)-1-azabicyclo[2.2.2]oct-3-ylamino]-3-(1H-benzimidazol-2-yl)-7-fluoro-2-oxo-1,2-dihydroquinolin-6-yl]benzoic acid | 524.6 |
| 631 | 4-[(3S)-1-azabicyclo[2.2.2]oct-3-ylamino]-3-(1H-benzimidazol-2-yl)-7-fluoro-6-(2-methylphenyl)quinolin-2(1H)-one | 494.6 |
| 632 | 4-[(3R)-1-azabicyclo[2.2.2]oct-3-ylamino]-3-(1H-benzimidazol-2-yl)-7-(2-methyl-1H-imidazol-1-yl)-6-[4-(methylsulfonyl)phenyl]quinolin-2(1H)-one | 620.7 |
| 633 | N-{3-[4-[(3R)-1-azabicyclo[2.2.2]oct-3-ylamino]-3-(1H-benzimidazol-2-yl)-7-(2-methyl-1H-imidazol-1-yl)-2-oxo-1,2-dihydroquinolin-6-yl]phenyl}acetamide | 599.7 |
| 634 | N-{3-[4-[(3R)-1-azabicyclo[2.2.2]oct-3-ylamino]-3-(1H-benzimidazol-2-yl)-2-oxo-7-piperidin-1-yl-1,2-dihydroquinolin-6-yl]phenyl}acetamide | 602.8 |
| 635 | N-{3-[7-(3-acetyl-1H-pyrrol-1-yl)-4-[(3R)-1-azabicyclo[2.2.2]oct-3-ylamino]-3-(1H-benzimidazol-2-yl)-2-oxo-1,2-dihydroquinolin-6-yl]phenyl}acetamide | 626.7 |
| 636 | N-{3-[4-[(3R)-1-azabicyclo[2.2.2]oct-3-ylamino]-3-(1H-benzimidazol-2-yl)-7-(dimethylamino)-2-oxo-1,2-dihydroquinolin-6-yl]phenyl}acetamide | 562.7 |
| 637 | N-{3-[4-[(3R)-1-azabicyclo[2.2.2]oct-3-ylamino]-3-(1H-benzimidazol-2-yl)-7-(2-ethyl-1H-imidazol-1-yl)-2-oxo-1,2-dihydroquinolin-6-yl]phenyl}acetamide | 613.7 |
| 638 | 4-[(3R)-1-azabicyclo[2.2.2]oct-3-ylamino]-3-(1H-benzimidazol-2-yl)-7-(2-ethyl-1H-imidazol-1-yl)-6-fluoroquinolin-2(1H)-one | 498.6 |
| 639 | 4-[(3R)-1-azabicyclo[2.2.2]oct-3-ylamino]-3-(1H-benzimidazol-2-yl)-6-fluoro-7-(2-isopropyl-1H-imidazol-1-yl)quinolin-2(1H)-one | 512.6 |
| 640 | 1-[4-[(3R)-1-azabicyclo[2.2.2]oct-3-ylamino]-3-(1H-benzimidazol-2-yl)-6-fluoro-2-oxo-1,2-dihydroquinolin-7-yl]-1H-pyrrole-3-carboxylic acid | 513.5 |
| 641 | 4-[(3S)-1-azabicyclo[2.2.2]oct-3-ylamino]-3-(1H-benzimidazol-2-yl)-7-chloro-6-iodoquinolin-2(1H)-one | 546.8 |
| 642 | 4-[(3R)-1-azabicyclo[2.2.2]oct-3-ylamino]-3-(1H-benzimidazol-2-yl)-5-fluoro-6-iodoquinolin-2(1H)-one | 530.4 |
| 643 | 4-[(3S)-1-azabicyclo[2.2.2]oct-3-ylamino]-3-(1H-benzimidazol-2-yl)-7-fluoro-6-iodoquinolin-2(1H)-one | 530.4 |
| 644 | 6-chloro-3-(5-morpholin-4-yl-1H-benzimidazol-2-yl)-4-[(2-pyridin-3-ylethyl)amino]quinolin-2(1H)-one | 502.0 |
| 645 | 4-{[4-(aminomethyl)benzyl]amino}-3-(1H-benzimidazol-2-yl)-7-chloroquinolin-2(1H)-one | 430.9 |
| 646 | 3-(1H-benzimidazol-2-yl)-7-chloro-4-{[2-(dimethylamino)ethyl]amino}quinolin-2(1H)-one | 382.9 |
| 647 | 3-(1H-benzimidazol-2-yl)-4-(1,4'-bipiperidin-1'-yl)-7-chloroquinolin-2(1H)-one | 463.0 |
| 648 | 3-(1H-benzimidazol-2-yl)-7-chloro-4-{[3-(4-methylpiperazin-1-yl)propyl]amino}quinolin-2(1H)-one | 452.0 |
| 649 | 3-(1H-benzimidazol-2-yl)-7-chloro-4-[(2-piperidin-1-ylethyl)amino]quinolin-2(1H)-one | 422.9 |
| 650 | 3-(1H-benzimidazol-2-yl)-7-chloro-4-{[3-(1H-imidazol-1-yl)propyl]amino}quinolin-2(1H)-one | 419.9 |
| 651 | 3-(1H-benzimidazol-2-yl)-7-chloro-4-(pyridin-3-ylamino)quinolin-2(1H)-one | 388.8 |
| 652 | 3-(1H-benzimidazol-2-yl)-7-chloro-4-(pyridin-4-ylamino)quinolin-2(1H)-one | 388.8 |
| 653 | 3-(1H-benzimidazol-2-yl)-7-chloro-4-({[6-(piperidin-3-yloxy)pyridin-3-yl]methyl}amino)quinolin-2(1H)-one | 502.0 |
| 654 | 3-(1H-benzimidazol-2-yl)-7-chloro-4-{[3-(2-oxopyrrolidin-1-yl)propyl]amino}quinolin-2(1H)-one | 436.9 |
| 655 | 4-[4-[(3R)-1-azabicyclo[2.2.2]oct-3-ylamino]-3-(1H-benzimidazol-2-yl)-7-methoxy-2-oxo-1,2-dihydroquinolin-6-yl]benzoic acid | 536.6 |
| 656 | 4-[4-[(3R)-1-azabicyclo[2.2.2]oct-3-ylamino]-3-(1H-benzimidazol-2-yl)-7-methoxy-2-oxo-1,2-dihydroquinolin-6-yl]benzamide | 535.6 |

-continued

TABLE of Additional Exemplary Compounds

| Example | Name | LC/MS m/z (MH+) |
|---|---|---|
| 657 | 6-(4-acetylphenyl)-4-[(3R)-1-azabicyclo[2.2.2]oct-3-ylamino]-3-(1H-benzimidazol-2-yl)-7-methoxyquinolin-2(1H)-one | 534.6 |
| 658 | methyl 4-[4-[(3R)-1-azabicyclo[2.2.2]oct-3-ylamino]-3-(1H-benzimidazol-2-yl)-7-methoxy-2-oxo-1,2-dihydroquinolin-6-yl]benzoate | 550.6 |
| 659 | methyl 3-amino-4-[4-[(3R)-1-azabicyclo[2.2.2]oct-3-ylamino]-3-(1H-benzimidazol-2-yl)-7-methoxy-2-oxo-1,2-dihydroquinolin-6-yl]benzoate | 565.6 |
| 660 | N-{3-[4-[(3R)-1-azabicyclo[2.2.2]oct-3-ylamino]-3-(1H-benzimidazol-2-yl)-7-methoxy-2-oxo-1,2-dihydroquinolin-6-yl]phenyl}acetamide | 549.6 |
| 661 | 6-(3-acetylphenyl)-4-[(3R)-1-azabicyclo[2.2.2]oct-3-ylamino]-3-(1H-benzimidazol-2-yl)-7-methoxyquinolin-2(1H)-one | 534.6 |
| 662 | methyl 3-[4-[(3R)-1-azabicyclo[2.2.2]oct-3-ylamino]-3-(1H-benzimidazol-2-yl)-7-methoxy-2-oxo-1,2-dihydroquinolin-6-yl]benzoate | 550.6 |
| 663 | 3-[4-[(3R)-1-azabicyclo[2.2.2]oct-3-ylamino]-3-(1H-benzimidazol-2-yl)-7-methoxy-2-oxo-1,2-dihydroquinolin-6-yl]benzoic acid | 536.6 |
| 664 | 4-[(3R)-1-azabicyclo[2.2.2]oct-3-ylamino]-3-(1H-benzimidazol-2-yl)-7-methoxy-6-(2-methylphenyl)quinolin-2(1H)-one | 506.6 |
| 665 | 4-[(3R)-1-azabicyclo[2.2.2]oct-3-ylamino]-3-(1H-benzimidazol-2-yl)-6-(2-ethylphenyl)-7-methoxyquinolin-2(1H)-one | 520.6 |
| 666 | 4-[(3R)-1-azabicyclo[2.2.2]oct-3-ylamino]-3-(1H-benzimidazol-2-yl)-7-methoxy-6-(2-methoxyphenyl)quinolin-2(1H)-one | 522.6 |
| 667 | 4-[(3R)-1-azabicyclo[2.2.2]oct-3-ylamino]-3-(1H-benzimidazol-2-yl)-6-(2,4-dichlorophenyl)-7-methoxyquinolin-2(1H)-one | 561.5 |
| 668 | 4-[(3R)-1-azabicyclo[2.2.2]oct-3-ylamino]-3-(1H-benzimidazol-2-yl)-7-[2-(dimethylamino)ethoxy]-6-fluoroquinolin-2(1H)-one | 491.6 |
| 669 | 4-[(3R)-1-azabicyclo[2.2.2]oct-3-ylamino]-3-(1H-benzimidazol-2-yl)-6-fluoro-7-[(2S)-pyrrolidin-2-ylmethoxy]quinolin-2(1H)-one | 503.6 |
| 670 | 4-[(3R)-1-azabicyclo[2.2.2]oct-3-ylamino]-3-(1H-benzimidazol-2-yl)-6-fluoro-7-[2-(2-oxopyrrolidin-1-yl)ethoxy]quinolin-2(1H)-one | 531.6 |
| 671 | 4-[(3R)-1-azabicyclo[2.2.2]oct-3-ylamino]-3-(1H-benzimidazol-2-yl)-6-fluoro-7-{[(2S)-1-(4-nitrophenyl)pyrrolidin-2-yl]methoxy}quinolin-2(1H)-one | 624.7 |
| 672 | 4-[(3R)-1-azabicyclo[2.2.2]oct-3-ylamino]-3-(1H-benzimidazol-2-yl)-6-fluoro-7-[(1-methylpiperidin-2-yl)methoxy]quinolin-2(1H)-one | 531.6 |
| 673 | 3-(1H-benzimidazol-2-yl)-6,7-dimethoxy-4-{[2-(1-methylpyrrolidin-2-yl)ethyl]amino}quinolin-2(1H)-one | 448.5 |
| 674 | 3-(1H-benzimidazol-2-yl)-6,7-dimethoxy-4-{[2-(methylsulfonyl)ethyl]amino}quinolin-2(1H)-one | 443.5 |
| 675 | 3-(1H-benzimidazol-2-yl)-6,7-dimethoxy-4-[(2-morpholin-4-yl-2-pyridin-3-ylethyl)amino]quinolin-2(1H)-one | 527.6 |
| 676 | 7-[(2-aminoethyl)amino]-4-[(3R)-1-azabicyclo[2.2.2]oct-3-ylamino]-3-(1H-benzimidazol-2-yl)-6-fluoroquinolin-2(1H)-one | 462.5 |
| 677 | 4-[(3R)-1-azabicyclo[2.2.2]oct-3-ylamino]-3-(1H-benzimidazol-2-yl-6-fluoro-7-(3-phenylthiomorpholin-4-yl)quinolin-2(1H)-one | 581.7 |
| 678 | 4-[(3R)-1-azabicyclo[2.2.2]oct-3-ylamino]-3-(1H-benzimidazol-2-yl-6-fluoro-7-(2-phenylthiomorpholin-4-yl)quinolin-2(1H)-one | 581.7 |
| 679 | 4-[(3R)-1-azabicyclo[2.2.2]oct-3-ylamino]-3-(1H-benzimidazol-2-yl)-6-fluoro-7-{2-(phenylsulfonyl)ethyl]amino}quinolin-2(1H)-one | 587.7 |
| 680 | 4-[(3R)-1-azabicyclo[2.2.2]oct-3-ylamino]-3-(1H-benzimidazol-2-yl)-6-fluoro-7-{[2-(methylsulfonyl)ethyl]amino}quinolin-2(1H)-one | 525.6 |
| 681 | 7-{[(2R)-2-aminopropyl]amino}-4-[(3R)-1-azabicyclo[2.2.2]oct-3-ylamino]-3-(1H-benzimidazol-2-yl)-6-fluoroquinolin-2(1H)-one | 476.6 |
| 682 | 4-[(3R)-1-azabicyclo[2.2.2]oct-3-ylamino]-3-(1H-benzimidazol-2-yl)-6-flouro-7-[(2-moropholin-4-yl-2-pyridin-3-ylethyl)amino]quionolin-2(1H)-one | 609.7 |
| 683 | 3-[4-[(3R)-1-azabicyclo[2.2.2]oct-3-ylamino]-3-(1H-benzimidazol-2-yl)-7-fluoro-2-oxo-1,2-dihydroquinolin-6-yl]benzoic acid | 524.6 |
| 684 | 4-[4-[(3S)-1-azabicyclo[2.2.2]oct-3-ylamino]-3-(1H-benzimidazol-2-yl)-7-(1H-imidazol-1-yl)-2-oxo-1,2-dihydroquinolin-6-yl]benzoic acid | 572.6 |

-continued

TABLE of Additional Exemplary Compounds

| Example | Name | LC/MS m/z (MH+) |
|---|---|---|
| 685 | 4-[4-[(3S)-1-azabicyclo[2.2.2]oct-3-ylamino]-3-(1H-benzimidazol-2-yl)-7-(2-methyl-1H-imidazol-1-yl)-2-oxo-1,2-dihydroquinolin-6-yl]benzoic acid | 586.7 |
| 686 | 4-[4-[(3S)-1-azabicyclo[2.2.2]oct-3-ylamino]-3-(1H-benzimidazol-2-yl)-2-oxo-7-piperidin-1-yl-1,2-dihydroquinolin-6-yl]benzoic acid | 589.7 |
| 687 | 4-[4-[(3R)-1-azabicyclo[2.2.2]oct-3-ylamino]-3-(1H-benzimidazol-2-yl)-7-(2-ethyl-1H-imidazol-1-yl)-2-oxo-1,2-dihydroquinolin-6-yl]benzoic acid | 600.7 |
| 688 | 3-[4-[(3R)-1-azabicyclo[2.2.2]oct-3-ylamino]-3-(1H-benzimidazol-2-yl)-7-(2-methyl-1H-imidazol-1-yl)-2-oxo-1,2-dihydroquinolin-6-yl]benzoic acid | 586.7 |
| 689 | 3-[4-[(3R)-1-azabicyclo[2.2.2]oct-3-ylamino]-3-(1H-benzimidazol-2-yl)-2-oxo-7-piperidin-1-yl-1,2-dihydroquinolin-6-yl]benzoic acid | 589.7 |
| 690 | 6-chloro-3-[5-(4-methylpiperazin-1-yl)-1H-benzimidazol-2-yl]-4[(piperidin-3-ylmethyl)amino]quinolin-2(1H)-one | 507.1 |
| 691 | 3-[4-[(3S)-1-azabicyclo[2.2.2]oct-3-ylamino]-3-(1H-benzimidazol-2-yl)-7-(1H-imidazol-1-yl)-2-oxo-1,2-dihydroquinolin-6-yl]benzoic acid | 572.6 |
| 692 | 6-chloro-3-[5-(4-methylpiperazin-1-yl)-1H-benzimidazol-2-yl]-4-[(piperidin-4-ylmethyl)amino]quinolin-2(1H)-one | 507.1 |
| 693 | 3-[4-[(3S)-1-azabicyclo[2.2.2]oct-3-ylamino]-3-(1H-benzimidazol-2-yl)-7-(2-methyl-1H-imidazol-1-yl)-2-oxo-1,2-dihydroquinolin-6-yl]benzoic acid | 586.7 |
| 694 | 6-chloro-3-[5-(4-methylpiperazin-1-yl)-1H-benzimidazol-2-yl]-4-[(pyrrolidin-2-ylmethyl)amino]quinolin-2(1H)-one | 493.0 |
| 695 | 3-[4-[(3S)-1-azabicyclo[2.2.2]oct-3-ylamino]-3-(1H-benzimidazol-2-yl)-2-oxo-7-piperidin-1-yl-1,2-dihydroquinolin-6-yl]benzoic acid | 589.7 |
| 696 | 4-{[(2R)-2-aminobutyl]amino}-6-chloro-3-[5-(4-methylpiperazin-1-yl)-1H-benzimidazol-2-yl]quinolin-2(1H)-one | 481.0 |
| 697 | 4-{[(2S)-2-amino-3-methylbutyl]amino}-6-chloro-3-[5-(4-methylpiperazin-1-yl)-1H-benzimidazol-2-yl]quinolin-2(1H)-one | 495.0 |
| 698 | 4-{[(1S)-2-amino-1-benzylethyl]amino}-6-chloro-3-[5-(4-methylpiperazin-1-yl)-1H-benzimidazol-2-yl]quinolin-2(1H)-one | 543.1 |
| 699 | 4-[(3S)-1-azabicyclo[2.2.2]oct-3-ylamino]-6-chloro-3-[5-(4-methylpiperazin-1-yl)-1H-benzimidazol-2-yl]quinolin-2(1H)-one | 519.1 |
| 700 | 6-chloro-3-[5-(4-methylpiperazin-1-yl)-1H-benzimidazol-2-yl]-4-(piperidin-3-ylamino)quinolin-2(1H)-one | 493.0 |
| 701 | 6-chloro-4-{[2-(dimethylamino)ethyl]amino}-3-[5-(4-methylpiperazin-1-yl)-1H-benzimidazol-2-yl]quinolin-2(1H)-one | 481.0 |
| 702 | 7-chloro-3-(5-morpholin-4-yl-1H-benzimidazol-2-yl)-4-(piperidin-4-ylamino)quinolin-2(1H)-one | 480.0 |
| 703 | 4-{[(1R,2R)-2-aminocyclohexyl]amino}-3-(1H-benzimidazol-2-yl)-7-chloroquinolin-2(1H)-one | 408.9 |
| 704 | 3-(1H-benzimidazol-2-yl)-7-chloro-4-[(3-morpholin-4-ylpropyl)amino]quinolin-2(1H)-one | 438.9 |
| 705 | 3-(1H-benzimidazol-2-yl)-7-chloro-4-[(pyridin-3-ylmethyl)amino]quinolin-2(1H)-one | 402.9 |
| 706 | 3-(1H-benzimidazol-2-yl)-7-chloro-4-[(2-pyridin-3-ylethyl)amino]quinolin-2(1H)-one | 416.9 |
| 707 | 4-{[(1R,2R)-2-aminocyclohexyl]amino}-7-chloro-3-(5-morpholin-4-yl-1H-benzimidazol-2-yl)quinolin-2(1H)-one | 494.0 |
| 708 | 4-[(4-aminocyclohexyl)amino]-7-chloro-3-(5-morpholin-4-yl-1H-benzimidazol-2-yl)quinolin-2(1H)-one | 494.0 |
| 709 | 7-chloro-4-{[2-(methylamino)ethyl]amino}-3-(5-morpholin-4-yl-1H-benzimidazol-2-yl)quinolin-2(1H)-one | 453.9 |
| 710 | 7-chloro-3-(5-morpholin-4-yl-1H-benzimidazol-2-yl)-4-[(pyrrolidin-2-ylmethyl)amino]quinolin-2(1H)-one | 480.0 |
| 711 | 4-{[(1S)-2-amino-1-benzylethyl]amino}-7-chloro-3-(5-morpholin-4-yl-1H-benzimidazol-2-yl)quinolin-2(1H)-one | 530.0 |
| 712 | 7-chloro-3-(5-morpholin-4-yl-1H-benzimidazol-2-yl)-4-(pyrrolidin-3-ylamino)quinolin-2(1H)-one | 466.0 |
| 713 | 3-(1H-benzimidazol-2-yl)-7-chloro-4-[(2-pyrrolidin-1-ylethyl)amino]quinolin-2(1H)-one | 408.9 |
| 714 | 3-(1H-benzimidazol-2-yl)-7-chloro-4-[(2-piperidin-2-ylethyl)amino]quinolin-2(1H)-one | 422.9 |
| 715 | 3-(1H-benzimidazol-2-yl)-7-chloro-4-[(piperidin-3-ylmethyl)amino]quinolin-2(1H)-one | 408.9 |
| 716 | 3-(1H-benzimidazol-2-yl)-7-chloro-4-[(piperidin-4-ylmethyl)amino]quinolin-2(1H)-one | 408.9 |
| 717 | 3-(1H-benzimidazol-2-yl)-7-chloro-4-{[(2-methyl-1-piperidin-4-yl-1H-benzimidazol-5-yl)methyl]amino}quinolin-2(1H)-one | 539.1 |

-continued

TABLE of Additional Exemplary Compounds

| Example | Name | LC/MS m/z (MH$^+$) |
|---|---|---|
| 718 | 4-[(4-aminocyclohexyl)amino]-3-(1H-benzimidazol-2-yl)-7-chloroquinolin-2(1H)-one | 408.9 |
| 719 | 3-(1H-benzimidazol-2-yl)-7-chloro-4-(pyrrolidin-3-ylamino)quinolin-2(1H)-one | 380.8 |
| 720 | 4-[(3S)-1-azabicyclo[2.2.2]oct-3-ylamino]-3-(1H-benzimidazol-2-yl)-6-[4-(trifluoromethyl)phenyl]quinolin-2(1H)-one | 530.6 |
| 721 | 4-[(3S)-1-azabicyclo[2.2.2]oct-3-ylamino]-3-(1H-benzimidazol-2-yl)-6-[3-(trifluoromethyl)phenyl]quinolin-2(1H)-one | 530.6 |
| 722 | 4-amino-5-fluoro-3-[6-(4-isopropylpiperazin-1-yl)-1H-benzimidazol-2-yl]quinolin-2(1H)-one | 421.5 |
| 723 | 7-chloro-3-(5-morpholin-4-yl-1H-benzimidazol-2-yl)-4-{[(2S)-pyrrolidin-2-ylmethyl]amino}quinolin-2(1H)-one | 480.0 |
| 724 | 7-chloro-3-(5-morpholin-4-yl-1H-benzimidazol-2-yl)-4-{[(2R)-pyrrolidin-2-ylmethyl]amino}quinolin-2(1H)-one | 480.0 |
| 725 | 7-chloro-4-({[(2S)-1-ethylpyrrolidin-2-yl]methyl}amino)-3-(5-morpholin-4-yl-1H-benzimidazol-2-yl)quinolin-2(1H)-one | 508.0 |
| 726 | 7-chloro-4-({[(2R)-1-ethylpyrrolidin-2-yl]methyl}amino)-3-(5-morpholin-4-yl-1H-benzimidazol-2-yl)quinolin-2(1H)-one | 508.0 |
| 727 | 4-[(3R)-1-azabicyclo[2.2.2]oct-3-ylamino]-7-chloro-3-(5-morpholin-4-yl-1H-benzimidazol-2-yl)quinolin-2(1H)-one | 506.0 |
| 728 | 7-chloro-3-(5-morpholin-4-yl-1H-benzimidazol-2-yl)-4-[(piperidin-3-ylmethyl)amino]quinolin-2(1H)-one | 494.0 |
| 729 | 7-chloro-3-(5-morpholin-4-yl-1H-benzimidazol-2-yl)-4-[(piperidin-4-ylmethyl)amino]quinolin-2(1H)-one | 494.0 |
| 730 | 4-{[(2S)-2-amino-3-methylbutyl]amino}-7-chloro-3-(5-morpholin-4-yl-1H-benzimidazol-2-yl)quinolin-2(1H)-one | 482.0 |
| 731 | 4-{[4-(aminomethyl)benzyl]amino}-7-chloro-3-(5-morpholin-4-yl-1H-benzimidazol-2-yl)quinolin-2(1H)-one | 516.0 |
| 732 | 4-{[(1R)-1-(aminomethyl)propyl]amino}-7-chloro-3-(5-morpholin-4-yl-1H-benzimidazol-2-yl)quinolin-2(1H)-one | 468.0 |
| 733 | 7-choro-4-{[3-(4-methylpiperazin-1-yl)propyl]amino}-3-(5-morpholin-4-yl-1H-benzimidazol-2-yl)quinolin-2(1H)-one | 537.1 |
| 734 | 7-chloro-4-{[3-(1H-imidazol-1-yl)propyl]amino}-3-(5-morpholin-4-yl-1H-benzimidazol-2-yl)quinolin-2(1H)-one | 505.0 |
| 735 | 7-chloro-3-(5-morpholin-4-yl-1H-benzimidazol-2-yl)-4-[(2-pyrrolidin-1-ylethyl)amino]quinolin-2(1H)-one | 494.0 |
| 736 | 7-chloro-3-(5-morpholin-4-yl-1H-benzimidazol-2-yl)-4-[(piperidin-2-ylmethyl)amino]quinolin-2(1H)-one | 494.0 |
| 737 | 7-chloro-4-{[2-(dimethylamino)ethyl]amino}-3-(5-morpholin-4-yl-1H-benzimidazol-2-yl)quinolin-2(1H)-one | 468.0 |
| 738 | 7-chloro-3-(5-morpholin-4-yl-1H-benzimidazol-2-yl)-4-[(3S)-pyrrolidin-3-ylamino]quinolin-2(1H)-one | 466.0 |
| 739 | 4-[(3S)-1-azabicyclo[2.2.2]oct-3-ylamino]-3-(1H-benzimidazol-2-yl)-6-(4-hydroxyphenyl)quinolin-2(1H)-one | 478.6 |
| 740 | 4-[(3S)-1-azabicyclo[2.2.2]oct-3-ylamino]-3-(1H-benzimidazol-2-yl)-6-(3-hydroxyphenyl)quinolin-2(1H)-one | 478.6 |
| 741 | 4-[(3S)-1-azabicyclo[2.2.2]oct-3-ylamino]-3-(1H-benzimidazol-2-yl)-6-(2-hydroxyphenyl)quinolin-2(1H)-one | 478.6 |
| 742 | 3-(1H-benzimidazol-2-yl)-7-chloro-4-{[(2S)-pyrrolidin-2-ylmethyl]amino}quinolin-2(1H)-one | 394.9 |
| 743 | 3-(1H-benzimidazol-2-yl)-7-chloro-4-({[(2S)-1-ethylpyrrolidin-2-yl]methyl}amino)quinolin-2(1H)-one | 422.9 |
| 744 | 3-(1H-benzimidazol-2-yl)-7-chloro-4-({[(2R)-1-ethylpyrrolidin-2-yl]methyl}amino)quinolin-2(1H)-one | 422.9 |
| 745 | 3-(1H-benzimidazol-2-yl)-7-chloro-4-[(3S)-pyrrolidin-3-ylamino]quinolin-2(1H)-one | 380.8 |
| 746 | 3-(1H-benzimidazol-2-yl)-6-chloro-4-{[(2S)-pyrrolidin-2-ylmethyl]amino}quinolin-2(1H)-one | 394.9 |
| 747 | 3-(1H-benzimidazol-2-yl)-6-chloro-4-{[(2R)-pyrrolidin-2-ylmethyl]amino}quinolin-2(1H)-one | 394.9 |
| 748 | 3-(1H-benzimidazol-2-yl)-6-chloro-4-({[(2S)-1-ethylpyrrolidin-2-yl]methyl}amino)quinolin-2(1H)-one | 422.9 |
| 749 | 3-(1H-benzimidazol-2-yl)-6-chloro-4-({[(2R)-1-ethylpyrrolidin-2-yl]methyl}amino)quinolin-2(1H)-one | 422.9 |
| 750 | 4-amino-3-[5-(1,4'-bipiperidin-1'-ylcarbonyl)-1H-benzimidazol-2-yl]quinolin-2(1H)-one | 380.8 |
| 751 | 4-[(3R)-1-azabicyclo[2.2.2]oct-3-ylamino]-7-bromo-3-(5-morpholin-4-yl-1H-benzimidazol-2-yl)quinolin-2(1H)-one | 550.5 |
| 752 | 4-[(3R)-1-azabicyclo[2.2.2]oct-3-ylamino]-7-bromo-3-(6-methoxy-1H-benzimidazol-2-yl)quinolin-2(1H)-one | 495.4 |
| 753 | 3-{[3-(1H-benzimidazol-2-yl)-6,7-dimethoxy-2-oxo-1,2-dihydroquinolin-4-yl]amino}bicyclo[2.2.1]heptane-2-carboxamide | 474.5 |

-continued

TABLE of Additional Exemplary Compounds

| Example | Name | LC/MS m/z (MH+) |
|---|---|---|
| 754 | 4-[(3-amino-2,2-dimethylpropyl)amino]-3-(1H-benzimidazol-2-yl)-6,7-dimethoxyquinolin-2(1H)-one | 422.5 |
| 755 | 3-(1H-benzimidazol-2-yl)-4-{[3-(dimethylamino)-2,2-dimethylpropyl]amino}-6,7-dimethoxyquinolin-2(1H)-one | 450.6 |
| 756 | 3-(1H-benzimidazol-2-yl)-7-chloro-4-[(pyridin-2-ylmethyl)amino]quinolin-2(1H)-one | 402.9 |
| 757 | 3-(1H-benzimidazol-2-yl)-7-chloro-4-[(2-pyridin-2-ylethyl)amino]quinolin-2(1H)-one | 416.9 |
| 758 | 3-(1H-benzimidazol-2-yl)-7-chloro-4-{[2-(methylamino)ethyl]amino}quinolin-2(1H)-one | 368.8 |
| 759 | 3-(1H-benzimidazol-2-yl)-7-chloro-4-[(piperidin-2-ylmethyl)amino]quinolin-2(1H)-one | 408.9 |
| 760 | 3-(1H-benzimidazol-2-yl)-7-chloro-4-(piperidin-4-ylamino)quinolin-2(1H)-one | 394.9 |
| 761 | 4-amino-3-[5-(1,4'-bipiperidin-1'-ylcarbonyl)-1H-benzimidazol-2-yl]quinolin-2(1H)-one | 471.6 |
| 762 | 4-amino-3-{5-[(3S)-3-(dimethylnitroryl)pyrrolidin-1-yl]-1H-benzimidazol-2-yl}quinolin-2(1H)-one | 405.5 |
| 763 | 4-amino-3-(5-{2-[(dimethylamino)methyl]morpholin-4-yl}-1H-benzimidazol-2-yl)quinolin-2(1H)-one | 419.5 |
| 764 | methyl 4-[4-[(3R)-1-azabicyclo[2.2.2]oct-3-ylamino]-3-(1H-benzimidazol-2-yl)-5-methyl-2-oxo-1,2-dihydroquinolin-6-yl]benzoate | 534.6 |
| 765 | 3-[4-[(3R)-1-azabicyclo[2.2.2]oct-3-ylamino]-3-(1H-benzimidazol-2-yl)-5-methyl-2-oxo-1,2-dihydroquinolin-6-yl]benzoic acid | 520.6 |
| 766 | 4-[4-[(3R)-1-azabicyclo[2.2.2]oct-3-ylamino]-3-(1H-benzimidazol-2-yl)-5-methyl-2-oxo-1,2-dihydroquinolin-6-yl]benzamide | 519.6 |
| 767 | 4-[4-[(3R)-1-azabicyclo[2.2.2]oct-3-ylamino]-3-(1H-benzimidazol-2-yl)-5-methyl-2-oxo-1,2-dihydroquinolin-6-yl]benzoic acid | 520.6 |
| 768 | 4-amino-3-{5-[(2S)-2-(pyrrolidin-1-ylmethyl)pyrrolidin-1-yl]-1H-benzimidazol-2-yl}quinolin-2(1H)-one | 429.5 |
| 769 | 2-(4-amino-5-fluoro-2-oxo-1,2-dihydroquinolin-3-yl)-N-methyl-N-(1-methylpiperidin-4-yl)-1H-benzimidazole-6-carboxamide | 449.5 |
| 770 | 4-amino-3-(1H-benzimidazol-2-yl)-5-[(1-methylpiperidin-4-yl)oxy]quinolin-2(1H)-one | 390.5 |
| 771 | 4-amino-5-(1-azabicyclo[2.2.2]oct-3-yloxy)-3-(1H-benzimidazol-2-yl)quinolin-2(1H)-one | 402.5 |
| 772 | 4-amino-5-fluoro-3-{6-[(2-piperidin-1-ylethyl)amino]-1H-benzimidazol-2-yl}quinolin-2(1H)-one | 421.5 |
| 773 | 4,6-diamino-3-[6-(4-methylpiperazin-1-yl)-1H-benzimidazol-2-yl]quinolin-2(1H)-one | 390.5 |
| 774 | 2-(4-amino-5-fluoro-2-oxo-1,2-dihydroquinolin-3-yl)-1H-benzimidazole-5-carboxylic acid | 339.3 |
| 775 | 2-(4-amino-2-oxo-1,2-dihydroquinolin-3-yl)-N-pyridin-3-yl-1H-benzimidazole-5-carboxamide | 397.4 |
| 776 | 4-amino-3-(5-{[(3R)-3-hydroxypyrrolidin-1-yl]carbonyl}-1H-benzimidazol-2-yl)quinolin-2(1H)-one | 390.4 |
| 777 | N-{4-amino-3-[6-(4-methylpiperazin-1-yl)-1H-benzimidazol-2-yl]-2-oxo-1,2-dihydroquinolin-6-yl}acetamide | 432.5 |
| 778 | 4-amino-5-fluoro-3-(6-morpholin-4-yl-1H-benzimidazol-2-yl)quinolin-2(1H)-one | 380.4 |
| 779 | 3-(5-chloro-1H-benzimidazol-2-yl)-4-{[2-(dimethylamino)ethyl]amino}-6-methylquinolin-2(1H)-one | 396.9 |
| 780 | 4-{[(1R,2R)-2-aminocyclohexyl]amino}-3-(5-chloro-1H-benzimidazol-2-yl)-6-methylquinolin-2(1H)-one | 422.9 |
| 781 | 3-(5-chloro-1H-benzimidazol-2-yl)-6-methyl-4-[(piperidin-3-ylmethyl)amino]quinolin-2(1H)-one | 422.9 |
| 782 | 3-(5-chloro-1H-benzimidazol-2-yl)-6-methyl-4-[(piperidin-4-ylmethyl)amino]quinolin-2(1H)-one | 422.9 |
| 783 | 4-[(4-aminocyclohexyl)amino]-3-(5-chloro-1H-benzimidazol-2-yl)-6-methylquinolin-2(1H)-one | 422.9 |
| 784 | 3-(5-chloro-1H-benzimidazol-2-yl)-6-methyl-4-{[2-(methylamino)ethyl]amino}quinolin-2(1H)-one | 382.9 |
| 785 | 3-(5-chloro-1H-benzimidazol-2-yl)-6-methyl-4-(pyrrolidin-3-ylamino)quinolin-2(1H)-one | 394.9 |
| 786 | 3-(5-chloro-1H-benzimidazol-2-yl)-6-methyl-4-[(piperidin-2-ylmethyl)amino]quinolin-2(1H)-one | 422.9 |
| 787 | 4-[(3S)-1-azabicyclo[2.2.2]oct-3-ylamino]-3-(5-chloro-1H-benzimidazol-2-yl)-6-methylquinolin-2(1H)-one | 434.9 |
| 788 | 4-[(3R)-1-azabicyclo[2.2.2]oct-3-ylamino]-3-(5-chloro-1H-benzimidazol-2-yl)-6-methylquinolin-2(1H)-one | 434.9 |

-continued

TABLE of Additional Exemplary Compounds

| Example | Name | LC/MS m/z (MH+) |
|---|---|---|
| 789 | 4-amino-3-(6-{(2R,5R)-2-[(dimethylamino)methyl]-5-methylmorpholin-4-yl}-1H-benzimidazol-2-yl)quinolin-2(1H)-one | 433.5 |
| 790 | 4-amino-3-(5-{[(3R)-3-hydroxypiperidin-1-yl]carbonyl}-1H-benzimidazol-2-yl)quinolin-2(1H)-one | 404.4 |
| 791 | 2-(4-amino-2-oxo-1,2-dihydroquinolin-3-yl)-N-(2-piperidin-1-ylethyl)-1H-benzimidazole-5-carboxamide | 431.5 |
| 792 | 4-amino-3-[5-(piperazin-1-ylcarbonyl)-1H-benzimidazol-2-yl]quinolin-2(1H)-one | 389.4 |
| 793 | N-{4-amino-3-[6-(4-methylpiperazin-1-yl)-1H-benzimidazol-2-yl]-2-oxo-1,2-dihydroquinolin-6-yl}-2,2-dimethylpropanamide | 474.6 |
| 794 | N-{4-amino-3-[6-(4-methylpiperazin-1-yl)-1H-benzimidazol-2-yl]-2-oxo-1,2-dihydroquinolin-6-yl}-3-phenylpropanamide | 522.6 |
| 795 | N-{4-amino-3-[6-(4-methylpiperazin-1-yl)-1H-benzimidazol-2-yl]-2-oxo-1,2-dihydroquinolin-6-yl}-2-(benzyloxy)acetamide | 538.6 |
| 796 | N-{4-amino-3-[6-(4-methylpiperazin-1-yl)-1H-benzimidazol-2-yl]-2-oxo-1,2-dihydroquinolin-6-yl}-2-thien-2-ylacetamide | 514.6 |
| 797 | N-{4-amino-3-[6-(4-methylpiperazin-1-yl)-1H-benzimidazol-2-yl]-2-oxo-1,2-dihydroquinolin-6-yl}-2-furamide | 484.5 |
| 798 | 2-(4-amino-2-oxo-1,2-dihydroquinolin-3-yl)-N-(2-pyrrolidin-1-ylethyl)-1H-benzimidazole-5-carboxamide | 417.5 |
| 799 | ethyl (4-{[2-(4-amino-2-oxo-1,2-dihydroquinolin-3-yl)-1H-benzimidazol-5-yl]carbonyl}piperazin-1-yl)acetate | 475.5 |
| 800 | N-{4-amino-3-[6-(4-methylpiperazin-1-yl)-1H-benzimidazol-2-yl]-2-oxo-1,2-dihydroquinolin-6-yl}-N'-phenylurea | 509.6 |
| 801 | N-{4-amino-3-[6-(4-methylpiperazin-1-yl)-1H-benzimidazol-2-yl]-2-oxo-1,2-dihydroquinolin-6-yl}-N'-benzylurea | 523.6 |
| 802 | N-{4-amino-3-[6-(4-methylpiperazin-1-yl)-1H-benzimidazol-2-yl]-2-oxo-1,2-dihydroquinolin-6-yl}-N'-(2-phenylethyl)urea | 537.6 |
| 803 | N-{4-amino-3-[6-(4-methylpiperazin-1-yl)-1H-benzimidazol-2-yl]-2-oxo-1,2-dihydroquinolin-6-yl}benzamide | 494.6 |
| 804 | 2-(4-amino-2-oxo-1,2-dihydroquinolin-3-yl)-N-piperidin-3-yl-1H-benzimidazole-5-carboxamide | 403.5 |
| 805 | 2-(4-amino-2-oxo-1,2-dihydroquinolin-3-yl)-N-[(3R)-1-azabicyclo[2.2.2]oct-3-yl]-1H-benzimidazole-6-carboxamide | 429.5 |
| 806 | 2-(4-amino-2-oxo-1,2-dihydroquinolin-3-yl)-N-[2-(diethylamino)ethyl]-N-ethyl-1H-benzimidazole-5-carboxamide | 447.6 |
| 807 | 4-amino-3-[6-(pyridin-4-yloxy)-1H-benzimidazol-2-yl]quinolin-2(1H)-one | 370.4 |
| 808 | 4-amino-5-fluoro-3-{6-[(4-methylpiperazin-1-yl)carbonyl]-1H-benzimidazol-2-yl}quinolin-2(1H)-one | 421.4 |
| 809 | 4-amino-5-fluoro-3-{6-[(4-isopropylpiperazin-1-yl)carbonyl]-1H-benzimidazol-2-yl}quinolin-2(1H)-one | 449.5 |
| 810 | 4-amino-3-{6-[(4-cyclohexylpiperazin-1-yl)carbonyl]-1H-benzimidazol-2-yl}-5-fluoroquinolin-2(1H)-one | 489.6 |
| 811 | 4-amino-6-(isobutylamino)-3-[6-(4-methylpiperazin-1-yl)-1H-benzimidazol-2-yl]quinolin-2(1H)-one | 446.6 |
| 812 | 2-(4-amino-5-fluoro-2-oxo-1,2-dihydroquinolin-3-yl)-N-methyl-N-(1-methylpyrrolidin-3-yl)-1H-benzimidazole-6-carboxamide | 488.6 |
| 813 | 4-amino-6-[(2-methylbutyl)amino]-3-[6-(4-methylpiperazin-1-yl)-1H-benzimidazol-2-yl]quinolin-2(1H)-one | 460.6 |
| 814 | 4-amino-6-[(cyclohexylmethyl)amino]-3-[6-(4-methylpiperazin-1-yl)-1H-benzimidazol-2-yl]quinolin-2(1H)-one | 486.6 |
| 815 | 4-amino-3-(6-{[(3S)-3-methylpiperazin-1-yl]carbonyl}-1H-benzimidazol-2-yl)quinolin-2(1H)-one | 403.5 |
| 816 | 2-(4-amino-2-oxo-1,2-dihydroquinolin-3-yl)-N-[(3S)-1-azabicyclo[2.2.2]oct-3-yl]-1H-benzimidazole-6-carboxamide | 429.5 |
| 817 | 4-amino-3-[6-(1,4'-bipiperidin-1'-ylcarbonyl)-1H-benzimidazol-2-yl]-5-fluoroquinolin-2(1H)-one | 489.6 |
| 818 | 2-(4-amino-5-fluoro-2-oxo-1,2-dihydroquinolin-3-yl)-N-methyl-N-(1-methylpyrrolidin-3-yl)-1H-benzimidazole-6-carboxamide | 435.5 |
| 819 | 4-amino-3-(1H-benzimidazol-2-yl)-5-[(4-methoxyphenyl)thio]quinolin-2(1H)-one | 415.5 |
| 820 | 4-amino-3-(1H-benzimidazol-2-yl)-5-[(4-methoxyphenyl)sulfonyl]quinolin-2(1H)-one | 447.5 |
| 821 | 4-amino-3-(1H-benzimidazol-2-yl)-5-[(2-methoxyphenyl)thio]quinolin-2(1H)-one | 415.5 |
| 822 | N-(4-{[2-(4-amino-2-oxo-1,2-dihydroquinolin-3-yl)-1H-benzimidazol-5-yl]oxy}phenyl)acetamide | 426.4 |
| 823 | 4-amino-6-(benzylamino)-3-[6-(4-methylpiperazin-1-yl)-1H-benzimidazol-2-yl]quinolin-2(1H)-one | 480.6 |
| 824 | 4-amino-3-[6-(4-methylpiperazin-1-yl)-1H-benzimidazol-2-yl]-6-{[(3-phenoxythien-2-yl)methyl]amino}quinolin-2(1H)-one | 578.7 |

-continued

TABLE of Additional Exemplary Compounds

| Example | Name | LC/MS m/z (MH+) |
|---|---|---|
| 825 | 4-amino-3-[6-(4-methylpiperazin-1-yl)-1H-benzimidazol-2-yl]-6-{[(3-methylthien-2-yl)methyl]amino}quinolin-2(1H)-one | 500.6 |
| 826 | 4-amino-3-[6-(4-methylpiperazin-1-yl)-1H-benzimidazol-2-yl]-6-[(1,3-thiazol-2-ylmethyl)amino]quinolin-2(1H)-one | 487.6 |
| 827 | 4-amino-3-[6-(4-methylpiperazin-1-yl)-1H-benzimidazol-2-yl]-6-[(pyrazin-2-ylmethyl)amino]quinolin-2(1H)-one | 482.6 |
| 828 | 4-amino-3-(5-{2-[(dimethylamino)methyl]-1,4-oxazepan-4-yl}-1H-benzimidazol-2-yl)-5-fluoroquinolin-2(1H)-one | 433.5 |
| 829 | 4-amino-3-(5-{2-[(dimethylamino)methyl]-1,4-oxazepan-4-yl}-1H-benzimidazol-2-yl)-5-fluoroquinolin-2(1H)-one | 451.5 |
| 830 | 6-chloro-4-{[2-(dimethylamino)-2-pyridin-3-ylethyl]amino}-3-(5-morpholin-4-yl-1H-benzimidazol-2-yl)quinolin-2(1H)-one | 545.1 |
| 831 | 6-amino-4-[(3S)-1-azabicyclo[2.2.2]oct-3-ylamino]-3-(1H-benzimidazol-2-yl)quinolin-2(1H)-one | 401.5 |
| 832 | 6-chloro-3-(5-chloro-1H-benzimidazol-2-yl)-4-{[2-(dimethylamino)ethyl]amino}quinolin-2(1H)-one | 417.3 |
| 833 | 4-{[(1R,2R)-2-aminocyclohexyl]amino}-6-chloro-3-(5-chloro-1H-benzimidazol-2-yl)quinolin-2(1H)-one | 443.3 |
| 834 | 6-chloro-3-(5-chloro-1H-benzimidazol-2-yl)-4-[(piperidin-3-ylmethyl)amino]quinolin-2(1H)-one | 443.3 |
| 835 | 6-chloro-3-(5-chloro-1H-benzimidazol-2-yl)-4-[(piperidin-4-ylmethyl)amino]quinolin-2(1H)-one | 443.3 |
| 836 | 4-[(4-aminocyclohexyl)amino]-6-chloro-3-(5-chloro-1H-benzimidazol-2-yl)quinolin-2(1H)-one | 443.3 |
| 837 | 6-chloro-3-(5-chloro-1H-benzimidazol-2-yl)-4-{[2-(methylamino)ethyl]amino}quinolin-2(1H)-one | 403.3 |
| 838 | 6-chloro-3-(5-chloro-1H-benzimidazol-2-yl)-4-(pyrrolidin-3-ylamino)quinolin-2(1H)-one | 415.3 |
| 839 | 6-chloro-3-(5-chloro-1H-benzimidazol-2-yl)-4-[(piperidin-2-ylmethyl)amino]quinolin-2(1H)-one | 443.3 |
| 840 | 4-[(3S)-1-azabicyclo[2.2.2]oct-3-ylamino]-6-chloro-3-(5-chloro-1H-benzimidazol-2-yl)quinolin-2(1H)-one | 455.4 |
| 841 | 4-[(3R)-1-azabicyclo[2.2.2]oct-3-ylamino]-6-chloro-3-(5-chloro-1H-benzimidazol-2-yl)quinolin-2(1H)-one | 455.4 |
| 842 | 4-amino-3-[6-(4-methylpiperazin-1-yl)-1H-benzimidazol-2-yl]-6-{[(2S)-pyrrolidin-2-ylmethyl]amino}quinolin-2(1H)-one | 473.6 |
| 843 | 4-amino-6-{[(5-methylisoxazol-3-yl)methyl]amino}-3-[6-(4-methylpiperazin-1-yl)-1H-benzimidazol-2-yl]quinolin-2(1H)-one | 485.6 |
| 844 | 4-amino-3-(5-{(2S,5R)-2-[(dimethylamino)methyl]-5-methylmorpholin-4-yl}-1H-benzimidazol-2-yl)quinolin-2(1H)-one | 433.5 |
| 845 | 3-(5-chloro-1H-benzimidazol-2-yl)-4-{[2-(dimethylamino)ethyl]amino}-6,7-difluoroquinolin-2(1H)-one | 418.8 |
| 846 | 4-{[(1R,2R)-2-aminocyclohexyl]amino}-3-(5-chloro-1H-benzimidazol-2-yl)-6,7-difluoroquinolin-2(1H)-one | 444.9 |
| 847 | 3-(5-chloro-1H-benzimidazol-2-yl)-6,7-difluoro-4-[(piperidin-3-ylmethyl)amino]quinolin-2(1H)-one | 444.9 |
| 848 | 3-(5-chloro-1H-benzimidazol-2-yl)-6,7-difluoro-4-[(piperidin-4-ylmethyl)amino]quinolin-2(1H)-one | 444.9 |
| 849 | 4-[(4-aminocyclohexyl)amino]-3-(5-chloro-1H-benzimidazol-2-yl)-6,7-difluoroquinolin-2(1H)-one | 444.9 |
| 850 | 3-(5-chloro-1H-benzimidazol-2-yl)-6,7-difluoro-4-{[2-(methylamino)ethyl]amino}quinolin-2(1H)-one | 404.8 |
| 851 | 3-(5-chloro-1H-benzimidazol-2-yl)-6,7-difluoro-4-(pyrrolidin-3-ylamino)quinolin-2(1H)-one | 416.8 |
| 852 | 3-(5-chloro-1H-benzimidazol-2-yl)-6,7-difluoro-4-[(piperidin-2-ylmethyl)amino]quinolin-2(1H)-one | 444.9 |
| 853 | 4-[(3S)-1-azabicyclo[2.2.2]oct-3-ylamino]-3-(5-chloro-1H-benzimidazol-2-yl)-6,7-difluoroquinolin-2(1H)-one | 456.9 |
| 854 | 4-[(3R)-1-azabicyclo[2.2.2]oct-3-ylamino]-3-(5-chloro-1H-benzimidazol-2-yl)-6,7-difluoroquinolin-2(1H)-one | 456.9 |
| 855 | 4-amino-3-(6-{[(3R)-3-methylpiperazin-1-yl]carbonyl}-1H-benzimidazol-2-yl)quinolin-2(1H)-one | 403.5 |
| 856 | 4-amino-3-(5-{[(3S)-3-hydroxypyrrolidin-1-yl]carbonyl}-1H-benzimidazol-2-yl)quinolin-2(1H)-one | 390.4 |
| 857 | 4-amino-3-(5-{[4-(2-hydroxyethyl)piperazin-1-yl]carbonyl}-1H-benzimidazol-2-yl)quinolin-2(1H)-one | 433.5 |
| 858 | 4-amino-3-[6-(4-isopropylpiperazin-1-yl)-1H-benzimidazol-2-yl]-5-methoxyquinolin-2(1H)-one | 433.5 |
| 859 | 4-amino-3-(5-{3-[(dimethylamino)methyl]pyrrolidin-1-yl}-1H-benzimidazol-2-yl)quinolin-2(1H)-one | 403.5 |
| 860 | 4-amino-3-(5-{3-[(dimethylamino)methyl]pyrrolidin-1-yl}-1H-benzimidazol-2-yl)-5-fluoroquinolin-2(1H)-one | 421.5 |

-continued

TABLE of Additional Exemplary Compounds

| Example | Name | LC/MS m/z (MH+) |
|---|---|---|
| 861 | 4-amino-3-(6-{(2R,5S)-2-[(dimethylamino)methyl]-5-methylmorpholin-4-yl}-1H-benzimidazol-2-yl)quinolin-2(1H)-one | 433.5 |
| 862 | 4-amino-3-[6-(4-methylpiperazin-1-yl)-1H-benzimidazol-2-yl]-6-(piperidin-4-ylamino)quinolin-2(1H)-one | 473.6 |
| 863 | 6-chloro-3-[5-(4-methylpiperazin-1-yl)-1H-benzimidazol-2-yl]-4-[(3S)-pyrrolidin-3-ylamino]quinolin-2(1H)-one | 479.0 |
| 864 | 4-amino-3-{5-[(3R)-3-(dimethylamino)pyrrolidin-1-yl]-1H-benzimidazol-2-yl}-5-fluoroquinolin-2(1H)-one | 407.5 |
| 865 | 4-amino-3-{5-[(3S)-3-(dimethylamino)pyrrolidin-1-yl]-1H-benzimidazol-2-yl}-5-fluoroquinolin-2(1H)-one | 407.5 |
| 866 | 4-amino-3-[6-(2,6-dimethylmorpholin-4-yl)-1H-benzimidazol-2-yl]-5-fluoroquinolin-2(1H)-one | 408.4 |
| 867 | 4-amino-3-{6-[(3-aminopyrrolidin-1-yl)carbonyl]-1H-benzimidazol-2-yl}quinolin-2(1H)-one | 389.4 |
| 868 | ethyl (3S,4R)-4-({[2-(4-amino-2-oxo-1,2-dihydroquinolin-3-yl)-1H-benzimidazol-6-yl]carbonyl}amino)-3-methoxypiperidine-1-carboxylate | 505.5 |
| 869 | 6-amino-3-(1H-benzimidazol-2-yl)-4-[(3S)-pyrrolidin-3-ylamino]quinolin-2(1H)-one | 361.4 |
| 870 | 4-amino-3-(6-{(2R,5S)-2-[(dimethylamino)methyl]-5-methylmorpholin-4-yl}-1H-benzimidazol-2-yl)-5-fluoroquinolin-2(1H)-one | 451.5 |
| 871 | N-{(3S)-1-[2-(4-amino-2-oxo-1,2-dihydroquinolin-3-yl)-1H-benzimidazol-6-yl]pyrrolidin-3-yl}-N-methylacetamide | 417.5 |
| 872 | 2-(4-amino-2-oxo-1,2-dihydroquinolin-3-yl)-N-piperidin-4-yl-1H-benzimidazole-6-carboxamide | 403.5 |
| 873 | 2-(4-amino-2-oxo-1,2-dihydroquinolin-3-yl)-N-[2-(1-methylpyrrolidin-2-yl)ethyl]-1H-benzimidazole-6-carboxamide | 431.5 |
| 874 | N-{4-amino-3-[6-(4-methylpiperazin-1-yl)-1H-benzimidazol-2-yl]-2-oxo-1,2-dihydroquinolin-6-yl}-N'-isopropylurea | 475.6 |
| 875 | N-{4-amino-3-[6-(4-methylpiperazin-1-yl)-1H-benzimidazol-2-yl]-2-oxo-1,2-dihydroquinolin-6-yl}-N'-(3,5-dimethylphenyl)urea | 537.6 |
| 876 | N-allyl-N'-{4-amino-3-[6-(4-methylpiperazin-1-yl)-1H-benzimidazol-2-yl]-2-oxo-1,2-dihydroquinolin-6-yl}urea | 473.6 |
| 877 | N-{4-amino-3-[6-(4-methylpiperazin-1-yl)-1H-benzimidazol-2-yl]-2-oxo-1,2-dihydroquinolin-6-yl}-N'-(tert-butyl)urea | 489.6 |
| 878 | N-{4-amino-3-[6-(4-methylpiperazin-1-yl)-1H-benzimidazol-2-yl]-2-oxo-1,2-dihydroquinolin-6-yl}-N'-[2-(methylthio)phenyl]urea | 555.7 |
| 879 | N-{4-amino-3-[6-(4-methylpiperazin-1-yl)-1H-benzimidazol-2-yl]-2-oxo-1,2-dihydroquinolin-6-yl}heptanamide | 502.6 |
| 880 | 4-amino-3-[6-(4-methylpiperazin-1-yl)-1H-benzimidazol-2-yl]-6-(neopentylamino)quinolin-2(1H)-one | 460.6 |
| 881 | N-{4-amino-3-[6-(4-methylpiperazin-1-yl)-1H-benzimidazol-2-yl]-2-oxo-1,2-dihydroquinolin-6-yl}-N'-(3,4-dichlorophenyl)urea | 578.5 |
| 882 | N-{4-amino-3-[6-(4-methylpiperazin-1-yl)-1H-benzimidazol-2-yl]-2-oxo-1,2-dihydroquinolin-6-yl}-N'-[3-(trifluoromethyl)phenyl]urea | 577.6 |
| 883 | N-{4-amino-3-[6-(4-methylpiperazin-1-yl)-1H-benzimidazol-2-yl]-2-oxo-1,2-dihydroquinolin-6-yl}-N'-heptylurea | 531.7 |
| 884 | N-{4-amino-3-[6-(4-methylpiperazin-1-yl)-1H-benzimidazol-2-yl]-2-oxo-1,2-dihydroquinolin-6-yl}-N'-(2-ethoxyphenyl)urea | 553.6 |
| 885 | N-{4-amino-3-[6-(4-methylpiperazin-1-yl)-1H-benzimidazol-2-yl]-2-oxo-1,2-dihydroquinolin-6-yl}-2-methylpropanamide | 460.6 |
| 886 | N-{4-amino-3-[6-(4-methylpiperazin-1-yl)-1H-benzimidazol-2-yl]-2-oxo-1,2-dihydroquinolin-6-yl}-4-ethylbenzamide | 522.6 |
| 887 | N-{4-amino-3-[6-(4-methylpiperazin-1-yl)-1H-benzimidazol-2-yl]-2-oxo-1,2-dihydroquinolin-6-yl}-4-cyanobenzamide | 519.6 |
| 888 | N-{4-amino-3-[6-(4-methylpiperazin-1-yl)-1H-benzimidazol-2-yl]-2-oxo-1,2-dihydroquinolin-6-yl}cyclohexanecarboxamide | 500.6 |
| 889 | N-{4-amino-3-[6-(4-methylpiperazin-1-yl)-1H-benzimidazol-2-yl]-2-oxo-1,2-dihydroquinolin-6-yl}pyrazine-2-carboxamide | 496.5 |
| 890 | N-{4-amino-3-[6-(4-methylpiperazinyl)benzimidazol-2-yl]-2-oxo(6-hydroquinolyl)}-2-[benzylamino]acetamide | 537.6 |
| 891 | 4-amino-6-[methyl(1-methylpiperidin-4-yl)amino]-3-[6-(4-methylpiperazin-1-yl)-1H-benzimidazol-2-yl]quinolin-2(1H)-one | 501.6 |
| 892 | 4-amino-6-[({5-[(dimethylamino)methyl]-2-furyl}methyl)amino]-3-[6-(4-methylpiperazin-1-yl)-1H-benzimidazol-2-yl]quinolin-2(1H)-one | 527.6 |
| 893 | 4-amino-6-{[(2-ethyl-5-methyl-4H-imidazol-4-yl)methyl]amino}-3-[6-(4-methylpiperazin-1-yl)-1H-benzimidazol-2-yl]quinolin-2(1H)-one | 512.6 |

-continued

TABLE of Additional Exemplary Compounds

| Example | Name | LC/MS m/z (MH+) |
|---|---|---|
| 894 | N-{4-amino-3-[6-(4-methylpiperazin-1-yl)-1H-benzimidazol-2-yl]-2-oxo-1,2-dihydroquinolin-6-yl}butanamide | 460.6 |
| 895 | 4-amino-3-(5-{[(2R)-2-(pyrrolidin-1-ylmethyl)pyrrolidin-1-yl]carbonyl}-1H-benzimidazol-2-yl)quinolin-2(1H)-one | 457.5 |
| 896 | 4-amino-3-[5-({(2R,5R)-2-[(dimethylamino)methyl]-5-methylmorpholin-4-yl}carbonyl)-1H-benzimidazol-2-yl]quinolin-2(1H)-one | 461.5 |
| 897 | 4-amino-3-[5-({(2S,5R)-2-[(dimethylamino)methyl]-5-methylmorpholin-4-yl}carbonyl)-1H-benzimidazol-2-yl]quinolin-2(1H)-one | 461.5 |
| 898 | 4-amino-5-fluoro-3-(6-{[(3S)-3-methylpiperazin-1-yl]carbonyl}-1H-benzimidazol-2-yl)quinolin-2(1H)-one | 421.4 |
| 899 | 4-amino-5-fluoro-3-(6-{[(3R)-3-methylpiperazin-1-yl]carbonyl}-1H-benzimidazol-2-yl)quinolin-2(1H)-one | 421.4 |
| 900 | 4-amino-5-fluoro-3-(5-{[(2R)-2-(pyrrolidin-1-ylmethyl)pyrrolidin-1-yl]carbonyl}-1H-benzimidazol-2-yl)quinolin-2(1H)-one | 475.5 |
| 901 | 4-amino-6-(dimethylamino)-3-[5-(4-methylpiperazin-1-yl)-1H-benzimidazol-2-yl]quinolin-2(1H)-one | 418.5 |
| 902 | 4-amino-6-(methylamino)-3-[5-(4-methylpiperazin-1-yl)-1H-benzimidazol-2-yl]quinolin-2(1H)-one | 404.5 |
| 903 | 4-amino-5-fluoro-3-[5-fluoro-6-(4-methylpiperazin-1-yl)-1H-benzimidazol-2-yl]quinolin-2(1H)-one | 411.4 |
| 904 | 4-amino-3-[6-({(2R,5S)-2-[(dimethylamino)methyl]-5-methylmorpholin-4-yl}carbonyl)-1H-benzimidazol-2-yl]quinolin-2(1H)-one | 461.5 |
| 905 | 4-amino-3-[6-({(2S,5S)-2-[(dimethylamino)methyl]-5-methylmorpholin-4-yl}carbonyl)-1H-benzimidazol-2-yl]quinolin-2(1H)-one | 461.5 |
| 906 | 4-amino-3-{6-[(3,5-dimethylpiperazin-1-yl)carbonyl]-1H-benzimidazol-2-yl}quinolin-2(1H)-one | 417.5 |
| 907 | 4-amino-3-[5-(4-ethylpiperazin-1-yl)-1H-benzimidazol-2-yl]-5-fluoroquinolin-2(1H)-one | 407.5 |
| 908 | 4-amino-3-[6-({(2R,5S)-2-[(dimethylamino)methyl]-5-methylmorpholin-4-yl}carbonyl)-1H-benzimidazol-2-yl]-5-fluoroquinolin-2(1H)-one | 479.5 |
| 909 | 4-amino-3-[6-({(2S,5S)-2-[(dimethylamino)methyl]-5-methylmorpholin-4-yl}carbonyl)-1H-benzimidazol-2-yl]-5-fluoroquinolin-2(1H)-one | 479.5 |
| 910 | 4-amino-3-[5-({(2R,5R)-2-[(dimethylamino)methyl]-5-methylmorpholin-4-yl}carbonyl)-1H-benzimidazol-2-yl]-5-fluoroquinolin-2(1H)-one | 479.5 |
| 911 | 4-amino-3-[5-({(2S,5R)-2-[(dimethylamino)methyl]-5-methylmorpholin-4-yl}carbonyl)-1H-benzimidazol-2-yl]-5-fluoroquinolin-2(1H)-one | 479.5 |
| 912 | N-[3-({4-amino-3-[6-(4-methylpiperazin-1-yl)-1H-benzimidazol-2-yl]-2-oxo-1,2-dihydroquinolin-5-yl}oxy)phenyl]acetamide | 524.6 |
| 913 | 4-amino-3-{6-[(4-ethylpiperazin-1-yl)carbonyl]-1H-benzimidazol-2-yl}quinolin-2(1H)-one | 417.5 |
| 914 | 2-(4-amino-2-oxo-1,2-dihydroquinolin-3-yl)-N,N'-dimethyl-1H-benzimidazole-6-carbohydrazide | 363.4 |
| 915 | 2-(4-amino-2-oxo-1,2-dihydroquinolin-3-yl)-N-(tetrahydrofuran-2-ylmethyl)-1H-benzimidazole-6-carboxamide | 404.4 |
| 916 | 4-amino-5-[3-(dimethylamino)phenoxy]-3-[6-(4-methylpiperazin-1-yl)-1H-benzimidazol-2-yl]quinolin-2(1H)-one | 510.6 |
| 917 | 4-amino-5-(4-aminophenoxy)-3-[6-(4-methylpiperazin-1-yl)-1H-benzimidazol-2-yl]quinolin-2(1H)-one | 482.6 |
| 918 | 6-chloro-4-{[2-(dimethylamino)ethyl]amino}-3-(6-fluoro-1H-benzimidazol-2-yl)quinolin-2(1H)-one | 400.9 |
| 919 | 4-{[(1R,2R)-2-aminocyclohexyl]amino}-6-chloro-3-(6-fluoro-1H-benzimidazol-2-yl)quinolin-2(1H)-one | 426.9 |
| 920 | 6-chloro-3-(6-fluoro-1H-benzimidazol-2-yl)-4-[(piperidin-3-ylmethyl)amino]quinolin-2(1H)-one | 426.9 |
| 921 | 6-chloro-3-(6-fluoro-1H-benzimidazol-2-yl)-4-[(piperidin-4-ylmethyl)amino]quinolin-2(1H)-one | 426.9 |
| 922 | 4-[(4-aminocyclohexyl)amino]-6-chloro-3-(6-fluoro-1H-benzimidazol-2-yl)quinolin-2(1H)-one | 426.9 |
| 923 | 6-chloro-3-(6-fluoro-1H-benzimidazol-2-yl)-4-{[2-(methylamino)ethyl]amino}quinolin-2(1H)-one | 386.8 |
| 924 | 6-chloro-3-(6-fluoro-1H-benzimidazol-2-yl)-4-[(3S)-pyrrolidin-3-ylamino]quinolin-2(1H)-one | 398.8 |
| 925 | 6-chloro-3-(6-fluoro-1H-benzimidazol-2-yl)-4-[(3R)-pyrrolidin-3-ylamino]quinolin-2(1H)-one | 398.8 |

-continued

TABLE of Additional Exemplary Compounds

| Example | Name | LC/MS m/z (MH⁺) |
|---|---|---|
| 926 | 6-chloro-3-(6-fluoro-1H-benzimidazol-2-yl)-4-[(piperidin-2-ylmethyl)amino]quinolin-2(1H)-one | 426.9 |
| 927 | 4-[(3S)-1-azabicyclo[2.2.2]oct-3-ylamino]-6-chloro-3-(6-fluoro-1H-benzimidazol-2-yl)quinolin-2(1H)-one | 438.9 |
| 928 | 6-bromo-4-{[2-(dimethylamino)ethyl]amino}-3-(6-fluoro-1H-benzimidazol-2-yl)quinolin-2(1H)-one | 445.3 |
| 929 | 4-{[(1R,2R)-2-aminocyclohexyl]amino}-6-bromo-3-(6-fluoro-1H-benzimidazol-2-yl)quinolin-2(1H)-one | 471.3 |
| 930 | 6-bromo-3-(6-fluoro-1H-benzimidazol-2-yl)-4-[(piperidin-3-ylmethyl)amino]quinolin-2(1H)-one | 471.3 |
| 931 | 6-bromo-3-(6-fluoro-1H-benzimidazol-2-yl)-4-[(piperidin-4-ylmethyl)amino]quinolin-2(1H)-one | 471.3 |
| 932 | 4-[(4-aminocyclohexyl)amino]-6-bromo-3-(6-fluoro-1H-benzimidazol-2-yl)quinolin-2(1H)-one | 471.3 |
| 933 | 6-bromo-3-(6-fluoro-1H-benzimidazol-2-yl)-4-{[2-(methylamino)ethyl]amino}quinolin-2(1H)-one | 431.3 |
| 934 | 6-bromo-3-(6-fluoro-1H-benzimidazol-2-yl)-4-[(3S)-pyrrolidin-3-ylamino]quinolin-2(1H)-one | 443.3 |
| 935 | 6-bromo-3-(6-fluoro-1H-benzimidazol-2-yl)-4-[(piperidin-2-ylmethyl)amino]quinolin-2(1H)-one | 471.3 |
| 936 | 4-[(3S)-1-azabicyclo[2.2.2]oct-3-ylaminol]-6-bromo-3-(6-fluoro-1H-benzimidazol-2-yl)quinolin-2(1H)-one | 483.4 |
| 937 | 6-bromo-3-(6-fluoro-1H-benzimidazol-2-yl)-4-[(3R)-pyrrolidin-3-ylamino]quinolin-2(1H)-one | 443.3 |
| 938 | N-[4-({4-amino-3-[6-(4-methylpiperazin-1-yl)-1H-benzimidazol-2-yl]-2-oxo-1,2-dihydroquinolin-5-yl}oxy)phenyl]acetamide | 524.6 |
| 939 | 4-amino-3-{6-[(4-ethylpiperazin-1-yl)carbonyl]-1H-benzimidazol-2-yl}-5-fluoroquinolin-2(1H)-one | 435.5 |
| 940 | ethyl (3S,4R)-4-({[2-(4-amino-5-fluoro-2-oxo-1,2-dihydroquinolin-3-yl)-1H-benzimidazol-6-yl]carbonyl}amino)-3-methoxypiperidine-1-carboxylate | 523.5 |
| 941 | 2-(4-amino-5-fluoro-2-oxo-1,2-dihydroquinolin-3-yl)-N-[(3R)-1-azabicyclo[2.2.2]oct-3-yl]-1H-benzimidazole-6-carboxamide | 447.5 |
| 942 | 2-(4-amino-5-fluoro-2-oxo-1,2-dihydroquinolin-3-yl)-N-[(3S)-1-azabicyclo[2.2.2]oct-3-yl]-1H-benzimidazole-6-carboxamide | 447.5 |
| 943 | 4-amino-5-fluoro-3-{5-[(5-methyl-2,5-diazabicyclo[2.2.1]hept-2-yl)carbonyl]-1H-benzimidazol-2-yl}quinolin-2(1H)-one | 433.5 |
| 944 | 4-amino-3-[5-(1,4'-bipiperidin-1'-yl)-1H-benzimidazol-2-yl]-5-fluoroquinolin-2(1H)-one | 461.6 |
| 945 | 4-[(3S)-1-azabicyclo[2.2.2]oct-3-ylamino]-6-chloro-3-(7-morpholin-4-yl-1H-benzimidazol-2-yl)quinolin-2(1H)-one | 506.0 |
| 946 | 6-chloro-3-(7-morpholin-4-yl-1H-benzimidazol-2-yl)-4-(piperidin-4-ylamino)quinolin-2(1H)-one | 480.0 |
| 947 | 6-chloro-3-(7-morpholin-4-yl-1H-benzimidazol-2-yl)-4-[(3S)-pyrrolidin-3-ylamino]quinolin-2(1H)-one | 466.0 |
| 948 | 4-amino-7-fluoro-3-[5-(4-methylpiperazin-1-yl)-1H-benzimidazol-2-yl]quinolin-2(1H)-one | 393.4 |
| 949 | 4-amino-3-{6-[(2,6-dimethylpiperazin-1-yl)carbonyl]-1H-benzimidazol-2-yl}quinolin-2(1H)-one | 417.5 |
| 950 | 4-amino-3-(5-{(2S,5R)-2-[(dimethylamino)methyl]-5-methylmorpholin-4-yl}-1H-benzimidazol-2-yl)-5-fluoroquinolin-2(1H)-one | 451.5 |
| 951 | 6-chloro-3-(5-morpholin-4-yl-1H-benzimidazol-2-yl)-4-[(3S)-pyrrolidin-3-ylamino]quinolin-2(1H)-one | 466.0 |
| 952 | 4-amino-3-(5-{(2S,5S)-2-[(dimethylamino)methyl]-5-methylmorpholin-4-yl}-1H-benzimidazol-2-yl)-5-fluoroquinolin-2(1H)-one | 451.5 |
| 953 | 4-amino-3-(1H-benzimidazol-2-yl)-6-[methyl(1-methylpiperidin-4-yl)amino]quinolin-2(1H)-one | 403.5 |
| 954 | 4-amino-6-[isobutyl(methyl)amino]-3-[6-(4-methylpiperazin-1-yl)-1H-benzimidazol-2-yl]quinolin-2(1H)-one | 460.6 |
| 955 | 4-amino-6-[(cyclohexylmethyl)(methyl)amino]-3-[6-(4-methylpiperazin-1-yl)-1H-benzimidazol-2-yl]quinolin-2(1H)-one | 500.7 |
| 956 | 4,6-diamino-3-(6,7-dimethyl-1H-benzimidazol-2-yl)quinolin-2(1H)-one | 320.4 |
| 957 | 4-amino-3-(6,7-dimethyl-1H-benzimidazol-2-yl)-6-(methylamino)quinolin-2(1H)-one | 334.4 |
| 958 | 4-amino-3-(5,6-dimethyl-1H-benzimidazol-2-yl)-6-(methylamino)quinolin-2(1H)-one | 334.4 |
| 959 | 4,6-diamino-3-(1H-benzimidazol-2-yl)quinolin-2(1H)-one | 292.3 |
| 960 | 4-amino-3-(6,7-dimethyl-1H-benzimidazol-2-yl)-6-(isobutylamino)quinolin-2(1H)-one | 376.5 |
| 961 | 4-amino-3-(5,6-dimethyl-1H-benzimidazol-2-yl)-6-(isobutylamino)quinolin-2(1H)-one | 376.5 |

-continued

TABLE of Additional Exemplary Compounds

| Example | Name | LC/MS m/z (MH+) |
|---|---|---|
| 962 | N-(3-{[2-(4-amino-2-oxo-1,2-dihydroquinolin-3-yl)-1H-benzimidazol-6-yl]oxy}phenyl)acetamide | 426.4 |
| 963 | 4-amino-3-[6-(3,4-dimethylpiperazin-1-yl)-1H-benzimidazol-2-yl]quinolin-2(1H)-one | 389.5 |
| 964 | N-[3-({4-amino-3-[6-(4-methylpiperazin-1-yl)-1H-benzimidazol-2-yl]-2-oxo-1,2-dihydroquinolin-6-yl}oxy)phenyl]acetamide | 524.6 |
| 965 | 4-amino-3-(6-{(2R,5R)-2-[(dimethylamino)methyl]-5-methylmorpholin-4-yl}-1H-benzimidazol-2-yl)-5-fluoroquinolin-2(1H)-one | 451.5 |
| 966 | 4-{[(1R,2R)-2-aminocyclohexyl]amino}-6-bromo-3-(6-chloro-5-fluoro-1H-benzimidazol-2-yl)quinolin-2(1H)-one | 505.8 |
| 967 | 6-bromo-3-(6-chloro-5-fluoro-1H-benzimidazol-2-yl)-4-[(piperidin-4-ylmethyl)amino]quinolin-2(1H)-one | 505.8 |
| 968 | 4-[(4-aminocyclohexyl)amino]-6-bromo-3-(6-chloro-5-fluoro-1H-benzimidazol-2-yl)quinolin-2(1H)-one | 505.8 |
| 969 | 6-bromo-3-(6-chloro-5-fluoro-1H-benzimidazol-2-yl)-4-{[2-(methylamino)ethyl]amino}quinolin-2(1H)-one | 465.7 |
| 970 | 6-bromo-3-(6-chloro-5-fluoro-1H-benzimidazol-2-yl)-4-(pyrrolidin-3-ylamino)quinolin-2(1H)-one | 477.7 |
| 971 | 6-bromo-3-(6-chloro-5-fluoro-1H-benzimidazol-2-yl)-4-[(3R)-pyrrolidin-3-ylamino]quinolin-2(1H)-one | 477.7 |
| 972 | 6-bromo-3-(6-chloro-5-fluoro-1H-benzimidazol-2-yl)-4-[(piperidin-2-ylmethyl)amino]quinolin-2(1H)-one | 505.8 |
| 973 | 4-[(3S)-1-azabicyclo[2.2.2]oct-3-ylamino]-6-bromo-3-(6-chloro-5-fluoro-1H-benzimidazol-2-yl)quinolin-2(1H)-one | 517.8 |
| 974 | 4-[(3R)-1-azabicyclo[2.2.2]oct-3-ylamino]-6-bromo-3-(6-chloro-5-fluoro-1H-benzimidazol-2-yl)quinolin-2(1H)-one | 517.8 |
| 975 | 4-[(3R)-1-azabicyclo[2.2.2]oct-3-ylamino]-6-bromo-3-(6-fluoro-1H-benzimidazol-2-yl)quinolin-2(1H)-one | 483.4 |
| 976 | 4-[(3R)-1-azabicyclo[2.2.2]oct-3-ylamino]-6-chloro-3-(6-fluoro-1H-benzimidazol-2-yl)quinolin-2(1H)-one | 438.9 |
| 977 | 4-amino-6-[bis(cyclohexylmethyl)amino]-3-(6,7-dimethyl-1H-benzimidazol-2-yl)quinolin-2(1H)-one | 512.7 |
| 978 | 4-amino-6-[bis(cyclohexylmethyl)amino]-3-(5,6-dimethyl-1H-benzimidazol-2-yl)quinolin-2(1H)-one | 512.7 |
| 979 | 4-amino-5-(methylamino)-3-[6-(4-methylpiperazin-1-yl)-1H-benzimidazol-2-yl]quinolin-2(1H)-one | 404.5 |
| 980 | 4-amino-6-[(cyclohexylmethyl)amino]-3-(6,7-dimethyl-1H-benzimidazol-2-yl)quinolin-2(1H)-one | 416.5 |
| 981 | 4-amino-6-[(cyclohexylmethyl)amino]-3-(5,6-dimethyl-1H-benzimidazol-2-yl)quinolin-2(1H)-one | 416.5 |
| 982 | 4-amino-6,7-difluoro-3-[5-(4-methylpiperazin-1-yl)-1H-benzimidazol-2-yl]quinolin-2(1H)-one | 411.4 |
| 983 | 4-amino-5-fluoro-3-[6-(2-methylpiperazin-1-yl)-1H-benzimidazol-2-yl]quinolin-2(1H)-one | 393.4 |
| 984 | 4-amino-7-fluoro-3-{6-[(4-isopropylpiperazin-1-yl)carbonyl]-1H-benzimidazol-2-yl}quinolin-2(1H)-one | 449.5 |
| 985 | 4-amino-3-[6-(2,4-dimethylpiperazin-1-yl)-1H-benzimidazol-2-yl]-5-fluoroquinolin-2(1H)-one | 407.5 |
| 986 | 2-(4-amino-7-fluoro-2-oxo-1,2-dihydroquinolin-3-yl)-N-methyl-N-(1-methylpiperidin-4-yl)-1H-benzimidazole-5-carboxamide | 449.5 |
| 987 | 6-chloro-3-(5-chloro-1H-benzimidazol-2-yl)-4-[(3S)-pyrrolidin-3-ylamino]quinolin-2(1H)-one | 415.3 |
| 988 | 4-amino-7-fluoro-3-(5-{[(2R)-2-(pyrrolidin-1-ylmethyl)pyrrolidin-1-yl]carbonyl}-1H-benzimidazol-2-yl)quinolin-2(1H)-one | 475.5 |
| 989 | 4-amino-3-{6-[4-(2-methoxyethyl)piperazin-1-yl]-1H-benzimidazol-2-yl}quinolin-2(1H)-one | 419.5 |
| 990 | 4-amino-3-[5-(methylamino)-1H-benzimidazol-2-yl]quinolin-2(1H)-one | 306.3 |
| 991 | 6-chloro-3-[5-(4-methylpiperazin-1-yl)-1H-benzimidazol-2-yl]-4-{[(3S)-1-methylpyrrolidin-3-yl]amino}quinolin-2(1H)-one | 493.0 |
| 992 | 6-chloro-3-(5-chloro-1H-benzimidazol-2-yl)-4-{[(3S)-1-methylpyrrolidin-3-yl]amino}quinolin-2(1H)-one | 429.3 |
| 993 | 3-(1H-benzimidazol-2-yl)-6-chloro-4-{[(3S)-1-methylpyrrolidin-3-yl]amino}quinolin-2(1H)-one | 394.9 |
| 994 | 3-(1H-benzimidazol-2-yl)-6-chloro-4-[(1-methylpiperidin-4-yl)amino]quinolin-2(1H)-one | 408.9 |
| 995 | 6-chloro-3-(5-chloro-1H-benzimidazol-2-yl)-4-[(1-methylpiperidin-4-yl)amino]quinolin-2(1H)-one | 443.3 |
| 996 | 6-chloro-3-[5-(4-methylpiperazin-1-yl)-1H-benzimidazol-2-yl]-4-[(1-methylpiperidin-4-yl)amino]quinolin-2(1H)-one | 507.1 |
| 997 | 6-chloro-3-[5-(4-methylpiperazin-1-yl)-1H-benzimidazol-2-yl]-4-{[(1-methylpiperidin-2-yl)methyl]amino}quinolin-2(1H)-one | 521.1 |

-continued

TABLE of Additional Exemplary Compounds

| Example | Name | LC/MS m/z (MH+) |
|---|---|---|
| 998 | 4-[(3S)-1-azabicyclo[2.2.2]oct-3-ylamino]-6-chloro-3-{5-[methyl(1-methylpiperidin-4-yl)amino]-1H-benzimidazol-2-yl}quinolin-2(1H)-one | 547.1 |
| 999 | 6-chloro-3-{5-[methyl(1-methylpiperidin-4-yl)amino]-1H-benzimidazol-2-yl}-4-(piperidin-4-ylamino)quinolin-2(1H)-one | 521.1 |
| 1000 | 6-chloro-3-{5-[methyl(1-methylpiperidin-4-yl)amino]-1H-benzimidazol-2-yl}-4-[(3S)-pyrrolidin-3-ylamino]quinolin-2(1H)-one | 507.1 |
| 1001 | 4-{[(2R)-2-aminobutyl]amino}-6-chloro-3-{5-[methyl(1-methylpiperidin-4-yl)amino]-1H-benzimidazol-2-yl}quinolin-2(1H)-one | 509.1 |
| 1002 | 4-amino-3-{6-[(3S)-3,4-dimethylpiperazin-1-yl]-1H-benzimidazol-2-yl}quinolin-2(1H)-one | 389.5 |
| 1003 | 4-amino-3-[5-(4-methylpiperazin-1-yl)-1H-benzimidazol-2-yl]-2-oxo-1,2-dihydroquinoline-6-carbonitrile | 400.5 |
| 1004 | 4-amino-3-[5-(4-methylpiperazin-1-yl)-1H-benzimidazol-2-yl]-2-oxo-1,2-dihydroquinoline-6-carboxylic acid | 419.5 |
| 1005 | 4-amino-5-fluoro-3-{5-[(8aS)-hexahydropyrrolo[1,2-a]pyrazin-2(1H)-yl]-1H-benzimidazol-2-yl}quinolin-2(1H)-one | 419.5 |
| 1006 | 4-amino-3-{6-[(3S)-3,4-dimethylpiperazin-1-yl]-1H-benzimidazol-2-yl}-5-fluoroquinolin-2(1H)-one | 407.5 |
| 1007 | 4-[(3S)-1-azabicyclo[2.2.2]oct-3-ylamino]-6-chloro-3-{6-[(3R)-3-(dimethylamino)pyrrolidin-1-yl]-1H-benzimidazol-2-yl}quinolin-2(1H)-one | 533.1 |
| 1008 | 6-chloro-3-{6-[(3R)-3-(dimethylamino)pyrrolidin-1-yl]-1H-benzimidazol-2-yl}-4-(piperidin-4-ylamino)quinolin-2(1H)-one | 507.1 |
| 1009 | 6-chloro-3-{6-[(3R)-3-(dimethylamino)pyrrolidin-1-yl]-1H-benzimidazol-2-yl}-4-[(3S)-pyrrolidin-3-ylamino]quinolin-2(1H)-one | 493.0 |
| 1010 | 4-{[(2R)-2-aminobutyl]amino}-6-chloro-3-{6-[(3R)-3-(dimethylamino)pyrrolidin-1-yl]1H-benzimidazol-2-yl}quinolin-2(1H)-one | 495.0 |
| 1011 | 6-chloro-3-{6-[(3R)-3-(dimethylamino)pyrrolidin-1-yl]-1H-benzimidazol-2-yl}-4-{[(3S)-1-methylpyrrolidin-3-yl]amino}quinolin-2(1H)-one | 507.1 |
| 1012 | 6-chloro-3-{6-[(3R)-3-(dimethylamino)pyrrolidin-1-yl]-1H-benzimidazol-2-yl}-4-[(1-methylpiperidin-4-yl)amino]quinolin-2(1H)-one | 521.1 |
| 1013 | 4-amino-7-(methylamino)-3-[6-(4-methylpiperazin-1-yl)-1H-benzimidazol-2-yl]quinolin-2(1H)-one | 404.5 |
| 1014 | 3-(1H-benzimidazol-2-yl)-6-chloro-4-[(2-morpholin-4-yl-2-pyridin-3-ylethyl)amino]quinolin-2(1H)-one | 502.0 |
| 1015 | 3-(1H-benzimidazol-2-yl)-6-chloro-4-{[2-(dimethylamino)-2-pyridin-3-ylethyl]amino}quinolin-2(1H)-one | 460.0 |
| 1016 | 4-[(3S)-1-azabicyclo[2.2.2]oct-3-ylamino]-6-chloro-3-(6-{3-[(dimethylamino)methyl]pyrrolidin-1-yl}-1H-benzimidazol-2-yl)quinolin-2(1H)-one | 547.1 |
| 1017 | 6-chloro-3-(6-{3-[(dimethylamino)methyl]pyrrolidin-1-yl}-1H-benzimidazol-2-yl)-4-(piperidin-4-ylamino)quinolin-2(1H)-one | 521.1 |
| 1018 | 6-chloro-3-(6-{3-[(dimethylamino)methyl]pyrrolidin-1-yl}-1H-benzimidazol-2-yl)-4-[(3S)-pyrrolidin-3-ylamino]quinolin-2(1H)-one | 507.1 |
| 1019 | 4-{[(2R)-2-aminobutyl]amino}-6-chloro-3-(6-{3-[(dimethylamino)methyl]pyrrolidin-1-yl}-1H-benzimidazol-2-yl)quinolin-2(1H)-one | 509.1 |
| 1020 | chloro-3-(6-{3-[(dimethylamino)methyl]pyrrolidin-1-yl}-1H-benzimidazol-2-yl)-4-{[(3S)-1-methylpyrrolidin-3-yl]amino}quinolin-2(1H)-one | 521.1 |
| 1021 | 6-chloro-3-(6-{3-[(dimethylamino)methyl]pyrrolidin-1-yl}-1H-benzimidazol-2-yl)-4-[(1-methylpiperidin-4-yl)amino]quinolin-2(1H)-one | 535.1 |
| 1022 | 3-(1H-benzimidazol-2-yl)-6-chloro-4-{[(3S)-piperidin-3-ylmethyl]amino}quinolin-2(1H)-one | 408.9 |
| 1023 | 3-(1H-benzimidazol-2-yl)-6-chloro-4-{[(3R)-piperidin-3-ylmethyl]amino}quinolin-2(1H)-one | 408.9 |
| 1024 | N-(3-{[4-amino-3-(1H-benzimidazol-2-yl)-2-oxo-1,2-dihydroquinolin-5-yl]oxy}phenyl)acetamide | 426.4 |
| 1025 | 4-[(3S)-1-azabicyclo[2.2.2]oct-3-ylamino]-6-chloro-3-{6-[3-(dimethylamino)pyrrolidin-1-yl]-1H-benzimidazol-2-yl}quinolin-2(1H)-one | 533.1 |
| 1026 | 6-chloro-3-{6-[3-(dimethylamino)pyrrolidin-1-yl]-1H-benzimidazol-2-yl}-4-(piperidin-4-ylamino)quinolin-2(1H)-one | 507.1 |

-continued

TABLE of Additional Exemplary Compounds

| Example | Name | LC/MS m/z (MH+) |
|---|---|---|
| 1027 | 4-{[(2R)-2-aminobutyl]amino}-6-chloro-3-{6-[3-(dimethylamino)pyrrolidin-1-yl]-1H-benzimidazol-2-yl}quinolin-2(1H)-one | 495.0 |
| 1028 | 6-chloro-3-{6-[3-(dimethylamino)pyrrolidin-1-yl]-1H-benzimidazol-2-yl}-4-[(1-methylpiperidin-4-yl)amino]quinolin-2(1H)-one | 521.1 |
| 1029 | 4-amino-7-[[2-(dimethylamino)ethyl](methyl)amino]-3-[6-(4-methylpiperazin-1-yl)-1H-benzimidazol-2-yl]quinolin-2(1H)-one | 475.6 |
| 1030 | 4-amino-5-fluoro-3-[6-(1,4-oxazepan-4-ylcarbonyl)-1H-benzimidazol-2-yl]quinolin-2(1H)-one | 422.4 |
| 1031 | methyl 4-amino-3-[5-(4-methylpiperazin-1-yl)-1H-benzimidazol-2-yl]-2-oxo-1,2-dihydroquinoline-6-carboxylate | 433.5 |
| 1032 | 4-amino-N-benzyl-3-[5-(4-methylpiperazin-1-yl)-1H-benzimidazol-2-yl]-2-oxo-1,2-dihydroquinoline-6-carboxamide | 508.6 |
| 1033 | 4-amino-3-{6-[4-(2-morpholin-4-ylethyl)piperazin-1-yl]-1H-benzimidazol-2-yl}quinolin-2(1H)-one | 474.6 |
| 1034 | 4-amino-7-fluoro-3-[6-(4-isopropylpiperazin-1-yl)-1H-benzimidazol-2-yl]quinolin-2(1H)-one | 421.5 |
| 1035 | 4-amino-3-[5-(4-ethylpiperazin-1-yl)-1H-benzimidazol-2-yl]-7-fluoroquinolin-2(1H)-one | 407.5 |
| 1036 | 4-amino-3-{6-[(2-aminoethyl)(methyl)amino]-1H-benzimidazol-2-yl}quinolin-2(1H)-one | 349.4 |
| 1037 | 4-amino-3-{6-[[(2-ethyl-4-methyl-1H-imidazol-5-yl)methyl](methyl)amino]-1H-benzimidazol-2-yl}quinolin-2(1H)-one | 428.5 |
| 1038 | 4-amino-3-[6-(hydroxymethyl)-1H-benzimidazol-2-yl]quinolin-2(1H)-one | 307.3 |
| 1039 | 4-amino-3-(6-{methyl[(2R)-pyrrolidin-2-ylmethyl]amino}-1H-benzimidazol-2-yl)quinolin-2(1H)-one | 389.5 |
| 1040 | 4-amino-3-{6-[(1H-imidazol-2-ylmethyl)(methyl)amino]-1H-benzimidazol-2-yl}quinolin-2(1H)-one | 386.4 |
| 1041 | 4-amino-3-{6-[(2-furylmethyl)(methyl)amino]-1H-benzimidazol-2-yl}quinolin-2(1H)-one | 386.4 |
| 1042 | 4-amino-3-{6-[methyl(piperidin-4-ylmethyl)amino]-1H-benzimidazol-2-yl}quinolin-2(1H)-one | 403.5 |
| 1043 | 4-amino-3-{6-[methyl(piperidin-3-ylmethyl)amino]-1H-benzimidazol-2-yl}quinolin-2(1H)-one | 403.5 |
| 1044 | 4-amino-3-(6-{methyl[2-(methylamino)ethyl]amino}-1H-benzimidazol-2-yl)quinolin-2(1H)-one | 363.4 |
| 1045 | 6-acetyl-4-amino-3-[6-(4-methylpiperazin-1-yl)-1H-benzimidazol-2-yl]quinolin-2(1H)-one | 417.5 |
| 1046 | 4-amino-5-[2-(methylamino)phenoxy]-3-[6-(4-methylpiperazin-1-yl)-1H-benzimidazol-2-yl]quinolin-2(1H)-one | 496.6 |
| 1047 | 3-(1H-benzimidazol-2-yl)-6-chloro-4-{[(2S)-piperidin-2-ylmethyl]amino}quinolin-2(1H)-one | 408.9 |
| 1048 | 4-amino-3-[6-(1,4-oxazepan-4-yl)-1H-benzimidazol-2-yl]quinolin-2(1H)-one | 376.4 |
| 1049 | 4-amino-3-[5-(4-ethylpiperazin-1-yl)-1H-benzimidazol-2-yl]-6-fluoroquinolin-2(1H)-one | 407.5 |
| 1050 | 6-chloro-3-(5-chloro-1H-benzimidazol-2-yl)-4-[(3R)-pyrrolidin-3-ylamino]quinolin-2(1H)-one | 415.3 |
| 1051 | 4-amino-6-fluoro-3-[5-(4-methylpiperazin-1-yl)-1H-benzimidazol-2-yl]-7-morpholin-4-ylquinolin-2(1H)-one | 478.5 |
| 1052 | 4-amino-6-fluoro-3-[5-(4-methylpiperazin-1-yl)-1H-benzimidazol-2-yl]-7-pyrrolidin-1-ylquinolin-2(1H)-one | 462.5 |
| 1053 | 4-amino-7-(dimethylamino)-6-fluoro-3-[5-(4-methylpiperazin-1-yl)-1H-benzimidazol-2-yl]quinolin-2(1H)-one | 436.5 |
| 1054 | 4-amino-6-fluoro-7-(4-methylpiperazin-1-yl)-3-[5-(4-methylpiperazin-1-yl)-1H-benzimidazol-2-yl]quinolin-2(1H)-one | 491.6 |
| 1055 | 4-amino-6-fluoro-7-[(4-methoxybenzyl)amino]-3-[5-(4-methylpiperazin-1-yl)-1H-benzimidazol-2-yl]quinolin-2(1H)-one | 528.6 |
| 1056 | 4-amino-6-fluoro-3-[5-(4-methylpiperazin-1-yl)-1H-benzimidazol-2-yl]-7-[(pyridin-4-ylmethyl)amino]quinolin-2(1H)-one | 499.6 |
| 1057 | 4-amino-7-[[2-(dimethylamino)ethyl](methyl)amino]-6-fluoro-3-[5-(4-methylpiperazin-1-yl)-1H-benzimidazol-2-yl]quinolin-2(1H)-one | 493.6 |
| 1058 | 4-amino-3-[6-(4-cyclopentylpiperazin-1-yl)-1H-benzimidazol-2-yl]-5-fluoroquinolin-2(1H)-one | 447.5 |
| 1059 | 4-amino-6-[1-(methylamino)ethyl]-3-[6-(4-methylpiperazin-1-yl)-1H-benzimidazol-2-yl]quinolin-2(1H)-one | 432.5 |
| 1060 | 4-amino-5-fluoro-3-[6-(1,4-oxazepan-4-yl)-1H-benzimidazol-2-yl]quinolin-2(1H)-one | 394.4 |

-continued

TABLE of Additional Exemplary Compounds

| Example | Name | LC/MS m/z (MH+) |
|---|---|---|
| 1061 | 4-amino-3-{6-[methyl(pyridin-3-ylmethyl)amino]-1H-benzimidazol-2-yl}quinolin-2(1H)-one | 397.5 |
| 1062 | 4-amino-3-{6-[({5-[(dimethylamino)methyl]-2-furyl}methyl)(methyl)amino]-1H-benzimidazol-2-yl}quinolin-2(1H)-one | 443.5 |
| 1063 | 4-amino-3-[6-(4-oxopiperidin-1-yl)-1H-benzimidazol-2-yl]quinolin-2(1H)-one | 374.4 |
| 1064 | 4-amino-3-{6-[4-(4-methylpiperazin-1-yl)piperidin-1-yl]-1H-benzimidazol-2-yl}quinolin-2(1H)-one | 458.6 |
| 1065 | 4-amino-3-[6-(4-{[(4-benzylmorpholin-2-yl)methyl]amino}piperidin-1-yl)-1H-benzimidazol-2-yl]quinolin-2(1H)-one | 564.7 |
| 1066 | 3-(1H-benzimidazol-2-yl)-6-bromo-4-{[2-(dimethylamino)ethyl]amino}quinolin-2(1H)-one | 427.3 |
| 1067 | 4-{[(1R,2R)-2-aminocyclohexyl]amino}-3-(1H-benzimidazol-2-yl)-6-bromoquinolin-2(1H)-one | 453.4 |
| 1068 | 3-(1H-benzimidazol-2-yl)-6-bromo-4-[(piperidin-4-ylmethyl)amino]quinolin-2(1H)-one | 453.4 |
| 1069 | 4-[(4-aminocyclohexyl)amino]-3-(1H-benzimidazol-2-yl)-6-bromoquinolin-2(1H)-one | 453.4 |
| 1070 | 3-(1H-benzimidazol-2-yl)-6-bromo-4-{[2-(methylamino)ethyl]amino}quinolin-2(1H)-one | 413.3 |
| 1071 | 3-(1H-benzimidazol-2-yl)-6-bromo-4-[(3S)-pyrrolidin-3-ylamino]quinolin-2(1H)-one | 425.3 |
| 1072 | 3-(1H-benzimidazol-2-yl)-6-bromo-4-[(3R)-pyrrolidin-3-ylamino]quinolin-2(1H)-one | 425.3 |
| 1073 | 3-(1H-benzimidazol-2-yl)-6-bromo-4-[(piperidin-2-ylmethyl)amino]quinolin-2(1H)-one | 453.4 |
| 1074 | 4-amino-N-[(3S)-1-azabicyclo[2.2.2]oct-3-yl]-3-[5-(4-methylpiperazin-1-yl)-1H-benzimidazol-2-yl]-2-oxo-1,2-dihydroquinoline-6-carboxamide | 527.6 |
| 1075 | 4-amino-N-methyl-3-[5-(4-methylpiperazin-1-yl)-1H-benzimidazol-2-yl]-N-(1-methylpiperidin-4-yl)-2-oxo-1,2-dihydroquinoline-6-carboxamide | 529.7 |
| 1076 | 4-amino-3-[5-(4-methylpiperazin-1-yl)-1H-benzimidazol-2-yl]-2-oxo-N-(tetrahydrofuran-2-ylmethyl)-1,2-dihydroquinoline-6-carboxamide | 502.6 |
| 1077 | 3-(1H-benzimidazol-2-yl)-6-chloro-4-[(3R)-pyrrolidin-3-ylamino]quinolin-2(1H)-one | 380.8 |
| 1078 | 3-(1H-benzimidazol-2-yl)-6-chloro-4-{[(2R)-piperidin-2-ylmethyl]amino}quinolin-2(1H)-one | 408.9 |
| 1079 | 4-amino-3-{6-[(3R)-3,4-dimethylpiperazin-1-yl]-1H-benzimidazol-2-yl}-5-fluoroquinolin-2(1H)-one | 407.5 |
| 1080 | 6-chloro-3-(6-chloro-5-fluoro-1H-benzimidazol-2-yl)-4-{[2-(dimethylamino)ethyl]amino}quinolin-2(1H)-one | 435.3 |
| 1081 | 4-{[(1R,2R)-2-aminocyclohexyl]amino}-6-chloro-3-(6-chloro-5-fluoro-1H-benzimidazol-2-yl)quinolin-2(1H)-one | 461.3 |
| 1082 | 6-chloro-3-(6-chloro-5-fluoro-1H-benzimidazol-2-yl)-4-[(piperidin-4-ylmethyl)amino]quinolin-2(1H)-one | 461.3 |
| 1083 | 4-[(4-aminocyclohexyl)amino]-6-chloro-3-(6-chloro-5-fluoro-1H-benzimidazol-2-yl)quinolin-2(1H)-one | 461.3 |
| 1084 | 6-chloro-3-(6-chloro-5-fluoro-1H-benzimidazol-2-yl)-4-{[2-(methylamino)ethyl]amino}quinolin-2(1H)-one | 421.3 |
| 1085 | 6-chloro-3-(6-chloro-5-fluoro-1H-benzimidazol-2-yl)-4-[(3S)-pyrrolidin-3-ylamino]quinolin-2(1H)-one | 433.3 |
| 1086 | 6-chloro-3-(6-chloro-5-fluoro-1H-benzimidazol-2-yl)-4-[(3R)-pyrrolidin-3-ylamino]quinolin-2(1H)-one | 433.3 |
| 1087 | 6-chloro-3-(6-chloro-5-fluoro-1H-benzimidazol-2-yl)-4-[(piperidin-2-ylmethyl)amino]quinolin-2(1H)-one | 461.3 |
| 1088 | 4-[(3S)-1-azabicyclo[2.2.2]oct-3-ylamino]-6-chloro-3-(6-chloro-5-fluoro-1H-benzimidazol-2-yl)quinolin-2(1H)-one | 473.3 |
| 1089 | 4-[(3R)-1-azabicyclo[2.2.2]oct-3-ylamino]-6-chloro-3-(6-chloro-5-fluoro-1H-benzimidazol-2-yl)quinolin-2(1H)-one | 473.3 |
| 1090 | 4-amino-6-fluoro-3-[6-(4-methylpiperazin-1-yl)-1H-benzimidazol-2-yl]quinolin-2(1H)-one | 393.4 |
| 1091 | 4-amino-3-(1H-benzimidazol-2-yl)-5-(methylamino)quinolin-2(1H)-one | 306.3 |
| 1092 | 4-amino-3-{6-[(2S)-2,4-dimethylpiperazin-1-yl]-1H-benzimidazol-2-yl}-5-fluoroquinolin-2(1H)-one | 407.5 |
| 1093 | 4-amino-5-fluoro-3-{6-[(2S)-2-methylpiperazin-1-yl]-1H-benzimidazol-2-yl}quinolin-2(1H)-one | 393.4 |
| 1094 | 4-amino-3-{6-[(2S)-4-isopropyl-2-methylpiperazin-1-yl]-1H-benzimidazol-2-yl}quinolin-2(1H)-one | 417.5 |

-continued

TABLE of Additional Exemplary Compounds

| Example | Name | LC/MS m/z (MH+) |
|---|---|---|
| 1095 | 4-amino-5,7-difluoro-3-[5-(4-methylpiperazin-1-yl)-1H-benzimidazol-2-yl]quinolin-2(1H)-one | 411.4 |
| 1096 | 3-(1H-benzimidazol-2-yl)-6-bromo-4-{[(2S)-piperidin-2-ylmethyl]amino}quinolin-2(1H)-one | 453.4 |
| 1097 | 3-(1H-benzimidazol-2-yl)-6-bromo-4-{[(2R)-piperidin-2-ylmethyl]amino}quinolin-2(1H)-one | 453.4 |
| 1098 | 4-amino-3-{6-[methyl(1,3-thiazol-2-ylmethyl)amino]-1H-benzimidazol-2-yl}quinolin-2(1H)-one | 403.5 |
| 1099 | 4-amino-3-{6-[(1-ethylpiperidin-4-yl)(methyl)amino]-1H-benzimidazol-2-yl}quinolin-2(1H)-one | 417.5 |
| 1100 | 4-amino-3-[6-(4-morpholin-4-ylpiperidin-1-yl)-1H-benzimidazol-2-yl]quinolin-2(1H)-one | 445.5 |
| 1101 | 4-amino-3-[6-(4-isopropylpiperazin-1-yl)-1H-benzimidazol-2-yl]-5-(methylamino)quinolin-2(1H)-one | 432.5 |
| 1102 | 4-amino-3-{6-[methyl(pyridin-2-ylmethyl)amino]-1H-benzimidazol-2-yl}quinolin-2(1H)-one | 397.5 |
| 1103 | 4-amino-3-{6-[(2S)-2,4-dimethylpiperazin-1-yl]-1H-benzimidazol-2-yl}quinolin-2(1H)-one | 389.5 |
| 1104 | 4-amino-3-{6-[(2S)-2-methylpiperazin-1-yl]-1H-benzimidazol-2-yl}quinolin-2(1H)-one | 375.4 |
| 1105 | N-[2-(4-amino-2-oxo-1,2-dihydroquinolin-3-yl)-1H-benzimidazol-6-yl]-N-methylacetamide | 348.4 |
| 1106 | 4-amino-5-fluoro-3-{6-[(2S)-4-isopropyl-2-methylpiperazin-1-yl]-1H-benzimidazol-2-yl}quinolin-2(1H)-one | 435.5 |
| 1107 | 4-amino-3-{6-[(3R)-3,4-dimethylpiperazin-1-yl]-1H-benzimidazol-2-yl}quinolin-2(1H)-one | 389.5 |
| 1108 | 4-[(3S)-1-azabicyclo[2.2.2]oct-3-ylamino]-3-(1H-benzimidazol-2-yl)-6-(dimethylamino)quinolin-2(1H)-one | 429.5 |
| 1109 | 4-amino-3-{6-[(2S)-4-cyclobutyl-2-methylpiperazin-1-yl]-1H-benzimidazol-2-yl}quinolin-2(1H)-one | 429.5 |
| 1110 | 4-amino-5-fluoro-3-[6-(methylamino)-1H-benzimidazol-2-yl]quinolin-2(1H)-one | 324.3 |
| 1111 | 4-amino-3-(1H-benzimidazol-2-yl)-5-(dimethylamino)quinolin-2(1H)-one | 320.4 |
| 1112 | 4-amino-3-(1H-benzimidazol-2-yl)-5-{[2-(dimethylamino)ethyl]amino}quinolin-2(1H)-one | 363.4 |
| 1113 | 4-amino-5-fluoro-3-(5-piperazin-1-yl-1H-benzimidazol-2-yl)quinolin-2(1H)-one | 379.4 |
| 1114 | 4-amino-3-{5-[[2-(dimethylamino)ethyl](methyl)amino]-1H-benzimidazol-2-yl}-5-fluoroquinolin-2(1H)-one | 395.5 |
| 1115 | 4-amino-5-fluoro-3-{5-[methyl(piperidin-3-ylmethyl)amino]-1H-benzimidazol-2-yl}quinolin-2(1H)-one | 421.5 |
| 1116 | 4-amino-3-(1H-benzimidazol-2-yl)-5-[[2-(dimethylamino)ethyl](methyl)amino]quinolin-2(1H)-one | 377.5 |
| 1117 | 4-amino-5-fluoro-3-{5-[(2R)-4-isopropyl-2-methylpiperazin-1-yl]-1H-benzimidazol-2-yl}quinolin-2(1H)-one | 435.5 |
| 1118 | 4-amino-3-{5-[(2S)-4-ethyl-2-methylpiperazin-1-yl]-1H-benzimidazol-2-yl}-5-fluoroquinolin-2(1H)-one | 421.5 |
| 1119 | 4-amino-3-(5-{[(1-ethylpyrrolidin-2-yl)methyl]amino}-1H-benzimidazol-2-yl)-5-fluoroquinolin-2(1H)-one | 421.5 |
| 1120 | 4-amino-3-(5-{[2-(dimethylamino)-1-methylethyl]amino}-1H-benzimidazol-2-yl)-5-fluoroquinolin-2(1H)-one | 395.5 |
| 1121 | 4-amino-3-{5-[[2-(dimethylamino)-1-methylethyl](methyl)amino]-1H-benzimidazol-2-yl}-5-fluoroquinolin-2(1H)-one | 409.5 |
| 1122 | 4-amino-3-(1H-benzimidazol-2-yl)-5-(1,2-dimethylhydrazino)quinolin-2(1H)-one | 335.4 |
| 1123 | 4-amino-5-fluoro-3-{6-[4-(2-methoxyethyl)piperazin-1-yl]-1H-benzimidazol-2-yl}quinolin-2(1H)-one | 437.5 |
| 1124 | 4-amino-5-fluoro-3-{6-[methyl(1-methylpiperidin-4-yl)amino]-1H-benzimidazol-2-yl}quinolin-2(1H)-one | 421.5 |
| 1125 | 4-amino-5-fluoro-3-(6-{[3-(4-methylpiperazin-1-yl)propyl]amino}-1H-benzimidazol-2-yl)quinolin-2(1H)-one | 450.5 |
| 1126 | 4-amino-5-fluoro-3-(6-{methyl[3-(4-methylpiperazin-1-yl)propyl]amino}-1H-benzimidazol-2-yl)quinolin-2(1H)-one | 464.6 |
| 1127 | N-[2-(4-amino-5-fluoro-2-oxo-1,2-dihydroquinolin-3-yl)-1H-benzimidazol-6-yl]-N-methylacetamide | 366.4 |
| 1128 | 4-amino-6-fluoro-3-(5-{[(2R)-2-(pyrrolidin-1-ylmethyl)pyrrolidin-1-yl]carbonyl}-1H-benzimidazol-2-yl)quinolin-2(1H)-one | 475.5 |
| 1129 | 4-amino-3-(1H-benzimidazol-2-yl)-5-(ethylamino)quinolin-2(1H)-one | 320.4 |
| 1130 | 4-amino-3-{5-[(2R)-2,4-dimethylpiperazin-1-yl]-1H-benzimidazol-2-yl}-5-fluoroquinolin-2(1H)-one | 407.5 |

-continued

TABLE of Additional Exemplary Compounds

| Example | Name | LC/MS m/z (MH+) |
|---|---|---|
| 1131 | 4-amino-5-fluoro-3-{5-[(2R)-2-methylpiperazin-1-yl]-1H-benzimidazol-2-yl}quinolin-2(1H)-one | 393.4 |
| 1132 | 4-amino-3-{5-[(2R)-4-cyclobutyl-2-methylpiperazin-1-yl]-1H-benzimidazol-2-yl}-5-fluoroquinolin-2(1H)-one | 447.5 |
| 1133 | 4-amino-5-(dimethylamino)-3-[6-(4-isopropylpiperazin-1-yl)-1H-benzimidazol-2-yl]quinolin-2(1H)-one | 446.6 |
| 1134 | 4-amino-5-{[2-(dimethylamino)ethyl]amino}-3-[6-(4-isopropylpiperazin-1-yl)-1H-benzimidazol-2-yl]quinolin-2(1H)-one | 489.6 |
| 1135 | 4-amino-5-[[2-(dimethylamino)ethyl](methyl)amino]-3-[6-(4-isopropylpiperazin-1-yl)-1H-benzimidazol-2-yl]quinolin-2(1H)-one | 503.7 |
| 1136 | 4-amino-5-(ethylamino)-3-[6-(4-isopropylpiperazin-1-yl)-1H-benzimidazol-2-yl]quinolin-2(1H)-one | 446.6 |
| 1137 | N-[2-(4-amino-2-oxo(3-hydroquinolyl))benzimidazol-6-yl]-2-(dimethylamino)-N-methylacetamide | 391.4 |
| 1138 | 4-amino-5-fluoro-3-[6-(9-isopropyl-1-oxa-4,9-diazaspiro[5.5]undec-4-yl)-1H-benzimidazol-2-yl]quinolin-2(1H)-one | 491.6 |
| 1139 | 4-amino-7-fluoro-3-[6-fluoro-5-(4-methylpiperazin-1-yl)-1H-benzimidazol-2-yl]quinolin-2(1H)-one | 411.4 |
| 1140 | 4-amino-3-(5-{(2S,5S)-2-[(dimethylamino)methyl]-5-methylmorpholin-4-yl}-6-fluoro-1H-benzimidazol-2-yl)-5-fluoroquinolin-2(1H)-one | 469.5 |
| 1141 | 4-amino-3-(5-{(2S,5S)-2-[(dimethylamino)methyl]-5-methylmorpholin-4-yl}-6-fluoro-1H-benzimidazol-2-yl)quinolin-2(1H)-one | 451.5 |
| 1142 | 4-amino-5-methyl-3-[5-(4-methylpiperazin-1-yl)-1H-benzimidazol-2-yl]quinolin-2(1H)-one | 389.5 |
| 1143 | 4-amino-3-[5-(4-methylpiperazin-1-yl)-1H-benzimidazol-2-yl]-5-(trifluoromethyl)quinolin-2(1H)-one | 443.4 |
| 1144 | 4-amino-5-fluoro-3-[6-(2-isopropyl-5-oxa-2,8-diazaspiro[3.5]non-8-yl)-1H-benzimidazol-2-yl]quinolin-2(1H)-one | 463.5 |
| 1145 | 4-amino-6-fluoro-3-[5-(4-isopropylpiperazin-1-yl)-1H-benzimidazol-2-yl]quinolin-2(1H)-one | 421.5 |
| 1146 | N-[2-(4-amino-5-fluoro-2-oxo-1,2-dihydroquinolin-3-yl)-1H-benzimidazol-6-yl]-N-methyl-2-(4-methylpiperazin-1-yl)acetamide | 464.5 |
| 1147 | N-[2-(4-amino-5-fluoro-2-oxo-1,2-dihydroquinolin-3-yl)-1H-benzimidazol-6-yl]-N-methyl-2-morpholin-4-ylacetamide | 451.5 |
| 1148 | N-[2-(4-amino-5-fluoro-2-oxo(3-hydroquinolyl))benzimidazol-6-yl]-N-methyl-2-morpholin-4-ylacetamide | 492.6 |
| 1149 | 4-amino-5-fluoro-3-(6-methyl-1H-benzimidazol-2-yl)quinolin-2(1H)-one | 309.3 |
| 1150 | 4-amino-3-[5-(4-ethylpiperazin-1-yl)-1H-benzimidazol-2-yl]-5-methylquinolin-2(1H)-one | 403.5 |
| 1151 | 4-amino-3-{6-[(4-methylpiperazin-1-yl)methyl]-1H-benzimidazol-2-yl}quinolin-2(1H)-one | 389.5 |
| 1152 | 4-amino-3-[6-(1,4-diazepan-1-yl)-1H-benzimidazol-2-yl]-5-fluoroquinolin-2(1H)-one | 393.4 |
| 1153 | 4-amino-5-fluoro-3-[6-(4-methyl-1,4-diazepan-1-yl)-1H-benzimidazol-2-yl]quinolin-2(1H)-one | 407.5 |
| 1154 | 3-[6-(4-acetylpiperazin-1-yl)-1H-benzimidazol-2-yl]-4-amino-5-fluoroquinolin-2(1H)-one | 421.4 |
| 1155 | 4-amino-3-[6-(4-ethyl-1,4-diazepan-1-yl)-1H-benzimidazol-2-yl]-5-fluoroquinolin-2(1H)-one | 421.5 |
| 1156 | 4-amino-5-fluoro-3-[6-(4-isopropyl-1,4-diazepan-1-yl)-1H-benzimidazol-2-yl]quinolin-2(1H)-one | 435.5 |

In yet another embodiment, the compound of Structure I is a compound of Structure II, where Structure II has the following formula:

II wherein,
A is a group having one of the following Structures:

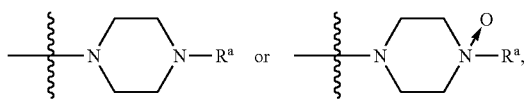

wherein,
$R^a$ is selected from H or straight or branched chain alkyl groups having from 1 to 6 carbon atoms.

In some embodiments, where the compound of Structure I is a compound of Structure II, $R^a$ is a methyl group, and the compound of Structure II is a compound of Structure IIA

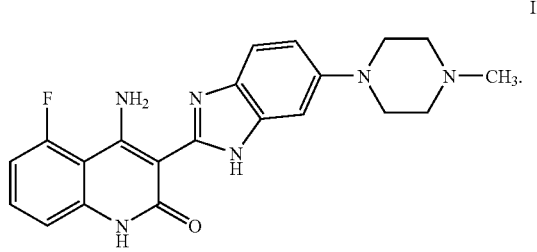

IIA

In some specific embodiments, the pharmaceutically acceptable salt of the compound of Structure IIA, the pharmaceutically acceptable salt of the tautomer, or the mixture thereof is administered to the subject, and the salt is a lactate salt.

In some embodiments, where the compound of Structure I is a compound of Structure II, $R^a$ is a H, and the compound of Structure II is a compound of Structure IIB

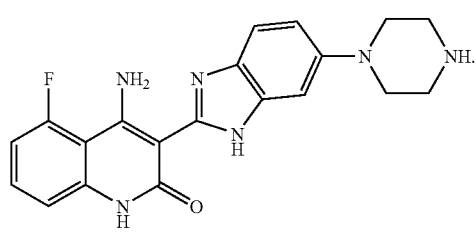

IIB

In some embodiments, where the compound of Structure I is a compound of Structure II, $R^a$ is a methyl group, and the compound of Structure II is a compound of Structure IIC

IIC

The compounds of any of the embodiments may be used to prepare medicaments or pharmaceutical formulations for use in any of the methods of the invention.

Pharmaceutical formulations for use with the invention may include any of the compounds, tautomers, or salts of any of the embodiments described above in combination with a pharmaceutically acceptable carrier such as those described herein.

The instant invention also provides for compositions which may be prepared by mixing one or more compounds of the instant invention, or pharmaceutically acceptable salts tautomers thereof, or mixtures thereof with pharmaceutically acceptable carriers, excipients, binders, diluents or the like to treat or ameliorate disorders related to metastacized tumors. The compositions of the inventions may be used to create formulations for use in any of the methods of the invention. Such compositions can be in the form of, for example, granules, powders, tablets, capsules, syrup, suppositories, injections, emulsions, elixirs, suspensions or solutions. The instant compositions can be formulated for various routes of administration, for example, by oral administration, by nasal administration, by rectal administration, subcutaneous injection, intravenous injection, intramuscular injections, or intraperitoneal injection. The following dosage forms are given by way of example and should not be construed as limiting the instant invention.

For oral, buccal, and sublingual administration, powders, suspensions, granules, tablets, pills, capsules, gelcaps, and caplets are acceptable as solid dosage forms. These can be prepared, for example, by mixing one or more compounds of the instant invention, pharmaceutically acceptable salts, tautomers, or mixtures thereof, with at least one additive such as a starch or other additive. Suitable additives are sucrose, lactose, cellulose sugar, mannitol, maltitol, dextran, starch, agar, alginates, chitins, chitosans, pectins, tragacanth gum, gum arabic, gelatins, collagens, casein, albumin, synthetic or semi-synthetic polymers or glycerides. Optionally, oral dosage forms can contain other ingredients to aid in administration, such as an inactive diluent, or lubricants such as magnesium stearate, or preservatives such as paraben or sorbic acid, or anti-oxidants such as ascorbic acid, tocopherol or cysteine, a disintegrating agent, binders, thickeners, buffers, sweeteners, flavoring agents or perfuming agents. Tablets and pills may be further treated with suitable coating materials known in the art.

Liquid dosage forms for oral administration may be in the form of pharmaceutically acceptable emulsions, syrups, elixirs, suspensions, and solutions, which may contain an inactive diluent, such as water. Pharmaceutical formulations and medicaments may be prepared as liquid suspensions or solutions using a sterile liquid, such as, but not limited to, an oil, water, an alcohol, and combinations of these. Pharmaceutically suitable surfactants, suspending agents, emulsifying agents, may be added for oral or parenteral administration.

As noted above, suspensions may include oils. Such oil include, but are not limited to, peanut oil, sesame oil, cottonseed oil, corn oil and olive oil. Suspension preparation may also contain esters of fatty acids such as ethyl oleate, isopropyl myristate, fatty acid glycerides and acetylated fatty acid glycerides. Suspension formulations may include alcohols, such as, but not limited to, ethanol, isopropyl alcohol, hexadecyl alcohol, glycerol and propylene glycol. Ethers, such as but not limited to, poly(ethyleneglycol), petroleum hydrocarbons such as mineral oil and petrolatum; and water may also be used in suspension formulations.

For nasal administration, the pharmaceutical formulations and medicaments may be a spray or aerosol containing an appropriate solvent(s) and optionally other compounds such as, but not limited to, stabilizers, antimicrobial agents, antioxidants, pH modifiers, surfactants, bioavailability modifiers and combinations of these. A propellant for an aerosol formulation may include compressed air, nitrogen, carbon dioxide, or a hydrocarbon based low boiling solvent.

Injectable dosage forms generally include aqueous suspensions or oil suspensions which may be prepared using a suitable dispersant or wetting agent and a suspending agent. Injectable forms may be in solution phase or in the form of a suspension, which is prepared with a solvent or diluent. Acceptable solvents or vehicles include sterilized water, Ringer's solution, or an isotonic aqueous saline solution. Alternatively, sterile oils may be employed as solvents or suspending agents. Preferably, the oil or fatty acid is nonvolatile, including natural or synthetic oils, fatty acids, mono-, di- or tri-glycerides.

For injection, the pharmaceutical formulation and/or medicament may be a powder suitable for reconstitution with an appropriate solution as described above. Examples of these include, but are not limited to, freeze dried, rotary dried or spray dried powders, amorphous powders, granules, precipitates, or particulates. For injection, the formulations may optionally contain stabilizers, pH modifiers, surfactants, bioavailability modifiers and combinations of these.

For rectal administration, the pharmaceutical formulations and medicaments may be in the form of a suppository, an ointment, an enema, a tablet or a cream for release of compound in the intestines, sigmoid flexure and/or rectum. Rectal suppositories are prepared by mixing one or more compounds of the instant invention, or pharmaceutically acceptable salts or tautomers of the compound, with acceptable vehicles, for example, cocoa butter or polyethylene glycol, which is present in a solid phase at normal storing temperatures, and present in a liquid phase at those temperatures suitable to release a drug inside the body, such as in the rectum. Oils may also be employed in the preparation of formulations of the soft gelatin type and suppositories. Water, saline, aqueous dextrose and related sugar solutions, and glycerols may be employed in the preparation of suspension formulations which may also contain suspending agents such as pectins, carbomers, methyl cellulose, hydroxypropyl cellulose or carboxymethyl cellulose, as well as buffers and preservatives.

Besides those representative dosage forms described above, pharmaceutically acceptable excipients and carriers are generally known to those skilled in the art and are thus included in the instant invention. Such excipients and carriers are described, for example, in "Remingtons Pharmaceutical Sciences" Mack Pub. Co., New Jersey (1991), which is incorporated herein by reference in its entirety for all purposes as if fully set forth herein.

The formulations of the invention may be designed to be short-acting, fast-releasing, long-acting, and sustained-releasing as described below. Thus, the pharmaceutical formulations may also be formulated for controlled release or for slow release.

The instant compositions may also comprise, for example, micelles or liposomes, or some other encapsulated form, or may be administered in an extended release form to provide a prolonged storage and/or delivery effect. Therefore, the pharmaceutical formulations and medicaments may be compressed into pellets or cylinders and implanted intramuscularly or subcutaneously as depot injections or as implants such as stents. Such implants may employ known inert materials such as silicones and biodegradable polymers.

Specific dosages may be adjusted depending on conditions of disease, the age, body weight, general health conditions, sex, and diet of the subject, dose intervals, administration routes, excretion rate, and combinations of drugs. Any of the above dosage forms containing effective amounts are well within the bounds of routine experimentation and therefore, well within the scope of the instant invention.

A therapeutically effective dose may vary depending upon the route of administration and dosage form. The preferred compound or compounds of the instant invention is a formulation that exhibits a high therapeutic index. The therapeutic index is the dose ratio between toxic and therapeutic effects which can be expressed as the ratio between $LD_{50}$ and $ED_{50}$. The $LD_{50}$ is the dose lethal to 50% of the population and the $ED_{50}$ is the dose therapeutically effective in 50% of the population. The $LD_{50}$ and $ED_{50}$ are determined by standard pharmaceutical procedures in animal cell cultures or experimental animals.

Pharmaceutical formulations and medicaments according to the invention include the compound of Structure I or the tautomers, salts, or mixtures thereof in combination with a pharmaceutically acceptable carrier. Thus, the compounds of the invention may be used to prepare medicaments and pharmaceutical formulations. Such medicaments and pharmaceutical formulations may be used in any of the methods of treatment described herein.

The compounds and formulations of the present invention are particularly suitable for use in combination therapy. Kinase inhibitors for use as anticancer agents in conjunction with the methods or compositions of the present invention include inhibitors of Epidermal Growth Factor Receptor (EGFR) kinases such as small molecule quinazolines, for example gefitinib (U.S. Pat. No. 5,457,105, U.S. Pat. No. 5,616,582, and U.S. Pat. No. 5,770,599), ZD-6474 (WO 01/32651), erlotinib (Tarceva®, U.S. Pat. No. 5,747,498 and WO 96/30347), and lapatinib (U.S. Pat. No. 6,727,256 and WO 02/02552). Kinase inhibitors for use as anticancer agents in conjunction with the methods of compositions of the present invention also include inibitors of Vascular Endothelial Growth Factor Receptor (VEGFR) kinase inhibitor such as, but not limited to, SU-11248 (WO 01/60814), SU 5416 (U.S. Pat. No. 5,883,113 and WO 99/61422), SU 6668 (U.S. Pat. No. 5,883,113 and WO 99/61422), CHIR-258 (U.S. Pat. No. 6,605,617 and U.S. Pat. No. 6,774,237), vatalanib or PTK-787 (U.S. Pat. No. 6,258,812), VEGF-Trap (WO 02/57423), B43-Genistein (WO-09606116), fenretinide (retinoic acid p-hydroxyphenylamine) (U.S. Pat. No. 4,323,581), IM-862 (WO 02/62826), bevacizumab or Avastin® (WO 94/10202), KRN-951, 3-[5-(methylsulfonylpiperadine methyl)-indolyl]-quinolone, AG-13736 and AG-13925, pyrrolo[2,1-f][1,2,4]triazines, ZK-304709, Veglin®, VMDA-3601, EG-004, CEP-701 (U.S. Pat. No. 5,621,100), and Cand5 (WO 04/09769).

The compounds of the invention may be used to treat a variety of subjects. Suitable subjects include animals such as mammals and humans. Suitable mammals include, but are not limited to, primates such as, but not limited to lemurs, apes, and monkeys; rodents such as rats, mice, and guinea pigs; rabbits and hares; cows; horses; pigs; goats; sheep; marsupials; and carnivores such as felines, canines, and ursines. In some embodiments, the subject or patient is a human. In other embodiments, the subject or patient is a rodent such as a mouse or a rat. In some embodiments, the subject or patient is an animal other than a human and in some such embodiments, the subject or patient is a mammal other than a human.

Purification and Characterization of Compounds

Compounds of the present invention were characterized by high performance liquid chromatography (HPLC) using a Waters Millenium chromatography system with a 2690 Separation Module (Milford, Mass.). The analytical columns were Alltima C-18 reversed phase, 4.6×250 mm from Alltech (Deerfield, Ill.). A gradient elution was used, typically starting with 5% acetonitrile/95% water and progressing to 100% acetonitrile over a period of 40 minutes. All solvents contained 0.1% trifluoroacetic acid (TFA). Compounds were detected by ultraviolet light (UV) absorption at either 220 or 254 nm. HPLC solvents were from Burdick and Jackson (Muskegan, Mich.), or Fisher Scientific (Pittsburg, Pa.). In some instances, purity was assessed by thin layer chromatography (TLC) using glass or plastic backed silica gel plates, such as, for example, Baker-Flex Silica Gel 1B2-F flexible sheets. TLC results were readily detected visually under ultraviolet light, or by employing well known iodine vapor and other various staining techniques.

Mass spectrometric analysis was performed on one of two LCMS instruments: a Waters System (Alliance HT HPLC and a Micromass ZQ mass spectrometer; Column: Eclipse XDB-C18, 2.1×50 mm; Solvent system: 5-95% acetonitrile in water with 0.05% TFA; Flow rate 0.8 mL/minute; Molecular weight range 150-850; Cone Voltage 20 V; Column temperature 40° C.) or a Hewlett Packard System (Series 1100 HPLC; Column: Eclipse XDB-C18, 2.1×50 mm; Solvent system: 1-95% acetonitrile in water with 0.05% TFA; Flow rate 0.4 mL/minute; Molecular weight range 150-850; Cone Voltage 50 V; Column temperature 30° C.). All masses are reported as those of the protonated parent ions.

GCMS analysis was performed on a Hewlet Packard instrument (HP6890 Series gas chromatograph with a Mass Selective Detector 5973; Injector volume: 1 µL; Initial column temperature: 50° C.; Final column temperature: 250° C.; Ramp time: 20 minutes; Gas flow rate: 1 mL/minute; Column: 5% Phenyl Methyl Siloxane, Model #HP 190915-443, Dimensions: 30.0 m×25 µm×0.25 µm).

Preparative separations were carried out using either a Flash 40 chromatography system and KP-Sil, 60A (Biotage, Charlottesville, Va.), or by HPLC using a C-18 reversed phase column. Typical solvents employed for the Flash 40 Biotage system were dichloromethane, methanol, ethyl acetate, hexane and triethyl amine. Typical solvents employed for the reverse phase HPLC were varying concentrations of acetonitrile and water with 0.1% trifluoroacetic acid.

Synthesis of 4-Amino-5-fluoro-3-[6-(4-methylpiperazin-1-yl)-1H-benzimidazol-2-yl]-1H-quinolin-2-one

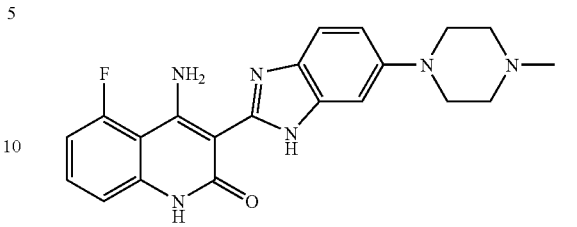

A. Synthesis of 5-(4-Methyl-piperazin-1-yl)-2-nitroaniline

Procedure A

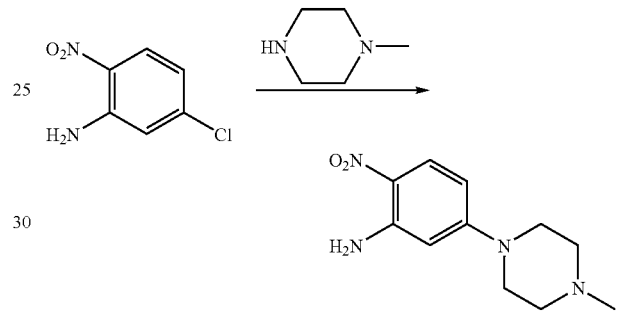

5-Chloro-2-nitroaniline (500 g, 2.898 mol) and 1-methyl piperazine (871 g, 8.693 mol) were placed in a 2000 mL flask fitted with a condenser and purged with $N_2$. The flask was placed in an oil bath at 100° C. and heated until the 5-chloro-2-nitroaniline was completely reacted (typically overnight) as determined by HPLC. After HPLC confirmed the disappearance of the 5-chloro-2-nitroaniline, the reaction mixture was poured directly (still warm) into 2500 mL of room temperature water with mechanical stirring. The resulting mixture was stirred until it reached room temperature and then it was filtered. The yellow solid thus obtained was added to 1000 mL of water and stirred for 30 minutes. The resulting mixture was filtered, and the resulting solid was washed with TBME (500 mL, 2×) and then was dried under vacuum for one hour using a rubber dam. The resulting solid was transferred to a drying tray and dried in a vacuum oven at 50° C. to a constant weight to yield 670 g (97.8%) of the title compound as a yellow powder.

Procedure B

5-Chloro-2-nitroaniline (308.2 g, 1.79 mol) was added to a 4-neck 5000 mL round bottom flask fitted with an overhead stirrer, condenser, gas inlet, addition funnel, and thermometer probe. The flask was then purged with $N_2$. 1-Methylpiperazine (758.1 g, 840 mL, 7.57 mol) and 200 proof ethanol (508 mL) were added to the reaction flask with stirring. The flask was again purged with $N_2$, and the reaction was maintained under $N_2$. The flask was heated in a heating mantle to an internal temperature of 97° C. (+/−5° C.) and maintained at that temperature until the reaction was complete (typically about 40 hours) as determined by HPLC. After the reaction was complete, heating was discontinued and the reaction was cooled to an internal temperature of about 20° C. to 25° C.

with stirring, and the reaction was stirred for 2 to 3 hours. Seed crystals (0.20 g, 0.85 mmol) of 5-(4-methyl-piperazin-1-yl)-2-nitroaniline were added to the reaction mixture unless precipitation had already occurred. Water (2,450 mL) was added to the stirred reaction mixture over a period of about one hour while the internal temperature was maintained at a temperature ranging from about 20° C. to 30° C. After the addition of water was complete, the resulting mixture was stirred for about one hour at a temperature of 20° C. to 30° C. The resulting mixture was then filtered, and the flask and filter cake were washed with water (3×2.56 L). The golden yellow solid product was dried to a constant weight of 416 g (98.6% yield) under vacuum at about 50° C. in a vacuum oven.

Procedure C

5-Chloro-2-nitroaniline (401 g, 2.32 mol) was added to a 4-neck 12 L round bottom flask fitted with an overhead stirrer, condenser, gas inlet, addition funnel, and thermometer probe. The flask was then purged with $N_2$. 1-Methylpiperazine (977 g, 1.08 L, 9.75 mol) and 100% ethanol (650 mL) were added to the reaction flask with stirring. The flask was again purged with $N_2$, and the reaction was maintained under $N_2$. The flask was heated in a heating mantle to an internal temperature of 97° C. (+/−5° C.) and maintained at that temperature until the reaction was complete (typically about 40 hours) as determined by HPLC. After the reaction was complete, heating was discontinued and the reaction was cooled to an internal temperature of about 80° C. with stirring, and water (3.15 L) was added to the mixture via an addition funnel over the period of 1 hour while the internal temperature was maintained at 82° C. (+/−3° C.). After water addition was complete, heating was discontinued and the reaction mixture was allowed to cool over a period of no less than 4 hours to an internal temperature of 20-25° C. The reaction mixture was then stirred for an additional hour at an internal temperature of 20-30° C. The resulting mixture was then filtered, and the flask and filter cake were washed with water (1×1 L), 50% ethanol (1×1 L), and 95% ethanol (1×1 L). The golden yellow solid product was placed in a drying pan and dried to a constant weight of 546 g (99% yield) under vacuum at about 50° C. in a vacuum oven.

B. Synthesis of [6-(4-Methyl-piperazin-1-yl)-1H-benzimidazol-2-yl]-acetic acid ethyl ester Procedure A

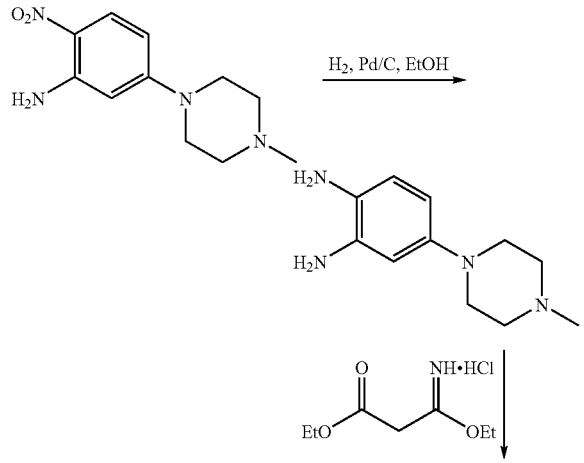

-continued

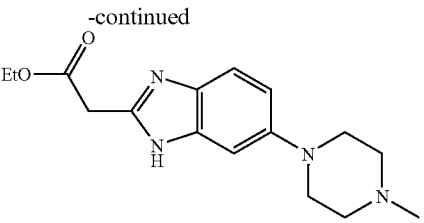

A 5000 mL, 4-neck flask was fitted with a stirrer, thermometer, condenser, and gas inlet/outlet. The equipped flask was charged with 265.7 g (1.12 mol. 1.0 eq) of 5-(4-methyl-piperazin-1-yl)-2-nitroaniline and 2125 mL of 200 proof EtOH. The resulting solution was purged with $N_2$ for 15 minutes. Next, 20.0 g of 5% Pd/C (50% $H_2O$ w/w) was added. The reaction was vigorously stirred at 40-50° C. (internal temperature) while $H_2$ was bubbled through the mixture. The reaction was monitored hourly for the disappearance of 5-(4-methyl-piperazin-1-yl)-2-nitroaniline by HPLC. The typical reaction time was 6 hours.

After all the 5-(4-methyl-piperazin-1-yl)-2-nitroaniline had disappeared from the reaction, the solution was purged with $N_2$ for 15 minutes. Next, 440.0 g (2.25 mol) of ethyl 3-ethoxy-3-iminopropanoate hydrochloride was added as a solid. The reaction was stirred at 40-50° C. (internal temperature) until the reaction was complete. The reaction was monitored by following the disappearance of the diamino compound by HPLC. The typical reaction time was 1-2 hours. After the reaction was complete, it was cooled to room temperature and filtered through a pad of Celite filtering material. The Celite filtering material was washed with absolute EtOH (2×250 mL), and the filtrate was concentrated under reduced pressure providing a thick brown/orange oil. The resulting oil was taken up in 850 mL of a 0.37% HCl solution. Solid NaOH (25 g) was then added in one portion, and a precipitate formed. The resulting mixture was stirred for 1 hour and then filtered. The solid was washed with $H_2O$ (2×400 mL) and dried at 50° C. in a vacuum oven providing 251.7 g (74.1%) of [6-(4-methyl-piperazin-1-yl)-1H-benzoimidazol-2-yl]-acetic acid ethyl ester as a pale yellow powder.

Procedure B

A 5000 mL, 4-neck jacketed flask was fitted with a mechanical stirrer, condenser, temperature probe, gas inlet, and oil bubbler. The equipped flask was charged with 300 g (1.27 mol) of 5-(4-methyl-piperazin-1-yl)-2-nitroaniline and 2400 mL of 200 proof EtOH (the reaction may be and has been conducted with 95% ethanol and it is not necessary to use 200 proof ethanol for this reaction). The resulting solution was stirred and purged with $N_2$ for 15 minutes. Next, 22.7 g of 5% Pd/C (50% $H_2O$ w/w) was added to the reaction flask. The reaction vessel was purged with $N_2$ for 15 minutes. After purging with $N_2$, the reaction vessel was purged with $H_2$ by maintaining a slow, but constant flow of $H_2$ through the flask. The reaction was stirred at 45-55° C. (internal temperature) while $H_2$ was bubbled through the mixture until the 5-(4-methyl-piperazin-1-yl)-2-nitroaniline was completely consumed as determined by HPLC. The typical reaction time was 6 hours.

After all the 5-(4-methyl-piperazin-1-yl)-2-nitroaniline had disappeared from the reaction, the solution was purged with $N_2$ for 15 minutes. The diamine intermediate is air sensitive so care was taken to avoid exposure to air. 500 g (2.56 mol) of ethyl 3-ethoxy-3-iminopropanoate hydrochloride was added to the reaction mixture over a period of about 30 minutes. The reaction was stirred at 45-55° C. (internal temperature) under $N_2$ until the diamine was completely consumed as determined by HPLC. The typical reaction time was about 2 hours. After the reaction was complete, the reaction was filtered while warm through a pad of Celite. The reaction flask and Celite were then washed with 200 proof EtOH (3×285 mL). The filtrates were combined in a 5000 mL flask, and about 3300 mL of ethanol was removed under vacuum producing an orange oil. Water (530 mL) and then 1M HCL (350 mL) were added to the resulting oil, and the resulting mixture was stirred. The resulting solution was vigorously stirred while 30% NaOH (200 mL) was added over a period of about 20 minutes maintaining the internal temperature at about 25-30° C. while the pH was brought to between 9 and 10. The resulting suspension was stirred for about 4 hours while maintaining the internal temperature at about 20-25° C. The resulting mixture was filtered, and the filter cake was washed with $H_2O$ (3×300 mL). The collected solid was dried to a constant weight at 50° C. under vacuum in a vacuum oven providing 345.9 g (90.1%) of [6-(4-methyl-piperazin-1-yl)-1H-benzoimidazol-2-yl]-acetic acid ethyl ester as a pale yellow powder. In an alternative work up procedure, the filtrates were combined and the ethanol was removed under vacuum until at least about 90% had been removed. Water at a neutral pH was then added to the resulting oil, and the solution was cooled to about 0° C. An aqueous 20% NaOH solution was then added slowly with rapid stirring to bring the pH up to 9.2 (read with pH meter). The resulting mixture was then filtered and dried as described above. The alternative work up procedure provided the light tan to light yellow product in yields as high as 97%.

Method for Reducing Water Content of [6-(4-Methyl-piperazin-1-yl)-1H-benzoimidazol-2-yl]-acetic acid ethyl ester

[6-(4-Methyl-piperazin-1-yl)-1H-benzimidazol-2-yl]-acetic acid ethyl ester (120.7 grams) that had been previously worked up and dried to a water content of about 8-9% $H_2O$ was placed in a 2000 mL round bottom flask and dissolved in absolute ethanol (500 mL). The amber solution was concentrated to a thick oil using a rotary evaporator with heating until all solvent was removed. The procedure was repeated two more times. The thick oil thus obtained was left in the flask and placed in a vacuum oven heated at 50° C. overnight. Karl Fisher analysis results indicated a water content of 5.25%. The lowered water content obtained by this method provided increased yields in the procedure of the following Example. Other solvents such as toluene and THF may be used in place of the ethanol for this drying process.

C. Synthesis of 4-Amino-5-fluoro-3-[6-(4-methyl-piperazin-1-yl)-1H-benzimidazol-2-yl]-1H-quinolin-2-one Procedure A

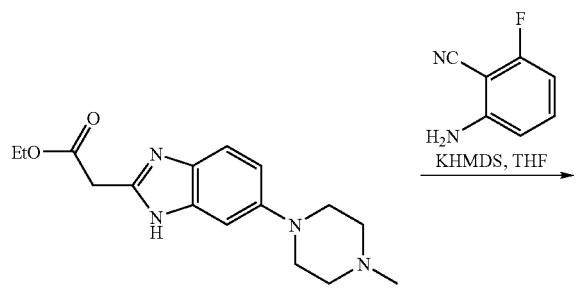

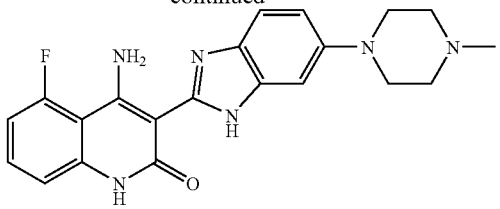

[6-(4-Methyl-piperazin-1-yl)-1H-benzimidazol-2-yl]-acetic acid ethyl ester (250 g, 820 mmol) (dried with ethanol as described above) was dissolved in THF (3800 mL) in a 5000 mL flask fitted with a condenser, mechanical stirrer, temperature probe, and purged with argon. 2-Amino-6-fluoro-benzonitrile (95.3 g, 700 mmol) was added to the solution, and the internal temperature was raised to 40° C. When all the solids had dissolved and the solution temperature had reached 40° C., solid KHMDS (376.2 g, 1890 mmol) was added over a period of 5 minutes. When addition of the potassium base was complete, a heterogeneous yellow solution was obtained, and the internal temperature had risen to 62° C. After a period of 60 minutes, the internal temperature decreased back to 40° C., and the reaction was determined to be complete by HPLC (no starting material or uncyclized intermediate was present). The thick reaction mixture was then quenched by pouring it into $H_2O$ (6000 mL) and stirring the resulting mixture until it had reached room temperature. The mixture was then filtered, and the filter pad was washed with water (1000 mL 2×). The bright yellow solid was placed in a drying tray and dried in a vacuum oven at 50° C. overnight providing 155.3 g (47.9%) of the desired 4-amino-5-fluoro-3-[6-(4-methyl-piperazin-1-yl)-1H-benzimidazol-2-yl]-1H-quinolin-2-one.

Procedure B

A 5000 mL 4-neck jacketed flask was equipped with a distillation apparatus, a temperature probe, a $N_2$ gas inlet, an addition funnel, and a mechanical stirrer. [6-(4-Methyl-piperazin-1-yl)-1H-benzimidazol-2-yl]-acetic acid ethyl ester (173.0 g, 570 mmol) was charged into the reactor, and the reactor was purged with $N_2$ for 15 minutes. Dry THF (2600 mL) was then charged into the flask with stirring. After all the solid had dissolved, solvent was removed by distillation (vacuum or atmospheric (the higher temperature helps to remove the water) using heat as necessary. After 1000 mL of solvent had been removed, distillation was stopped and the reaction was purged with $N_2$. 1000 mL of dry THF was then added to the reaction vessel, and when all solid was dissolved, distillation (vacuum or atmospheric) was again conducted until another 1000 mL of solvent had been removed. This process of adding dry THF and solvent removal was repeated at least 4 times (on the $4^{th}$ distillation, 60% of the solvent is removed instead of just 40% as in the first 3 distillations) after which a 1 mL sample was removed for Karl Fischer analysis to determine water content. If the analysis showed that the sample contained less than 0.20% water, then reaction was continued as described in the next paragraph. However, if the analysis showed more than 0.20% water, then the drying process described above was continued until a water content of less than 0.20% was achieved.

After a water content of less than or about 0.20% was achieved using the procedure described in the previous paragraph, the distillation apparatus was replaced with a reflux condenser, and the reaction was charged with 2-amino-6-fluoro-benzonitrile (66.2 g, 470 mmol) (in some procedures 0.95 equivalents is used). The reaction was then heated to an internal temperature of 38-42° C. When the internal temperature had reached 38-42° C., KHMDS solution (1313 g, 1.32 mol, 20% KHMDS in THF) was added to the reaction via the additional funnel over a period of 5 minutes maintaining the internal temperature at about 38-50° C. during the addition. When addition of the potassium base was complete, the reaction was stirred for 3.5 to 4.5 hours (in some examples it was stirred for 30 to 60 minutes and the reaction may be complete within that time) while maintaining the internal temperature at from 38-42° C. A sample of the reaction was then removed and analyzed by HPLC. If the reaction was not complete, additional KHMDS solution was added to the flask over a period of 5 minutes and the reaction was stirred at 38-42° C. for 45-60 minutes (the amount of KHMDS solution added was determined by the following: If the IPC ratio is <3.50, then 125 mL was added; if 10.0≧IPC ratio≧3.50, then 56 mL was added; if 20.0≧IPC ratio≧10, then 30 mL was added. The IPC ratio is equal to the area corresponding to 4-amino-5-fluoro-3-[6-(4-methyl-piperazin-1-yl)-1H-benzimidazol-2-yl]-1H-quinolin-2-one) divided by the area corresponding to the uncyclized intermediate). Once the reaction was complete (IPC ratio>20), the reactor was cooled to an internal temperature of 25-30° C., and water (350 mL) was charged into the reactor over a period of 15 minutes while maintaining the internal temperature at 25-35° C. (in one alternative, the reaction is conducted at 40° C. and water is added within 5 minutes. The quicker quench reduces the amount of impurity that forms over time). The reflux condenser was then replaced with a distillation apparatus and solvent was removed by distillation (vacuum or atmospheric) using heat as required. After 1500 mL of solvent had been removed, distillation was discontinued and the reaction was purged with N$_2$. Water (1660 mL) was then added to the reaction flask while maintaining the internal temperature at 20-30° C. The reaction mixture was then stirred at 20-30° C. for 30 minutes before cooling it to an internal temperature of 5-10° C. and then stirring for 1 hour. The resulting suspension was filtered, and the flask and filter cake were washed with water (3×650 mL). The solid thus obtained was dried to a constant weight under vacuum at 50° C. in a vacuum oven to provide 103.9 g (42.6% yield) of 4-amino-5-fluoro-3-[6-(4-methyl-piperazin-1-yl)-1H-benzimidazol-2-yl]-1H-quinolin-2-one as a yellow powder.

Procedure C

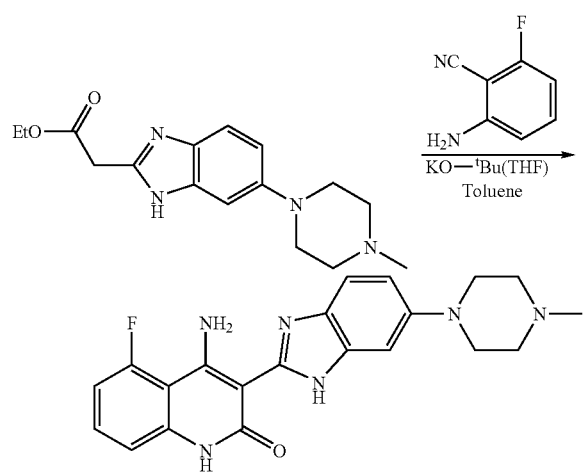

[6-(4-Methyl-piperazin-1-yl)-1H-benzimidazol-2-yl]-acetic acid ethyl ester (608 g, 2.01 mol) (dried) and 2-amino-6-fluoro-benzonitrile (274 g, 2.01 mol) were charged into a 4-neck 12 L flask seated on a heating mantle and fitted with a condenser, mechanical stirrer, gas inlet, and temperature probe. The reaction vessel was purged with N$_2$, and toluene (7.7 L) was charged into the reaction mixture while it was stirred. The reaction vessel was again purged with N$_2$ and maintained under N$_2$. The internal temperature of the mixture was raised until a temperature of 63° C. (+/−3° C.) was achieved. The internal temperature of the mixture was maintained at 63° C. (+/−3° C.) while approximately 2.6 L of toluene was distilled from the flask under reduced pressure (380+/−10 torr, distilling head t=40° C. (+/−10° C.) (Karl Fischer analysis was used to check the water content in the mixture. If the water content was greater than 0.03%, then another 2.6 L of toluene was added and distillation was repeated. This process was repeated until a water content of less than 0.03% was achieved). After a water content of less than 0.03% was reached, heating was discontinued, and the reaction was cooled under N$_2$ to an internal temperature of 17-19° C. Potassium t-butoxide in THF (20% in THF; 3.39 kg, 6.04 moles potassium t-butoxide) was then added to the reaction under N$_2$ at a rate such that the internal temperature of the reaction was kept below 20° C. After addition of the potassium t-butoxide was complete, the reaction was stirred at an internal temperature of less than 20° C. for 30 minutes. The temperature was then raised to 25° C., and the reaction was stirred for at least 1 hour. The temperature was then raised to 30° C., and the reaction was stirred for at least 30 minutes. The reaction was then monitored for completion using HPLC to check for consumption of the starting materials (typically in 2-3 hours, both starting materials were consumed (less than 0.5% by area % HPLC)). If the reaction was not complete after 2 hours, another 0.05 equivalents of potassium t-butoxide was added at a time, and the process was completed until HPLC showed that the reaction was complete. After the reaction was complete, 650 mL of water was added to the stirred reaction mixture. The reaction was then warmed to an internal temperature of 50° C. and the THF was distilled away (about 3 L by volume) under reduced pressure from the reaction mixture. Water (2.6 L) was then added dropwise to the reaction mixture using an addition funnel. The mixture was then cooled to room temperature and stirred for at least 1 hour. The mixture was then filtered, and the filter cake was washed with water (1.2 L), with 70% ethanol (1.2 L), and with 95% ethanol (1.2 L). The bright yellow solid was placed in a drying tray and dried in a vacuum oven at 50° C. until a constant weight was obtained providing 674 g (85.4%) of the desired 4-amino-5-fluoro-3-[6-(4-methyl-piperazin-1-yl)-1H-benzimidazol-2-yl]-1H-quinolin-2-one.

Purification of 4-Amino-5-fluoro-3-[6-(4-methyl-piperazin-1-yl)-1H-benzimidazol-2-yl]-1H-quinolin-2-one A 3000 mL 4-neck flask equipped with a condenser, temperature probe, N$_2$ gas inlet, and mechanical stirrer was placed in a heating mantle. The flask was then charged with 4-amino-5-fluoro-3-[6-(4-methyl-piperazin-1-yl)-1H-benzimidazol-2-yl]-1H-quinolin-2-one (101.0 g, 0.26 mol), and the yellow solid was suspended in 95% ethanol (1000 mL) and stirred. In some cases an 8:1 solvent ratio is used. The suspension was then heated to a gentle reflux (temperature of about 76° C.) with stirring over a period of about 1 hour. The reaction was then stirred for 45-75 minutes while refluxed. At this point, the heat was removed from the flask and the suspension was allowed to cool to a temperature of 25-30° C. The suspension was then filtered, and the filter pad was washed with water (2×500 mL). The yellow solid was then placed in a drying tray and dried in a vacuum oven at 50° C. until a constant weight was obtained (typically 16 hours) to obtain 97.2 g (96.2%) of the purified product as a yellow powder.

D. Preparation of Lactic Acid Salt of 4-Amino-5-fluoro-3-[6-(4-methyl-piperazin-1-yl)-1H-benzimidazol-2-yl]-1H-quinolin-2-one

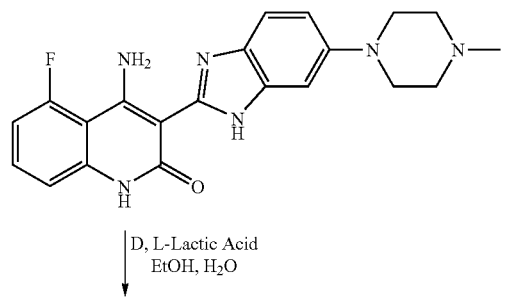

D, L-Lactic Acid
EtOH, H₂O

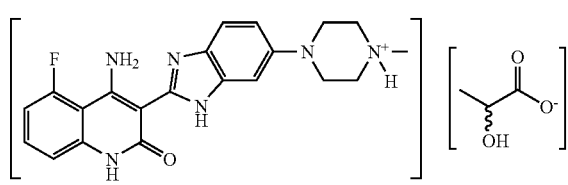

A 3000 mL 4-necked jacketed flask was fitted with a condenser, a temperature probe, a N₂ gas inlet, and a mechanical stirrer. The reaction vessel was purged with N₂ for at least 15 minutes and then charged with 4-amino-5-fluoro-3-[6-(4-methyl-piperazin-1-yl)-1H-benzimidazol-2-yl]-1H-quinolin-2-one (484 g, 1.23 mol). A solution of D,L-Lactic acid (243.3 g, 1.72 mol of monomer-see the following paragraph), water (339 mL), and ethanol (1211 mL) was prepared and then charged to the reaction flask. Stirring was initiated at a medium rate, and the reaction was heated to an internal temperature of 68-72° C. The internal temperature of the reaction was maintained at 68-72° C. for 15-45 minutes and then heating was discontinued. The resulting mixture was filtered through a 10-20 micron frit collecting the filtrate in a 12 L flask. The 12 L flask was equipped with an internal temperature probe, a reflux condenser, an addition funnel, a gas inlet an outlet, and an overhead stirrer. The filtrate was then stirred at a medium rate and heated to reflux (internal temperature of about 78° C.). While maintaining a gentle reflux, ethanol (3,596 mL) was charged to the flask over a period of about 20 minutes. The reaction flask was then cooled to an internal temperature ranging from about 64-70° C. within 15-25 minutes and this temperature was maintained for a period of about 30 minutes. The reactor was inspected for crystals. If no crystals were present, then crystals of the lactic acid salt of 4-amino-5-fluoro-3-[6-(4-methyl-piperazin-1-yl)-1H-benzimidazol-2-yl]-1H-quinolin-2-one (484 mg, 0.1 mole %) were added to the flask, and the reaction was stirred at 64-70° C. for 30 minutes before again inspecting the flask for crystals. Once crystals were present, stirring was reduced to a low rate and the reaction was stirred at 64-70° C. for an additional 90 minutes. The reaction was then cooled to about 0° C. over a period of about 2 hours, and the resulting mixture was filtered through a 25-50 micron fritted filter. The reactor was washed with ethanol (484 mL) and stirred until the internal temperature was about 0° C. The cold ethanol was used to wash the filter cake, and this procedure was repeated 2 more times. The collected solid was dried to a constant weight at 50° C. under vacuum in a vacuum oven yielding 510.7 g (85.7%) of the crystalline yellow lactic acid salt of 4-amino-5-fluoro-3-[6-(4-methyl-piperazin-1-yl)-1H-benzimidazol-2-yl]-1H-quinolin-2-one. A rubber dam or inert conditions were typically used during the filtration process. While the dry solid did not appear to be very hygroscopic, the wet filter cake tends to pick up water and become sticky. Precautions were taken to avoid prolonged exposure of the wet filter cake to the atmosphere.

Commercial lactic acid generally contains about 8-12% w/w water, and contains dimers and trimers in addition to the monomeric lactic acid. The mole ratio of lactic acid dimer to monomer is generally about 1.0:4.7. Commercial grade lactic acid may be used in the process described in the preceding paragraph as the monolactate salt preferentially precipitates from the reaction mixture.

Identification of Metabolites

Two metabolites of 4-amino-5-fluoro-3-[6-(4-methyl-piperazin-1-yl)-1H-benzimidazol-2-yl]-1H-quinolin-2-one (Compound 1) have been identified and characterized in pooled rat plasma from a 2 week toxicology study as described in the references incorporated herein. The two identified metabolites were the piperazine N-oxide compound (Compound 2) and the N-demethylated compound (Compound 3) shown below.

Compound 2

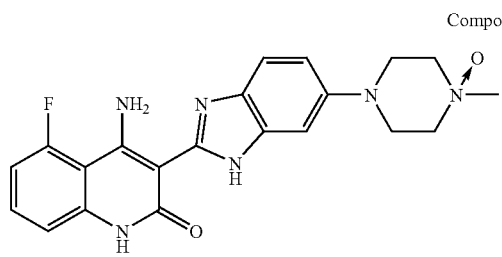

Compound 3

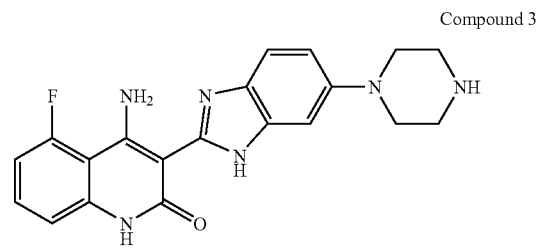

$IC_{50}$s of Compounds 1-3

The kinase activity of a number of protein tyrosine kinases was measured using the procedures described in the various references incorporated herein. Some of these are shown in the following Table.

Table. IC$_{50}$s of Compounds 1-3

| Compound | IC$_{50}$ (μM) | | | | | |
| --- | --- | --- | --- | --- | --- | --- |
| | VEGFR flt | VEGFR flk1 | bFGFR | PDGFR | Flt3 | c-kit |
| Compound 1 | 0.010 | 0.013 | 0.008 | 0.027 | 0.0001 | 0.0015 |
| Compound 2 | 0.004 | 0.009 | 0.005 | 0.010 | 0.0004 | 0.0002 |
| Compound 3 | 0.019 | 0.012 | 0.019 | 0.037 | 0.0001 | 0.0002 |

Synthesis of 4-Amino-5-fluoro-3-[6-(4-methyl-4-oxidopiperazin-1-yl)-1H-benzimidazol-2-yl]quinolin-2(1H)-one (Compound 2) and 4-Amino-5-fluoro-3-(6-piperazin-1-yl-1H-benzimidazol-2-yl)quinolin-2(1H)-one (Compound 3)

To confirm the structures of the identified metabolites of Compound 1, the metabolites were independently synthesized.

Compound 2, the N-oxide metabolite of Compound 1, was synthesized as shown in the scheme below. Compound 1 was heated in a mixture of ethanol, dimethylacetamide and hydrogen peroxide. Upon completion of the reaction, Compound 2 was isolated by filtration and washed with ethanol. If necessary, the product could be further purified by column chromatography.

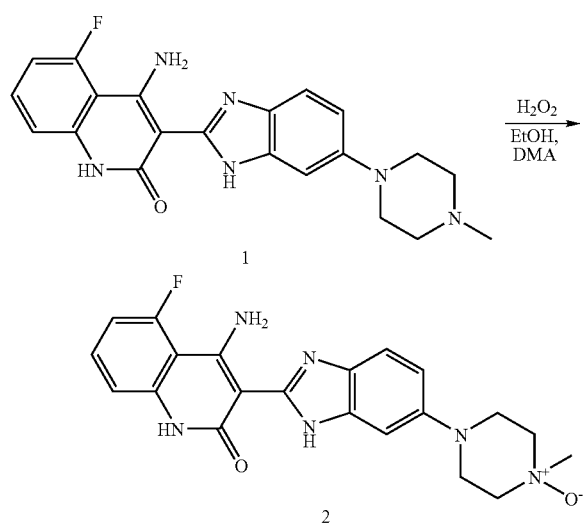

Compound 3, the N-desmethyl metabolite of Compound 1, was synthesized as shown in the scheme below. 5-Chloro-2-nitroaniline was treated with piperazine to yield 4 which was subsequently protected with a butyloxycarbonyl (Boc) group to yield 5. Reduction of the nitro group followed by condensation with 3-ethoxy-3-iminopropionic acid ethyl ester gave 6. Condensation of 6 with 6-fluoroanthranilonitrile using potassium hexamethyldisilazide as the base yielded 7. Crude 7 was treated with aqueous HCl to yield the desired metabolite as a yellow/brown solid after purification.

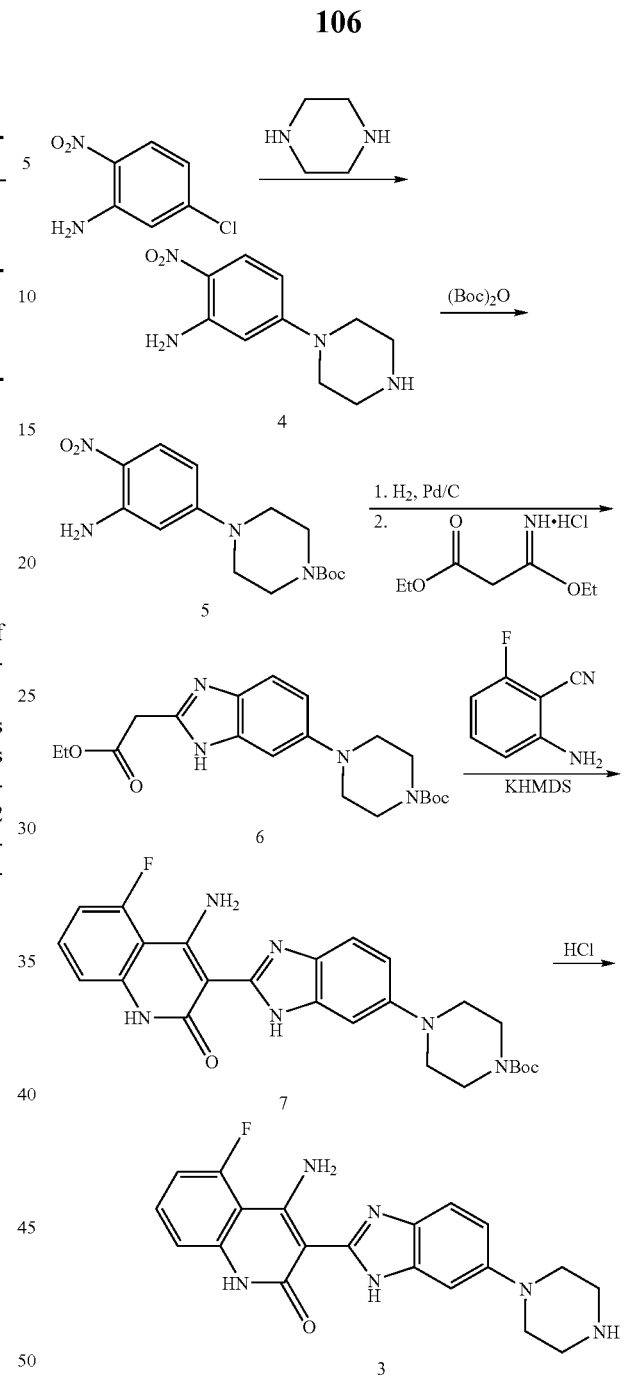

To identify plasma biomarkers of 4-amino-5-fluoro-3-[6-(4-methylpiperazin-1-yl)-1H-benzimidazol-2-yl]quinolin-2 (1H)-one treatment, the 4T1 spontaneously metastatic mouse breast tumor model was used, and circulating serum markers were analyzed by ELISA.

4T1 breast tumor cells were grown as subcutaneous tumors in BALB/C mice, and treatment (10, 30, 60, 100, and 150 mg/kg) with 4-amino-5-fluoro-3-[6-(4-methylpiperazin-1-yl)-1H-benzimidazol-2-yl]quinolin-2(1H)-one (Compound 1) were initiated when tumors were approximately 150 mm$^3$. Mice were dosed orally, daily for 18 days.

The serum was collected from individual animals after 18 days, and the levels of circulating cell adhesion molecules, soluble ICAM, VCAM, and E-selectin, were measured by ELISA assay.

FIG. 1 is a graph showing the effects of 4-amino-5-fluoro-3-[6-(4-methylpiperazin-1-yl)-1H-benzimidazol-2-yl]quinolin-2(1H)-one in the 4T1 murine breast tumor model. The growth of subcutaneous tumors was inhibited (40-80% compared to control), liver metastases were completely inhibited, and lung metastases were inhibited by 60-97% after 18 days of dosing. Various data regarding the incidence of metastases is shown in FIG. 1 and included in the following Table

| Liver Metastases Treatment Group (n) | Incidence of Metastases | # of Liver Metastases Mean +/− SD | % Inhibition vs. Vehicle | P values vs. Vehicle |
|---|---|---|---|---|
| Vehicle (water) (9) | 8/9 | 17.9 +/− 15.4 | n/a | n/a |
| 10 mpk (8) | 7/8 | 22.0 +/− 32.3 | 0 | 0.810 |
| 30 mpk (10) | 6/10 | 3.1 +/− 3.5 | 83 | 0.014 |
| 60 mpk (10) | 5/10 | 0.7 +/− 0.9 | 94 | 0.002 |
| 100 mpk (10) | 1/10 | 4.1 +/− 13.0 | 77 | 0.010 |
| 150 mpk (9) | 0/9 | 0.0 +/− 0.0 | 100 | 0.002 |

Wells of a Nunc Maxisorb "U" bottom microtiter plate (#449824) were coated with monoclonal capture antibody, rat anti-mouse VCAM-1 (R&D Systems #BCA12), at 5 µg/mL in phosphate buffered saline (PBS), 50 µL/well, and incubated at 37° C. for 1 hour. The plates were washed 3 times with wash buffer [PBS containing 0.1% Tween 20 and 1% goat serum (Gibco BRL #16210-072)]. Wells were blocked with 150 µL/well wash buffer and incubated at 37° C. for 1 hour. The blocking solution was removed from the wells and the standard (recombinant mouse VCAM-1/Fc Chimera NOS derived R&D Systems #643-VM) and samples were diluted in wash buffer and added to the wells.

The standard was used at a range of 4000 pg/mL to 31 pg/mL. The serum samples were diluted 1/200 followed by 3-fold serial dilutions. The samples and standards were added at 50 µL/well and incubated at 37° C. for 1 hour. The plates were washed three times and incubated at 37° C. for 1 hour with the primary antibody (biotinylated goat anti-mouse VCAM-1, R&D Systems #BAF643) diluted 1/200 in wash buffer, 50 µL/well. The plates were washed as described above and incubated at 37° C. for 1 hour with stepavidin-HRP (R&D Systems #DY998) 1/200 in PBS/1% goat serum without Tween 20.

The plates were washed three times with wash buffer and three times with PBS. They were then developed with TMB substrate (Kirkegaard & Perry labs # 50-76-00) 50 µL/well and incubated at room temperature for 10 minutes. The reaction was stopped with the addition of 50 µL/well 4N $H_2SO_4$, and the plates were read at 450-550 dual wavelength on the Molecular Devices Vmax plate reader.

Wells of a Nunc Maxisorb "U" bottom microtiter plate (#449824) were coated with monoclonal capture antibody, rat anti-mouse ICAM-1 (R&D Systems #BSA2), at 5 µg/mL in phosphate buffered saline (PBS), 50 µL/well and incubated at 37° C. for 1 hour. The plates were washed 3 times with wash buffer [PBS containing 0.1% Tween 20 and 1% Carnation Nonfat Dry Milk]. Wells were blocked with 150 µL/well wash buffer and incubated at 37° C. for 1 hour. The blocking solution was removed from the wells and the standard (a pool of serum from mice implanted with KM12L4a or 4T1 tumors) and samples were diluted in wash buffer and added to the wells.

The standard was used at a dilution range of 1/10-1/1280. The serum samples were diluted 1/15 followed by 3-fold serial dilutions. The samples and standards were added at 50 µL/well and incubated at 37° C. for 1 hour. The plates were washed three times and incubated at 37° C. for 1 hour with the primary antibody (goat anti-ICAM-1, Santa Cruz Biotechnology #sc-1511) diluted 1/250 in wash buffer, 50 µL/well. The plates were washed as above and incubated at 37° C. for 1 hour with 50 µL/well of the secondary antibody (swine anti-goat IgG HRPO labeled, Caltag #G50007) 1/2000 in wash buffer.

The plates were washed three times with wash buffer and three times with PBS, then developed with TMB substrate (Kirkegaard & Perry labs # 50-76-00) 50 µL/well and incubated at room temperature for 10 minutes. The reaction was stopped with the addition of 50 µL/well 4N $H_2SO_4$, and the plates were read at 450-550 dual wavelength on the Molecular Devices Vmax plate reader.

Serum samples were assayed by the R&D Systems Quantikine M, Mouse sE-Selectin Immunoassay kit #MESOO according to the manufacturer's protocol.

In Vivo KM12L4a Human Colon Xenografts

Female Nu/nu mice (6-8 weeks old, 18-22 grams) were obtained from Charles River Laboratories (Wilmington, Mass.). Tumor cells ($2 \times 10^6$ KM12L4a) were implanted subcutaneously into the flank of mice and allowed to grow to the desired size before treatment was initiated. Tumor bearing mice were administered with 100 mg/kg of 4-amino-5-fluoro-3-[6-(4-methylpiperazin-1-yl)-1H-benzimidazol-2-yl]quinolin-2(1H)-one for 7 days, and individual mice were euthanized. The tumors were resected and flash frozen in liquid nitrogen.

Zymography for MMP-2 and MMP-9 Activity

Resected tumors were lysed in RIPA buffer (1% Nonidet P-40, 0.5% sodium deoxycholate, 0.1% Sodium Dodecylsulphate in 1× Phosphate Buffered Saline, pH 7.2) containing protease inhibitors (Roche Molecular Biochemicals) and phosphatase inhibitors (Sigma). 50 µg of total proteins were analyzed by gelatin zymography on 12% SDS polyacrylamide with gelatin substrate. After electrophoresis, gels were washed twice for 15 minutes in 2.5% Triton X-100, incubated overnight at 37° C. in 50 mM Tris-HCl and 10 mM $CaCl_2$, pH 7.6, and stained with 0.5% Comassie Blue and destained with 50% methanol.

ELISA

VEGF-A protein levels in KM12L4a tumor lysates were quantified using a commercially available ELISA kit (R and D Systems, Minneapolis, Minn.) according to the manufacturer's procedures.

Analysis of KM12L4a human colon tumors, removed after in vivo administration of 4-amino-5-fluoro-3-[6-(4-methylpiperazin-1-yl)-1H-benzimidazol-2-yl]quinolin-2(1H)-one, showed reduced VEGF production and decreased MMP-9 activity. These changes were accompanied by decreased tumor cell proliferation (Ki67), induced apoptosis (increased PARP cleavage and caspase-3) and reduced vascular density (CD31) as seen by antibody immunohistochemistry staining.

The preparation of numerous quinolinone benzimidazole compounds useful in inhibiting angiogenesis and vascular endothelial growth factor receptor tyrosine kinases and in inhibiting other tyrosine and serine/threonine kinases including 4-amino-5-fluoro-3-[5-(4-methylpiperazin-1-yl)-1H-benzimidazol-2-yl]quinolin-2(1H)-one or a tautomer thereof is disclosed in the following documents which are each hereby incorporated by reference in their entireties and for all purposes as if fully set forth herein: U.S. Pat. No. 6,605,617; U.S. Pat. No. 6,756,383; U.S. patent application Ser. No.

10/116,117 filed (published on Feb. 6, 2003, as U.S. 2003/0028018 A1); U.S. patent application Ser. No. 10/644,055 (published on May 13, 2004, U.S. Patent Application No. 2004/0092535); U.S. patent application Ser. No. 10/983,174; U.S. patent application Ser. No. 10/706,328 (published on Nov. 4, 2004, as 2004/0220196); U.S. patent application Ser. No. 10/982,757; and U.S. patent application Ser. No. 10/982,543.

Western Blot Analysis

HUVECs were cultured in EGM (Endothelial Cell Growth Media) with or without 100 nM 4-amino-5-fluoro-3-[6-(4-methylpiperazin-1-yl)-1H-benzimidazol-2-yl]quinolin-2(1H)-one (Compound 1), and cell lysates were collected at 0, 16, and 24 hours post-treatment. Equal amounts of proteins were loaded in 4-20% SDS-PAGE, and the gels were probed with antibodies against ICAM, VCAM, α5 integrin, and αv integrin. The equal loading and efficiency was evaluated by probing with anti β-actin antibody. The expression of ICAM, VCAM, and α5 integrin was decreased with 4-amino-5-fluoro-3-[6-(4-methylpiperazin-1-yl)-1H-benzimidazol-2-yl]quinolin-2(1H)-one treatment in HUVECs in vitro.

It should be understood that the organic compounds according to the invention may exhibit the phenomenon of tautomerism. As the chemical structures within this specification can only represent one of the possible tautomeric forms at a time, it should be understood that the invention encompasses any tautomeric form of the drawn structure. For example, the compound of Structure IIIB is shown below with one tautomer, Tautomer IIIBa:

IIIB

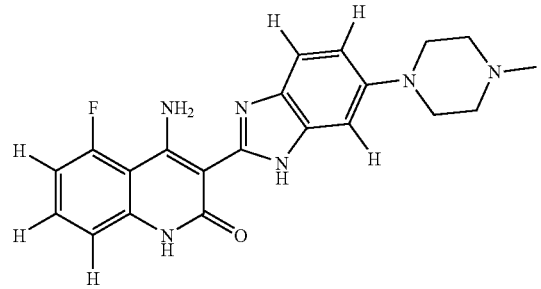

Tautomer IIIBa

Other tautomers of the compound of Structure IIIB, Tautomer IIIBb and Tautomer IIIBc, are shown below:

Tautomer IIIBb

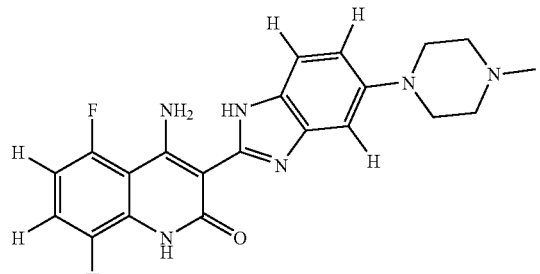

Tautomer IIIBc

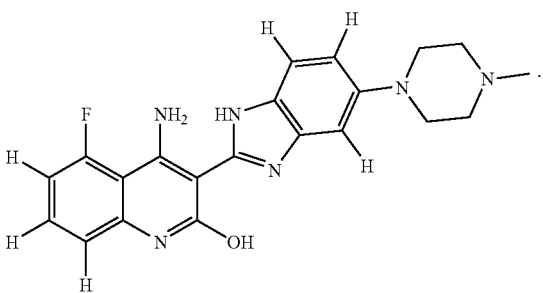

All documents or references cited herein are hereby incorporated by reference in their entireties and for all purposes as if fully set forth herein.

It is understood that the invention is not limited to the embodiments set forth herein for illustration, but embraces all such forms thereof as come within the scope of the invention.

What is claimed is:

1. A method of reducing cellular adhesion in a cancer patient, comprising: administering to the cancer patient a compound of Structure II, a tautomer of the compound, a pharmaceutically acceptable salt of the compound, a pharmaceutically acceptable salt of the tautomer, or a mixture thereof, and measuring the amount of at least one of inducible cell adhesion molecule, vascular cell adhesion molecule, or endothelial leukocyte adhesion molecule in at least a portion of a blood sample withdrawn from the cancer patient after administration of the compound, the tautomer, the pharmaceutically acceptable salt of the compound, the pharmaceutically acceptable salt of the tautomer, or the mixture thereof, wherein cellular adhesion and the levels of circulating adhesion molecules are reduced in the cancer patient after administration, and Structure II has the following formula:

II

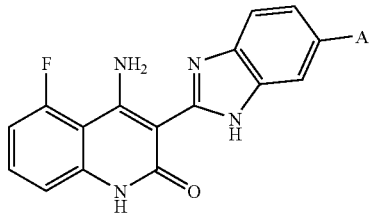

wherein,
A is a group having one of the following Structures:

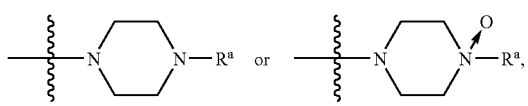

wherein,
$R^a$ is selected from H or straight or branched chain alkyl groups having from 1 to 6 carbon atoms.

2. A method of monitoring the progression of a cancer or cancer treatment in a cancer patient, comprising: measuring the amount of at least one cell adhesion molecule in at least a portion of a blood sample withdrawn from the cancer patient after administration of a compound of Structure II, a tautomer of the compound, a pharmaceutically acceptable salt of the compound, a pharmaceutically acceptable salt of the tautomer, or a mixture thereof to the cancer patient, wherein the cell adhesion molecule is selected from inducible cell adhesion molecule, vascular cell adhesion molecule, or endothelial leukocyte adhesion molecule, and Structure II has the following formula:

wherein,
A is a group having one of the following Structures:

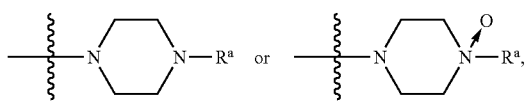

wherein,
$R^a$ is selected from H or straight or branched chain alkyl groups having from 1 to 6 carbon atoms.

3. The method of claim 2, wherein $R^a$ is a methyl group, and the compound of Structure II has the Structure IIA having the following formula:

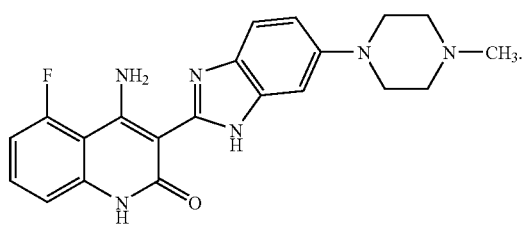

4. The method of claim 3, wherein the pharmaceutically acceptable salt of the compound of Structure IIA, the pharmaceutically acceptable salt of the tautomer, or the mixture thereof is administered to the cancer patient, and the salt is a lactate salt.

5. The method of claim 2, wherein $R^a$ is a hydrogen, and the compound of Structure II has the Structure IIB having the following formula:

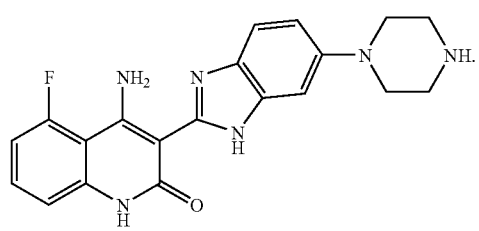

6. The method of claim 2, wherein $R^a$ is a methyl group, and the compound of Structure II has the Structure IIC having the following formula:

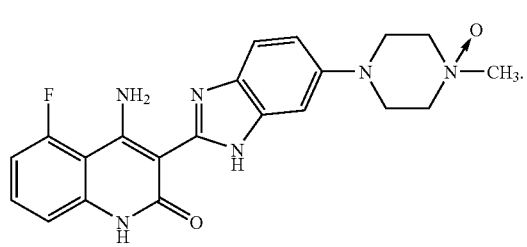

7. The method of claim 1, wherein the amount of at least one of inducible cell adhesion molecule, vascular cell adhesion molecule, or endothelial leukocyte adhesion molecule is reduced in the cancer patient after administration.

8. The method of claim 1, wherein the amount of a matrix metalloprotease is reduced in the cancer patient after administration.

9. The method of claim 8, wherein the matrix metalloprotease is matrix metalloprotease-2 or matrix metalloprotease-9.

10. The method of claim 1, wherein $R^a$ is a methyl group, and the compound of Structure II has the Structure IIA having the following formula:

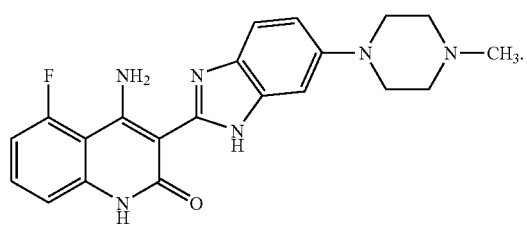

11. The method of claim 10, wherein the pharmaceutically acceptable salt of the compound of Structure IIA, the pharmaceutically acceptable salt of the tautomer, or the mixture thereof is administered to the cancer patient, and the salt is a lactate salt.

12. The method of claim 1, wherein the pharmaceutically acceptable salt of the compound of Structure II, the pharmaceutically acceptable salt of the tautomer, or the mixture thereof is administered to the cancer patient, and the salt is a lactate salt.

13. The method of claim 1, wherein the cancer is selected from the group consisting of bladder cancer, breast cancer, gastrointestinal cancer, ovarian cancer, renal cancer, Hodgkin's lymphoma, and non-Hodgkin's lymphoma.

14. The method of claim 13, wherein the cancer is breast cancer.

15. The method of claim 2, wherein the levels of circulating adhesion molecules are reduced in the cancer patient after administration.

16. The method of claim 2, wherein the amount of at least one of inducible cell adhesion molecule, vascular cell adhesion molecule, or endothelial leukocyte adhesion molecule is reduced in the cancer patient after administration.

17. The method of claim 2, wherein the cancer is selected from the group consisting of bladder cancer, breast cancer, gastrointestinal cancer, ovarian cancer, renal cancer, Hodgkin's lymphoma, and non-Hodgkin's lymphoma.

18. The method of claim 17, wherein the cancer is breast cancer.

\* \* \* \* \*